United States Patent
Chetverin et al.

(12) 
(10) Patent No.: US 6,322,971 B1
(45) Date of Patent: Nov. 27, 2001

(54) OLIGONUCLEOTIDE ARRAYS AND THEIR USE FOR SORTING, ISOLATING, SEQUENCING, AND MANIPULATING NUCLEIC ACIDS

(75) Inventors: Alexander B. Chetverin, Moscow Region (RU); Fred Russell Kramer, Riverdale, NY (US)

(73) Assignee: The Public Health Research Institute of the city of New York, Inc., New York, NY (US)

( * ) Notice: Subject to any disclaimer, the term of this patent is extended or adjusted under 35 U.S.C. 154(b) by 0 days.

(21) Appl. No.: 09/164,249

(22) Filed: Sep. 30, 1998

Related U.S. Application Data

(62) Division of application No. 08/247,530, filed on May 23, 1994, which is a continuation of application No. 07/838,607, filed on Feb. 19, 1992, now abandoned.

(51) Int. Cl.[7] .......................................... C12Q 1/68
(52) U.S. Cl. .................. 435/6; 435/6; 435/91.1; 435/810; 436/501; 436/808; 536/28; 536/29; 536/24.33; 536/25.3; 935/77
(58) Field of Search ................ 435/6, 91.1, 810; 436/501, 808; 536/28, 29, 24.33, 25.3; 935/77

(56) References Cited

U.S. PATENT DOCUMENTS 4,797,355 * 1/1989 Stabinsky ........................... 435/6

FOREIGN PATENT DOCUMENTS

WO89/10977 * 5/1998 (WO) ........................... 435/6

* cited by examiner

Primary Examiner—W. Gary Jones
Assistant Examiner—Janell E. Taylor
(74) Attorney, Agent, or Firm—Fish & Richardson, PC

(57) ABSTRACT

Ligation methods for manipulating nucleic acid stands and oligonucleotides utilizing hybridization arrays of immobilized oligonucleotides. The oligonucleotide arrays may be plain or sectioned, comprehensive or non-comprehensive. The immobilized oligonucleotides may in some cases be binary oligonucleotides having constant as well as variable segments. Some embodiments include amplification of ligated products.

32 Claims, 50 Drawing Sheets

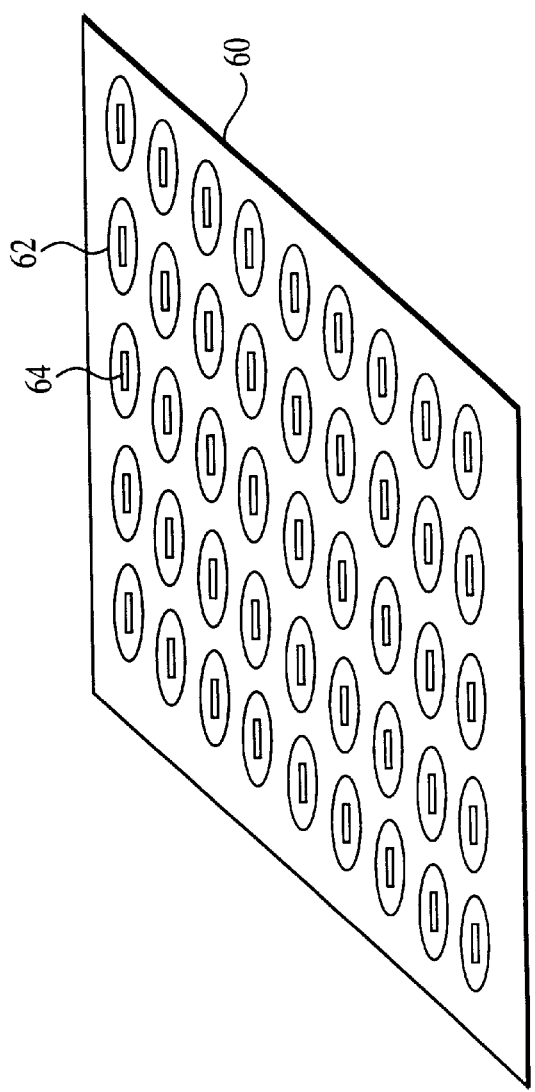
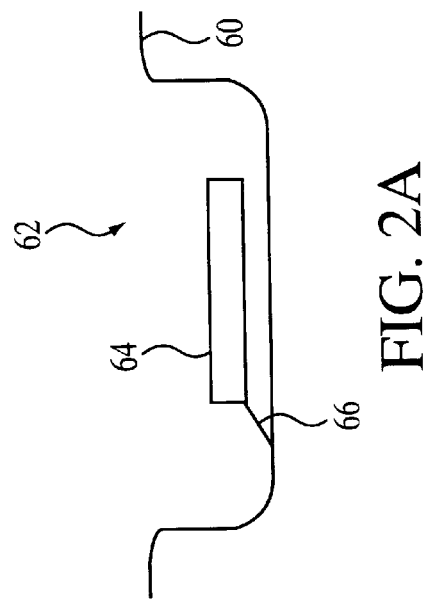
FIG. 2
FIG. 2A

ORIGINAL STRAND:
5'-ATGAGCCTAGATCGGT-3' (SEQ ID NO: 1)

PARTIALS:
5'-ATGAGCC TAG ATCGGT (SEQ ID NO: 1)
5'-ATGAGCC TAG ATCGG (SEQ ID NO: 7)
5'-ATGAGCC TAG ATCG (SEQ ID NO: 8)       ADDRESSES COMPRISING
5'-ATGAGCC TAG ATC (SEQ ID NO: 9)        THE DOWNSTREAM SUBSET
5'-ATGAGCC TAG AT (SEQ ID NO: 10)        OF THE TAG ADDRESS
5'-ATGAGCC TAG A (SEQ ID NO: 11)

5'-ATGAGCC TAG (SEQ ID NO: 12)   THE TAG ADDRESS

5'-ATGAGCC TA
5'-ATGAGCC T
5'-ATGAGCC           ADDRESSES COMPRISING
5'-ATGAGC            THE UPSTREAM SUBSET
5'-ATGAG             OF THE TAG ADDRESS
5'-ATGA
5'-ATG

THE TAG ADDRESS SET:

UPSTREAM SUBSET                DOWNSTREAM SUBSET
5'-[AGC, ATG, CCT, CTA, GAG, GCC, TAG, TGA] TAG [AGA, ATC, CGG, GAT, GGT, TAG, TCG]-3'
(SEQ ID NO: 13)

FIG. 9

OLIGONUCLEOTIDES IN STRAND SET ( n = 3 )

| AGA, | AGC, | ATC, | ATG, | CCT, | CGG, | CTA, |
|------|------|------|------|------|------|------|
| GAG, | GAT, | GCC, | GGT, | TAG, | TCG, | TGA, |

OVERLAPPING SEGMENTS IN OLIGONUCLEOTIDES

| (AG,GA), | (AG,GC), | (AT,TC), | (AT,TG), | (CC,CT), | (CG,GG), | (CT,TA), |
|----------|----------|----------|----------|----------|----------|----------|
| (GA,AG), | (GA,AT), | (GC,CC), | (GG,GT), | (TA,AG), | (TC,CG), | (TG,GA), |

ASSEMBLY USING UNIQUE OVERLAPS

SEQUENCE BLOCKS

AGCCTAG, ATCGGT, ATGA, AGA, GAG, GAT

STRAND SET

GROUPS OF UNIQUELY OVERLAPPING OLIGONUCLEOTIDES

SEQUENCE BLOCKS

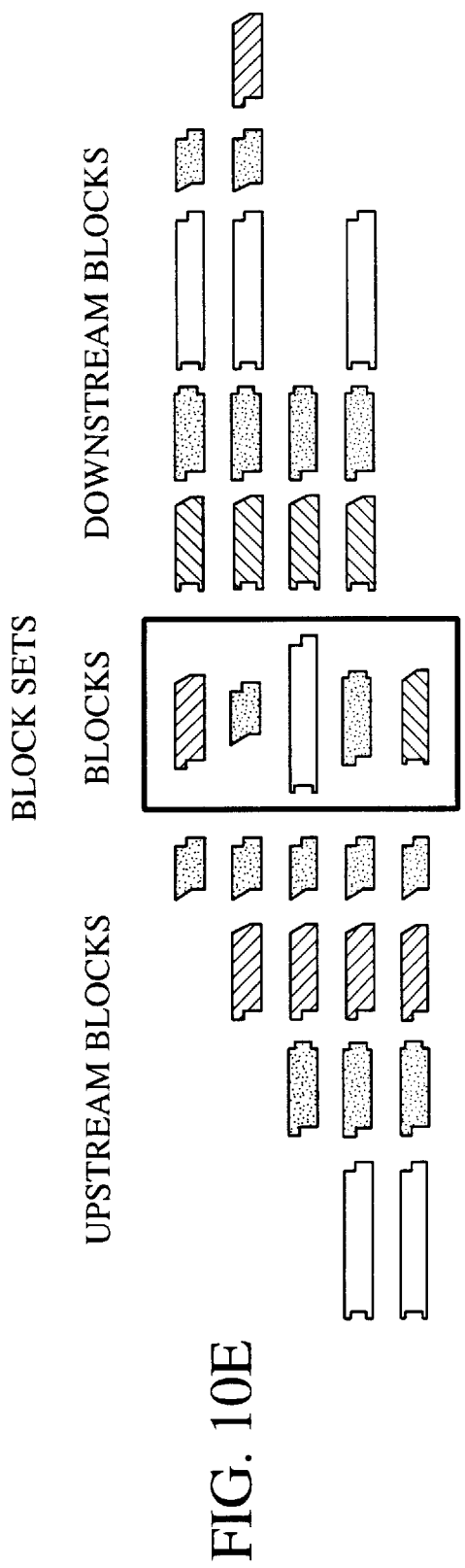

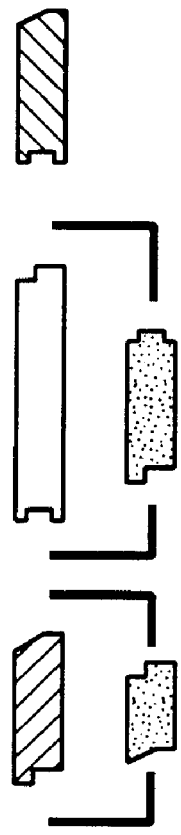
FIG. 10G — ORDERING THE BLOCKS
FIG. 10H — ASSEMBLING THE BLOCKS

UPSTREAM OLIGONUCLEOTIDES
(SURVEYED)

DOWNSTREAM OLIGONUCLEOTIDES
(INFERRED)

SUPERIMPOSITION OF UPSTREAM AND DOWNSTREAM SUBSETS

UNINDEXED ADDRESS SETS

GROUPS OF IDENTICAL
UNINDEXED ADDRESS SETS

FIG. 12A

STRAND SET:
d f g h l m n q

FIG. 12B

STRAND SET:

STRAND SET:

a b d e f g i k p r a b c d e f g h i j k l m n o p q r

III [ b e k p ]

PSEUDO-PRIME SET
a b d f g h l m o p q s t

FIG. 13A

STRAND SET
a d f h l m o p q s t

FIG. 13B

STRAND SET a b d g h l m o q s t

FIG. 13C

UNDIGESTED DNA

FRAGMENTS PRODUCED BY THE A-TYPE RESTRICTION ENDONUCLEASE

FRAGMENTS PRODUCED BY THE B-TYPE RESTRICTION ENDONUCLEASE

STRANDS PRODUCED BY MELTING THE B-TYPE RESTRICTION FRAGMENTS

STRANDS BINDING AND REPLICATION AT THE ADDRESSES:

SEQUENCED DNA FRAGMENTS
PRODUCED BY
RESTRICTION ENDONUCLEASE A

FRAGMENTS FROM THE SAME
DNA REGIONS, PRODUCED BY
RESTRICTION RNDONUCLEASE B

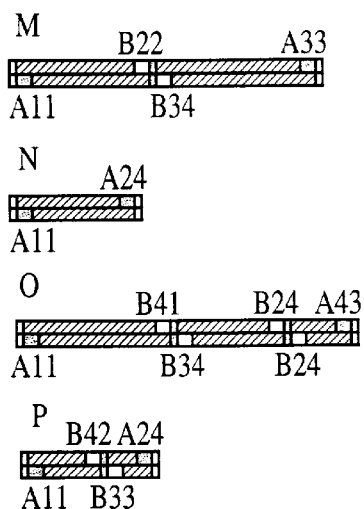
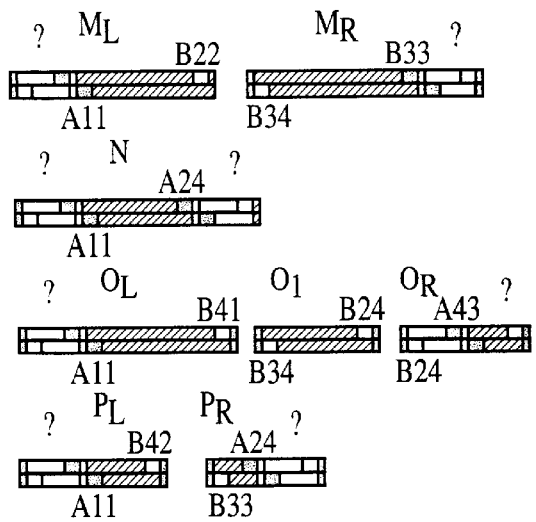

FIG. 15A

ADDRESS OF THE A-TYPE
SORTING ARRAY, OCCUPIED BY
THE B-TYPE FRAGMENTS

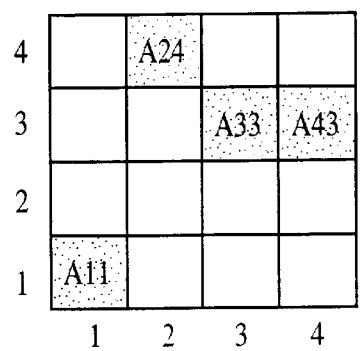

SIGNATURES OF THE INTERSITE
SEGMENTS ABLE TO BIND TO
AN A-TYPE SORTING ARRAY

| INTERSITE SEGMENT | SIGNATURE |
|---|---|
| N | A11-A24 |
| $M_L$ | A11-B22 |
| $O_L$ | A11-B41 |
| $P_L$ | A11-B42 |
| $P_R$ | A24-B33 |
| $M_R$ | A33-B34 |
| $O_R$ | A43-B24 |

FIG. 15B

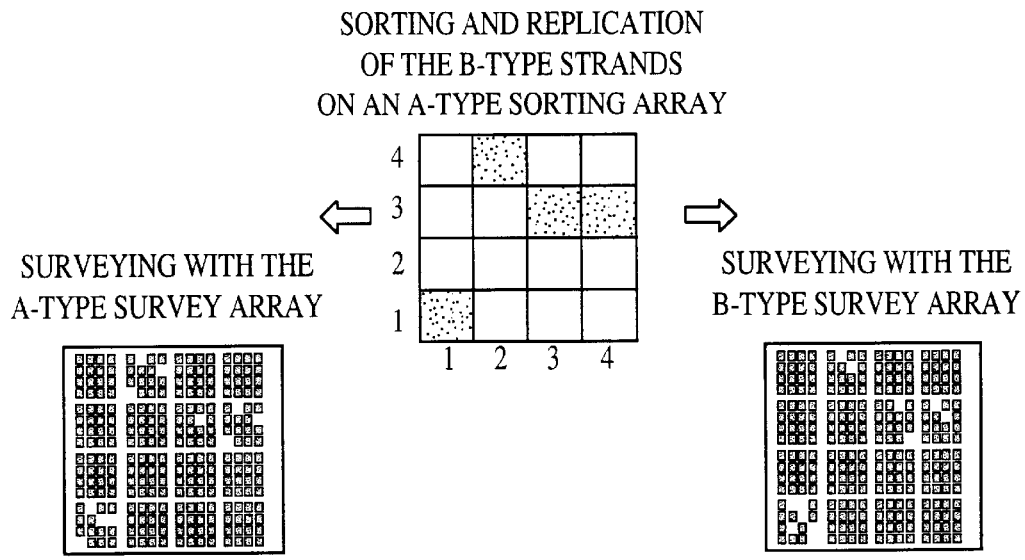

FIG. 16A

| KEY | | RESULTS | | | | |
|---|---|---|---|---|---|---|
| SIGNATURE | INTERSITE SEGMENT | ADDRESS | A-TYPE OLIGOS | B-TYPE OLIGOS | SIGNATURE | INTERSITE SEGMENTS | COMPANION SEGMENTS |
| A11-A24 | N | A11 | A11 A24 A33 A43 | B22 B24 B33 B34 B41 B42 | A11-A24 A11-B22 A11-B41 A24-B33 A33-B34 A43-B24 | N $M_L$ $O_L$ $P_L$ $P_R$ $M_R$ $O_R$ | $\boxed{N P_R O_R}$ $\boxed{O_L M_R}$ $\boxed{M_L}$ $\boxed{P_L}$ |
| A11-B22 | $M_L$ |
| A11-B41 | $O_L$ |
| A11-B42 | $P_L$ | A24 | A11 A24 A43 | B24 B33 | A11-A24 A24-B33 A43-B24 | N $P_R$ $O_R$ | $\boxed{N P_R O_R}$ |
| A24-B33 | $P_R$ |
| A33-B34 | $M_R$ | A33 | A11 A33 | B34 B41 | A11-B41 A33-B34 | $O_L$ $M_R$ | $\boxed{O_L M_R}$ |
| A43-B24 | $O_R$ | A43 | A11 A24 A43 | B24 B33 | A11-A24 A24-B33 A43-B24 | N $P_R$ $O_R$ | $\boxed{N P_R O_R}$ |

FIG. 16B

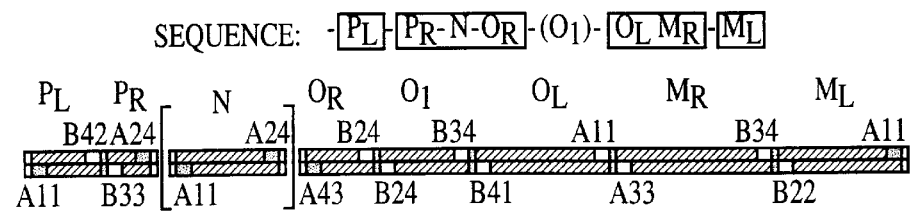

FIG. 16C

CHOSING A RESTRICTION FRAGMENT
THAT SPANS ALLELIC DIFFERENCES

TAKING A SAMPLE AT THE RELEVANT ADDRESS OF A SORTING ARRAY

MELTING THE STRANDS APART

PREPARING PARTICALS AT THE ADDRESSES
THAT ENCOMPASS THE ALLELIC DIFFERENCE
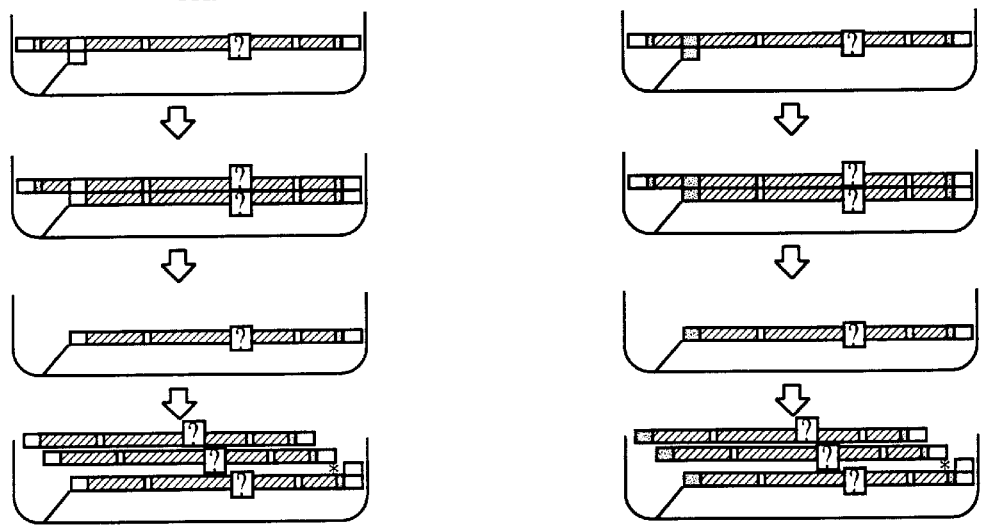
FIG. 17D
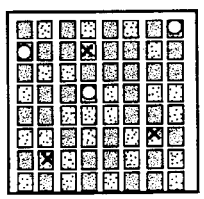 SURVEYING THE OLIGONUCLEOTIDES
AT THOSE ADDRESSES 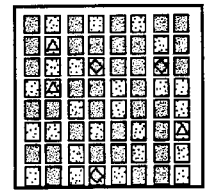
CONCLUSION:

FIG. 18A

STRANDS IN THE MIXTURE

CATGGTACCTTGGTAA (SEQ ID NO: 14)
ATGGTCCTTGGTACCTA (SEQ ID NO: 15)

FIG. 18Bi

UPSTREAM OLIGONUCLEOTIDES (SURVEYED)     ADDRESSES

| | | | | | | | | | | | | | | ADDRESSES |
|---|---|---|---|---|---|---|---|---|---|---|---|---|---|---|
| ACC | ATG | CAT | CCT | | CTT | GGT | GTA | GTC | | TAC | TCC | TGG | TTG | ACC |
| | ATG | CAT | | | | | | | | | | | | ATG |
| | | CAT | | | | | | | | | | | | CAT |
| ACC | ATG | CAT | CCT | | CTT | GGT | GTA | GTC | | TAC | TCC | TGG | TTG | CCT |
| ACC | ATG | CAT | CCT | CTA | CTT | GGT | GTA | GTC | | TAC | TCC | TGG | TTG | CTA |
| ACC | ATG | CAT | CCT | | CTT | GGT | GTA | GTC | | TAC | TCC | TGG | TTG | CTT |
| ACC | ATG | CAT | CCT | | CTT | GGT | GTA | GTC | | TAC | TCC | TGG | | GGT |
| ACC | ATG | CAT | CCT | | CTT | GGT | GTA | GTC | | TAC | TCC | TGG | TTG | GTA |
| | ATG | | | | | GGT | | GTC | | | | TGG | | GTC |
| ACC | | | | | CTT | GGT | GTA | | TAA | TAC | TCC | TGG | TTG | TAA |
| ACC | ATG | CAT | CCT | | CTT | GGT | GTA | GTC | | TAC | TCC | TGG | TTG | TAC |
| | ATG | CAT | | | | GGT | | GTC | | | TCC | TGG | | TCC |
| ACC | ATG | CAT | CCT | | CTT | GGT | GTA | GTC | | TAC | TCC | TGG | TTG | TGG |
| ACC | ATG | CAT | CCT | | CTT | GGT | GTA | GTC | | TAC | TCC | TGG | TTG | TTG |

FIG. 18Bii

| ADDRESSES | DOWNSTREAM OLIGONUCLEOTIDES (INFERRED) | | | | | | | | | | | | | |
|---|---|---|---|---|---|---|---|---|---|---|---|---|---|---|
| | ACC | ATG | CAT | CCT | CTA | CTT | GGT | GTA | GTC | TAA | TAC | TCC | TGG | TTG |
| ACC | ACC | | | CCT | CTA | CTT | GGT | GTA | | TAA | TAC | | TGG | TTG |
| ATG | ACC | ATG | | CCT | CTA | CTT | GGT | GTA | GTC | TAA | TAC | TCC | TGG | TTG |
| CAT | ACC | ATG | CAT | CCT | | CTT | GGT | GTA | | TAA | TAC | | TGG | TTG |
| CCT | ACC | | | CCT | CTA | CTT | GGT | GTA | | TAA | TAC | | TGG | TTG |
| CTA | | | | | CTA | | | | | | | | | |
| CTT | ACC | | | CCT | CTA | CTT | GGT | GTA | | TAA | TAC | | TGG | TTG |
| GGT | ACC | | | CCT | CTA | CTT | GGT | GTA | GTC | TAA | TAC | TCC | TGG | TTG |
| GTA | ACC | | | CCT | CTA | CTT | GGT | GTA | | TAA | TAC | | TGG | TTG |
| GTC | ACC | | | CCT | CTA | CTT | GGT | GTA | GTC | TAA | TAC | TCC | TGG | TTG |
| TAA | | | | | | | | | | TAA | | | | |
| TAC | ACC | | | CCT | CTA | CTT | GGT | GTA | | TAA | TAC | TCC | TGG | TTG |
| TCC | ACC | | | CCT | CTA | CTT | GGT | GTA | GTC | TAA | TAC | TCC | TGG | TTG |
| TGG | ACC | | | CCT | CTA | CTT | GGT | GTA | | TAA | TAC | TCC | TGG | TTG |
| TTG | ACC | | | CCT | CTA | | GGT | GTA | | TAA | TAC | | TGG | TTG |

UNINDEXED ADDRESS SETS

| | ACC | ATG | CAT | CCT | CTA | CTT | GGT | GTA | GTC | TAA | TAC | TCC | TGG | TTG |
|---|---|---|---|---|---|---|---|---|---|---|---|---|---|---|
| ACC | | ATG | CAT | CCT | CTA | CTT | GGT | GTA | GTC | TAA | TAC | TCC | TGG | TTG |
| ATG | ACC | | CAT | CCT | CTA | CTT | GGT | GTA | GTC | TAA | TAC | TCC | TGG | TTG |
| CAT | ACC | ATG | | CCT | CTA | CTT | GGT | GTA | GTC | TAA | TAC | TCC | TGG | TTG |
| CCT | ACC | ATG | CAT | | CTA | CTT | GGT | GTA | GTC | TAA | TAC | | TGG | TTG |
| CTA | ACC | ATG | CAT | CCT | | CTT | GGT | GTA | GTC | TAA | TAC | TCC | TGG | TTG |
| CTT | ACC | ATG | | CCT | CTA | | GGT | GTA | GTC | TAA | TAC | TCC | TGG | TTG |
| GGT | ACC | ATG | CAT | CCT | CTA | CTT | | GTA | GTC | TAA | TAC | TCC | TGG | TTG |
| GTA | ACC | ATG | CAT | CCT | CTA | CTT | GGT | | GTC | TAA | TAC | TCC | TGG | TTG |
| GTC | ACC | ATG | CAT | CCT | CTA | CTT | GGT | GTA | | | TAC | TCC | TGG | TTG |
| TAA | ACC | ATG | CAT | CCT | CTA | CTT | GGT | GTA | GTC | | TAC | TCC | TGG | TTG |
| TAC | ACC | ATG | CAT | CCT | CTA | CTT | GGT | GTA | GTC | TAA | | TCC | TGG | TTG |
| TCC | ACC | ATG | | CCT | CTA | CTT | GGT | GTA | GTC | TAA | TAC | | TGG | TTG |
| TGG | ACC | ATG | CAT | CCT | CTA | CTT | GGT | GTA | GTC | TAA | TAC | TCC | | TTG |
| TTG | ACC | ATG | CAT | CCT | CTA | CTT | GGT | GTA | GTC | TAA | TAC | TCC | TGG | |

GROUPED ADDRESS SETS

I, II, III

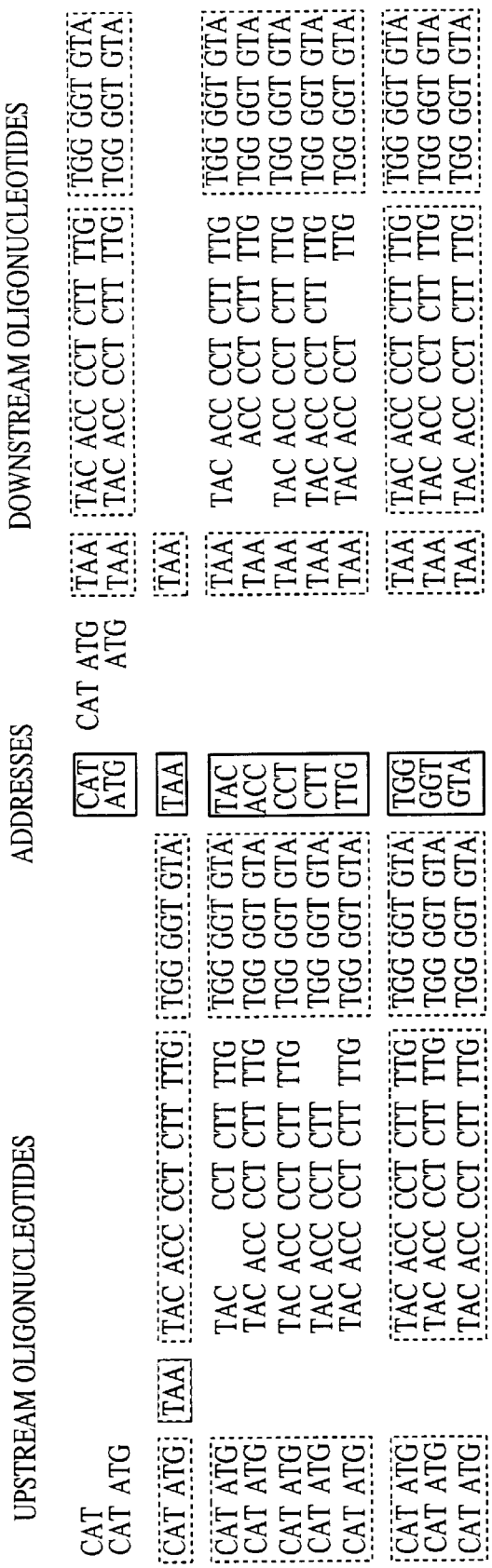

FIG. 20D

UPSTREAM BLOCKS          BLOCKS          DOWNSTREAM BLOCKS

BLOCKS THAT ARE KNOWN TO BE UNIQUE

CATG | TGGTA | CATG | TACCTTG | TAA | TACCTTG | TGGTA
              TAA

OTHER BLOCKS

CATG | TAA | TACCTTG | TGGTA | TAA | TGGTA
CATG | TACCTTG | TGGTA | TAA | TACCTTG | TGGTA

FIG. 20E

ORDERING THE BLOCKS

CATG | TACCTTG | TAA
       TGGTA
⇒
CATG
 TGGTA
  TACCTTG
   TGGTA
    TAA

FIG. 20F    SEQUENCE: CATGGTACCTTGGTAA (SEQ ID NO: 14)

FIG. 21A

STRAND SET B

ACC ATG CCT CTA CTT GGT GTA GTC TAC TCC TGG TTG

FIG. 21B

ASSEMBLING OLIGONUCLEOTIDES INTO BLOCKS

ATG CCT CTA CTT TTG GTA GTC TCC TAC ACC TGG GGT

ATG CCT CTA CTTG GTA GTCC TACC TGGT

FIG. 21C

CONVERTING FILTERED ADDRESS SETS INTO BLOCK SETS

ADDRESSES: ATG CCT CTA CTT/TTG GTA GTC/TCC TAC/ACC TGG/GGT

FIG. 21D

UPSTREAM BLOCKS | BLOCKS | DOWNSTREAM BLOCKS

BLOCKS THAT ARE KNOWN TO BE UNIQUE

OTHER BLOCKS

FIG. 21E ORDERING THE BLOCKS

FIG. 21F  SEQUENCE: ATGGTCCTTGGTACCTA (SEQ ID NO: 15)

STRANDS IN THE MIXTURE

ATGCTGGTATAA (SEQ ID NO: 16)
ATGCTTAGCTAA (SEQ ID NO: 17)
CGCTTAGCTAA (SEQ ID NO: 18)
CGCTTATAA

FIG. 22A

UPSTREAM OLIGONUCLEOTIDES (SURVEYED)

| | | | | | | | | | | ADDRESSES |
|---|---|---|---|---|---|---|---|---|---|---|
| AGC | ATG | CGC | | | | | | TAG | TTA | AGC |
| | ATA | ATG | CGC | | | CTT | GCT | TAG | TTA | ATA |
| | | ATG | | | | | | | | ATG |
| AGC | | ATG | CGC | CTA | CTG | CTT | GCT | | TAT | TGC | TTA | CGC |
| | | ATG | CGC | | CTG | | | TAG | | TGC | | CTA |
| AGC | | ATG | CGC | | | CTT | GCT | | | TGC | | CTG |
| | | ATG | CGC | | CTG | CTT | GCT | GGT | | TGC | | CTT |
| | | ATG | CGC | | CTG | CTT | GCT | GGT | | TGC | TGG | TTA | GGT |
| AGC | ATA | ATG | CGC | CTA | CTG | CTT | GCT | GGT | GTA | TAA | TAG | TAT | TGC | TGG | TTA | GTA |
| | | ATG | CGC | | CTG | CTT | GCT | GGT | GTA | | TAG | | TGC | TGG | TTA | TAA |
| | | ATG | CGC | | | | | | | | | TAG |

UPSTREAM OLIGONUCLEOTIDES (INFERRED)

| ADDRESSES | | | | | | | | | | | | | | |
|---|---|---|---|---|---|---|---|---|---|---|---|---|---|---|
| AGC | AGC | | | | CTA | | | | | | | | | |
| ATA | | ATA | ATG | | | | | | | | | | | |
| ATG | AGC | ATA | | CGC | | | | | | | | | | |
| CGC | AGC | ATA | | | | | | | | | | | | |
| CTA | AGC | | | | CTA | | | GCT | | | TAA | | TGC | TGG | TTA |
| CTG | AGC | ATA | | | CTA | CTG | CTT | GCT | GGT | | TAA | TAG | TAT | | | TTA |
| CTT | AGC | ATA | | | CTA | CTG | CTT | GCT | | | TAA | TAG | TAT | | TGG | TTA |
| GGT | | ATA | | | | CTG | | | GGT | GTA | TAA | | TAT | | TGG | |
| GTA | AGC | ATA | | | CTA | CTG | CTT | GCT | GGT | GTA | TAA | TAG | TAT | | | |
| TAA | AGC | ATA | | | CTA | CTG | | | GGT | GTA | TAA | TAG | TAT | | TGG | TTA |
| TAG | | ATA | | | | | | | | | TAA | TAG | TAT | | | |
| TAT | AGC | ATA | | | CTA | CTG | CTT | GCT | GGT | GTA | TAA | TAG | TAT | TGC | TGG | TTA |
| TGC | AGC | ATA | | | CTA | CTG | | | GGT | GTA | TAA | TAG | TAT | | TGG | TTA |
| TGG | AGC | ATA | | | | | | | | | | TAG | TAT | | | |
| TTA | AGC | ATA | | | CTA | | | GCT | | | | TAG | TAT | | | TTA |

FIG. 22C

UNINDEXED ADDRESS SETS

| ADDRESSES | | | | | | | | | | | | | | | | |
|---|---|---|---|---|---|---|---|---|---|---|---|---|---|---|---|---|
| AGC |     |     | ATG |     |     |     |     |     |     |     |     |     |     |     |     |     |
| ATA |     | ATA | ATG | CGC | CTA |     | CTT | GCT | GGT | GTA | TAA | TAG |     | TGC |     | TTA |
| ATG |     | ATA | ATG | CGC | CTA | CTG | CTT | GCT | GGT | GTA | TAA | TAG | TAT | TGC | TGG | TTA |
| CGC |     | ATA | ATG | CGC | CTA | CTG | CTT | GCT | GGT | GTA | TAA | TAG | TAT | TGC | TGG | TTA |
| CTA |     |     |     |     |     |     | CTT | GCT | GGT | GTA | TAA |     | TAT | TGC |     | TTA |
| CTG |     | ATA | ATG |     |     |     | CTT | GCT | GGT | GTA | TAA | TAG | TAT | TGC | TGG |     |
| CTT |     | ATA | ATG |     | CTA | CTG |     | GCT | GGT | GTA | TAA | TAG | TAT | TGC | TGG |     |
| GCT |     | ATA | ATG | CGC | CTA | CTG | CTT |     | GGT | GTA | TAA |     | TAT | TGC |     |     |
| GGT |     | ATA | ATG | CGC | CTA |     | CTT | GCT |     | GTA | TAA | TAG | TAT | TGC | TGG |     |
| GTA |     | ATA | ATG | CGC | CTA | CTG | CTT | GCT | GGT |     | TAA | TAG | TAT | TGC | TGG | TTA |
| TAA |     | ATA | ATG | CGC | CTA | CTG | CTT | GCT | GGT | GTA |     | TAG | TAT | TGC | TGG | TTA |
| TAG |     | ATA | ATG | CGC | CTA | CTG | CTT | GCT | GGT | GTA | TAA |     | TAT | TGC | TGG | TTA |
| TAT |     |     | ATG |     | CTA | CTG | CTT | GCT | GGT | GTA | TAA | TAG |     | TGC | TGG | TTA |
| TGC |     | ATA | ATG | CGC | CTA | CTG | CTT | GCT | GGT | GTA | TAA | TAG | TAT |     | TGG | TTA |
| TGG |     |     |     |     |     |     |     |     |     |     | TAA | TAG |     | TGC |     | TTA |
| TTA |     | ATA | ATG | CGC | CTA | CTG | CTT | GCT | GGT | GTA | TAA | TAG | TAT | TGC | TGG |     |

GROUPED ADDRESS SETS

C: PSEUDO-PRIME SET

| | | | | | | | | | | | |
|---|---|---|---|---|---|---|---|---|---|---|---|
| AGC | ATA | | CGC | CTA | | CTT | GCT | | TAA | TAG | TAT | | |
| AGC | ATA | ATG | CGC | CTA | CTG | CTT | GCT | GGT | TAA | TAG | TAT | TGC | | TTA | IV |
| AGC | ATA | ATG | CGC | CTA | CTG | CTT | GCT | GGT | TAA | TAG | TAT | TGC | TGG | TTA | VI |
| AGC | ATA | ATG | CGC | CTA | CTG | CTT | GCT | GTA | TAA | TAG | TAT | TGC | TGG | TTA | VII |

CGC
CTT  TTA
GCT  TAA

FIG. 23C

DECOMPOSING PSEUDO-PRIME SETS

A1: AGC CTA ATG CGC CTA CTT GCT TAA TAG TGC TTA

| | | | | | | | | | | |
|---|---|---|---|---|---|---|---|---|---|---|
| AGC | ATA | ATG | CGC | CTA | | CTT | GCT | TAA | TAG | TGC | TTA |
| AGC | ATA | ATG | CGC | CTA | | CTT | GCT | TAA | TAG | TGC | TTA |
| AGC | | ATG | CGC | CTA | | CTT | GCT | TAA | TAG | TGC | TTA |
| AGC | ATA | ATG | CGC | CTA | | CTT | GCT | TAA | TAG | | |
| AGC | ATA | ATG | CGC | | CTG | CTT | GCT | TAA | TAG | TGC | TTA |
| AGC | ATA | ATG | | | CTG | CTT | GGT | TAA | TAG | TGC | TTA |
| AGC | ATA | ATG | CGC | CTA | CTG | CTT | GGT | TAA | TAG | TAT | TGC | TTA |
| AGC | ATA | ATG | CGC | CTA | CTG | CTT | GGT | TAA | TAG | TAT | TGC | TTA |

— I
VI
III
VII

AGC CTA TAG
CTT TTA
ATG TGC
GCT TAA

FIG. 24A

A2: AGC CGC CTA CTT GCT TAA TAG TAT TGC TGG TTA

| | | | | | | | | | | |
|---|---|---|---|---|---|---|---|---|---|---|
| AGC | ATA | ATG | CGC | CTA | | CTT | GCT | TAA | TAG | | TGC | | TTA |
| AGC | ATA | ATG | CGC | CTA | | CTT | GCT | TAA | TAG | | TGC | | TTA |
| AGC | ATA | ATG | CGC | CTA | | CTT | GCT | TAA | TAG | | TGC | | TTA |
| AGC | ATA | | CGC | CTA | | CTT | GCT | TAA | TAG | TAT | TGC | | TTA |
| AGC | | ATG | CGC | CTA | | CTT | | TAA | TAG | TAT | TGC | | TTA |
| AGC | ATA | ATG | CGC | CTA | | CTT | GCT | TAA | TAG | TAT | TGC | TGG | TTA |
| AGC | ATA | ATG | CGC | CTA | CTG | CTT | GGT | TAA | TAG | TAT | TGC | TGG | TTA |
| AGC | ATA | ATG | CGC | CTA | CTG | CTT | GGT | TAA | TAG | TAT | TGC | TGG | TTA |

— I
IV
VI
VII

AGC CTA TAG TTA
CGC
CTT TTA
GCT TAA

FIG. 24B

DECOMPOSING PSEUDO-PRIME SETS

FIG. 24C

C1: ATA

| | AGC | ATA | ATG | CGC | CTA | CTG | CTT | GCT | GGT | GTA | TAA | TAG | TAT | TGC | TGG | TTA | |
|---|---|---|---|---|---|---|---|---|---|---|---|---|---|---|---|---|---|
| CGC | AGC | ATA | | CGC | CTA | | CTT | GCT | | | TAA | TAG | TAT | | | TTA | IV |
| CTT/TTA | AGC | ATA | ATG | CGC | CTA | | CTT | GCT | | | TAA | TAG | TAT | TGC | TGG | TTA | VI |
| ATA/TAT | | ATA | ATG | CGC | | CTG | CTT | GCT | GGT | GTA | TAA | | TAT | TGC | TGG | TTA | II |
| GCT/TAA | AGC | ATA | ATG | CGC | CTA | CTG | CTT | GCT | GGT | GTA | TAA | TAG | TAT | TGC | TGG | TTA | VII |

FIG. 24D

C2: AGC

| | AGC | ATA | ATG | CGC | CTA | CTG | CTT | GCT | GGT | GTA | TAA | TAG | TAT | TGC | TGG | TTA | |
|---|---|---|---|---|---|---|---|---|---|---|---|---|---|---|---|---|---|
| CGC | AGC | ATA | | CGC | CTA | | CTT | GCT | | | TAA | TAG | TAT | | | TTA | IV |
| AGC/CTA/TAG | | | ATG | CGC | CTA | | CTT | GCT | | | TAA | TAG | TAT | TGC | TGG | TTA | I |
| CTT/TTA | AGC | ATA | ATG | CGC | CTA | | CTT | GCT | | | TAA | TAG | TAT | TGC | TGG | TTA | VI |
| GCT/TAA | AGC | ATA | ATG | CGC | CTA | CTG | CTT | GCT | GGT | GTA | TAA | TAG | TAT | TGC | TGG | TTA | VII |

FIG. 25A

STRAND SET A1

AGC ATG CTA CTT GCT TAA TAG TGC TTA

FIG. 25B

ASSEMBLING OLIGONUCLEOTIDES INTO BLOCKS

| ATG TGC | CTA | CTT TTA | GCT | TAA | TAG AGC |
|---------|-----|---------|-----|-----|---------|
| ATGC    | CTA | CTTA    | GCT | TAA | TAGC    |

FIG. 25C

CONVERTING FILTERED ADDRESS SETS INTO BLOCK SETS

UPSTREAM OLIGONUCLEOTIDES     ADDRESSES     DOWNSTREAM OLIGONUCLEOTIDES

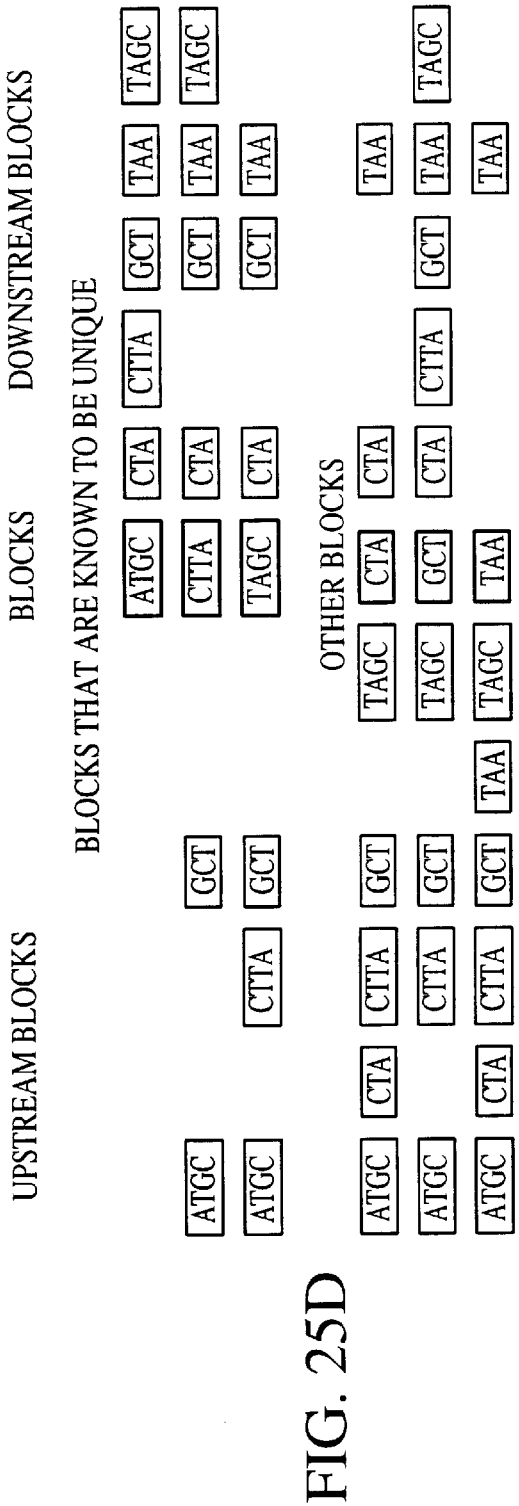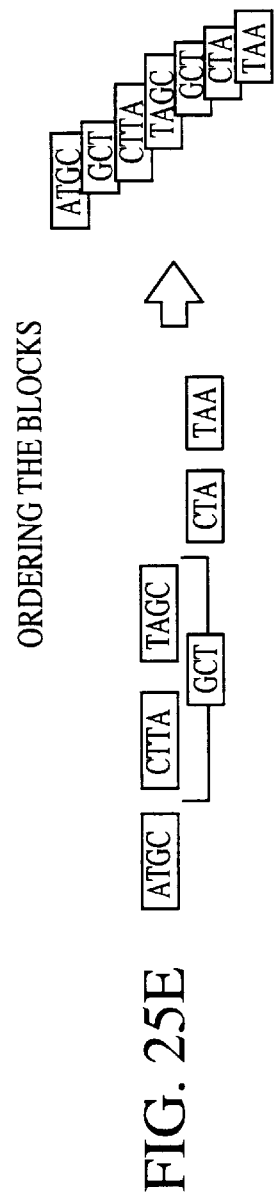
FIG. 25D
FIG. 25E   ORDERING THE BLOCKS
FIG. 25F   SEQUENCE: ATGCTTAGCTAA (SEQ ID NO: 17)

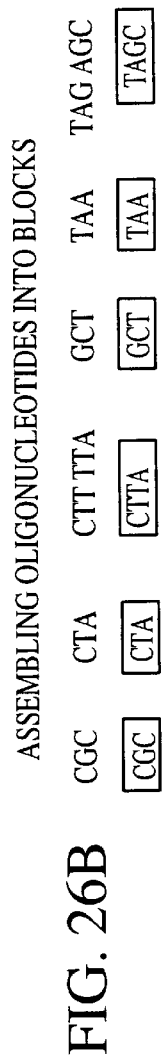
FIG. 26A
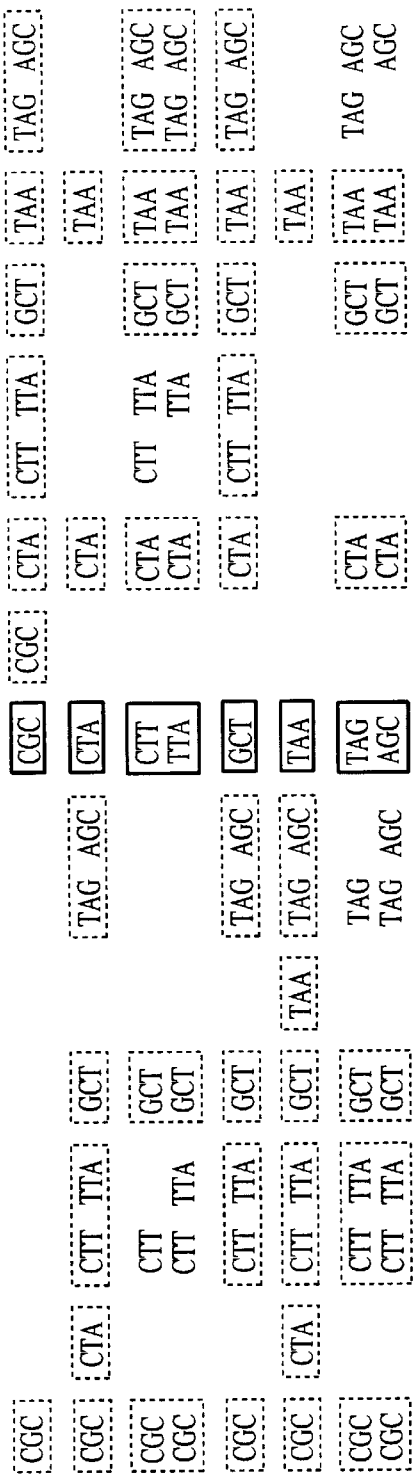
FIG. 26B
FIG. 26C

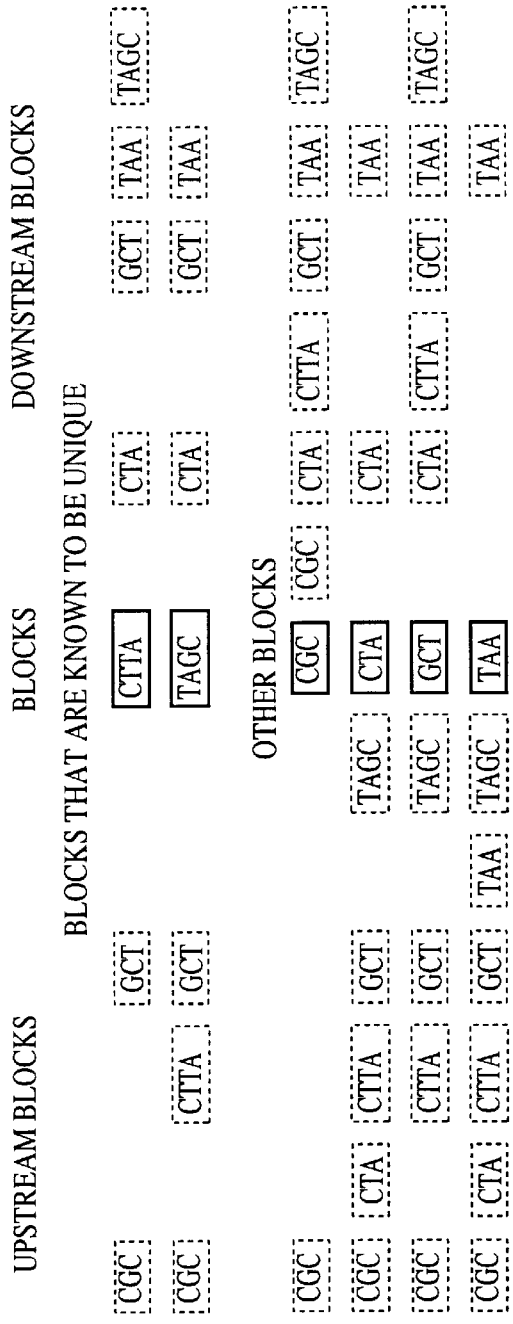
FIG. 26D
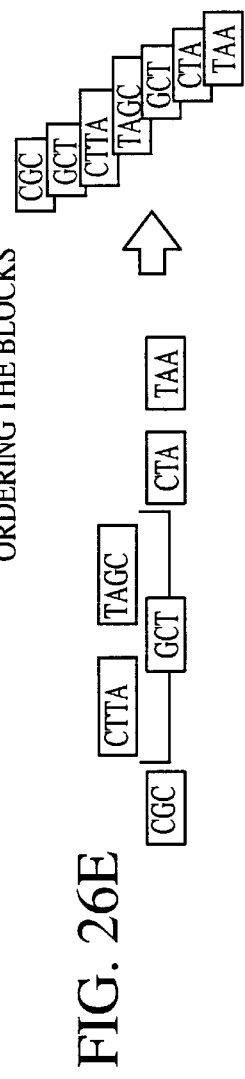
FIG. 26E  ORDERING THE BLOCKS
FIG. 26F  SEQUENCE: CGCTTAGCTAA (SEQ ID NO: 18)

FIG. 27A  STRAND SET B  ATA ATG ATG CTG GCT GGT GTA TAA TAT TGC TGG

ASSEMBLING OLIGONUCLEOTIDES INTO BLOCKS

FIG. 27B

| ATA | ATG | TAA | TAT | TGC GCT CTG | TGG GGT GTA |
|-----|-----|-----|-----|-------------|-------------|
| ATA | ATG | TAA | TAT | TGCTG       | TGGTA       |

CONVERTING FILTERED ADDRESS SETS INTO BLOCK SETS

FIG. 27C

UPSTREAM OLIGONUCLEOTIDES        ADDRESSES        DOWNSTREAM OLIGONUCLEOTIDES

FIG. 27F  SEQUENCE: ATGCTGGTATAA

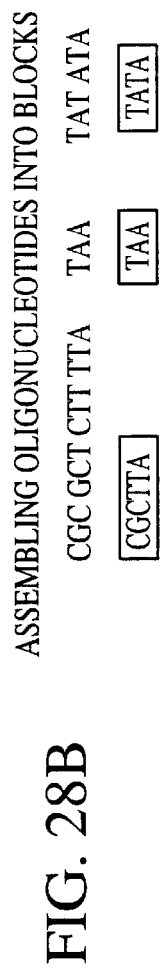
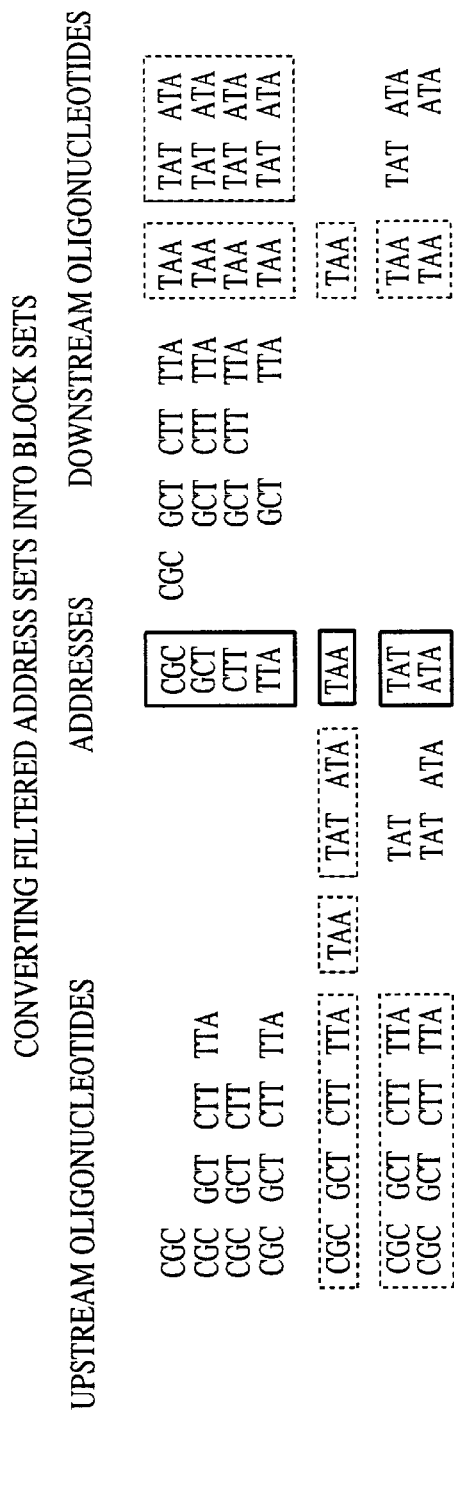
FIG. 28A
FIG. 28B
FIG. 28C

OLIGONUCLEOTIDE ARRAYS AND THEIR USE FOR SORTING, ISOLATING, SEQUENCING, AND MANIPULATING NUCLEIC ACIDS

This application is a division of Ser. No. 08/247,530, filed May 23, 1994, which is a continuation of Ser. No. 07/838,607, filed Feb. 19, 1992, now abandoned.

FIELD OF THE INVENTION

BACKGROUND OF THE INVENTION

Ordered arrays of oligonucleotides immobilized on a solid support have been proposed for sequencing DNA fragments. It has been recognized that hybridization of a cloned single-stranded DNA fragment to all possible oligonucleotide probes of a given length can identify the corresponding, complementary oligonucleotide segments that are present somewhere in the fragment, and that this information can sometimes be used to determine the DNA sequence. Use of arrays can greatly facilitate the surveying of a DNA fragment's oligonucleotide segments. There are two approaches currently being employed.

In one approach, each oligonucleotide probe is immobilized on a solid support at a different predetermined position, forming an array of oligonucleotides. The array allows one to simultaneously survey all the oligonucleotide segments in a DNA fragment strand. Many copies of the strand are required, of course. Ideally, surveying is carried out under conditions to ensure that only perfectly matched hybrids will form. Oligonucleotide segments present in the strand can be identified by determining those positions in the array where hybridization occurs. The nucleotide sequence of the DNA sometimes can be ascertained by ordering the identified oligonucleotide segments in an overlapping fashion. For every identified oligonucleotide segment, there must be another oligonucleotide segment whose sequence overlaps it by all but one nucleotide. The entire sequence of the DNA strand can be represented by a series of overlapping oligonucleotides, each of equal length, and each located one nucleotide further along the sequence. As long as every overlap is unique, all of the identified oligonucleotides can be assembled into a contiguous sequence block [Bains, W. and Smith, G. (1988). A Novel Method for Nucleic Acid Sequence Determination, *J. Theor. Biol.* 135, 303–307; Lysov, Yu. P., Florentiev, V. L., Khorlin, A. A., Khrapko, K. R., Shik, V. V. and Mirzabekov, A. D., (1988). Determination of the Nucleotide Sequence of DNA Using Hybridization to Oligonucleotides. A New Method, *Doklady Akademii Nauk SSSR* 303, 1508–1511]. The practical feasibility of using oligonucleotide arrays for sequencing nucleic acid fragments has been demonstrated in model experiments in which short synthetic DNA strands made of pyrimidines were hybridized to an array containing the 4,096 possible octapurines [Maskos, U. and Southern, E. M. (1991). Analyzing Nucleic Acids by Hybridization to Arrays of Oligonucleotides: Evaluation of Sequence Analysis, In *Genome Mapping and Sequencing* (Abstracts of papers presented at the 1991 meeting arranged by M. Olson, C. Cantor and R. Roberts), p. 143, Cold Spring Harbor Laboratory, Cold Spring Harbor, N.Y.].

An attractive feature of sequencing by oligonucleotide hybridization is its suitability for being automated. Another attractive feature is its tolerance of detection errors. There is an inherent redundancy in the data, due to the overlapping nature of the oligonucleotides. In contradistinction, current prevalent sequencing methods are based on the reading of sequences one nucleotide at a time, and it is common to overlook a legitimate nucleotide or to insert an illegitimate nucleotide. There is, however, an important limitation to sequencing by known surveying techniques. As relatively longer DNA strands are surveyed, there is an increasing probability that more than two identified oligonucleotides will share the same overlapping sequence, i.e., the overlap is not unique. When this occurs, the sequence of the DNA cannot be unambiguously determined. Instead of one contiguous sequence block that contains the entire DNA sequence, the oligonucleotides can only be assembled into a number of smaller sequence blocks, whose order is not known. Lysov et al. have estimated that, if oligonucleotide probes 8 nucleotides in length are used, then at least 20 percent of all random sequences merely 200 nucleotides in length can not be assembled into a single sequence block, because of the presence of non-unique overlaps. The longer the DNA sequence, the worse this problem becomes. Khrapko et al. suggested that the ambiguities in reconstruction of a DNA sequence caused by the presence of non-unique overlaps between surveyed oligonucleotides could be resolved by a secondary hybridization of the DNA-oligonucleotide complexes to a series of short oligonucleotides, so that the two hybrids would stack on each other, thus producing a longer duplex [Khrapko, K. R., Lysov, Yu. P., Khorlin, A. A., Shik, V. V., Florentiev, V. L. and Mirzabekov, A. D. (1989). An Oligonucleotide Hybridization Approach to DNA Sequencing, *FEBS Lett.* 256, 118–122].

Another way of using arrays for DNA sequencing has been proposed by Drmanac et al. In their method, many different cloned DNA strands are each bound to a solid support at a different position. All are then tested in parallel for their ability to form a hybrid with each of the possible oligonucleotides of a given length. One oligonucleotide at a time is tested. To resolve ambiguities arising because of the presence of non-unique overlaps between the oligonucleotides revealed in a DNA strand, it has been suggested that a library of densely overlapping cloned fragments be prepared and analyzed. The library would be composed of approximately 500-nucleotide-long DNA strands with a 40-nucleotide average displacement. [Drmanac, R., Labat, I., Brukner, I. and Crkvenjakov, R. (1989). Sequencing of Megabase Plus DNA by Hybridization: Theory of the Method, *Genomics* 4, 114–128]. The feasibility of this method has also been demonstrated [Strezoska, Z., Paunesky, T., Radosavljevic, D., Labat, I., Drmanac, R. and Crkvenjakov, R. (1991). DNA Sequencing by Hybridization: 100 Bases Read by a Non-gel Method, *Proc. Natl. Acad. Sci U.S.A.* 88, 10089–10093].

The sequencing techniques described above, as well as conventional sequencing techniques, rely on cloning the fragments to be sequenced. Cloning of DNA fragments is well known. For cloning, DNA fragments are ligated into cloning vectors (e.g., plasmids or bacteriophage DNAs), which are then introduced by means of transformation into microbial cells, where they are amplified. At appropriate ratios of fragment-to-vector and vector-to-cell, there will be only one fragment ligated into a vector molecule, and only one recombinant molecule introduced into each transformed cell. By obtaining progeny from individual transformed cells (clones) individual DNA fragments can be isolated. If a large DNA (e.g., a genome) were to be sequenced, it first would be cleaved into pieces of suitable size by, for example, digestion with a restriction endonuclease. The goal of the cloning procedure, in this case, is to obtain a comprehensive library of cloned fragments, which, taken together, comprise every segment of the DNA to be sequenced. However, the completion of a clone library is essentially an asymptotic process. Because fragment cloning is intrinsically random, the number of clones that have to be isolated and analyzed is much greater than the number of different restriction fragments produced by digestion of the original DNA [Sambrook, J., Fritsch, E. F. and Maniatis, T. (1989). *Molecular Cloning: A Laboratory Manual;* 2nd edition, Cold Spring Harbor Laboratory Press, Cold Spring Harbor, N.Y.]. Moreover, there is no way to know whether the library is comprehensive or not, until the sequenced fragments are finally assembled. The cloning of fragments of an entire genome is extremely slow and tedious.

Recently, in place of classic cloning techniques, individual DNA fragments have been amplified by the polymerase chain reaction (PCR). Briefly, this method is based on the hybridization of two oligodeoxynucleotide probes (primers) to DNA strands and the extension of these primers by incubation with DNA polymerase. The primers are intended to hybridize to unique locations within complementary strands of the same DNA molecule, and their growing 3' termini are directed towards each other, so that their extension results in the replication of the DNA region included between them. The DNA template and product strands are then melted apart at elevated temperature to allow the next round of replication, where both the product strand and the template strand serve as templates for additional replication. This process is repeated many times by cycling between the annealing and melting temperatures, resulting in exponential amplification of the target region [see for example, Mullis et al., U.S. Pat. Nos. 4,800,159 and 4,965,188], incorporated by reference herein. The advantage of PCR over cloning is that fragment isolation becomes deterministic, instead of being random. However, in order to use PCR for preparing DNA fragments, two unique oligonucleotide primers must be synthesized for every new fragment that is amplified. Moreover, the terminal sequences of each fragment must be known in advance. Thus latter circumstance makes PCR, in its current form, barely useful for the preparation of individual fragments of unknown nucleotide sequences.

SUMMARY OF THE INVENTION

We have invented new oligonucleotide arrays and methods of using them.

A binary array according to the invention contains immobilized oligonucleotides comprised of two sequence segments of predetermined length, one variable and the other constant. The constant segment is the same in every oligonucleotide of the array. The variable segments can vary both in sequence and length. Binary arrays have advantages compared with ordinary arrays: (1) they can be used to sort strands according to their terminal sequences, so that each strand binds to a fixed location (an address) within the array; (2) longer oligonucleotides can be used on an array of a given size, thereby increasing the selectivity of hybridization; this allows strands to be sorted according to the identity of internal oligonucleotide segments adjacent to a particular constant sequence (such as a segment adjacent to a recognition site for a particular restriction endonuclease), and this allows strands to be surveyed for the presence of signature oligonucleotides that contain a constant segment in addition to a variable segment; (3) universal sequences, such as priming sites, can be introduced into the termini of sorted strands using the binary arrays, thereby enabling the strands' specific amplification without synthesizing primers specific for each strand, and without knowledge of each strand's terminal sequences; and (4) the specificity of hybridization during surveying can be increased by coupling hybridization to a ligation event that discriminates against terminal base-pair mismatches.

A sectioned array as used herein is an array that is divided into sections, so that every individual area is mechanically separated from all other areas, such as, for example, a depression on the surface, or a "well". The areas have different oligonucleotides immobilized thereon. A sectioned array allows many reactions to be performed simultaneously, both on the surface of the solid support and in solution, without mixing the products of different reactions. The reactions occurring in different wells are highly specific, the specificity of the reaction occurring in each well being determined by the nucleotide sequence of the oligonucleotide immobilized on the surface. This allows a large number of sortings and manipulations of nucleic acids to be carried out in parallel, by amplifying or modifying only those nucleic acids in each well that are perfectly hybridized to the immobilized oligonucleotides. Nucleic acids prepared on a sectioned array can be transferred to other arrays (replicated) by direct blotting of the wells' contents (printing), without mixing the contents of different wells of the same array. Furthermore, the presence of individual sections in arrays allows multiple re-hybridizations of bound nucleic acids to be performed, resulting in a significant increase in hybridization specificity. It is particularly advantageous according to this invention to use a binary array that is sectioned.

An important feature of arrays which determines their use in the methods described herein is the way oligonucleotides are attached to their surfaces. For many applications we prefer arrays in which the 3' end of each immobilized oligonucleotides is free, enabling it to be extended by incubation with a DNA polymerase, utilizing a strand hybridized to the oligonucleotide as a template. This provides: (1) a further increase in hybridization specificity, because hybrid extension by DNA polymerase is highly sensitive to terminal mismatches; (2) the ability to obtain strand copies (complementary to the hybridized strands) covalently linked to the array surface, which allows the arrays to be vigorously washed to remove non-covalently bound material, and allows the arrays to serve as permanent banks of sorted nucleic acid strands; and (3) the ability to generate partial copies of hybridized strands by extending the immobilized oligonucleotide after it has bound to an internal segment of the hybridized strand.

Our invention includes methods of using sectioned arrays to sort mixtures of nucleic acid strands, either RNA or DNA. As used herein, "strand" means not just a single strand, but multiple copies thereof; and "mixture of strands" means a mixture of copies of different strands no matter how many copies of each is present. Similarly "fragment" refers to multiple copies thereof, and "mixture of fragments" means a mixture of copies of different fragments. The methods include sorting nucleic acid strands either according to their terminal oligonucleotide segments (3'-terminal or 5'-terminal), or according to their internal oligonucleotide segments on a binary array. Before or after sorting, universal priming region(s) can be added to the strands' termini to enable their subsequent amplification. Binary sectioned arrays for sorting according to strands' terminal sequences ("terminal sequence sorting arrays") can be "comprehensive". A comprehensive array is one wherein any possible strand will hybridize to at least one immobilized oligonucleotide. This type of sorting is particularly useful for preparing comprehensive libraries of fragments of a large genome. For example, in one embodiment of the invention, strands of restriction fragments have their restriction sites restored and are sorted on a binary array. That array contains immobilized oligonucleotides whose constant segments contain the sequence complementary to the restriction site, and an adjacent variable segment. The array is complete, containing all variable sequences of each type in separate areas.

Our invention also includes methods of using sectioned arrays, preferably binary, for isolating individual strands (or pairs of allelic strands in the case of a diploid genome). If the starting material is a complex mixture of strands, such as resulting from a restriction digest of an entire human genome, the isolation is performed in two stages. In the first stage, the strands are sorted into groups according to the identity of their terminal sequences, and then amplified to produce direct and/or complementary copies of the bound strands. In the second stage, isolation of individual strands is achieved by sorting the strand copies in each area of the first array on a second array according to their terminal sequences. If the strands were sorted according to their 3' sequences on the first array, the direct copies are sorted by their 5' terminal sequences, or the complementary copies are sorted by their 3' terminal sequences. There are also embodiments wherein individual strands can be obtained by sorting strands according to their internal sequences.

Our invention also includes using sectioned arrays for preparing every possible partial copy of a strand or a group of strands. The term "partial" refers to multiple copies thereof. Partials are prepared by either of the following methods: (1) terminal sorting on a binary sectioned array of a mixture of all possible partial strands generated by random degradation of a parental strand; or (2) generation of partials directly on an array, through the sorting on an ordinary sectioned array of parental strands according to the identity of their internal oligonucleotide sequences, followed by the synthesis of partial copies of each parental strand by enzymatic extension of the immobilized oligonucleotides on the array utilizing the hybridized parental strands as templates. In either case, the partials that are generated correspond to a parental strand whose 3' or 5' end is truncated to all possible extents (at the "variable" end of the partial), and whose other end is preserved (at the "fixed" end of the partial). These are "one-sided partials." Unless otherwise indicated the word "partial" is used herein to refer to one-sided partials. Our invention also includes the preparation of "two-sided partials" that correspond to a parental strand that is truncated to any extent from both ends using our procedures for preparing one sided partials. These are prepared in a two-stage procedure, each stage resulting in the truncation of one of the ends. If a parental strand has been truncated at its 3' end in the first stage (its 5' end being fixed), the resulting partials are truncated in the second stage from the other side by either truncation of direct copies at their 5' ends (their 3' ends being fixed), or by truncation of complementary copies at their 3' ends (their 5' ends being fixed).

Our invention also includes using sectioned arrays to isolate individual partials from one parental strand or from a group of parental strands.

Our invention also includes methods of using sectioned arrays for carrying out recombinations between chosen segments of previously sequenced nucleic acids. The recombination can be performed on an array in a massively parallel and precisely directed procedure. The recombinants can be constructed from isolated strands or their partials, from mixtures of strands, or from mixtures of their partials.

Our invention also includes methods of using sectioned arrays for the massively parallel introduction of site-directed mutations into sequenced nucleic acids, including the introduction of nucleotide substitutions, deletions, and insertions, using isolated partials, or mixtures of partials. In particular, a single array can be used in one procedure, either to alter many single positions in a gene, or to introduce alterations in many genes. Sectioned arrays can also be subsequently used for the massively parallel testing of the biological effects of the introduced mutations.

Our invention also includes methods of using oligonucleotide arrays for obtaining oligonucleotide information as part of a process for determining the nucleotide sequence of a long nucleic acid strand, or of many nucleic acid strands in an unknown mixture. A complete set of one-sided partials of the strand or strands is prepared on a sectioned array, and the oligonucleotide content of the partial strands in each well of the array is separately surveyed (i.e. each group of partials sharing the same oligonucleotide at the partials' variable end is surveyed). Once the oligonucleotide information is obtained, we infer "address sets". Each address set is a complete list of all oligonucleotides that are contained in the parental strand, or strands, sharing a particular oligonucleotide. We then decompose the address sets into their constituent "strand sets", which are complete lists of all of the oligonucleotides that are contained in each parental strand. To arrive at the oligonucleotide sequence of the starting strand(s), the order of oligonucleotides in each strand is then inferred by analyzing the distribution of the oligonucleotides between the "upstream subset" (i.e., 5') and "downstream subset" (i.e., 3') of the relevant address sets.

Our invention also includes methods of using oligonucleotide arrays for ordering previously sequenced fragments from a first restriction digest of a large nucleic acid or even a genome. This involves sorting a second (alternate) restriction digest of long DNA into groups of strands on a sectioned array, preferably on a sectioned binary array, and preferably by the oligonucleotides adjacent to the first or second restriction site. Then the sorted strands in each well are amplified (preferably by symmetric PCR). Then two surveys of the strands in each well are carried out with binary arrays to identify "signature oligonucleotides" that are present in the strands of each well of the sorting array. A signature oligonucleotide is a variable sequence and an adjacent restriction recognition sequence, using the first restriction recognition sequence for one survey and the second restriction recognition sequence for the other survey. Then it is then determined which of all pairwise combinations of signature oligonucleotides found in each well correspond to the signatures of the "intersite segments" that actually occur among the sequenced fragments. An "intersite segment" is a segment of a DNA fragment between two closest restriction recognition sites of either type. Thus, an intersite segment always has two signature oligonucleotides, of either type, and they are always located at its termini. The pair of signature oligonucleotides is an "intersite segment signature" or, for short, a "signature". Then we determine which combinations of two or more intersite segments accompany each other in two or more different wells of the sorting array by determining which combination of two or more signatures accompany each other in two or more different wells of the sorting array. Then the sequenced fragments from the first digest are ordered according to which intersite segments accompany one another. Repetition of the process with further digests may be needed to accomplish the ordering of all sequenced fragments.

Our invention also includes methods of using oligonucleotide arrays for allocating sequenced and ordered allelic fragments into their chromosomal linkage groups. These methods include the preparation on a sectioned array of selected one-sided partials from selected fragments of an alternate digest. The selected partials span allelic differences in neighboring allelic pairs of sequenced fragments. Oligonucleotides in the selected partials which contain the allelic differences are surveyed, and the fragments thereby allocated.

Our invention also includes a method of using binary arrays for surveying the oligonucleotides contained in nucleic acid strands or their partials. This method provides improved comprehensive surveys over the conventional surveying of oligonucleotides on an ordinary array. The method is especially useful for strand sequencing, for allocating allelic fragments to their chromosomes, as well as for surveys of selected oligonucleotides in, for example, a clinical diagnostic procedure. The method can also be performed to survey special types of oligonucleotides, for example, surveying signature oligonucleotides to order sequenced fragments.

BRIEF DESCRIPTION OF THE DRAWINGS

FIG. 2 shows a sectioned array having depressions.

FIG. 2a shows a well of a sectioned array.

FIG. 9 shows a complete set of partials generated for a nucleic acid strand, and the assembly of one of its address sets from the oligonucleotide information obtained from those partials.

FIG. 12 shows, schematically, the decomposition of address sets into their constituent strand sets.

FIG. 13 shows, schematically, the decomposition of a pseudo-prime address set into its constituent strand sets.

FIG. 15 shows, schematically, the prediction of segment signatures and their locations within a sorting array.

FIG. 16 shows the ordering of fragments from the distribution of their signatures within a sorting array.

FIGS. 18 to 28 show examples of the determination of nucleotide sequences from indexed address sets obtained from analysis of mixtures of strands.

DETAILED DESCRIPTION OF THE INVENTION

Figure 1:
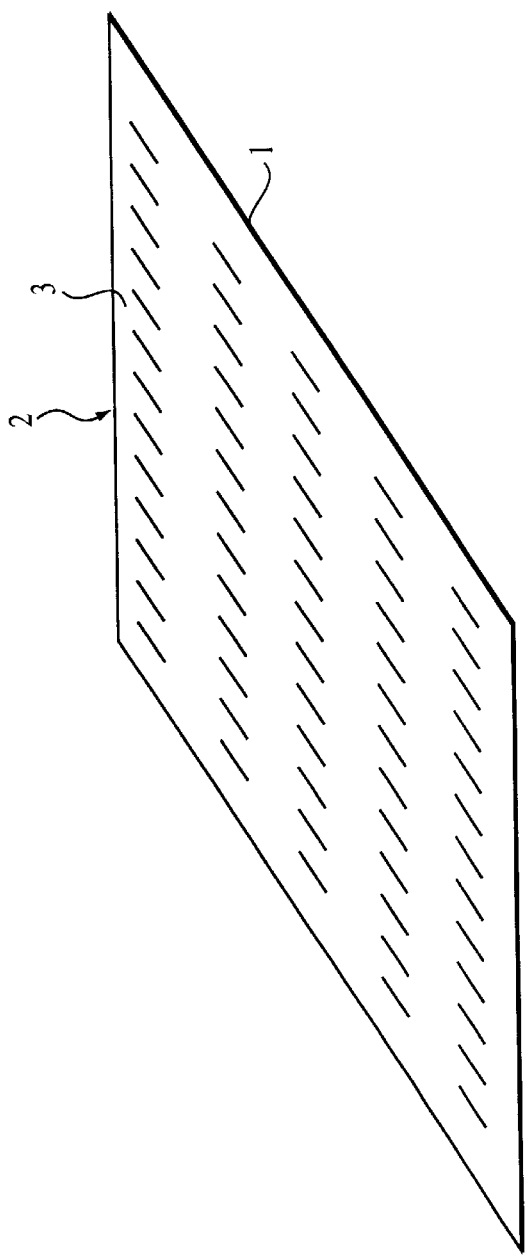
FIG. 1 shows a binary array.

Throughout the detailed description, references to the examples section are made to illustrate particular embodiments of the aspect of the invention discussed. Also, techniques described with respect to one embodiment may not be explicitly described in other embodiments. Their application to the several embodiments described herein, however, is understood.

All periodicals, patents and other references cited herein are hereby incorporated by reference.

I. Oligonucleotide Arrays

As used herein an "oligonucleotide array" is an array of regularly situated areas on a solid support wherein different oligonucleotides are immobilized, typically by covalent linkage. Each area contains a different oligonucleotide, and the location within the array of each oligonucleotide is predetermined. If the array is made of oligodeoxyribonucleotides, the nucleotides are: deoxyadenylate (dA), deoxycytidylate (dC), deoxyguanylate (dG), and deoxythymidylate (dT) (for brevity, the prefix "d" is often omitted herein). If the array is made of oligoribonucleotides, the nucleotides are: adenylate (A), cytidylate (C), guanylate (G), and uridylate (U). The array can also contain mixed oligonucleotides, comprised of both ribonucleotides and deoxyribonucleotides, and can include non-standard bases (such as inosine) or modified bases. The oligonucleotides can also possess modified ribose groups or modified phosphate groups (such as occur in the nucleoside phosphorothioates). During hybridization, C pairs with G, and A pairs with T (or U), irrespective of the nature of the sugar moiety. These basepairs are perfect "matches". All other pairwise combinations are "mismatches".

Arrays can be classified by the composition of their immobilized oligonucleotides. "Ordinary arrays" known in the art are arrays made of oligonucleotides that are comprised entirely of "variable segments". Every position of the oligonucleotide sequence in such a segment can be occupied by any one of the four commonly occurring nucleotides.

Comprehensive ordinary arrays are those wherein any segment of any possible strand will hybridize perfectly to the length of one or more of the immobilized oligonucleotides in the array. Therefore, any possible strand can be hybridized to one or more of the immobilized oligonucleotides, so that no strand is lost. An example of a comprehensive ordinary array is one having oligonucleotides all of the same length n, in which case the number of different oligonucleotides is 4n, each oligonucleotide being situated in a predetermined position; e.g., if the immobilized oligonucleotides are eight oligonucleotides long, the number of different areas required to make the array comprehensive is $4^8$ or 65,536. Another example of a functionally equivalent comprehensive ordinary array is one having oligonucleotides not all of the same length n, e.g., where a given oligonucleotide of length n is replaced by four oligonucleotides of length n+1 or sixteen oligonucleotides of length n+2 (as a concrete example, the eight-nucleotide oligonucleotide ACGTTGGG could be replaced by four nine-nucleotide oligonucleotides ACGTTGGGA, ACGTTGGGC, ACGTTGGGG and ACGCTGGGT). As used herein, "a comprehensive array of oligonucleotides of length n" refers to both of the above types. If the lengths of the oligonucleotides in a comprehensive array are not the same, the length n is the "basic length". In such an array, perfectly matched hybrids of the different lengths can be formed using methods described herein.

As a functional equivalent to an array with immobilized oligonucleotides of variable length as discussed above, the length of all of the immobilized oligonucleotides can be made the same by including degenerate positions at the free ends of shorter oligonucleotides in the array. It can be easier to discriminate against mismatched hybrids if the immobilized oligonucleotides are all of the same length. For example, a shorter immobilized oligonucleotide can be replaced with four oligonucleotides having "A", "T", "G" and "C" separately added at its free terminus. All four oligonucleotides should be immobilized in the same area of the array. Two degenerate positions can be added at an immobilized oligonucleotide's terminus resulting in sixteen oligonucleotides immobilized in the same area.

Figure 1A:
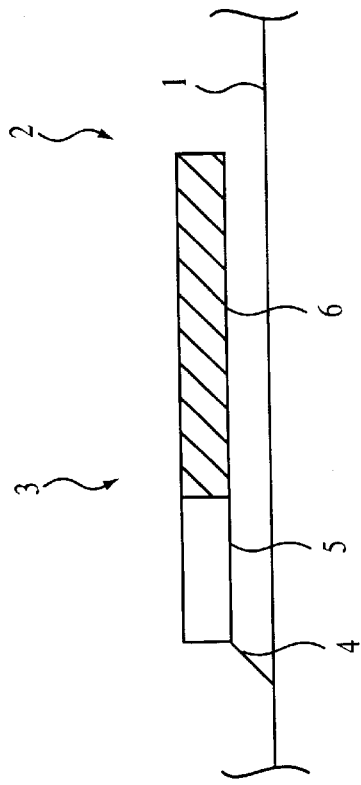
FIG. 1a shows an oligonucleotide immobilized in an area of a binary array.

"Binary arrays" according to this invention contain immobilized oligonucleotides that are comprised of two segments, one of which is variable, and the other of which is constant. The same sequence is present in the constant segment of all such oligonucleotides in the binary array. The variable segments can vary in both the sequence and the length. A binary array is illustrated in FIGS. 1 and 1a. FIG. 1 shows a substrate or support 1 having immobilized thereon an array of oligonucleotides 3, each oligonucleotide being in a separate area 2 of support 1. FIG. 1a shows one area 2. A binary oligonucleotide 3 comprised of constant region 5 and variable region 6 is covalently bound to support 1 by covalent linking moiety 4. Of course, many identical oligonucleotides are immobilized to the same area.

The number of different oligonucleotides as well as the number of areas is the same for a comprehensive binary array as for a comprehensive ordinary array having the same set of variable segments. In a comprehensive binary array, every possible segment adjacent to the chosen segment in a strand can be hybridized perfectly to one or more variable segments of the immobilized oligonucleotides, the chosen segment being complementary to all or part of the constant segment of the immobilized oligonucleotide. Such an array has the property that if a strand possesses the chosen segment it will be hybridized somewhere in the array.

It is possible, of course, to include on the same support additional areas having other oligonucleotides, for example, oligonucleotides not having a constant region.

Because of the constant segments in the immobilized oligonucleotides, binary arrays provide means for the hybridization of longer sequences without increasing the size of the array. The constant segment can be located within the immobilized oligonucleotide either "upstream" of the variable segment (i.e., toward or at the 5' end of the oligonucleotide) or "downstream" from the variable segment (i.e., toward or at the 3' end of the oligonucleotide). The type of array that is chosen depends on the specific application to which the array is put. The constant region preferably is or includes a good priming region for amplification of hybridized strands by PCR, or a promoter for copying the strand by transcription. Generally a length of 15 to 25 nucleotides is suitable for priming. The constant region can contain all or part of the complement of a restriction site. A binary array can be "plain" or "sectioned" (see below).

"Plain arrays" known in the art are arrays in which the individual oligonucleotide areas are not physically separated from one another. Many reactions can be carried out simultaneously on a plain array; however, they are limited to those in which the nucleic acid templates and the reaction products are bound in some manner to the surface of the array to avoid the intermixing of products generated in different areas.

"Sectioned arrays" are oligonucleotide arrays that are divided into sections, so that each area is physically separated by mechanical or other means (e.g., a gel) from all the other areas, e.g., depressions on the surface, called a "well". There are many techniques apparent to one skilled in the art for preventing the exchange of materials between areas; any such method can be used to make a "sectioned" array, as that term is used herein, even though there might not be a physical wall between areas. For example, the contents of the areas can be prevented from mixing by solidifying or gelling the solution.

Figure 3:
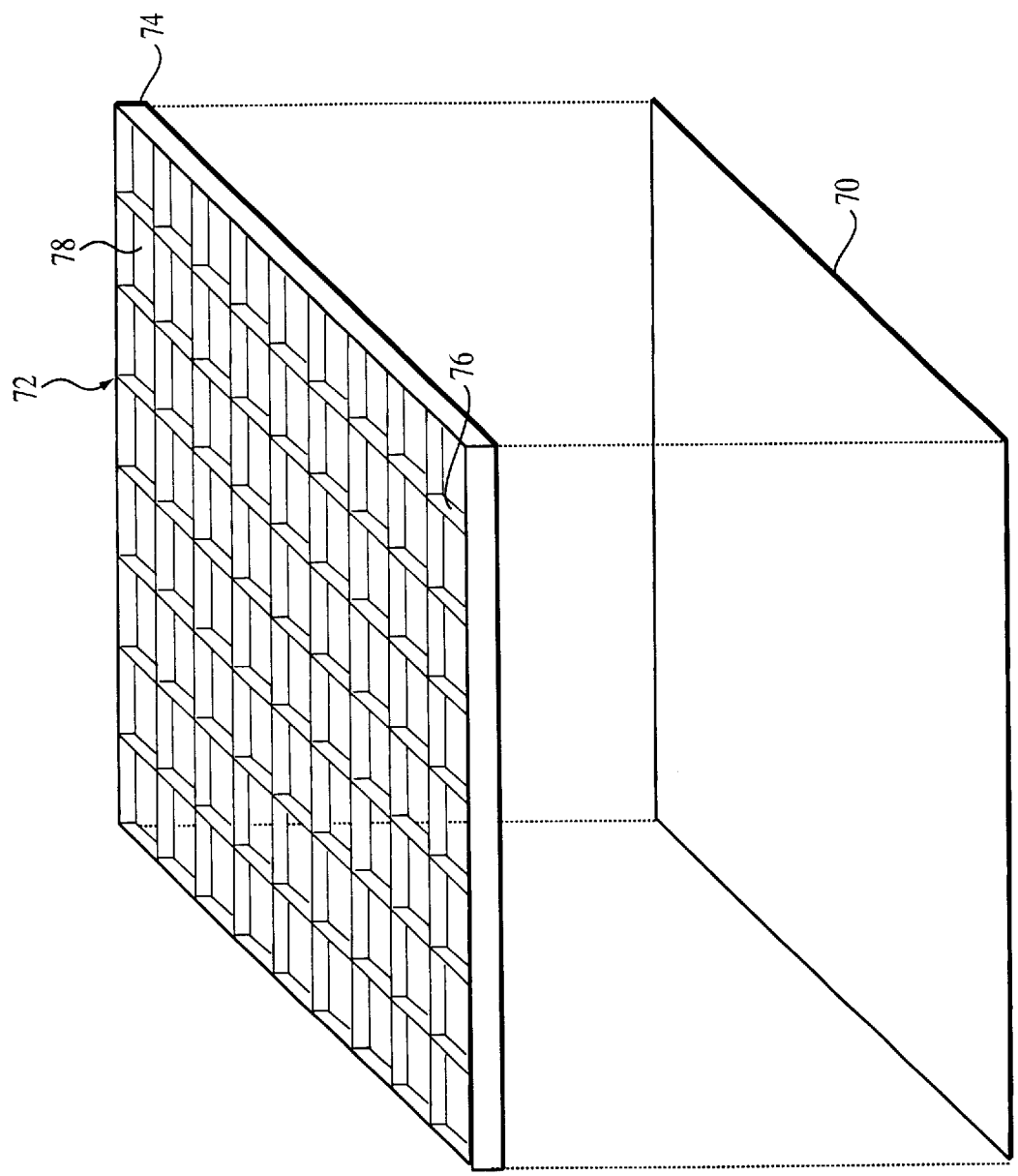
FIG. 3 shows addition of a lattice to a support to make a sectioned array.

One type of sectioned array is illustrated in FIGS. 2 and 2a. FIG. 2 shows a support sheet 60 having an array of depressions or wells 62, each containing an immobilized oligonucleotide 64. FIG. 2a shows one well 62 of the array of FIG. 2. Well 62 formed in support 60 has therein oligonucleotide 64 covalently bound to support 60 by covalent linking moiety 66. Of course, many identical oligonucleotides are bound to the surface of each well. In practice one may prepare a plain array, e.g., an array on a flat sheet, and then, at a point during a series of steps involving its use, convert the array into a sectioned array, e.g., by making physical depressions in a deformable solid support to isolate the individual areas in each depression. The sectioned array can also be created by applying a lattice to the solid support and bonding it to the surface so that each area is surrounded by impermeable walls. The technique of application of the lattice to the support is not critical; such means are well known in the art and include using adhesives and heat bonding. The areas of the array should be separated in a water tight manner. An exploded perspective view of such a sectioned array is shown in FIG. 3. Support or substrate 70, here a planar sheet, has mounted thereon and affixed thereto a lattice 72 comprised of a series of horizontal members 74, 76. The lattice members define a series of open areas which, in conjunction with support 70, define an array of wells 78. In some applications it is preferable to utilize a detachable lattice (or a removable cover sheet), so that the sectioned array can be converted back to a plain array. Oligonucleotides can be immobilized on the inner surface of the walls of the lattice, rather than on the bottoms of the wells. Irrespective of whether an array is sectioned permanently or temporarily, it is called herein a sectioned array. It is anticipated that the intermixing of the contents of an array can even be prevented by simply withdrawing materials by means of suction from each area as they are produced. A sectioned array allows reactions to be performed simultaneously in individual areas, both on the molecules attached to the surface of the array and on the molecules contained in the solution in each well. For some applications, it is particularly advantageous to use an array that is both sectioned and contains binary oligonucleotides, i.e., "sectioned binary arrays."

Sectioned arrays according to this invention can be used to increase the specificity of hybridization of nucleic acids to the immobilized oligonucleotides. After hybridization, unhybridized strands can be washed away. Hybridized strands can then be released into solution without mixing materials present in different wells. Released strands can be rebound to the oligonucleotides immobilized on the surface, and unhybridized strands can be washed away. Each successive release, rebinding, and washing increases the ratio of perfectly matched hybrids to mismatched hybrids.

"Replica arrays" are sectioned arrays that are used to receive nucleic acids from the wells of a first array, such as by printing or blotting. The replica array can contain immobilized oligonucleotides arranged in such a manner that the replica array is a mirror image of the original array, or the replica array can be a blank array. A blank array, unlike "arrays" as used elsewhere herein, does not contain immobilized oligonucleotides. Its surface can be modified by, for example, weak anion-exchange groups (such as diethylaminoethyl groups) to keep the transferred nucleic acids in place. A replica array can initially be a flat sheet, and after the transfer a lattice can be applied to the sheet, to produce a sectioned array. To make the transfer more accurate, the buffer filling the original array can contain a low-gelling-temperature agarose. This buffer remains liquid at the higher temperatures that are required for strand amplification, but a gel forms when the array is chilled. In this case, a cover sheet plus a lattice can serve as a replica array. The cover sheet is first bonded to the lattice that forms the wells of the original array. After the agarose is converted to a gel by chilling, the original array is detached from the lattice and replaced by a new sheet.

An array can be "3'" or "5'". "3' arrays" possess free 3' termini and "5' arrays" possess free 5' termini. The immobilized oligonucleotides in the arrays can be used for hybridization or ligation to nucleic acid strands present in solution as part of certain methods of the invention. The immobilized oligonucleotides in a 3' array can be extended at their 3' termini by incubation with a nucleic acid polymerase. If the nucleic acid polymerase is a template-directed polymerase, only immobilized oligonucleotides that are hybridized to a nucleic acid template strand can be extended. The immobilized oligonucleotides in a 5' array cannot be so extended because of the nature of currently known polymerases.

It is of course possible to add to the array, if desired, areas containing oligonucleotides having the same sequence as those in another area.

It is not necessary that all oligonucleotides immobilized in each area have the same sequence. For example, an array containing oligonucleotides might contain in an area the oligonucleotides (constant or variable) "AAAAAAA", "AAAAAAT", "AAAAAAG" and "AAAAAAC". Such a collection of oligonucleotides would be capable of hybridizing to the hexameric sequence "AAAAAA" in addition to any other nucleotide at its terminus. Such an increase in the length of the hybrids effectively results in the same strands being hybridized in that area, and increases the length of the oligonucleotides, possibly allowing the hybrid to be formed at a more convenient temperature. The added nucleotide can be, for example, at the free end or at the immobilized end of the oligonucleotide.

It is also not necessary that all of the constant regions be the same in all of the areas of the array. An array might be broken up into several regions, each utilizing a different constant region.

It is also possible to add additional sequences to the constant and variable segments in a binary array. For example, it is possible to make a trinary, or quaternary array according to the invention, in which the immobilized oligonucleotides in those arrays contain a constant segment and a variable segment in addition to further segments which are variable or constant.

In some applications, it may be advantageous to use a comprehensive array obtained by combining oligonucleotides in several areas into one area. This array will retain the property of a comprehensive array that any possible strand segment is able to be hybridized somewhere in the array, although the number of areas in such an array will be smaller. For example, rather than having four oligonucleotides that differ in one position and are immobilized in four separate areas of a comprehensive array, it may be convenient to immobilize all of these four oligonucleotide in one area. Thus, instead of having the sequences "AAAAAAA", "AAATAAA", "AAAGAAA", and "AAACAAA" in separate areas, a comprehensive array might be obtained if they are contained in the same area. This would be analogous to having in this area an oligonucleotide with one position that is degenerate.

The length of the immobilized oligonucleotides on the arrays used according to the invention depends upon many considerations discussed herein. One consideration is the ability to discriminate perfectly matched hybrids from mismatched hybrids. In an ordinary array, the length of the immobilized oligonucleotides should be between about six and about thirty nucleotides. In a binary array where the entire length of the immobilized oligonucleotide is intended to hybridize to a strand, the immobilized oligonucleotides should also be between six and thirty nucleotides long. If, however, only part of the oligonucleotide immobilized in a binary array is intended to hybridize to a strand, such as where the immobilized oligonucleotide is pre-hybridized to a masking oligonucleotide, then the length of the region intended to hybridize to the strand should preferably be between six and thirty nucleotides long, i.e., the immobilized oligonucleotide can be longer. This can be achieved by having the length of the constant segment be no longer than one nucleotide, in combination with a longer variable segment, or visa versa.

Suitable substrates or supports for arrays should be non-reactive with reagents to be used in processing, washable under stringent conditions, not interfere with hybridization, and not be subject to inordinate non-specific binding. They must be amenable to covalent linking of oligonucleotides. In many cases it is preferred that the supports be long lasting and not subject to deterioration. Suitable support materials are well known. They include, for example, treated glass, polymers of various kinds (e.g., polyamide and polyacrylmorpholide), latex-coated substrates, and silica chips.

There are a number of different ways to manufacture oligonucleotide arrays. Many methods for the immobilization of oligonucleotides on different solid supports are known in the art, examples of which follow. The support can be made of glass and the surface can be coated with long aminoalkyl chains [Ghosh, S. S. and Musso, G. F. (1987). Covalent Attachment of Oligonucleotides to a Solid Support, *Nucleic Acids Res.* 15, 5353–5372]. The support can be a polyacrylamide layer [Khrapko, K. R., Lysov, Yu. P., Khorlin, A. A., Shik, V. V., Florentiev, V. L., and Mirzabekov, A. D. (1989). An oligonucleotide Hybridization Approach to DNA Sequencing, *FEBS Lett.* 256, 118–122], or a latex-covered surface [Kremsky, J. N., Wooters, J. L., Dougherty, J. P., Meyers, R. E., Collins, M. and Brown, E. L. (1987). Immobilization of DNA via Oligonucleotides Containing an Aldehyde or Carboxylic Acid Group at the 5' Terminus, *Nucleic Acids Res.* 15, 2891–2909], or a surface covered with various polymers [Markham, A. F., Edge, M. D., Atkinson, T. C., Greene, A. R., Heathcliffe, G. R., Newton, C. R. and Scanlon, D. (1980). Solid Phase Phosphotriester Synthesis of Large Oligoribonucleotides on a Polyamide Support, *Nucleic Acids Res.* 8, 5193–5205; Norris, K. E., Norris, F. and Brunfeldt, K. (1980). Solid Phase Synthesis of Oligonucleotides on a Crosslinked Polyacrylmorpholide Support, *Nucleic Acids Symp. Ser.* 7, 233–241; Zhang, Y., Coyne, M. Y., Will, S. G., Levenson, C. H. and Kawasaki, E. S. (1991). Single-base Mutational Analysis of Cancer and Genetic Diseases Using Membrane Bound Modified Oligonucleotides, *Nucleic Acids Res.* 19, 3929–3933].

Methods of oligodeoxyribonucleotide synthesis directly on a solid support are also known in the art, including methods wherein synthesis occurs in the 3' to 5' direction (so that the oligonucleotides will possess free 5' termini) [Caruthers, M. H., Barone, A. D., Beaucage, S. L., Dodds, D. R., Fisher, E. F., McBride, L. J., Matteucci, M., Stabinski, Z. and Tang, J.-Y. (1987). Chemical Synthesis of Deoxyoligonucleotides by the Phosphoramidite Method, *Methods Enzymol.* 154, 287–313; Horvath, S. J., Firca, J. R., Hunkapiller, T., Hunkapiller, M. W. and Hood, L. (1987). An Automated DNA Synthesizer Employing Deoxynucleoside 3'-phosphoramidites, *Methods Enzymol.* 154, 314–326], and methods wherein synthesis occurs in the 5' to 3' direction (so that the oligonucleotides will possess free 3' termini) [Agalwal, K. L., Yamazaki, A., Cashion, P. J. and Khorana, H. G. (1972). Chemical Synthesis of Polynucleotides, *Angew. Chem.* 11, 451–459; Belagaje, R. and Brush, C. K. (1982). Polymer Supported Synthesis of Oligonucleotides by a Phosphotriester Method, *Nucleic Acids Res.* 10, 6295–6303; Rosenthal, A., Cech, D., Veiko, V, P., Orezkaja, T. S., Kuprijanova, E. A. and Shabarova, Z. A. (1983). Triester Solid Phase Synthesis of Oligodeoxyribonucleotides on a Polystyrene-teflon Support, *Tetrahedron Lett.* 24, 1691–1694; Barone, A. D., Tang, J.-Y. and Caruthers, M. H. (1984). In situ Activation of Bis-dialkylaminophosphines—A New Method for Synthesizing Deoxyoligonucleotides on Polymer Supports, *Nucleic Acids Res.* 12, 4051–4061].

Methods for synthesizing oligoribonucleotides, and methods for synthesizing mixed oligo(ribo/deoxyribo) nucleotides, on a solid support are also known in the art [Veniaminova, A. G., Gorn, V. V., Zenkova, M. A., Komarova, N. I. and Repkova, M. N. (1990). Automated H-Phosphonate Synthesis of Oligoribonucleotides Using 2'-O-tetrahydropyranyl Protective Groups, *Bioorg. Khim.* (Moscow) 16, 941–950; Romanova, E. A., Oretskaia, T. S., Sukhomlinov, V. V., Krynetskaia, N. F., Metelev, V. G. and Shabarova, Z. A. (1990). Hybridase Cleavage of RNA. II. Automatic Synthesis of Mixed Oligonucleotide Probes, *Bioorg. Khim.* (Moscow) 16, 1348–1354; Scaringe, S. A., Francklyn, C. and Usman, N. (1990). Chemical Synthesis of Biologically Active Oligoribonucleotides Using β-Cyanoethyl Protected Ribonucleoside Phosphoramidites, *Nucleic Acids Res.* 18, 5433–5441].

The simultaneous synthesis of many different oligonucleotides is also known in the art [Frank, R., Meyerhans, A., Schwellnus, K. and Blocker, H. (1987). Simultaneous Synthesis and Biological Applications of DNA Fragments: An Efficient and Complete Methodology, *Methods Enzymol.* 154, 221–249 (1987); Djurhuus, H. W., Staub, A. and Chambon, P. (1987). The Segmented Paper Method: DNA Synthesis and Mutagenesis by Rapid Microscale "Shotgun Gene Synthesis", *Methods Enzymol.* 154, 250–287].

Arrays are suitable for automated delivery of four different nucleotide precursors to precise locations within the array using a computer-controlled device similar to the devices used in multicolor inkjet printers (such as the DeskWriter C, manufactured by Hewlett-Packard), based on "drop-on-demand" technology. This method is particularly useful for the synthesis of oligonucleotides on arrays that are already sectioned. An even higher efficiency of oligonucleotide synthesis and a higher density of areas of immobilized oligonucleotides can be achieved by using photolithography techniques [Fodor, S. P., Read, J. L., Pirrung, M. C., Stryer, L., Lu, A. T. and Solas, D. (1991). Light-directed, Spatially Addressable Parallel Chemical Synthesis, *Science* 251, 767–773].

Arrays can be made over a wide range of sizes. In the example of a square sheet, the length of a side can vary from a few millimeters to several meters. An array of 256-by-256 areas on 2 mm centers, for example, would be more than a half meter on a side. Miniaturized arrays for surveying, manufactured by using microchip technology, would be orders of magnitude smaller.

There are many useful ways in which the elements of an array can be arranged. The most efficient shape for an array can depend on the particular design of any robotic array-handling device used, any method used to control temperature across the array (see below), and any method used to detect hybrids. The individual areas to which the oligonucleotides are immobilized can be arranged on a surface in various patterns, such as, for example, a square, rectangular, linear, concentric, or spiral pattern. The arrays may be rigid or flexible. For example, they may even be in the form of a tape that is wound up on a reel or cassette.

Sophisticated arrangements can be used in order to place the different oligonucleotides at positions that correspond to the stability ($T_m$) of the hybrids they form. Such an arrangement can be used to increase the specificity of hybridization to the array. For example, an array can be mounted on a plate constructed of a heat-conducting material, such as metal, whose opposite edges are kept at different controlled temperatures (for example, the side along one edge can be heated and the other cooled). These can be the opposite edges of a square, a rectangle, a cylinder, or the inner and outer edges of a disk with a hole in the middle. Moreover, the temperature gradient need not be uniform. The shape of the array or the thickness of the supporting material can be varied in order to alter the distribution of heat through the supporting material. The oligonucleotides should then be arranged on the support in such a manner that each area can be conveniently incubated at whatever temperature is optimal for a preselected operation—hybridization, washing, or a subsequent enzymatic reaction such as ligation or polymerization. Careful placement of the oligonucleotides within the array can ensure that the highest degree of discrimination against mismatched hybrids occurs. The optimal temperature for the formation of each perfect hybrid in the array can be determined in preliminary experiments, in which a mixture of all possible synthetic oligonucleotides, or a digest of nucleic acids of known sequence, are hybridized and then washed away at steadily increasing temperature, while simultaneously recording for each type of oligonucleotide the temperature at which its hybrid dissociates (i.e. a "melting curve" for each oligonucleotide can be established) [Khrapko et al., 1989].

There are a number of ways that solutions may be spread across large arrays, including sectioned arrays. For example, an array can be rolled on a rotating horizontally mounted cylinder that is slightly immersed in a tray filled with a solution, for example, a nucleic acid mixture. During hybridization or washing, the solution in the tray can be kept hot so that the nucleic acids will denature, and the cylinder can be cooled by having the opposite edges of the cylinder be at different temperatures, thus forming a temperature gradient across the surface of the cylinder. The array can also be placed against the inside wall of a rotating vertically mounted cylinder, such as a centrifuge, whose bottom and top are kept at different temperatures to form a temperature gradient. The thin film of solution contacting the array surface can continuously be withdrawn from the top and be pumped back into the bottom, with, for example, the aid of a peristaltic pump, through a heating coil, in order to ensure that the nucleic acids in the solution remain denatured. The progress of hybridization can be monitored with a densitometer that records the decrease in ultraviolet absorption in the solution being recirculated. The array can also be mounted on a rotating disk, with the liquid being collected at the outer edge and then reintroduced at the center.

II. Sorting Nucleic Acids

Our invention allows mixtures of nucleic acid strands, whether DNA or RNA, to be sorted according either to their terminal oligonucleotide segments ("terminal sorting") or their internal oligonucleotide segments ("internal sorting") on a binary array.

There are two important aspects of our invention for sorting nucleic acids. First, each strand in a mixture can be made to hybridize to an array at only a few, or a single, location. And second, each strand can be provided with universal terminal priming regions that enable all strands to be amplified by PCR without prior knowledge of the nucleotide sequences at the strands' termini, and without the need to synthesize individual primers for each strand.

For terminal sorting, the priming region(s) can be made essentially dissimilar from the sequences occurring in the nucleic acids that are present in the mixture to be sorted, so that priming does not occur anywhere but at the strands' termini (the addition of priming regions to strands is discussed below). The absence of priming within a strand's internal regions can be confirmed by checking the inability of the primers chosen to hybridize to the strand mixture at temperatures well below (e.g., by 10° C.) the temperature at which the polymerization reaction is carried out. When strands from a complete restriction digest of a DNA are to be sorted by their termini and then amplified, priming only at the strands termini can be promoted by restoring the terminal restriction sites (those sites having been eliminated from internal regions by complete digestion) concomitant with the generation of terminal priming regions (see Example 1.1, below). Restriction sites are thereby uniquely found within the sequence of the terminal priming regions.

Universal terminal priming regions (that preferably include a restored restriction site) serve as "tags" that distinguish the terminal oligonucleotide segments from all internal segments. Terminal sorting is carried out on a binary array, which preferably is a sectioned binary array. The immobilized oligonucleotides contain a constant segment complementary to either the strands' 3' priming region or 5' priming region. Thus, each strand can only be hybridized to one location within the array. By sorting on a comprehensive array, every strand is bound somewhere within the array. This is especially important for the preparation of a comprehensive library of fragments of a long nucleic acid or a genome.

The 3' and 5' terminal priming regions can be introduced before or after strand sorting. Also, one priming region can be introduced before sorting and another can be introduced after sorting (see Example 1.2, below). Methods of introducing the priming regions include ligation to oligonucleotide adaptors using either DNA ligase or RNA ligase, strand extension with a homopolymeric tail using terminal nucleotide transferases, and combinations of these methods (see Examples 1.1 to 1.3, below).

Strands can be sorted on either 3' or 5' arrays in which the constant segment is located either upstream or downstream of the variable segment. High specificity of sorting can be achieved by employing 3' arrays in which the constant segment of the immobilized oligonucleotides is located upstream from the variable segment. In that case, sorting can be followed by the generation of an immobilized copy of each sorted strand using the immobilized oligonucleotides as primers for the synthesis of a complementary copy of that strand when the array is incubated with an appropriate DNA polymerase. This procedure provides an increase in hybridization specificity, since hybrid extension by DNA polymerase is highly sensitive to terminal mismatches. A functionally equivalent array is a 5' array in which the constant segment is located downstream from the variable segment. In that case, a primer hybridized to the 3' end of the bound strand can be extended with a polymerase and the product ligated to the 5' end of the immobilized oligonucleotide. In both of these two cases the generation of nucleic acid copies that are covalently linked to the array surface enables the arrays to be vigorously washed to remove non-covalently bound material before strand amplification. It also enables the arrays to serve as permanent banks of sorted nucleic acid strands which can subsequently be amplified over and over to generate copies for further use. Exemplary methods are given below in Examples 1.1 to 1.3.

Figure 4A:
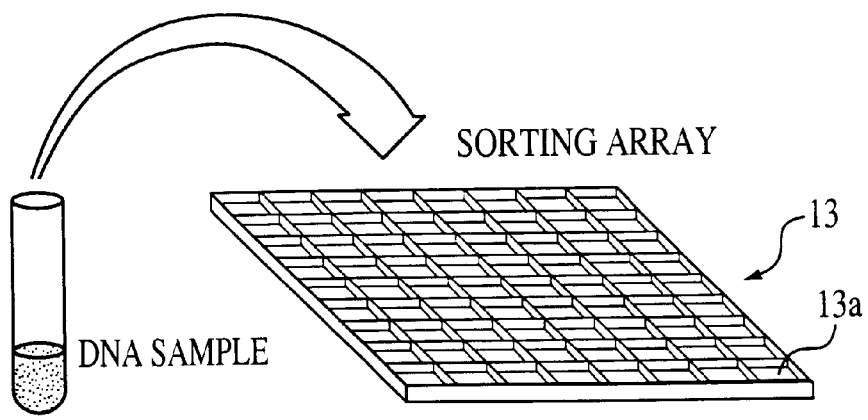
FIG. 4 shows an example of sorting and amplification of restriction fragments on a sectioned binary array.
Figure 4B:
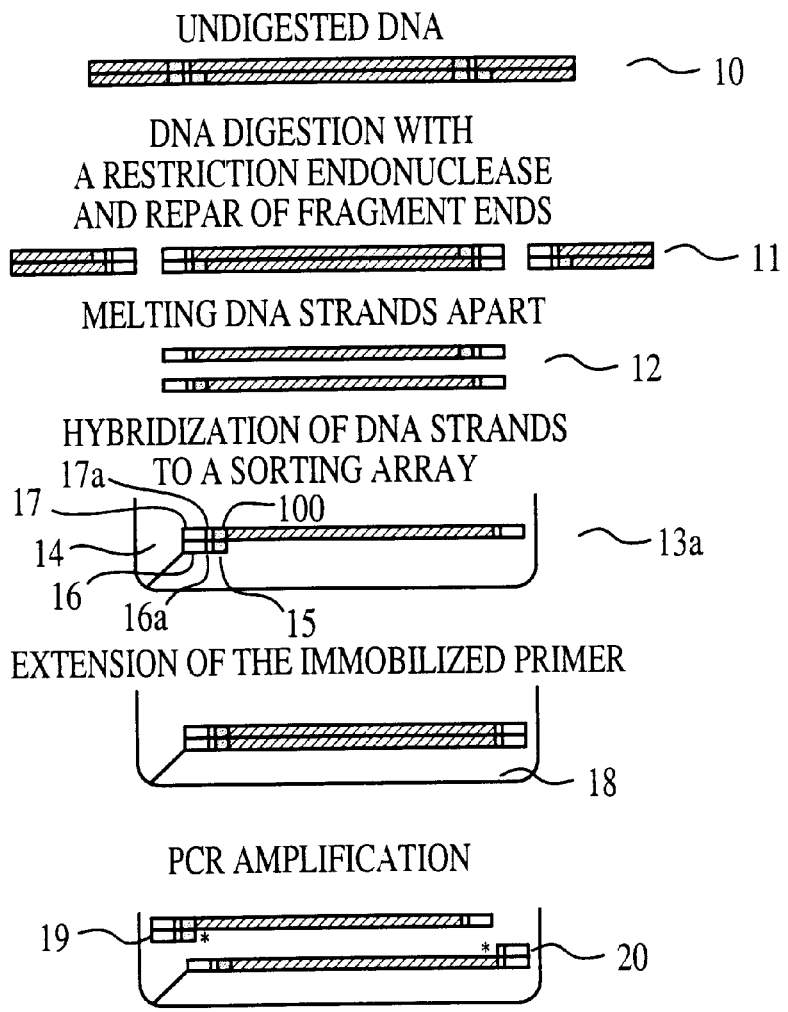

A strand sorting procedure of the invention is illustrated in FIG. 4. A DNA sample 10 is completely digested with a restriction endonuclease. The ends of each fragment are restored, and universal priming sequences 17 generated in the process to prepare fragments 11 for sorting. It is not necessary that priming sequences be added at both ends, if only linear amplification is desired. Nor is it necessary that the priming sequence at the 3' end of a strand be the same as the priming sequence at the 5' end.

The strands are then melted apart 12 and hybridized to a terminal sequence binary sorting array, whose immobilized oligonucleotides 14 contain a variable segment 15 and a constant segment 16 which is complementary to the universal priming region 17, including the restored recognition site of the restriction enzyme 16a, 17a. Each strand is at a location dependent upon its variable sequence 100 adjacent to its priming sequence. At this point the array need not be a sectioned array; it may be a plain array. The array is then washed to remove unhybridized strands. The entire array is then incubated with DNA polymerase. Consequently, a complementary copy 18 of each hybridized DNA strand is generated by extension of the 3' end of the oligonucleotide to which the strand is bound. The array is then vigorously washed to remove the original DNA strands and all other material not covalently bound to the surface (not shown).

The covalently bound copy strands can be amplified. During the amplification reaction it is usually desirable that the array be sectioned. The wells are filled with a solution containing universal primers 19, 20, an appropriate DNA polymerase, and the substrates and buffer needed to carry out a polymerase chain reaction. The array can, if desired, be sealed with a coversheet, further isolating the wells from each other. A polymerase chain reaction is carried out simultaneously in each well of the array. This procedure results in sorting the mixture of strands into groups of strands that share the same terminal oligonucleotide sequence, each strand (or each group of strands) being present in a different well of the array and amplified there.

The most important factor determining the purity of the sorted strands is the specificity of the hybridization between the nucleic acid strands and the immobilized oligonucleotides, i.e., the ratio of the amount of perfectly matched (legitimate) hybrids to the amount of mismatched (illegitimate) hybrids after the hybridization step is completed. In general, perfect hybrids are more stable than mismatched hybrids, and their relative stability is dependent upon a variety of factors, such as temperature, concentration of denaturing agents, the presence and concentration of divalent metal ions, and ionic strength. By adjusting these conditions, differences in stability between the perfect hybrids and hybrids containing a single mismatch can be increased to as high as two orders of magnitude [Wilson, K. H., Blitchington, R., Hindenach, B. and Greene, R. (1988). Species-specific Oligonucleotide Probes for rRNA of *Clostridium difficile* and Related Species, *J. Clin. Microbiol.* 26, 2484–2488; Zhang, Y., Coyne, M. Y., Will, S. G., Levenson, C. H. and Kawasaki, E. S. (1991). Single-base Mutational Analysis of Cancer and Genetic Diseases Using Membrane Bound Modified Oligonucleotides, *Nucleic Acids Res.* 19, 3929–3933].

Methods to increase hybridization specificity and the specificity of the polymerase chain reaction are known in the art [Wallace, R. B., Shaffer, J., Murphy, R. F., Bonner, J., Hirose, T. and Itakura, K. (1979). Hybridization of Synthetic Oligodeoxyribonucleotides to ΦX174 DNA: The Effect of Single Base Pair Mismatch, *Nucleic Acids Research* 6, 3543–3557; Conner, B. J., Reyes, A. A., Morin, C., Itakura, K., Teplitz, R. L. and Wallace, R. B. (1983). Detection of Sickle Cell β$^s$-globin Allele by Hybridization with Synthetic Oligonucleotides, *Proc. Natl. Acad. Sci., U.S.A.* 80, 278–282; Wallace, R. B., Studencki, A. B. and Murasugi, A. (1985). Application of Synthetic Oligonucleotides to the Diagnosis of Human Genetic Diseases, *Biochimie* 67, 755–762; Saiki, R. R., Bugawan, T. L., Horn, G. T., Mullis, K. B. and Erlich, H. A. (1986). Analysis of Enzymatically Amplified β-globin and HLA-DQα DNA with Allele-specific Oligonucleotide Probes, *Nature* 324, 163–166; Miyada, C. G. and Wallace, R. B. (1987). Oligonucleotide Hybridization Techniques, *Methods Enzymol.* 154, 94–107; Saiki, R. K., Walsh, P. S., Levenson, C. H. and Erlich, H. A. (1989). Genetic Analysis of Amplified DNA with Immobilized Sequence-specific Oligonucleotide Probes, *Proc. Natl. Acad. Sci., U.S.A.* 86, 6230–6234; Wu, D. Y., Nozari, G., Schold, M., Conner, B. J. and Wallace R. B. (1989). Direct Analysis of Single Nucleotide Variation in Human DNA and RNA Using in situ Dot Hybridization, *DNA* 8, 135–142; Wu, D. Y., Ugozzoli, L., Pal, B. K. and Wallace, R. B. (1989). Allele-specific Enzymatic Amplification of Beta-globin Genomic DNA for Diagnosis of Sickle Cell Anemia, *Proc. Natl. Acad. Sci., U.S.A.* 86, 2757–2760; Drmanac, R., Strezoska, Z. Labat, I., Drmanac, S. and Crkvenjakov, R. (1990). Reliable Hybridization of Oligonucleotides as Short as Six Nucleotides, *DNA Cell Biol.* 9, 527–534; Nielson, K. and Mathur, E. J. (1990). Perfect Match Enhancer: Limits False Priming Events During Amplification Reaction, Strategies In Molecular Biology (A Stratagene newsletter) 3, 17–22; Nielson, K., Wilbanks, A., Hansen., C. and Mathur, E. J. (1991). Improve Specificity of Long Amplification Products with Perfect Match Polymerase Enhancer, Strategies In Molecular Biology (A Stratagene newsletter) 4, 38; Erlich, H. A., Gelfand, D. and Sninsky, J. J. (1991). Recent Advances in the Polymerase Chain Reaction, *Science* 252, 1643–1651; Lundberg, K. S. and Mathur, E. J. (1991). Optimization of Perfect Match Polymerase Enhancer for the Polymerase Chain Reaction, Strategies In Molecular Biology (A Stratagene newsletter) 4, 4–5].

Terminal mismatches have the least effect on hybrid stability and are the most difficult to discriminate against [Drmanac, R., Strezoska, Z., Labat, I., Drmanac, S. and Crkvenjakov, R. (1990). Reliable Hybridization of Oligonucleotides as Short as Six Oligonucleotides, *DNA Cell Biol.* 9, 527–534]. Embodiments, discussed below, in which hybrids are extended at both ends, through enzymatic ligation to a masking oligonucleotide (an oligonucleotide that is hybridized to, and covers a part of, the constant segment of the immobilized oligonucleotide) at one end and through enzymatic extension at the other end, are highly sensitive to terminal mismatches (see Examples 1.2 and 1.3, below).

Another difficulty in achieving perfect hybrids in each area of an array is the different intrinsic stability of hybrids that contain A:T and G:C basepairs in different proportions. It has been found that high concentrations of tetraalkylammonium salts in a hybridization solution minimize these differences, so that the stability of the hybrids can be made to be dependent on only the length of the hybrids [Wood, W. I., Gitschier, J., Lasky, L. and Lawn, R. M. (1985). Base Composition-Independent Hybridization in Tetramethylammonium Chloride: A Method for Oligonucleotide Screening of Highly Complex Gene Libraries, *Proc. Natl. Acad. Sci. U.S.A.* 82, 1585–1588; Jacobs, K. A., Rudersdorf, R., Neill, S. D., Dougherty, J. P., Brown, E. L. and Fritsch, E. F. (1988). The Thermal Stability of Oligonucleotide Duplexes is Sequence Independent in Tetraalkylammonium Salt Solutions: Application to Identifying Recombinant DNA Clones, *Nucleic Acids Res.* 16, 4637–4650]. This approach can be used, for example, in hybridization of strands whose termini have been provided with priming regions prior to sorting and when the immobilized oligonucleotides are all of the same length. However, if hybridization is to be coupled to an enzymatic reaction, such as ligation to a masking oligonucleotide, high salt concentrations can be inhibitory. This method also does not apply when the length of the immobilized oligonucleotides vary. Another solution for overcoming the problem of different hybrid stabilities consists of applying a temperature gradient across an array, wherein different oligonucleotides are arranged according to the thermal stability of their corresponding hybrids (see Section I, above). In this case, enzymatic reactions can be carried out by utilizing mixtures of enzymes with different temperature optima, ensuring equal reaction efficiency in all wells.

By carrying out hybridizations on sectioned arrays the specificity of hybridization can be significantly increased above the level that is currently achievable. Because wells are physically isolated from one another, the hybridized strands can repeatedly be released into solution without mixing of material in different wells, and rebound to the immobilized oligonucleotides, followed by washing the array to remove unhybridized strands. Alternatively, the released strands can be rebound to a fresh replica array to eliminate the background that results from the non-specific binding of strands to the array surface. In each succeeding cycle of hybridization, only those strands that have been bound in the previous cycle are available to hybridize. Therefore, the ratio of the perfect hybrids to mismatched hybrids increases as an exponential function of the number of cycles. The number of cycles required to achieve a desired ratio of perfect hybrids to mismatched hybrids for a particular embodiment is determinable in preliminary experiments. If mixtures of nucleic acids of known sequences are used in these experiments, the cycling is repeated until only the legitimate strands are detected (for example, by gel electrophoresis or oligonucleotide probe hybridization) in each well after strand amplification. The test experiments can also be carried out with mixtures of nucleic acids whose sequences are unknown. In this case, the number of different strands in a mixture should be less than the number of different oligonucleotides in the array, and the cycles repeated until the number of empty wells after strand amplification remains constant. The inevitable loss of legitimate strands during the cycling procedure need not be troublesome, since the number of remaining strands needed to reliably initiate subsequent PCR can be as low as 100 [Myers, T. W. and Gelfand, D. H. (1991). Reverse Transcription and DNA Amplification by a *Thermus thermophilus* DNA Polymerase, *Biochemistry* 30, 7661–7666]. In those embodiments where priming regions are introduced into the termini of the strands prior to sorting, reversible hybridization cycling is performed after the strands are first bound to the array. If priming regions are introduced by ligation of the hybridized strands to masking oligonucleotides, then cycling is performed after the ligation step.

The results of hybridization can be improved further by "proofreading", or editing, the hybrids formed, by selectively destroying those hybrids that contain mismatches, without affecting perfect hybrids. Various means of hybrid proofreading by chemical and enzymatic methods are discussed in detail herein (see Example 5.1.1, below).

The necessary level of hybridization specificity depends on the complexity of the sorted nucleic acid mixture, and on the particular use to which the sorted strands will be put. Therefore, the above methods for improving specificity need not be used in every case.

The length of the immobilized oligonucleotides in a strand sorting array is chosen to suit the number of strands to be sorted. When sorting strands according to their terminal sequences, the number of different strands obtained in each well equals the number of times that a particular oligonucleotide complementary to the variable segment of the immobilized oligonucleotide occurs among the termini of different strands in the mixture. If the number of nucleotides in each variable segment is n, then the total number of such variable sequences is $4^n$, the mean number of different strands in a well is $N/4^n$, where N is the number of different strands in the mixture, provided that nucleotide sequence is random, and that each of the four nucleotides is present in equal proportion. If a random sequence that is the size of an entire diploid human genome ($6 \times 10^9$ basepairs) is completely digested by a restriction endonuclease that has a hexameric recognition site, then the resulting mixture will contain approximately $3 \times 10^6$ strands with an average length of 4,096 nucleotides. If this mixture is then applied to a comprehensive binary array having variable segments eight nucleotides long, then each well will contain, on average, approximately 45 different strands. A similar degree of sorting (i.e., approximately the same number of different strands in a well) will be achieved if a random sequence that is the size of an entire diploid Drosophila genome ($3 \times 10^8$ basepairs) is digested with a restriction endonuclease that has a hexameric recognition site, and is applied to an array whose variable segments are six nucleotides long, or if it is digested with a restriction endonuclease having a tetrameric recognition site and is applied to an array whose variable segments are eight nucleotides long. Similarly, the same degree of sorting can be achieved if a random sequence that is the size of an *Escherichia coli* genome ($5 \times 10^6$ basepairs) is sorted on an array containing trinucleotide-long variable segments after digestion by a restriction endonuclease that has a hexameric recognition site, or if it is sorted on an array containing pentameric variable segments after digestion by a restriction enzyme that has a tetrameric recognition site. An increase in the length of the variable segments, or the use of a restriction endonuclease that has a longer recognition site, will result in there being fewer different strands per well.

The actual number of strands in each well can differ significantly from the mean. This is especially true for real nucleic acids that do not have random sequences, and wherein the proportion of the four different nucleotides is usually unequal. For example, the content of A and T nucleotides in the human genome is about 1.5 times higher than that of G and C nucleotides. This will result in some wells containing fewer than the mean number of strands, and some wells containing many more. There may be too many strands in a well for some subsequent uses (e.g., for sequencing).

In cases where overloaded wells are a problem, our invention provides means to overcome the problem. If the material to be sorted is a mixture of double-stranded fragments, such as DNA fragments produced by restriction endonuclease digestion, the fragments are melted into single strands before hybridization to a sectioned oligonucleotide array. If, for example, the strands are sorted by their 3' termini on a binary sectioned array, the complementary strands from the same double-stranded fragment will sort into different wells of the array, because their 3'-terminal sequences are almost always different. A subsequent amplification of the sorted strands by symmetric PCR results in both the complementary strands being produced in each of the two wells of the array. If by chance one of the two wells is overloaded, it is highly unlikely that the other well will also be overloaded. Thus, despite the uneven distribution of strands among wells, virtually every strand can be found in a well that is occupied with a moderate number of strands (i.e., a number that does not significantly exceed the mean).

Our invention also provides an option for directly monitoring the number of different strands in each well, and for predicting whether the strands that are present in an overloaded well can each be found among wells that are not overloaded. After strands have been sorted and amplified by symmetric PCR, the wells are surveyed for "signature oligonucleotides" with special binary survey arrays discussed below. In this application, a signature oligonucleotide consists of the sequence of the terminal restriction site (such sites having been substantially eliminated from internal regions during the prior restriction endonuclease digestion) and an adjacent variable segment, and thus identify the terminal sequences of each strand in a well. If strands are sorted by their 3' termini, each strand in a well will possess the same 3' terminal signature oligonucleotide, but the strands will almost always possess different 5'-terminal signature oligonucleotides. Similarly, complementary copies of these strands (that are generated during symmetric PCR) will possess identical 5'-terminal signature oligonucleotides, but different 3'-terminal signature oligonucleotides. By determining the number and identity of signature oligonucleotides at either the 5' end or the 3' end of the strands in each well, it is possible to directly count the number of different strands in the well, and to determine in which other wells the strands from a particular well are also found (i.e. into which wells their complementary strands have been sorted). If each of these wells is not overloaded, the overloaded well can be ignored for sequencing.

If necessary or desired, the mixture of strands from a highly populated well can be further divided into smaller groups, by sorting according to their 5' termini (in which case, direct copies will be sorted into groups), or according to their 3' termini (in which case, complementary copies will be sorted into groups). Even very small arrays can be effective for this purpose. For example, if it is found by surveying, as described above, that after strand sorting by 3'-terminal sequences and amplification by symmetric PCR, a well contains, say 1,000 different 3'-terminal signature oligonucleotides (which means that there are some 2,000 strands in the well, including both direct and complementary copies), the mixture can then be sorted into 64 groups on a terminal binary sectioned array whose variable segments are as short as three nucleotides. If the second sorting is also carried out according to 3'-terminal sequences, one of the groups will contain slightly more than 1,000 strands (that includes all 1,000 direct copies from the first sorting), and the other groups will contain, on average, 1,000/64≈16 strands (due to the sorting of the complementary copies). This number will double after symmetric PCR amplification of the strands. If, from an examination of the survey results, it is determined that the well with slightly more than 1,000 strands does not contain strands found only in overloaded wells, that well can be ignored for sequencing. If, as is preferred, asymmetric PCR is carried out during the first sorting to only produce the complementary copies, then the mean number of strands will be ≈16 in all 64 groups (i.e., none of the wells will be overloaded).

The ability to monitor the distribution of strands among wells helps to control the number of strands in a group within certain limits, irrespective of the statistical nature of the sorting. If it is desired to sort 3,000,000 human genome strands into groups of about 45 strands (e.g., for the determination of their sequences with the aid of partialing arrays, see below), one may choose to sort the strands on a large binary sectioned array wherein the most populated well is expected to contain not more than 45 strands. It is not necessary that the variable segments in this array all be of the same length; rather, the length of the variable segments can be chosen to suit the expected frequencies of different oligonucleotide segments in the human genome. For example, taking into account the higher content of A and T nucleotides, the (A+T)-rich variable segments can be made longer than the (G+C)-rich variable segments. If it is desired to use a comprehensive array, then the array can be made comprehensive, as described above. In such an array, most wells will contain fewer than 45 strands, sometimes only a few strands. After each well of the array has been surveyed for terminal signature oligonucleotides to determine the actual distribution of strands among the wells, the strands from chosen wells can be combined to obtain ≈65,000 groups with about 45 strands in each.

According to our invention, as discussed further below, DNA fragments that are not bounded by restriction sites can also be sorted on sectioned binary arrays by their terminal sequences (see Example 1.4, below).

Our invention also includes methods for isolating individual strands by sorting them according to the identity of their terminal sequences on sectioned binary arrays. The strands can be from restriction fragments or not, so long as unique priming sequences are added to at least one of the strand's termini, such as by methods described herein. If the number of different DNA strands in a sample is rather small, there is a high probability that after the first stage of sorting, many wells in the sectioned array will either not be occupied, or be occupied by only one type of fragment. In the case of a complex mixture of DNA strands (such as the mixture of strands that are obtained from the digestion of an entire human genome), a number of different types of fragments will occupy each well of the sectioned array. In that case, the isolation of individual fragments can be achieved by PCR amplifying the strands in each well in the first stage of sorting and then sorting the group of fragments from each well on a fresh sectioned array. After symmetric PCR amplification, each well of the first array will contain copies of the strands that were originally hybridized there, and also their complementary copies. If the original strands were sorted by their 3' ends, then their copies in a given well will all possess the same 3'-terminal sequence, and their complementary copies will possess the same 5' end. However, the 3'-terminal sequences of the complementary copies of the original strands in each well will be different (as will be the 5' terminal sequences of the original copies). Therefore, the complementary strands will bind at different locations within the new sectioned array, according to the identity of their own 3'-terminal sequences, and with a high probability, each of them will occupy a separate well, where they can then be amplified. Alternatively, the second stage of sorting can be carried out according to the identity of the terminal sequences at the other end of each strand. For example, if the strands were sorted in the first stage by their 3' ends (on an array whose immobilized oligonucleotides contain constant segments that are upstream of the variable segments), then the groups of strands from each well in the first array can be sorted in a second stage by their 5' termini (on an array whose constant segments are downstream of the variable segments). In either procedure, as a result of the second round of sorting, almost all of the different types of fragments are separated from one another (with the exception of virtually identical allelic strands from a diploid genome, which usually have identical termini, and consequently are sorted into the same well). Other aspects of strand isolation are discussed herein (see Example 1.5, below). The isolated strands can then be used for any purpose. For example, they can be inserted into vectors and cloned, or they can be amplified and their sequences determined using methods known in the art.

Our invention also includes the use of binary arrays for isolating selected strands by sorting according to the identity of terminal sequences (see Example 1.6, below). Strands can, for example, be selected that contain particular regions (such as genes) of special interest from a clinical viewpoint. After the relevant portion of a genome has been sequenced, an array can be made using only preselected oligonucleotides whose variable segments uniquely match the terminal sequences of the strands of interest, i.e., they would be long enough to uniquely hybridize to the desired strands. Alternatively, strands of interest can be isolated by sorting on a sectioned array having immobilized thereon previously isolated selected genomic (single-stranded) fragments, rather than synthetic oligonucleotides. In this case, the isolation procedure will have much in common with the sorting of strands according to the identity of their internal sequences, which is discussed next.

Our invention also encompasses methods that include sorting DNA fragments according to their internal sequences (see Examples 2.1 and 2.2, below). When sorting by internal sequences, the specificity of sorting is, as a rule, lower than when sorting by terminal sequences because the strands may be bound at more than one internal oligonucleotide. Thus, strands may bind at more than one well in the array. However, this type of sorting can be useful for a number of applications, such as the isolation of strands that contain particular internal sequence segments (utilizing a sectioned ordinary array), or the sorting of strands according to the identity of variable oligonucleotide segments adjacent to internal restriction sites of a particular type (utilizing a sectioned binary array). The latter approach is useful for ordering sequenced restriction fragments (see Section V, below). The sorting of strands by their internal segments on a 3' sectioned ordinary array is useful for the generation of partial strands by virtue of extension of the immobilized oligonucleotides (see Section III, below).

Our invention includes the sorting, in particular for sequencing, of natural mixtures of RNA molecules, such as cellular RNAs. The sequences of eukaryotic genes are usually interrupted by many large non-coding inserts, called introns. Following transcription, the introns are excised from the RNA sequence, and the remaining segments, called exons, are linked together in a process called splicing, to produce messenger RNAs [Watson, J. D., Hopkins, N. H., Roberts, J. W., Steitz, J. A. and Weiner, A. M. (1987). *Molecular Biology of the Gene,* 4th edition, The Benjamin/Cummings Publishing Co., Menlo Park]. Establishing messenger RNA sequences is therefore useful not only for the identification and localization of genes in the genomic DNA, but also for providing information necessary to determine the coding gene sequences (i.e. the exon/intron structure of each gene). Furthermore, the analysis of cellular RNAs in different tissues, at different stages of development, and in the course of a disease, will clarify which genes are active in these instances and which are not. Usually, RNAs are short enough to be sorted and analyzed without preliminary fragmentation. Details of RNA sorting are provided in Example 1.7, below.

III. Preparing Partial Strands of Nucleic Acids and Manipulating Nucleic Acids on Sectioned Arrays Our invention includes methods of using sectioned arrays for preparing all possible partial copies of a strand or a group of strands. Preparing complete sets of partials of a strand(s), and sorting the partials by their variable ends is especially useful in a process for determining the sequence of the strand or strands, as described herein. The preparation of partials is accomplished by either of the following methods: (1) terminally sorting on sectioned binary arrays a mixture of partial strands generated by degradation of a "parental" strand(s) at random; or (2) generating partials on a sectioned ordinary array, through the sorting of a parental strand(s) according to the identity of the strand's internal sequences, followed by the synthesis of (complementary) partial copies of the parental strand(s) by the enzymatic extension of the immobilized oligonucleotides, utilizing the hybridized parental strands as templates, and then copying the immobilized partials. In either case, the partials that are generated correspond to a parental strand whose 3' or 5' end is truncated to a different extent (the "variable" end), and whose other end is preserved (the "fixed" end). These are "one-sided partials". By using comprehensive arrays, it is possible to prepare every possible one-sided partial of a strand.

In the first case (partialing before sorting), a strand, a double-stranded fragment, a group of strands, or a group of double-stranded fragments, carrying terminal priming regions, (these can be a strand or a group of strands sorted on a sectioned binary array as described above), is randomly degraded by a chemical or an enzymatic method, or by a combination of both (see Examples 3.1 and 3.2, below). Care is taken to ensure that partials of different length are produced in roughly equal proportion. Then the mixture of partials is sorted on a sectioned binary array according to the identity of their newly generated termini, essentially as described above for the sorting of full-length strands by their terminal sequences, with new priming sites being introduced at these new termini either before or after sorting. Only those partials that possess both the newly introduced priming site and the already existing priming site (at the opposite end), will be amplified by subsequent PCR. Partials can be sorted according to the identity of a variable sequence at either their 3' termini or their 5' termini. However, as is the case for the sorting of full-length strands, the highest specificity can be achieved by sorting according to the identity of a variable sequence at the 3' termini, and carrying out the sorting on 3' arrays having constant segments located upstream of the variable segments, or by sorting according to the identity of a variable sequence at the 5' termini, and carrying out the sorting on 5' arrays having constant segments located downstream of the variable segments. In these cases, sorting can be followed by the generation of immobilized (complementary) copies of the sorted partials. The arrays with the immobilized copies can serve as permanent banks of the sorted partials which can subsequently be amplified over and over to generate copies for further use. Following sorting, each well in the array will contain immobilized copies of all of those partials whose variable end is complementary to the variable segment of the immobilized oligonucleotide. The other (fixed) end of these partials will be identical to one of the ends of the parental strands. If an oligonucleotide segment occurs more than once in a strand, or if it occurs in more than one strand in the group of strands subjected to partialing, then the well will contain a corresponding number of different partials, all sharing the same sequence at their variable ends.

In the second case (sorting before partialing), partials are prepared directly from the parental strands that are hybridized to a sectioned ordinary array without prior degradation of the nucleic acids. A strand, or a mixture of strands, is hybridized to a 3' ordinary array. The immobilized oligonucleotides are then used as primers for copying the hybridized strands, beginning at the location within each bound strand where hybridization occurred, and ending at the upstream terminus of each bound strand. After extension of the immobilized oligonucleotides, the hybridized parental strands are discarded. At this point the wells contain immobilized (complementary) partial strands. The partials in one well all share a 5'-terminal oligonucleotide segment that is complementary to a particular internal oligonucleotide in the parental strand(s). The partial strands have 3'-terminal sequences that include the complement of the 5'-terminal region of the parental strand(s) (which contains a priming region). Again, if an oligonucleotide occurs more than once in a strand, or if it occurs in more than one strand in the group of strands subjected to partialing, then the well will contain a corresponding number of different partials. Unlike the methods described above for partialing before sorting, the immobilized complementary partials will contain a priming region at only one end and therefore can not be amplified exponentially. However, their linear amplification is possible, with the partials being synthesized as DNAs or RNAs. Where RNA partials are generated, the priming region at the partial copy's 3' terminus contains an RNA polymerase promoter. Synthesis of RNA copies is more efficient than linear synthesis of DNA copies. Alternatively, the synthesized copies can be provided with second priming regions by a variety of methods, and can then be amplified in an exponential manner by PCR. Examples of methods in which partials are generated on arrays are discussed in Example 3.3, below, and this approach for preparing partials is illustrated, schematically, in FIG. 5.

Figure 5A:
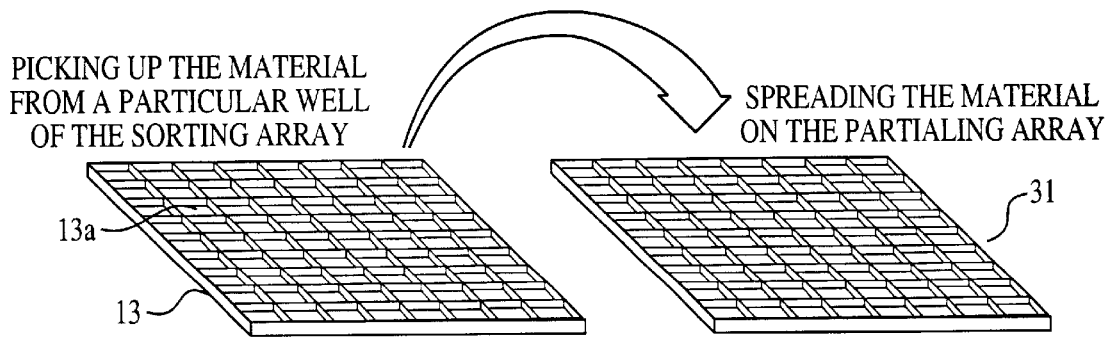
FIG. 5 shows an example of preparing partials on a sectioned ordinary array.
Figure 5B:
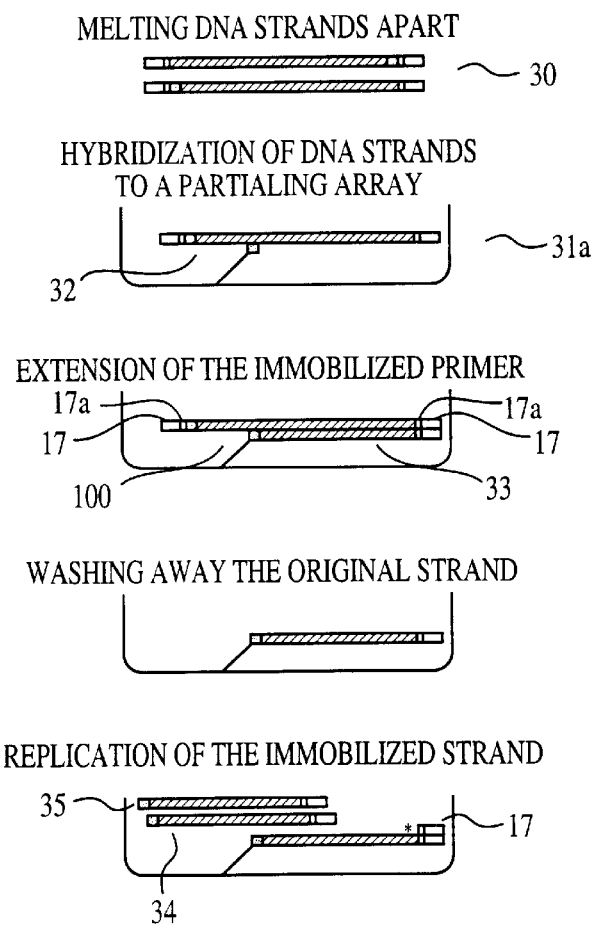

FIG. 5 illustrates the generation of partials for one DNA parental strand 30 on a 3' sectioned ordinary array. First, the strand 30 (many copies, of course) such as obtained from well 13*a* of sorting array 13, is hybridized to the partialing array 31, a 3 sectioned ordinary array, containing well 31*a*. The parental strand 30 binds to many different locations within the array, dependent on which oligonucleotide segments are present in the strand. A hybrid 32 is formed in each well at the array that contains an immobilized oligonucleotide complementary to a strand's oligonucleotide segment. After hybridization, the entire array is washed and incubated with an appropriate DNA polymerase in order to extend the immobilized oligonucleotides utilizing the hybridized strand as a template. Each extension product 33 strand is a partial (complementary) copy of the parental strand. Each partial begins at the place 32 in the strand where hybridization occurred and ends at the strand's terminus. The strand preferably terminates at its 5' terminus with a universal priming sequence 17, such as one introduced into all strands when sorting strands on a sectioned binary array as described previously. This allows for later amplification of the partials. That priming sequence can contain a restored restriction site 16a. The parental strand may also contain, if it was previously sorted on a binary sorting array, a priming sequence at its 3' terminus 17, adjacent to the variable sequence 100 that the strand was previously sorted by.

The entire array is then vigorously washed under conditions that remove the parental DNA strands and other material, preferably all, that is not covalently bound to the surface. The individual areas of the array then contain immobilized strands 33 that are complementary to a portion of the parental strand. The wells can then be filled with a solution containing the universal primer (or promoter complement), an appropriate polymerase, and the substrates and buffer needed to carry out multiple rounds of copying of the immobilized partial strands. The array can then be sealed, isolating the wells from each other, and (linear) copying can be carried out simultaneously in all of the wells in the array.

The partialing array, containing the covalently bound complementary partial copies 33 of the parental strands, can be stored and used at later time for the generation of additional copies of the complete set of partials, or, if desired, only for the generation of additional copies of the partials contained in selected wells.

Embodiments for generating partials which employ degradation of nucleic acids and then sorting the resulting degraded (partial) strands by their terminal sequences may have the following advantages as compared with the method of preparing partials directly on an array (by sorting strands by their internal segments): (1) introduction of priming regions at both ends of the partials for subsequent exponential PCR amplification can be accomplished more easily using certain methods, described herein, to introduce priming regions into the degraded strands; (2) secondary structures can interfere with hybridization of nucleic acids to immobilized oligonucleotides, which interference tends to be lessened when hybridization is by terminal sequences; and (3) it is often easier to prepare partials in roughly equimolar amounts, resulting in amplified products that also are roughly equimolar. On the other hand, the method of partialing directly on an internal sorting array has the significant advantage of economy of processing.

Our invention also includes the preparation of partial copies of RNAs on sectioned arrays (see Example 3.4, below).

Methods for sequencing using partialing are described in detail below. Partialing has other uses as well. Our invention also includes the use of sectioned arrays for the isolation of desired individual partials of nucleic acids whose sequences, or partial sequences, are already known. In most cases, these methods allow individual partials to be isolated, irrespective of whether one parental strand, or a group of parental strands, was used as the starting material for the partialing procedure, and irrespective of whether the particular oligonucleotide at the variable end of a partial to be isolated occurs in a strand only once, or more than once. According to this aspect of the invention, partials that originate from different parental strands, and that share the same variable end, are separated from each other by sorting according to their fixed ends if these ends were not yet used for sorting the parental strands. The fixed ends of these partials originating from different parental strands contain variable regions (adjacent to an added priming region at the fixed end) which are almost always different. Where the oligonucleotide at the variable end of a partial to be isolated occurs in a parental strand two or more times, the individual partials that share that oligonucleotide at their variable end, are isolated as follows. Instead of using parental strands as the starting material for the generation of partials, the desired partial is generated from another partial, which is chosen so that the desired partial will be the longest partial amongst those that share that variable end. Then, the longest partial is separated from the shorter partials by hybridizing it at an internal oligonucleotide that does not occur in the shorter partials (Example 4.1). (The sequence of the parental strand has previously been determined.)

Our invention also allows the preparation of partials that correspond to a parental strand that is truncated to any extent from both ends. These "two-sided partials" are prepared in a two-stage procedure, each stage resulting in the truncation of one of the ends. The ability to prepare two-sided partials means that the precise excision and isolation of any desired segment of a nucleic acid is possible using the invention, without the need for restriction sites at the boundaries of the segment, and without the need to synthesize specific primers that embrace that segment (Example 4.2).

In making two-sided partials, methods described for making one-sided partials are employed. One-sided partials can be prepared by the method of sorting strands by their internal segments on an array and then extending the immobilized oligonucleotides, or by degrading strands and then sorting them on an array according to their variable ends. The one-sided partials have fixed ends and variable ends. The fixed ends can contain priming regions. If the one-sided partials were prepared by degradation and sorting, then both the fixed and the variable end can also be provided with a priming region during sorting, as described herein. To prepare two-sided partials, the strands from one well of the first array are partialed to truncate their former fixed ends. This can be accomplished by using any of the means described for preparing one-sided partials. For example, complementary partials, preferably having primers at both ends, can be hybridized to wells of an array and the oligonucleotides immobilized in the array can then be extended to produce partial copies that have their former fixed ends truncated. Either direct copies of the partials in the first array, or their complements, may be partialed in the second round of partialing. The choice of whether to use 3' or 5' arrays will be apparent to one skilled in the art. The resulting partials will have both termini truncated.

Priming regions can be added to ends of the partials, using the methods described herein. If it is desired to obtain a two-sided partial with no added priming sequences, appropriate cleavable primers, described herein, can be used for amplification.

The same array can be used for both rounds of partialing, and only selected wells in the array need be used.

Our invention also includes the use of sectioned arrays for the manipulation in a great variety of ways of a nucleic acid whose sequence is known (or partially known), including methods for their recombination and site-directed mutagenesis. These methods are based on the ability to prepare any desired partial of a nucleic acid strand according to the invention, and utilize "cleavable primers" as discussed below. Cleavable primers allow the substitution of new terminal priming regions for old priming regions, and allow the removal of a priming region from a partial's, or strand's, end, after amplification has been carried out, when the presence of that priming region would interfere with subsequent manipulations. The cleavage of such a primer does not result in the degradation of a partial (or a strand), because the entire cleavable primer, or just the junction nucleotide that joins the primer to the remainder of the partial, is made chemically different from the rest of the partial (Example 4.3).

Our invention includes using sectioned arrays for carrying out precisely directed recombinations between chosen segments of previously sequenced nucleic acids. This recombination can be carried out on the arrays in a massively parallel fashion, resulting in production of many different recombinants, e.g., for screening, at the same time. The recombinants can be constructed from isolated strands or their partials, or from mixtures of strands or their partials. This method involves the ligation of nucleic acids to each other on the surface of arrays. The immobilized oligonucleotides either serve as sequence-specific "splints" that hold together the correct termini of nucleic acids, thereby ensuring their specific ligation, or they serve as protruding "sticky ends" that are added to the terminus of a double stranded fragment to be ligated, and that direct its ligation to the other desired fragment. In either case, each non-ligated end of the joined fragments has a priming region, so that the recombinant strands (and only the recombinant strands) possess the two terminal priming regions that are required for subsequent exponential amplification by PCR (Example 4.4).

Our invention also includes using sectioned arrays for introducing site-directed mutations into sequenced nucleic acids, including the introduction of nucleotide substitutions, deletions and insertions. This can be carried out in a massively parallel fashion. In one embodiment, a partial whose variable end has been deprived of a priming region, is ligated to the free terminus of an immobilized oligonucleotide that contains the mutation to be introduced. In another procedure, where the purpose of mutagenesis is to introduce a single-nucleotide substitution, then the substituting nucleotide can be added directly to the variable end of the partial. In both cases, the modified partials or their complementary copies are used to synthesize a mutant strand utilizing as a template either the complementary parental strand (i.e., from which the partials were generated) or a longer complementary partial, or any other strand or partial that encodes the missing region. The fixed end of the mutant partial is provided with a priming region that is different from the corresponding priming region of the template strand. Therefore, only mutant strands are capable of subsequent amplification by PCR. A single array can be used either to mutate many single positions in a gene, or to introduce mutations in many genes in one procedure. Sectioned arrays can also be used for the massively parallel testing of the biological effects of the introduced mutations. For example, parallel coupled transcription-translation reactions can be carried out in the wells of a sectioned array following amplification of the mutant strands. It is thus possible to determine simultaneously, on the same sectioned array, the effects of many different amino acid substitutions on the structure and function of a protein. This is useful for protein engineering (Example 4.5).

IV. Surveying Oligonucleotides with Binary Arrays

Our invention includes the use of binary arrays for surveying the oligonucleotides contained in nucleic acid strands and their partials to determine their oligonucleotide content (see Examples 5.1 and 5.2, below).

Surveying allows information to be obtained about which oligonucleotides are contained in a strand, in a partial, in a group of strands, or in a group of partials. Survey arrays can be comprehensive. Essentially comprehensive surveying is useful in sequencing nucleic acids. The information obtained can be used as a check on a sequence derived by some other means, and thus can be used even if only a partial sequence is obtainable from the survey. According to an important aspect of the invention, discussed elsewhere herein, however, surveying, preferably on a binary array, can be used in combination with other methods described herein to obtain complete sequences of longer nucleic acids than have been sequenced using conventional surveying techniques. Surveys can also be used for diagnostic purposes.

Surveying can also be selective, where only certain oligonucleotides of interest are identified. In selective surveying, the array contains only selected oligonucleotides, that can be rather long without increasing the size of the array. Selective surveying is useful for studying genetic variations, such as mutations and chromosomal rearrangements, when a reference sequence is known. It is also useful for ordering sequenced fragments in a longer nucleic acid, by identifying their "signature oligonucleotides" (discussed below). This method makes it unnecessary to repeat the complete sequencing of overlapping fragment libraries to obtain the sequence of a long nucleic acid.

The use of binary arrays also allows surveying to be improved as compared with the use of ordinary arrays, and it allows new types of selective surveying (such as surveying signature oligonucleotides) to be carried out.

A principle advantage of using binary arrays to survey oligonucleotides is to improve markedly the discrimination against terminal mismatches. Terminal mismatches are responsible for most errors that occur in oligonucleotide surveys that are carried out by hybridization [Drmanac et al., *DNA Cell Biol.*, 9, 527–534 (1990), supra]. According to this aspect of the invention, terminal basepairs are checked for a mismatch in two enzymatic reactions, ligation and primer extension, that are both highly sensitive. A further advantage of using binary arrays is that a hybrid can be labeled at each end after it has formed, and in a manner that is dependent upon the success of these two enzymatic reactions, thus enabling background levels to be significantly reduced. Also, binary arrays can increase hybrid length (by ligation and extension), which allows the detection of hybrids to occur under optimal conditions.

In surveying, nucleic acid strands first can be randomly degraded into pieces whose average length slightly exceeds the surveyed length. Degradation of DNA strands prior to hybridization has been proposed to overcome interference from internal secondary structures that are present in a single-stranded DNA molecule [Lysov, Yu. P., Florentiev, V. L., Khorlin, A. A., Khrapko, K. R., Shik, V. V. and Mirzabekov, A. D. (1988). Determination of the Nucleotide Sequence of DNA Using Hybridization to Oligonucleotides. A New Method, *Doklady Akademii Nauk SSSR* 303, 1508–1511]. There are, however, other advantages of degradation prior to hybridization. For example, degradation significantly increases the molar yield of hybridization that can be achieved with the same amount of material, especially in the case of long nucleic acid strands (or partials). Moreover, degradation equalizes the molar yield of individual hybrids that can be obtained from strands of different length. Without degradation, once a DNA or RNA molecule is bound by one of its oligonucleotide segments, the rest of that molecule is not available for hybridization. Therefore, the molar amount of hybrids that are produced by a strand is inversely proportional to its length, since longer strands are distributed among a larger number of areas in an array. Degradation breaks each strand into many pieces of the same average length, and each of these pieces can hybridize to the survey array independently of the others. For example, degradation of a 4,000-nucleotide-long strand into 20-nucleotide-long pieces can result in up to a 200-fold increase in the molar yield of hybridization at each relevant area in an array. Moreover, there is the same molar amount of hybrids at each relevant area in an array as would be produced by a similarly fragmented strand that is only 200 nucleotides in length. Finally, random strand degradation allows each nucleotide in the strand to become a terminal nucleotide. This observation is taken advantage of to increase specificity of hybridization in preferred methods of surveying oligonucleotides described below.

After degradation, each resulting nucleic acid piece is ligated to the same type of oligonucleotide (i.e., a constant sequence), that preferably does not occur anywhere in the internal regions of the analyzed nucleic acids. For example, the sequence of the added oligonucleotide can contain the recognition site of a restriction endonuclease that was used to digest the DNA prior to fragment sorting. The ligation can be carried out in solution prior to hybridization, or after hybridization of the pieces to binary immobilized oligonucleotides whose constant segment is complementary to the oligonucleotide to be ligated. Preferably, a 3' array is used, having constant segments upstream from variable segments. The immobilized oligonucleotides can then be extended with an appropriate DNA polymerase, using the hybridized nucleic acid pieces as templates. It is preferable that after extension all hybrids have the same length. This can be achieved by employing dideoxynucleotides as substrates for the DNA polymerase, which causes the immobilized oligonucleotides to be extended by only one nucleotide. These methods can be used to survey both DNA and RNA (see Examples 5.1.1 and 5.2).

Hybrids can be labeled in both a ligation-dependent and an extension-dependent manner to increase the specificity of hybrid detection, as described in Example 5.1.2, below. Also, the ligated oligonucleotides and the added dideoxynucleotides can be tagged with different labels, for example, fluorescent dyes of different colors. The array is then subsequently scanned at two different wavelengths, and only those areas in the array that emit fluorescence of both colors indicate perfect hybrids (see Example 5.1.2).

Survey results can be improved further by hybrid proofreading, by destroying hybrids containing mismatches, by using chemical or enzymatic methods (see Examples 5.1.1 and 5.2, below).

Selected oligonucleotides (see Example 5.1.3, below) and signature oligonucleotides (see Example 5.1.4, below) can also be surveyed on binary array, as is described below.

V. Use of the Oligonucleotide Arrays for the Sequencing of Nucleic Acids

The arrays and methods of this invention can be used to determine the nucleotide sequence of nucleic acids, including the sequence of an entire genome, whether it is haploid or diploid. This embodiment requires neither cloning of fragments nor preliminary mapping of chromosomes. It is especially significant that our method avoids cloning, a labor-intensive and time-consuming approach that is essentially a random search for fragments. In a preferred embodiment of our invention, a comprehensive collection of whole nucleic acids or nucleic acid fragments is sorted into discrete groups. The sorted nucleic acids are then amplified with a polymerase, preferably by a polymerase chain reaction.

This method has advantages over cloning. Cloning is a form of amplification that begins with a single DNA molecule. The cloned DNA can contain somatic mutations (including those caused by environmental factors) which were not present in the zygotic DNA, and which accumulate during an individual's lifetime. Also, sequence alterations can occur when the DNA is cloned in the host cell. Moreover, cloning involves selective steps that can reject some sequences in favor of others. In contrast, the use of a polymerase, especially in a polymerase chain reaction, to amplify sorted fragments begins with a large number of DNA strands, and the sequence obtained from the amplified material is an averaged representative of the DNA in the analyzed sample, for example the DNA from many somatic cells, thus reflecting the sequence of zygotic DNA.

Figure 6:
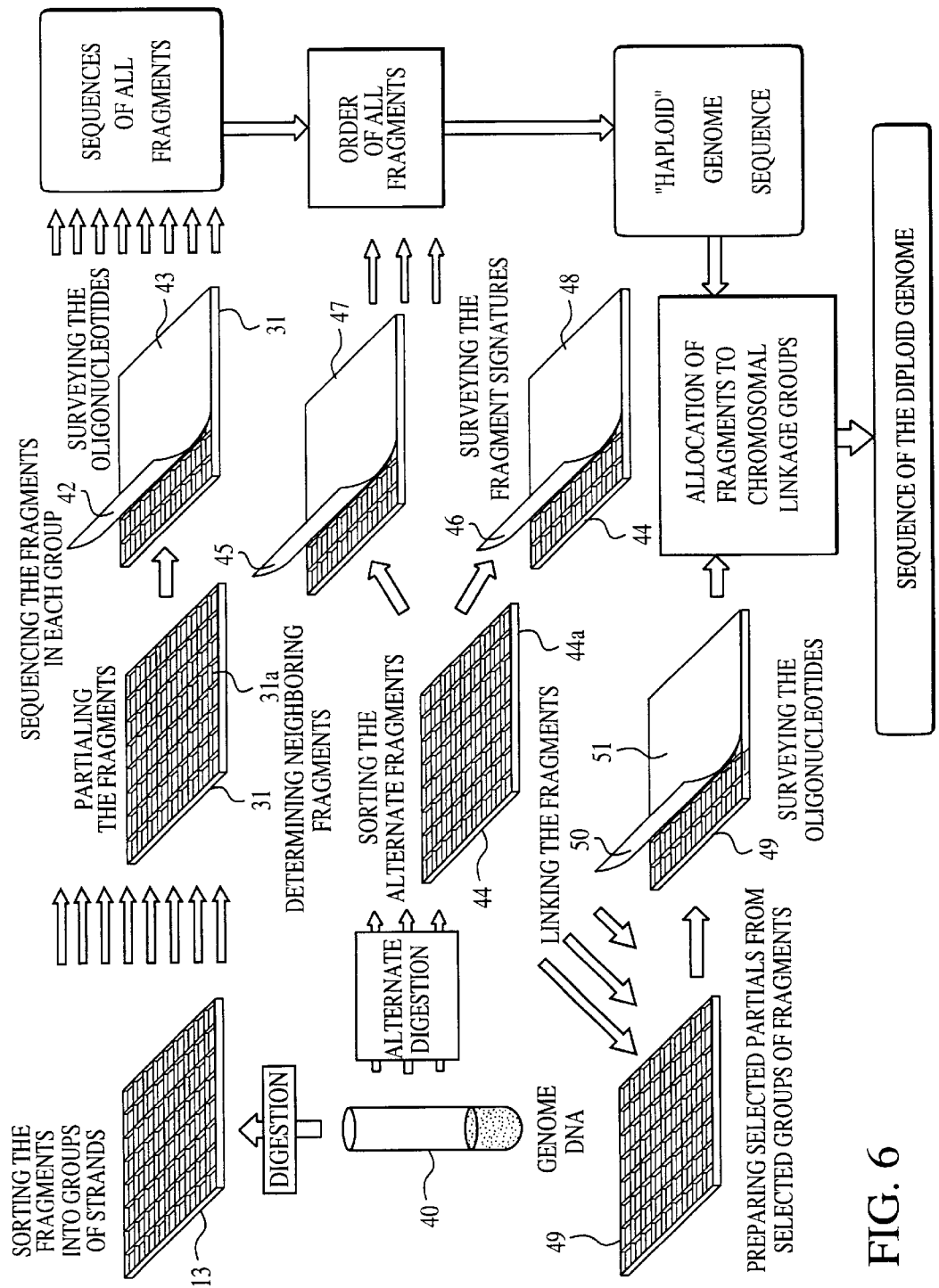
FIG. 6 shows, schematically, the order of steps for sequencing a complete genome.

Sequencing large diploid genomes, such as a human genome, using the arrays and methods of this invention is shown in FIG. 6. We will describe the overall method in general terms. The overall method employs several more specific methods already described. For details, reference should be made to the descriptions set forth above and in the examples. In the embodiment illustrated in FIG. 6 an individual's genomic DNA 40 is digested with a restriction endonuclease and sorted by terminal sequences into groups of strands using a 3' sectioned binary sorting array 13, as is described above in Section II and illustrated in FIG. 4.

Next, treating each well 13a of the sorting array separately, a complete set of partials is prepared for each group of sorted strands using a sectioned array 31, as is described above in Section III and illustrated in FIG. 5. The partials can be generated in any chosen manner to make them detectable.

Then the contents of each well 31a of the partialing array 31 is surveyed using a survey array 42, as is described above in Section IV. Preferably the survey array is a binary array, but an ordinary array may also be used. In the embodiment shown in FIG. 6, surveying is performed with a sheet 43 containing miniature survey arrays 42 that have been printed in a pattern that coincides with the number and location of the wells in the partialing array. Miniature survey arrays are discussed further below. Larger arrays can be used as well for surveying. The oligonucleotide information that is obtained can be used, according to our invention, to separately determine the nucleotide sequence of every strand in each of the groups isolated on the sorting array. The invention can also be used to determine incomplete sequences, such as when ambiguous results are obtained because of, for example, the presence of monotonous sequences or multiple repeats within the strands. The possibilities for ambiguous results, however, are minimized using methods described herein.

To determine the order of the fragments sequenced as illustrated in the embodiment of FIG. 6, genomic DNA 40 is digested with at least a second restriction endonuclease and sorted into groups of strands using a 3' sectioned binary sorting array 44, as is described above in Section II and illustrated in FIG. 4. The contents of each well 44a of the sorting array 44 is surveyed with special survey arrays 45, 46 that identify signature oligonucleotides (described below) in intersite segments of sorted fragments from different digests. This is done to determine the order of the fragments relative to one another without regard to differences between allelic pairs of fragments. In the embodiment shown in FIG. 6 this surveying is performed with printed sheets 47, 48 that have been printed with a pattern of miniature arrays 45, 46. Larger arrays can, of course, be used.

To allocate the ordered allelic fragments to their respective chromosomes in a diploid organism, fragments are linked by their allelic differences. In the embodiment illustrated in FIG. 6, the strands from selected wells of the sorting array 44 are transferred to a selected well of one of a series of partialing arrays 49, partials are generated, and the partials are surveyed using miniature survey arrays 50 on printed sheets 51. Only the presence of oligonucleotides containing allelic differences in the selected partials needs to be determined to link a pair of allelic fragments to their respective neighboring allelic fragments.

In some cases, abbreviated methods can be used for sequencing. For example, the final stage can be omitted when a haploid genome is sequenced, because in this case the ordering of the fragments will immediately result in their unambiguous linkage. If a mixture of undegraded cellular RNAs is to be sequenced, even the ordering step can be omitted.

As described above, this invention provides for comprehensive sequence analysis without resort to other methods (except for the resolution of a small number of ambiguities). Of course, portions of the entire procedure can be used independently, and in conjunction with other methods, if desired. For example, partialing and survey arrays and methods can be used to sequence cloned strands without sorting. Similarly, the fragment ordering procedure can be used to order fragments that have been sequenced by any method. Finally, allelic fragments can be allocated to their chromosomes by the method of this invention, no matter how fragment order has been established.

A detailed description of the sequencing procedure will now be provided. As will be apparent, some of the methods described can be carried out using conventional oligonucleotide arrays, as opposed to the novel arrays of the invention.

If the nucleic acid to be sequenced is a large DNA molecule, or a mixture of large DNA molecules (such as the genome of a prokaryotic or eukaryotic organism), it is first digested by a site-specific method that results in the cleavage of each type of DNA in the sample at specific locations within its sequence. One preferred method is to cleave with a restriction endonuclease and to sort by terminal sequences using a 3' sectioned binary sorting array as described in Section II above. Advantageously, the length of fragments should not exceed about ten thousand nucleotides, so that the fragments can be efficiently amplified by PCR. The array used for strand sorting should be comprehensive (see Section I, above) so that no strand is lost. The length of the variable segments chosen (and therefore, the overall number of different types of oligonucleotides in the array) will depend on the complexity of the sorted fragment mixture, and preferably should be chosen so that there will be no more than 100 or so different strands sorted into a well. The choice should be made according to considerations discussed in Section II, above.

For linear DNA (as opposed to a circular DNA) almost every strand is provided with two terminal priming regions, each of which includes the recognition site for the restriction endonuclease or other site-specific agent used for digesting the DNA. Almost every strand will therefore be exponentially amplifiable by PCR. Those strands that arise from the fragments at the ends of each DNA will only have one priming region. Strands originating from terminal (telomeric) fragments will possess a priming region at only one end, and cannot be exponentially amplified by PCR.

Telomeric fragments can be isolated in a separate procedure that utilizes affinity to characteristic telomeric sequences. For example, in human chromosomes the telomeres consist of many characteristic tandem repeats of TTAGGG, which will bind to their complement on an array [Alberts, B., Bray, D., Lewis, J., Raff, M., Roberts, K. and Watson, J. D. (1989). *Molecular Biology of the Cell,* 2nd edition, Garland Publishing, New York]. Alternatively, telomeric fragments can be isolated by specifically binding them to a telomere protein [see, for example, Raghuraman, M. K. and Cech, T. R. (1989). Assembly and Self-association of Oxytrichia Telomeric Nucleoprotein Complexes, *Cell* 59, 719–728].

When sorting according to the identity of terminal sequences, each strand occupies a particular "address" in the array. It is convenient to think of the address as the oligonucleotide sequence within a strand that directs the DNA strand to hybridize to a particular location within the array, i.e., the sequence that is perfectly complementary to the variable sequence of the oligonucleotide immobilized at that location. The "address" also identifies the location within the array where the DNA binds.

After sorting, each group of strands is amplified (described in the examples and Section II above) and subjected to partialing (see Examples 3.1 to 3.3, below). Importantly, the isolation of individual strands is not necessary, because our method allows the nucleotide sequence of each strand in a mixture to be determined. In particular, our method allows the sequences of strands in a well of the sorting array to be determined, separately from mixtures of strands in other wells. In a preferred embodiment, the partialing array is comprehensive (see Section I) in order to obtain all possible one-sided partials (i.e., a comprehensive array). At the same time, smaller partialing arrays having some oligonucleotides excluded, can also be used for partialing to obtain sequence information as discussed below in this section. Each group of partials is amplified prior to surveying. Most preferably, the amplification is carried out in such a manner that one of the two complementary partial strands is produced in great excess over the other.

Each group of partials is surveyed by hybridization to a survey array, in order to identify their constituent oligonucleotides. Surveying is preferably carried out using binary arrays (see Example 5.1, below) but can be performed with ordinary arrays. The arrays are preferably comprehensive, in order to obtain a complete list of the oligonucleotide segments that are contained in the partials.

The selection of the optimal lengths to use for variable segments in both the partialing arrays and the survey arrays depends on the complexity of the groups of strands to be analyzed and on the length of those strands, and should be based on both theoretical calculations, such as those discussed at the end of this section, and preliminary experiments (with model mixtures of fragments whose sequence is known) designed to evaluate the resolving capacity for each array size. Our calculations show that if the basic length (minimal length) of the variable segments in both the partialing arrays and the sorting arrays is eight nucleotides, the arrays should be adequate for sequencing groups of about 50 strands whose average length is 4,000 nucleotides. If octameric variable segments are used as a basic length, then a comprehensive partialing array will contain at least 65,536 wells. For sequencing smaller groups of similar fragments, or similar groups of shorter fragments, shorter variable segments, and consequently, smaller partialing arrays, can be used. The basic length of the variable segments in the oligonucleotides immobilized on the survey arrays must suit the combined length of all partials in each well of the partialing arrays, so that there are always unoccupied areas in a survey array. If a group of about 50 4,000-nucleotide-long strands is subjected to partialing on a single partialing array, then the basic length of eight nucleotides should be adequate for the variable segments in the oligonucleotides immobilized on the survey arrays. In this case, a comprehensive survey array will contain at least 65,536 different areas. The number of different areas in the survey arrays can be made approximately 50% greater due to the inclusion of special longer oligonucleotides, in order to read through regions of recursive sequences in the strands.

Figure 7:
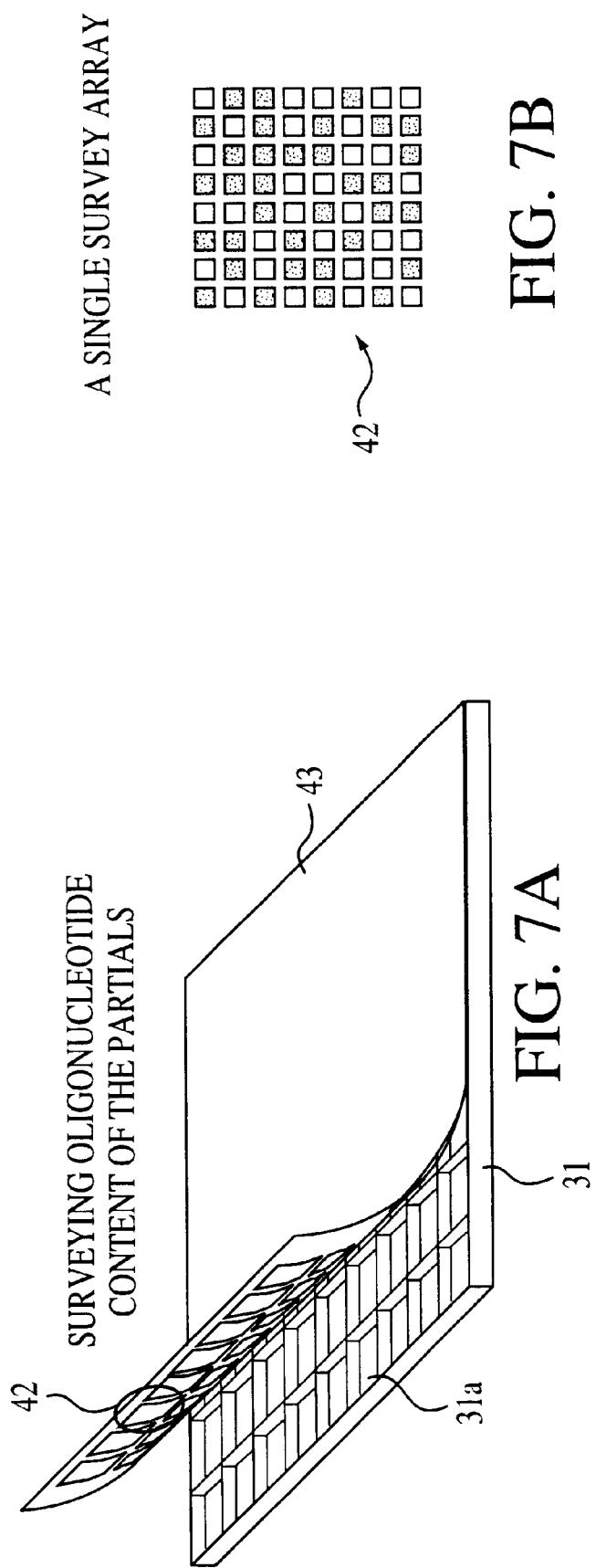
FIG. 7 shows, schematically, the use of a sheet with a number of miniature survey arrays for simultaneous surveying every well in a partialing array.

Although not necessary, it is preferable to have the survey arrays be as compact as possible. It is anticipated that surveying will be advantageously accomplished simultaneously for many or all wells of a partialing array by utilizing a sheet on which miniature survey arrays have been "printed" in a pattern that coincides with the arrangement of wells in the partialing array, in a manner similar to that shown in FIGS. 6 and 7. Referring to FIG. 7, partialing array 31, comprising an array of wells 31a, is surveyed using sheet 43, having printed thereon an array of miniaturized survey arrays 42. The pattern of arrays 42 corresponds to the pattern of wells 31a, whereby all wells 31a can be surveyed simultaneously.

Automated photolithography techniques for preparing miniature oligonucleotide arrays have been developed [Fodor, S. P., Read, J. L., Pirrung, M. C., Stryer, L., Lu, A. T. and Solas, D. (1991). Light-Directed, Spatially Addressable Parallel Chemical Synthesis, *Science* 251, 767–773]. The manufacture of miniature arrays on a "chip", for use in surveys also has been reported [Fisher, L. M. (Mar. 3, 1991). Microchips for Drug Compounds, *The New York Times, p. F7*]. It is not, however, necessary to practice the invention that printed arrays be used for surveying. The contents of wells to be surveyed can be transferred to large arrays instead, having sufficiently amplified the partials previously to make them abundant enough to be detectable.

Surveying with comprehensive arrays produces a complete list of oligonucleotides contained in the partials in each well of the partialing array. As discussed below, the partials in each well share the same terminal variable oligonucleotide. It is important to note that if an oligonucleotide occurs more than once in the same parental DNA strand (or in more than one of the different parental DNA strands) in the same well, there will be more than one different partial strand in that well of the partialing array. The survey will reveal all oligonucleotides that are present in all partials in that well. The method of this invention can determine the sequences of each of the original (parental) fragment strands.

Figure 8:
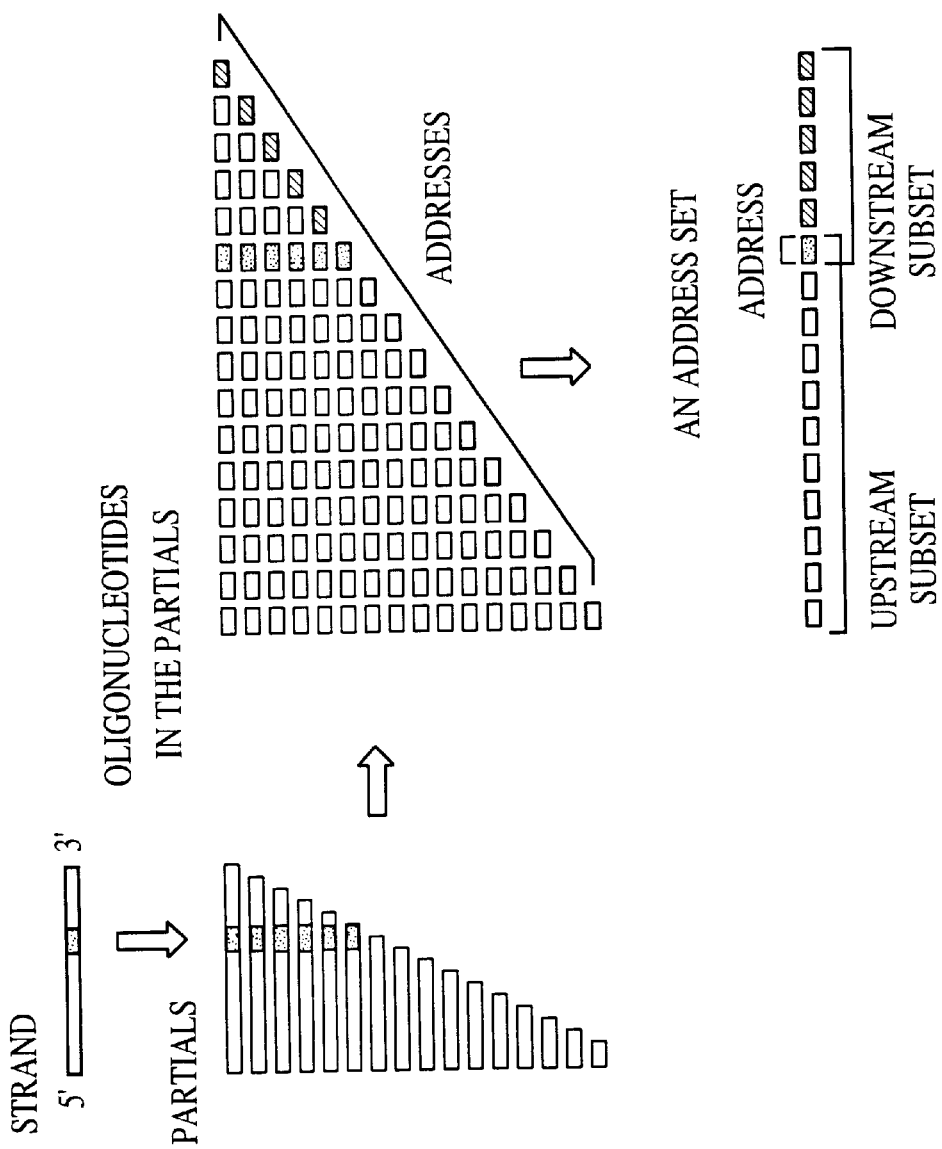
FIG. 8 shows, schematically, how a downstream subset and an address set are inferred from the oligonucleotide content of all possible partials of a strand.

Considering one parental strand, the partial strands are generated in such a manner that they all begin with the same parental terminal sequence, but terminate at a different nucleotide in the parental sequence. A different partial strand is generated for every nucleotide position in the parental sequence. The collection of partials will therefore consist of a nested set in which each successive partial strand is at least one nucleotide longer (if a comprehensive partialing array is used). An illustration of a nested set of partials is shown in FIGS. 8 and 9.

The "partials" referred to in this section are one-sided partial strands that begin at the 5' terminus of a parental nucleic acid strand (the fixed end) and end at different nucleotide positions in the strand (the variable end). Partials are sorted in the partialing array according to the identity of their variable ends, and therefore each partial has a particular "address" within the array. As with sorting arrays, an "address" in a partialing array is the oligonucleotide sequence that is present at the variable end of the partial strand and that is complementary to the variable segment of an immobilized oligonucleotide. The shortest partials used are as long as the oligonucleotide sequence at the variable end, i.e., the address plus priming region(s) at the partial's end(s). The "address" also relates to the location within the array where the partial strand is found, since the variable segment of the oligonucleotide immobilized in that well is complementary to the oligonucleotide at the partial's variable terminus. The "address" also relates to the location within the parental strand of a partial's terminal oligonucleotide. The location of this "address oligonucleotide" within a parental strand is characterized by an "upstream subset" of oligonucleotides that come before it in the parental sequence and by a "downstream subset" of oligonucleotides that come after it.

Our method of establishing nucleic acid sequences, for either a single strand or a group of parental strands sorted by their terminal sequences, begins by assembling an "address set" for each address in the partialing array. The "address set" is a comprehensive list of all of the oligonucleotides in all the parental strands which have the address oligonucleotide within their nucleotide sequences. The "upstream subset" contains all the oligonucleotides that occur upstream (i.e., towards the 5' end) of the address oligonucleotide in any parental strands that contain the address oligonucleotide. The "downstream subset" contains all the oligonucleotides that occur downstream (i.e., towards the 3' end) of the address oligonucleotide in any parental strands that contain the address oligonucleotide. Taken together, the upstream subset and the downstream subset form the "address set."

The upstream subset of each address can be determined directly from the survey of each well of a partialing array and consists of a list of all the oligonucleotides identified as being present in the partial strands in that well. The downstream subset of each address can be inferred by examining the upstream subsets of all the addresses in the partialing array: the downstream subset of a particular address consists of those addresses whose own upstream subset includes that particular address oligonucleotide. FIG. 8 illustrates how we infer the downstream subset of a particular address from the upstream subsets of the other addresses. Note that the address oligonucleotide is included in both its upstream and downstream subsets, and divides the address set into the two subsets.

The terms "partials" and "addresses" can perhaps be more easily understood by reference to FIG. 9, wherein a complete set of partials is shown for the strand 5'-ATGAGCCTAGATCGGT-3', which is sixteen nucleotides long. In this illustration, only one strand is being sequenced. The method of this invention is not so limited, however. It has the power to sequence simultaneously a mixture of strands. In FIG. 9, the oligonucleotides at the variable ends of the partials (i.e., their addresses) are three-nucleotide sequences, as are the oligonucleotides surveyed. Accordingly, both the partialing array and the survey arrays used to obtain these results would have $4^3$, or 64 areas, each coated with a different oligonucleotide sequence whose variable segment is three nucleotides long. The use of such a small array is presented here for ease of illustration, as larger arrays are generally to be used. Terminal priming regions are not shown for the same reason. (It should be noted that the length of the variable segments in the partialing arrays and in the survey arrays need not be the same, i.e., the length of the address oligonucleotides and the length of the surveyed oligonucleotides can be different.) The strand shown in FIG. 9 has fourteen addresses. Starting from the 5' end, the fourteen addresses are ATG, TGA, GAG . . . GGT. The shortest partial, ATG, is three nucleotides long, and has the address ATG (i.e., the partial was sorted on the partialing array by its variable terminal sequence: ATG). The next shortest partial, ATGA, is four nucleotides long, and has the address TGA. For the other twelve partials, the last three nucleotides in each is its address. The addresses, as they appear in the partials, are underlined in FIG. 9, depicting visually how the addresses propagate down the strand from the 5' end to the 3' end. The largest partial is the entire strand of sixteen nucleotides. The complete set of partials is shown nested in FIG. 9 with the longest partial shown on the top of the diagram, and the shortest partial shown on the bottom.

If an "address" were defined to be four nucleotides long, the first address in the strand of FIG. 9 would be ATGA, which would be the first of thirteen partials. If an "address" were five nucleotides long, the first address in the strand of FIG. 9 would be ATGAG, which would be the first of twelve partials.

Where the address contains eight nucleotides, a strand having a length of 4,096 base pairs would contain up to 4,089 different oligonucleotides which are eight nucleotides long, and therefore up to 4,089 different addresses; accordingly, up to 4,089 different partials would be a complete set generated for such a strand.

As shown in FIG. 9, according to the method of this invention the address set for an arbitrarily chosen address "TAG" contained in the parental strand is determined from the oligonucleotide information obtained from the partials. For the address "TAG", the upstream subset, i.e., those oligonucleotides that occur 5' of TAG in the parental strand (plus TAG itself), contains (in alphabetical order) AGC, ATG, CCT, CTA, GAG, GCC, TAG, and TGA. The downstream subset of this address contains AGA, ATC CGG, GAT, GGT, TAG, and TCG.

To obtain the upstream subset for the "TAG" address set we survey the oligonucleotide content of the well in the partialing array to which the partial that contains the TAG oligonucleotide at its variable terminus hybridized. That well contains the immobilized complementary oligonucleotide "CTA". (The partialing array, and other arrays used in this invention, are preferably arranged so that the identity of the immobilized oligonucleotides in each well or area is known from its position within the array.) A survey of the oligonucleotides in this well provides the upstream subset of the TAG address.

The downstream subset for the TAG address, i.e., those oligonucleotides that occur on the 3' side of TAG in the parental strand, is inferred by determining which other addresses contain the TAG oligonucleotide in their upstream subsets. For example, a survey of the well containing an immobilized CGA reveals that the partial with address TCG in FIG. 9, contains TAG among its constituent oligonucleotides. Therefore, TAG is contained in the upstream subset of the address TCG, and, consequently, the TCG oligonucleotide must be contained in the downstream subset of the TAG address. From the survey results of all the other addresses in the partially array, we similarly determine all other oligonucleotides in the downstream subset of the TAG address.

The upstream subset and the downstream subset of a particular address, taken together, are an "indexed address set". If an oligonucleotide occurs more than once in a strand, it can occur in both the upstream and the downstream subsets of an address. Indexed address sets provide the information required to order the oligonucleotides contained in a strand set, as will be described below. When a mixture of strands is examined, it is also useful to consider an address set without regard to which oligonucleotides occur upstream and downstream of an address. This is called an "unindexed address set". Unindexed address sets are decomposable into strand sets by the method of this invention.

FIGS. 8 and 9 depict a situation in which only one strand is analyzed. In this simple case, once the indexed address sets are inferred for every address contained in the parental strand (in this illustration there are 14 address sets), the relative position of each address oligonucleotide within the strand is determined by comparing address sets to each other. For example, the address set for "ATG" has no upstream addresses and thirteen downstream addresses. The address set for "TGA" has one upstream address (ATG) and twelve downstream addresses, etc. It follows that ATG comes in the strand before TGA. In this manner we determine the order of the address oligonucleotides within the parental strand.

We have discovered that when assembling big strand sets whose oligonucleotides do not all overlap uniquely, it is advantageous to work with "sequence blocks" rather than with individual oligonucleotides. Sequence blocks are composed of oligonucleotides that uniquely overlap one another in a given strand set. Two oligonucleotides contained in a strand set are said to overlap if they share a terminal (5' or 3') n−1 nucleotide sequence. An overlap is unique if no other oligonucleotide than those two in the strand set has this sequence at its termini. Here n is the length (in nucleotides) of each of the two oligonucleotides if they are of the same length or, if they are of different length, n is the length of the shorter one. We use unique overlaps to construct sequence blocks from the oligonucleotides in a strand set.

Figure 9A:
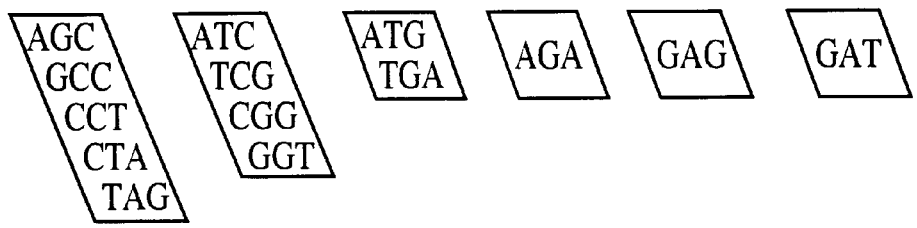
FIG. 9a shows how the oligonucleotides that are in a strand set can be assembled into sequence blocks.
Figure 10A:
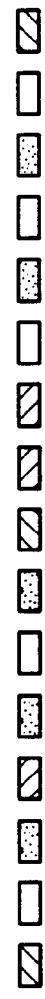
FIG. 10 shows, schematically, how the information obtained from indexed address sets can be used to determine the order of sequence blocks.
Figure 10B:
Figure 10C:
Figure 10D:
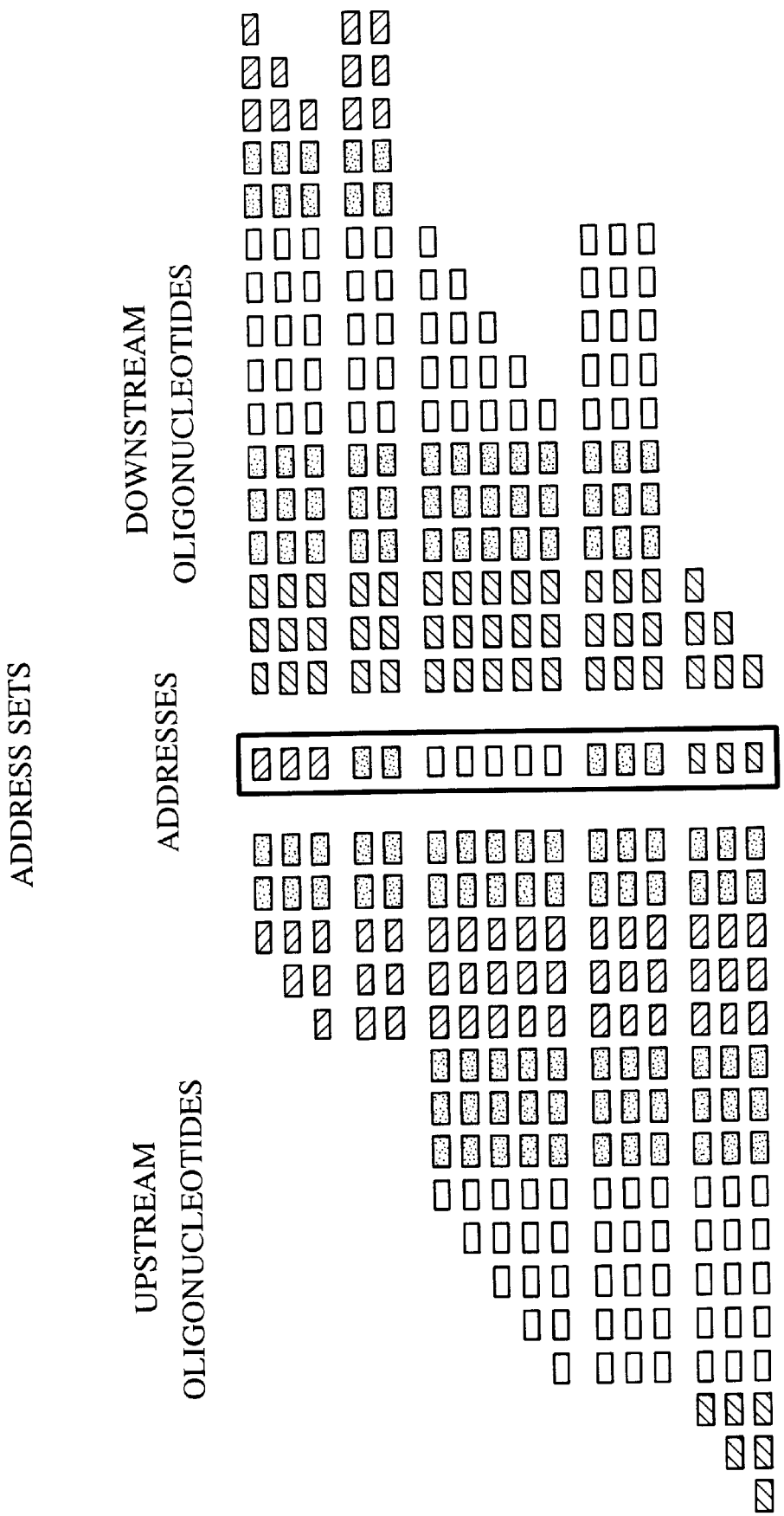
Figure 11A:
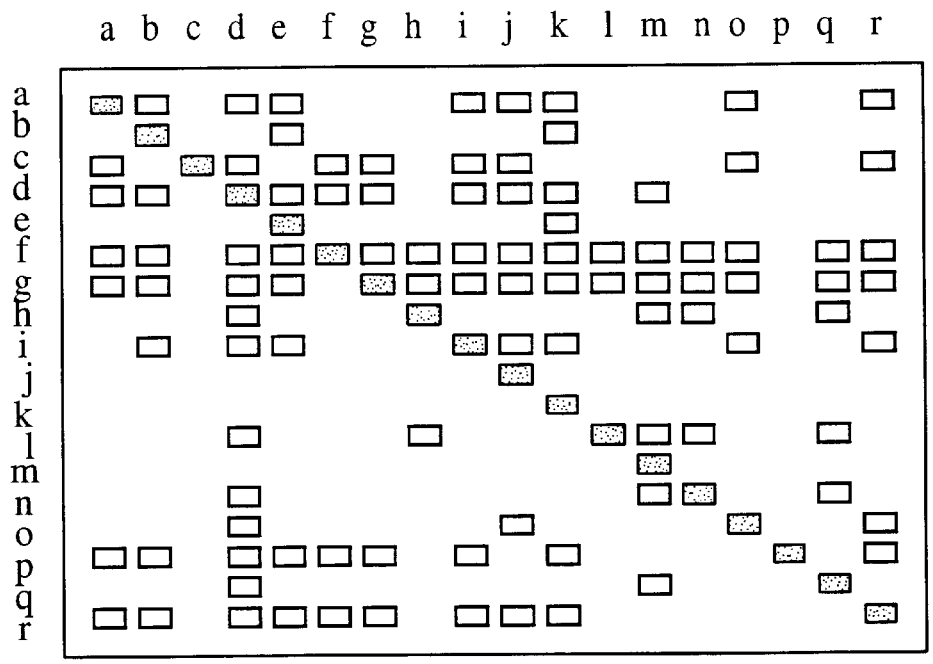
FIG. 11 shows, schematically, how unindexed address sets can be inferred from a survey of the oligonucleotides that are present in the partials generated at different addresses from a mixture of strands.
Figure 11B:
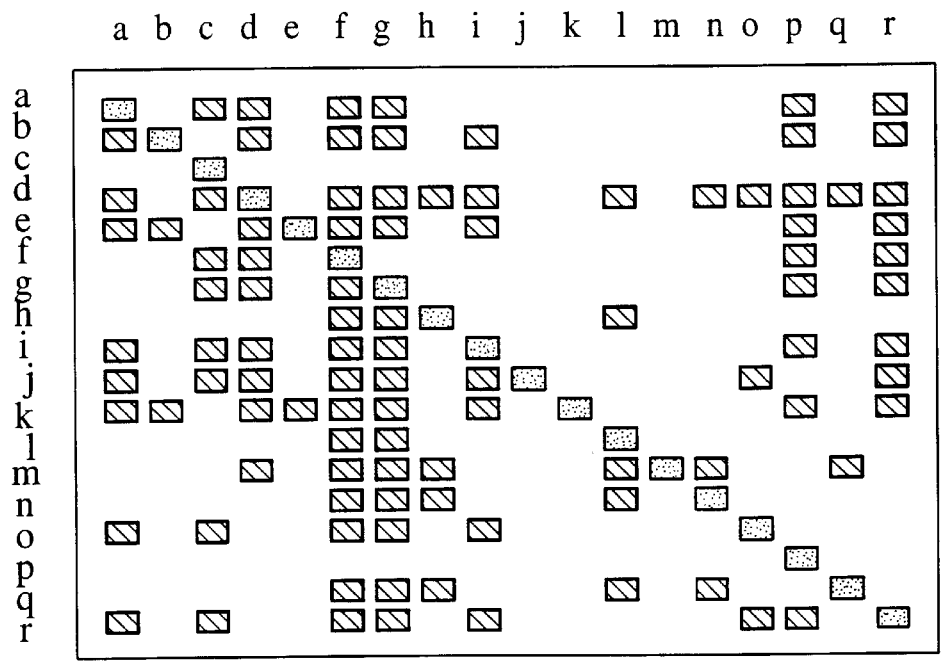
Figure 11C:
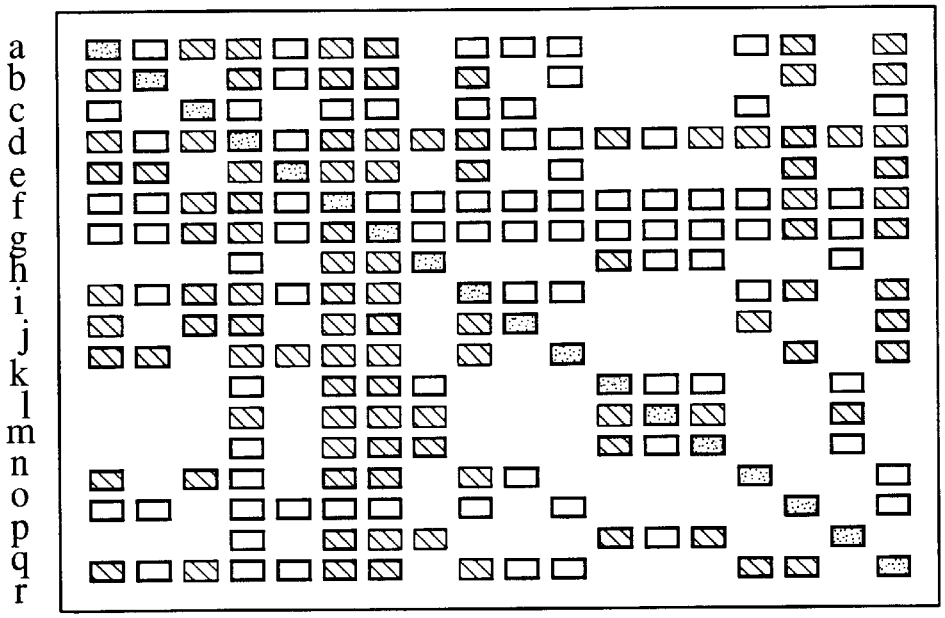
Figure 11D:
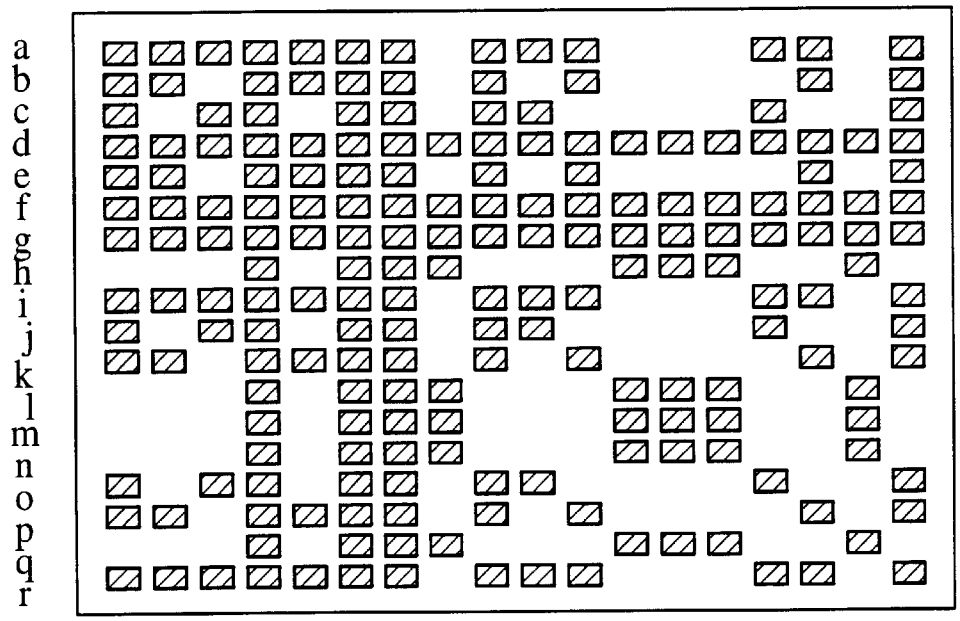
Figure 14A:
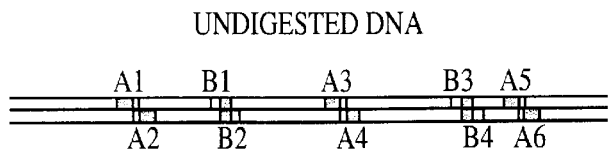
FIG. 14 shows, schematically, principles used to identify neighboring restriction fragments which have been sequenced.
Figure 14B:
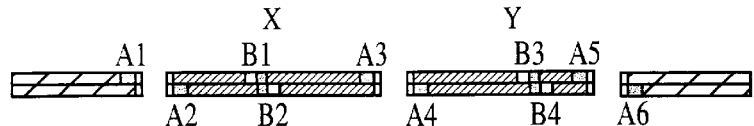
Figure 14C:
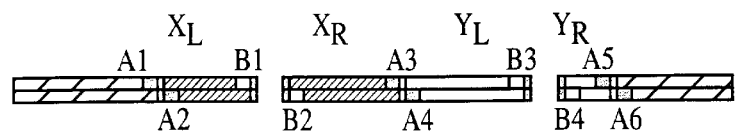
Figure 14D:
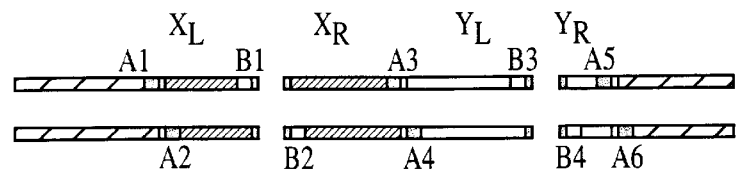
Figure 14E:
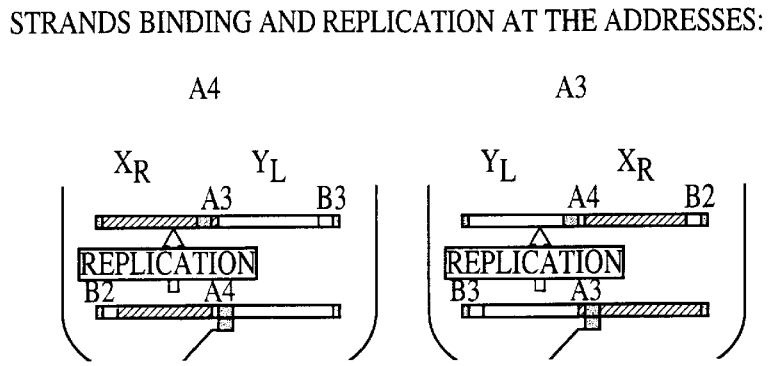

We can use the strand depicted in FIG. 9 as an illustration. By examining the address sets obtained using partialing and surveying methods (described above and discussed in more detail later), the set of all oligonucleotides in a strand will have been determined. For example, the set of oligonucleotides that occur in the strand shown in FIG. 9 will have been determined to be, in alphabetical order: AGA, AGC, ATC, ATG, CCT, CGG, CTA, GAG, GAT, GCC, GGT, TAG, TCG and TGA. To begin the method of assembling those oligonucleotides into the strand sequence shown in FIG. 9, we use unique overlaps to assemble sequence blocks, as will now be described in conjunction with FIG. 9A.

Because the oligonucleotides in the set are trinucleotides (n=3), n−1 is two. We examine, therefore, the first two nucleotides and the last two nucleotides of each address. Referring to FIG. 9A, the strand set of fourteen trinucleotides is shown first. Then each trinucleotide is shown as a pair of dinucleotides; e.g., AGA is shown as AG and GA. We examine those dinucleotides. If a dinucleotide occurs only twice, it indicates that two oligonucleotides uniquely overlap. The dinucleotide GC occurs only in trinucleotides A<u>GC</u> and <u>GC</u>C, so these two trinucleotides are assembled as shown in FIG. 9A, in the order shown there, AGCC. To see if this block can be enlarged, we examine its 5'-terminal and 3'-terminal dinucleotides. Its 5'-terminal dinucleotide, AG, occurs in four trinucleotides (<u>AG</u>A, <u>AG</u>C, G<u>AG</u> and T<u>AG</u>), therefore it is not a unique overlap. Thus, the block AGGC cannot be extended in the 5' direction. Its 3'-terminal dinucleotide, CC, in contrast, occurs in only two trinucleotides, G<u>CC</u> and <u>CC</u>T. Therefore, block AGCC can be extended at its 3' end to form AG<u>CCT</u>. For the same reason, the block can be extended at its 3' end by inclusion of oligonucleotides CTA and TAG to form AGCCTAG, but further extension of the block at its 3' end is not possible because of non-uniqueness of overlap AG. Similarly, blocks ATCGGT, ATGA, AGA, GAG, and GAT can be isolated from the rest of the strand set. Note that block ATCGGT cannot be extended at its 3' end because dinucleotide GT is only present in GGT, and in no other oligonucleotide. This means that, in this particular example, this block is the 3' terminal in the strand. Blocks AGA, GAG, and GAT are identical to oligonucleotides in the stand set, because the overlaps they can form (AG, GA, and AT) are not unique overlaps.

Whether an oligonucleotide is downstream or upstream of another in a strand set is not considered in the formation of the blocks, but this information is used at the next step, during ordering the sequence blocks.

FIG. 10 shows a schematic overview of the way in which a nucleic acid sequence is assembled from a strand set. This is done by examining the distribution of oligonucleotides in the upstream and downstream subsets of relevant address sets. A strand set, shown schematically, has sixteen unordered oligonucleotides (FIG. 10a). They are each identified by a pattern which indicates the particular group of uniquely overlapping oligonucleotides (FIG. 10b) which can be assembled into a sequence block, illustrated in FIG. 9A. The individual sequence blocks are schematically represented in FIG. 10c. Then, the position of each sequence block relative to the others is determined from the distribution of the oligonucleotides between the upstream and downstream subsets of every address (10d). This is accomplished by finding, for each of the blocks, which blocks occur upstream, and which blocks occur downstream, of that block by examining the address sets. The address sets are used in order to generate "block sets." The block sets are address sets wherein blocks have been substituted for the oligonucleotides that comprise the blocks, including the address oligonucleotide (FIG. 10e). Once the relative position of the sequence blocks has been determined, they can be assembled into the final sequence. The assembly is governed by the following rules: (1) each of the blocks must be used at least once, (2) the blocks must be assembled into a single sequence, (3) the ends of neighboring blocks must match each other (i.e., overlap by an n-1 nucleotide sequence, see above) and (4) the order of the blocks must be consistent with their positions relative to one another, as ascertained from the block sets.

A sequence block can occur either once in a sequence, or more than once, and this we determine by examining the block sets. If a block occurs more than once in a sequence, it will always be contained in both its own upstream and downstream subsets. On the other hand, if a block occurs only once in a sequence, it may or may not be present in its own upstream or downstream subset. But, if a block is absent from either its upstream subset, or from its downstream set, that block occurs in the strand only once. Therefore, from an examination of the block sets of FIG. 10, it can be seen that three of the blocks occur only once in the strand being sequenced (FIG. 10f). The relative order of these "unique" blocks can be determined by noting which of them occur in the upstream subset, and which of them occur in the downstream subset, of the others. Once the unique blocks have been ordered relative to each other, the gaps between them are filled with blocks that may be non-unique. However, not every gap can necessarily be filled in with a particular block. There is a range of locations within which each non-unique block (or presumably-non-unique block) can be present. The range for a particular block is determined by noting those blocks that always occur upstream of it, and those blocks that always occur downstream of it. In FIG. 10g, the range for each of the two potentially non-unique blocks is indicated by brackets. A gap can be filled in if, and only if, there is a block or a combination of blocks, whose outer ends have n−1 nucleotide-long perfect sequence overlaps with the ends of the blocks that form the gap (indicated in FIG. 10 by their having compatible shapes). Because at least two overlaps, each of low probability, must occur simultaneously, it is highly unlikely that more than one block, or one combination of blocks, can fill a gap. If a particular block occurs many times in a strand, it will have to be used to fill every gap it matches. This is why, using the method of the invention, it is possible to establish the sequence of a strand (as shown in FIG. 10h) without measuring how many times an oligonucleotide occurs in the partials. It is only necessary to determine whether an oligonucleotide is present or not.

We estimate that if the basic length of the variable segments used in a partialing array and a survey array is eight nucleotides, then this method can determine the sequence of strands that are many thousands of nucleotides long. Shorter variable segments can be used to determine the sequences of shorter strands.

While it is not always possible to avoid all ambiguities with this sequencing procedure, it is quite feasible to limit them to a small enough number so that they can be resolved, if desired, with an independent sequencing technique. The most significant source of ambiguities when utilizing our overall method is the presence within the strands of recursive, or monotonous, regions that consist of perfect repeats of identical units comprised of one, two, three, or more nucleotides, such as . . . AAAAAAAAA . . . or . . . ACACACACACAC . . . for example, the sequence 5'-GGTTGACTGACTGACTGACTGACGGTT-3' contains the tetrameric sequence TGAC repeated five times. The occurrence of such sequences will result in the appearance of sequence blocks possessing self-overlapping termini. If this occurs, it will not be possible to know how many times those blocks are repeated in a particular region of the analyzed strand. The smaller the recurring unit, the shorter is the sequence block and, therefore, the higher is the probability of its occurrence among the analyzed strands. The most difficult case is a homopolymeric region, where the recurring unit consists of one nucleotide. In that case, the length of the self-overlapping sequence block will be equal to the surveyed length. The probability of finding a recursive sequence with a longer recurring unit declines steeply with an increase in the length of the recurring unit. When the surveyed length is eight nucleotides, then almost all the ambiguities will arise from recursive sequences composed of recurring units that are seven nucleotides or less. Fortunately, the shorter the recurring unit, the fewer types there are. For example, there are only four unit types if the unit is a mononucleotide, twelve ($4^2$-4) types if it is a dinucleotide; sixty ($4^3$-4) types if it is a trinucleotide, and so on. It is thus practicable to include in the survey array an additional number of longer oligonucleotides which are complementary to recursive sequences that contain short recurring units. The use of longer probes for resolving recursive regions was suggested by Drmanac et al. for the analysis of arrays made of DNA strands [Drmanac, R., Labat, I., Brukner, I. and Crkvenjakov, R. (1989). Sequencing of Megabase Plus DNA by Hybridization: Theory of the Method, *Genomics* 4, 114–128]. For a survey array containing all variable octanucleotides, an approximately 1.5-fold increase in the number of oligonucleotides will drastically reduce the number of ambiguities caused by recursions. Any ambiguities that remain will not affect the assembly of the sequence blocks that occur within a strand outside of the recursive region. Consequently, the rest of the sequence will be determined unambiguously. Furthermore, it will be known where strands and partials that contain a particular recursion can be found in the sorting and partialing arrays. Therefore, if desired, the number of repeats in the unresolved recursive region can be determined by analyzing these strands or partials by conventional sequencing techniques.

An important aspect of this invention is the ability to sequence a mixture of strands simultaneously. The invention can be used for the determination of fragment sequences from an entire fragmented and sorted genome.

If one strand is being sequenced, then all the address sets determined from a partialing array will contain the same oligonucleotides that constitute the strand set. The only difference is that some oligonucleotides which are downstream in one set may be upstream in another address set. If a mixture of strands have been partialed on a single partialing array, certain addresses will be shared by more than one parental strand. Their address sets will be composite, containing all of the oligonucleotides from all of the strands that the address oligonucleotide is present in. Addresses that are only found in a particular strand in the mixture, however, will have address sets which only contain oligonucleotides from that strand. They are identical to the strand set, and each contain the same oligonucleotides. The mixture can contain up to a hundred or so different DNA strands, each of a different length and sequence, as can be obtained with an appropriate sorting array (or set of sorting arrays) and method described above. When a mixture of strands is analyzed on a partialing array, the data obtained by surveying the partials will reflect the diversity of the sequences in the mixture, and will appear to be very complex. However, we have discovered a way to decompose the unindexed address sets obtained by analysis of a strand mixture into their constituent strand sets. Then, as we have described for sequencing a single strand, the oligonucleotides in each of the identified strand sets can be grouped into sequence blocks and the blocks can be ordered from the information contained in the indexed address sets.

FIG. 11, diagram A, shows schematically data from a mixture of strands. For purposes of illustration, the mixture is limited to three strands, although the number of strands is not readily apparent in FIG. 11. The oligonucleotides found in a survey of the partial strands at each address are represented as unfilled bold rectangles and are identified by lower case letters on the top of the diagram. Address oligonucleotides are represented by filled black rectangles and are identified by lower case letters on the side of the diagram. Each horizontal line of rectangles shows which oligonucleotides are present in the upstream subset of the address oligonucleotide shown on that line. Diagram B shows the corresponding downstream subsets inferred from the data shown in diagram A. Each horizontal line of shaded rectangles in this diagram shows which oligonucleotides are present in the downstream subset of the address oligonucleotide shown on that line. Note that the pattern in diagram B can also be obtained from the pattern in diagram A by rotating the pattern in diagram A about the diagonal formed by the address oligonucleotides.

The oligonucleotides that constitute the downstream subset of an address ("first address") can also be determined directly from the survey data, provided that the mixture of strands applied to a partialing array contains both direct copies and complementary copies of each strand. Such a mixture of strands results from symmetric PCR amplification of strands in a well of a sorting array. In that case, the partial(s) sorted into the well with an address that is complementary to the first address will have been generated from the strands that are complementary copies of the parental strand(s). Their partials are complementary to the downstream portion of strands that are direct copies of the parental strand(s). That downstream portion contains the downstream subset of oligonucleotides missed from the partial(s) at the first address. In other words, oligonucleotides contained in the partials from the complementary address are complementary to the oligonucleotides that constitute the downstream subset of the first address.

Thus, the information obtainable by surveying the wells of a comprehensive partialing array is highly redundant. In fact, the information is repeated twice if complementary strands are partialed together: essentially the same information is collected from the analysis of complementary addresses. This fact can be taken advantage of, for example, in filtering out errors that can occur during surveying.

This redundancy also provides one way to reduce the number of wells in a partialing array without losing information that is essential for determining strand sequences. For example, a collection of oligonucleotides in a comprehensive array can be divided into two halves such that the (variable) sequences in one half have complementary counterparts in the other half. A partialing array containing either half can be used for partialing mixtures of complementary copies of strands to obtain comprehensive oligonucleotide information about each strand in the mixture. For this reason, it is not necessary to use comprehensive arrays to obtain the information usable to sequence strands.

The information contained in the upstream and downstream subsets of each address can be combined to form unindexed address sets. Diagram C shows how this information can be obtained by superimposing diagrams A and B. Oligonucleotides present in both the upstream and the downstream subset of the same address will occur at the same position in the superimposed pattern (represented as shaded bold rectangles). Consequently, each horizontal line of rectangles in the resulting pattern (diagram D) shows which oligonucleotides are present in either the upstream or the downstream subset of the address identified by the lower case letter on the side of the diagram. These unindexed address sets are used to identify the strand set of each DNA in the original mixture.

Each parental strand in a DNA mixture binds to many different areas (addresses) in the partialing array. The number of different parental strands that bind to a given address in the array depends on how many of the strands possess the address oligonucleotide. It follows that after partialing the mixture, an occupied address in the array may contain one, and possibly more than one, partial strand generated from each parental strand possessing that address. Accordingly, the upstream subset of an address will contain the address oligonucleotide and all the other oligonucleotides that occur upstream of the address oligonucleotide in every parental strand that binds to that address in the array. Put another way, the upstream subset of an address will be the union of the upstream subsets of each parental strand containing the address oligonucleotide. Similarly, the downstream subset of an address will be the union of the downstream subsets of each parental strand containing the address oligonucleotide. And finally, each unindexed address set (identified by the procedure shown in FIG. 11) will be the union of the strand sets of each parental strand containing the address oligonucleotide. No matter whether an address set is composed of one strand, or is composed of more than one strand, each strand will contribute all of its oligonucleotides to the address set.

Unindexed address sets can be either "prime" or "composite." A prime set consists of one strand set; while a composite set consists of more than one strand set. Accordingly, it is characteristic of a prime set that it cannot be decomposed into other address sets, i.e., there is no address set which is a subset of a prime set. Composite sets, however, can usually be decomposed into two or more simpler address sets.

FIG. 12 illustrates, schematically, how unindexed address sets can be decomposed into constituent strand sets. If a number of different address sets consist of the same strand set, or consist of a particular group of strand sets, then those address sets will be identical. Therefore, for the sake of simplicity, we can sort all the address sets into groups of identical address sets. For example, diagram A in FIG. 12 shows the different groups of identical address sets (I through V) that can be formed from the address sets identified in diagram D of FIG. 11. The address sets in three of these groups (I, II, and III) appear to be prime sets, because these address sets cannot be decomposed into other address sets. The address sets in the other two groups (IV and V) are clearly composite sets: they contain oligonucleotides that constitute two or more prime sets. Thus, group IV includes all oligonucleotides belonging to groups II and III, and group V includes all oligonucleotides that belong to three groups of prime sets (I, II and III).

By using the five groups of address sets, we can build three "pyramids" (FIG. 12, diagrams B, C and D), such that on the top of each there are prime sets (i.e., address sets that do not contain other address sets as their subsets). The rest of a pyramid is comprised of address sets that include the top address sets (i.e., prime sets) as a subset. These common oligonucleotides comprise full columns in the three pyramids, and the oligonucleotides common to each pyramid constitute three strand sets. It can be seen from diagrams B, C, and D of FIG. 12, that the oligonucleotides contained in a strand set are identical to the addresses whose address sets form a pyramid. This is exactly what is expected, since a strand set must contribute all of its oligonucleotides to each pertinent address set.

Specific examples of interpreting the oligonucleotide information obtained by partialing mixtures of strands and by surveying the oligonucleotide content of the partials that are present in the wells of the partialing array are given below (see Examples 6.1 and 6.2).

FIG. 12 illustrates how strand sets can be identified, when each strand set contains at least one oligonucleotide that is not present in any other strand set. The unindexed address set associated with a unique oligonucleotide contains only one strand set, and it is a prime set. However, there can be situations when there is no oligonucleotide in a strand set that is unique, in the sense used above. This is expected to occur frequently when fragments from diploid genomes are examined. Restriction fragments will occur as allelic pairs, and allelic strands will, as a rule, hybridize to the same address in a sorting array. In that case partial strands generated from the mixture of strands present in a single well of a sorting array will originate from pairs of allelic strands. Since allelic nucleotide differences occur roughly once in every thousand nucleotides, the two strand sets will, in general, be identical, except for a few oligonucleotides, and most of the addresses they occupy in the partialing array will also be identical. A similar situation will arise when strands originate from repeated genome regions that contain sequence microheterogeneities.

When there are many other different strands in a sample, there will be a high probability that the oligonucleotides that account for the few differences between quasi-identical strands will not be unique in a mixture of strands. In that case, there will be no prime address set for each of the quasi-identical strands. Even if an oligonucleotide occurs only in the quasi-identical strands, the address set associated with that oligonucleotide will be a composite of the strand sets of the quasi-identical strands. That address set will not be decomposable into other address sets, and it will therefore appear to be a prime set, as shown below.

Figure 13C:
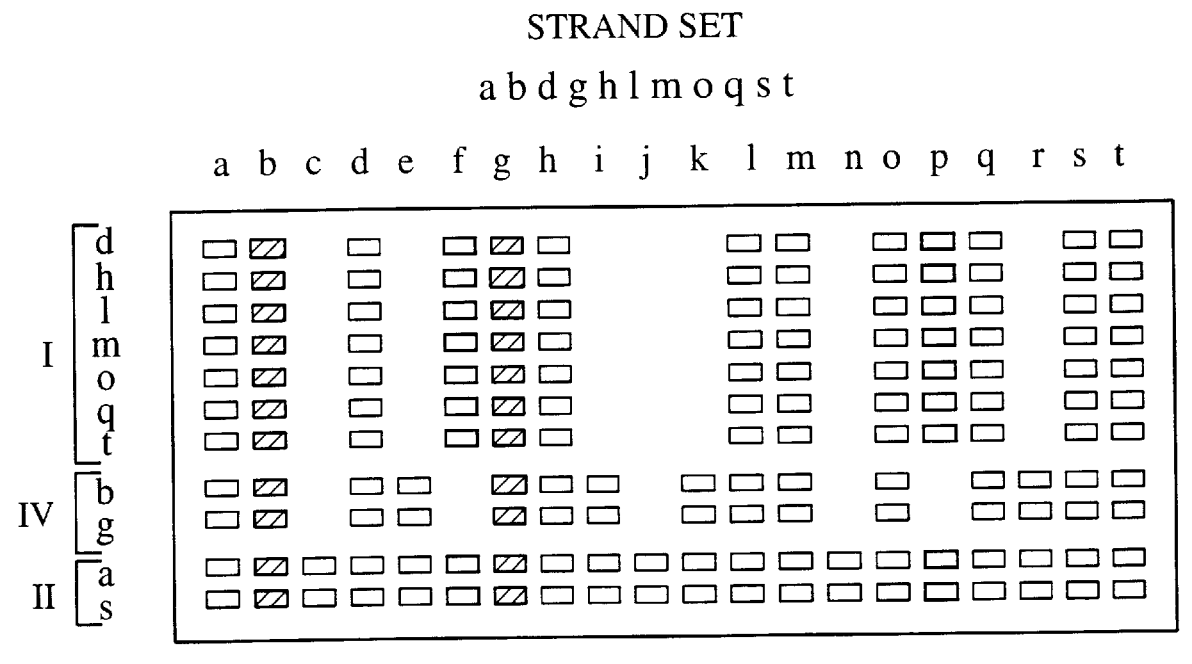

Such a "pseudo-prime set" is illustrated in FIG. 13. The address sets in group I of diagram A appear to be prime sets, because they cannot be decomposed into other address sets. However, inspection of the list of oligonucleotides contained in the group I address sets shows that not all of them are found among the addresses of the corresponding pyramid (made of the group I and group II address sets). The missed addresses are "b", "g", "f", and "p". At the same time, the respective address sets from groups III and IV (they are shown in diagram A beneath the dashed line) cannot be included in the pyramid, since address sets "b" and "g" do not contain oligonucleotides "f" and "p", and address sets "f" and "p" do not contain oligonucleotides "b" and "g", all of which are present among the group I oligonucleotides. This means that the address sets from group I do not consist of a single strand set (i.e., they are pseudo-prime sets). Pseudo-prime sets can be decomposed into their constituent strand sets by finding (building) pyramids that include some of the missed groups of address sets, and that have the property that the list of the oligonucleotides common to every address set in a pyramid is identical to the list of the pyramid's addresses. The result of such a decomposition is shown in diagrams B and C of FIG. 13. In each of these diagrams, there are oligonucleotides that are common to every address set, and they are seen as complete columns of rectangles. Every one of these oligonucleotides is found among the address oligonucleotides listed on the left side of the diagram. Note that a pyramid that includes both groups III and IV (in addition to groups I and II) would not satisfy the above criterion. In that case, the list of addresses would exceed the list of common oligonucleotides, since oligonucleotides "b", "g", "f", and "p" are not common to all these groups.

Pseudo-prime sets can not always be detected and decomposed into strands by this procedure. This situation occurs when the oligonucleotides that are unique within a pair of the quasi-identical strands, are all present in one other strand in the mixture. This is expected to be a rare situation, but one which may occur when analyzing DNA that is the size of the human genome. It can be diagnosed by the inability of the sequence blocks that are formed from a set that is supposed to be a prime set to be assembled into one contiguous sequence. When this happens, an analysis of the same quasi-identical strands within a different group of strands (obtained from a different well in the sorting array) can be helpful. This well is the well where strands complementary to those being analyzed were originally bound in the strand sorting array. In different wells, the strands from the same fragment will be enmeshed in a different group of strands. These different sequence contexts will interfere differently with the determination of the sequence of the strands and, thus, will often provide a way around the problem.

Once the individual strand sets have been identified, they can each be treated as though they were obtained from an analysis of a homogeneous strand. As was described earlier, the oligonucleotides in the strand set can be assembled into sequence blocks, and the location of these sequence blocks relative to one another can be determined from the presence or absence of these blocks in the upstream and downstream subsets of the relevant addresses. It is thus possible, in many cases, to sequence all the strands in an unknown heterogenous DNA sample without first isolating them from one another.

In this manner, the complete nucleotide sequence of every strand in a mixture can be determined. Occasional errors in the input data due to the presence of false hybrids on a survey array, or due to missing hybrids, are markedly reduced by the redundancy of having many different partials for each strand, and by the fact that each group of partials is analyzed separately. After each of the groups of sorted fragments has been analyzed by this partialing method, the sequence of almost every restriction fragment in the original digest will be known. Methods to minimize ambiguities in sequencing are discussed later.

The fragment sequences obtained by the methods outlined above or by any other method can then be put in their correct order using oligonucleotide arrays. Assembling restriction fragments into contiguous sequences can be accomplished by identifying each fragment's immediate neighbors. One method for obtaining this information is to use another restriction enzyme to cleave the same DNA at different positions, thus producing a set of fragments that partially overlap neighboring fragments from the first digest, and then to sequence these fragments in order to identify the neighbors. However, it is not necessary to sequence the fragments in the second restriction digest. It is only necessary to uniquely identify overlapping segments in the fragments from alternate restriction digests. This can be accomplished by surveying "signatures".

Signatures can be determined by hybridization of the fragment strands to complementary oligonucleotide probes. A signature of a fragment may consist of one, two, or more oligonucleotides, so long as it is unique within the DNA sequence being analyzed.

Neighboring fragments from one restriction digest can be determined by looking for their signatures in overlapping fragments from an alternate digest. This principle has been used by others to order an array of cloned fragments immobilized on a solid support. Overlapping fragments have been identified by the "fingerprint" pattern created when a series of short oligodeoxynucleotide probes are hybridized to the fragments [Craig, A. G., Nizetic, D., Hoheisel, J. D., Zehetner, G. and Lehrach, H. (1990). Ordering of Cosmid Clones Covering the Herpes Simplex Virus Type I (HSV-I) Genome: A Test for Fingerprinting by Hybridization, *Nucleic Acids Res.* 18, 2653–2660]. Overlapping fragments have also been identified by hybridization to groups of end-specific RNA transcripts [Evans, G. A. and Lewis, K. A. (1989). Physical Mapping of Complex Genomes by Cosmid Multiplex Analysis, *Proc. Natl. Acad. Sci., U.S.A.* 86, 5030–5034]. Both methods require preliminary cloning of the overlapping fragments.

We have devised a new method for identifying neighboring restriction fragments among the list of sequenced fragments that does not require either cloning or sequencing of overlapping fragments. If strands from an alternate digest are sorted, complementary strands of the same fragment will hybridize to different addresses in the sorting array. Whenever intersite segments from two or more fragments of the first digest are present within one fragment of the second digest, then all of these segments will be represented in both complementary strands of that one fragment, and all will be present wherever those strands bind in a sorting array. We identify the segments by obtaining their signatures through hybridization to specialized binary survey arrays. The signatures of intersite segments that occur in one fragment always accompany each other, whereas signatures of distant segments travel independently.

After the fragments from an original (first) restriction digest of a long DNA have been sequenced, the same DNA is digested with a second (different) restriction endonuclease, the termini of the generated fragments are provided with universal priming regions (that also restore the recognition sites at the termini), and the strands are sorted according to particular internal sequences, namely, a variable sequence adjacent to the recognition site for the first restriction enzyme. The sorting array used is a sectioned binary array (see Example 2.1, below). The array contains immobilized oligonucleotides having a variable sequence as well as an adjacent constant sequence that is complementary to the recognition sequence of the first restriction endonuclease. The sorted strands are amplified by "symmetric" PCR, so that in each well where a strand has been bound, copies of the bound strand, as well as their complements, are generated. In another embodiment, strands can be sorted according to their terminal sequences on an array whose oligonucleotides' constant segments include sequences that are complementary to the recognition site of the second restriction enzyme (see Examples 1.1 to 1.3, below). This alternative embodiment for identifying neighboring fragments is not detailed, but corresponds to the embodiment discussed below, but with terminal sorting. Any sorting technique that results in a sufficiently low number of strands in each group can be employed.

Each strand that hybridizes to the binary sorting array will possess at least two recognition sites for the second restriction enzyme (restored at the strand's termini), and at least one (internal) recognition site for the first restriction enzyme. The segments included between these two types of restriction sites (intersite segments) comprise the overlaps between the two types of restriction fragments, and each intersite segment is thus bounded by any two restriction sites of the two types. It follows, that each of these segments can be characterized by identifying these two restriction sites and variable sequences of preselected length within the segment that are immediately adjacent to each of the restriction sites. The combination of a recognition site (for either the first or the second restriction enzyme) and its adjacent variable oligonucleotide we call a "signature oligonucleotide". Every intersite segment can be characterized by two signature oligonucleotides (of either type) that bound that segment. The combination of the two signature oligonucleotides is defined herein as the intersite segment's "signature".

After strand amplification, the strands in the wells of the sorting array are surveyed to identify the signature oligonucleotides of each of the two types. This is carried out by using two types of binary survey arrays. The first of these binary survey arrays has immobilized oligonucleotides containing a variable oligonucleotide segment and a constant segment that is, or includes, an adjacent sequence that is complementary to the recognition site for the first restriction endonuclease. The immobilized oligonucleotides in the second of these binary survey arrays have a variable oligonucleotide segment of preferably the same length as the variable segment of the first specialized survey array, and a constant segment that is, or includes an adjacent sequence that is complementary to the recognition site for the second restriction endonuclease. The constant oligonucleotide segments in these binary survey arrays can be located either upstream or downstream of the variable oligonucleotide segments, resulting in the surveying of either the downstream or the upstream signature oligonucleotides in each strand of the intersite segments being surveyed. In a preferred embodiment the constant oligonucleotide segments are upstream from the variable segments, and the immobilized oligonucleotides have free 3' ends, so that they can be extended by incubation with a DNA polymerase (see Example 5.1.4, below). In the discussions below, we will assume that this preferred embodiment is used for surveying. From the oligonuclebtide information that is obtained, the sequenced fragments can be ordered relative to one another.

The principle of this method is illustrated in FIG. 14. The top diagram shows a region of a double-stranded DNA molecule that contains recognition sites for two different restriction endonucleases (A and B). Each recognition site is adjacent to an upstream oligonucleotide segment of a variable sequence (represented as a shaded square, and identified by a code, in which the first character is the type of restriction site). The sequence of a recognition site, in combination with the sequence of its adjacent oligonucleotide, is responsible for the hybridization of its DNA strand to the oligonucleotide arrays used in this method. Such a combination will be called an "A-type signature oligonucleotide" or a "B-type signature oligonucleotide". A digest of the DNA with the A-type restriction enzyme contains fragments X and Y. (Assume those fragments have been sequenced.) Digestion of the same DNA region with the B-type restriction enzyme gives rise to a chimeric fragment that contains the right intersite segment of fragment X (i.e., $X_R$) and the left intersite segment of fragment Y (i.e., $Y_L$). After digestion, the terminal recognition sites in the B-type restriction fragments are restored by the introduction of priming regions, and the strands are then melted apart and hybridized to an A-type sorting array.

Each of the immobilized oligonucleotides in the A-type sorting array consists of a sequence complementary to the A-type restriction site and a variable segment. The array is comprehensive as far as variable sequences are concerned, so that every strand is bound in one or more locations in the array. An A-type array, rather than a B-type array, is used to sort B-type restriction fragments in the illustrations of FIGS. 14, 15, and 16. Therefore, the strands bind to the array by their internal regions. The complementary strands of B-type fragment $X_RY_L$ will hybridize at two different addresses (i.e. wells) in the sorting array, as shown in the bottom diagram of FIG. 14. When the strands are amplified (in a polymerase chain reaction), each strand gives rise to its complementary copy, restoring each strand of the restriction fragment $X_RY_L$ at each of those two addresses.

Our method obtains the signature of every intersite segment. Intersite segments $X_R$ (whose signature consists of oligonucleotides B2 and A3) and $Y_L$ (whose signature consists of oligonucleotides B3 and A4) are seen together at two different addresses, A3 and A4 (i.e., wells) in the sorting array, indicating that segments $X_R$ and $Y_L$ are present in the same B-type fragment, and therefore neighbor each other in the undigested DNA. In addition to establishing that the two A-type fragments (X and Y) are neighbors, our method determines the orientation of their linkage, i.e., that the right side of fragment X is linked to the left side of fragment Y. This can be determined even if other fragments are present at each of the addresses, because the segments of these other fragments will appear together at different combinations of addresses, i.e., it is highly unlikely that the signatures of other intersite segments from the first well will also appear in the second well where $X_R$ and $Y_L$ are found.

After the B-type fragments have been sorted into groups on an A-type sorting array as discussed above and shown in FIG. 14, each group is analyzed (surveyed) by hybridization to the two types of binary survey arrays discussed above, A and B. Oligonucleotides of the A-type binary survey array contain in their constant segments a sequence that is complementary to the A-type restriction site, whereas the constant segments in the B-type binary survey array include a sequence that is complementary to the B-type restriction site. Since every intersite segment that occurs in a B-type fragment will be bordered by a pair of restriction sites (each of which can be either A-type or B-type), every segment hybridizes to two different areas in the survey arrays. If the two surveyed signature oligonucleotides in each intersite segment that constitute a signature are each fourteen nucleotides long (6-nucleotide-long restriction site plus an 8-nucleotide-long variable segment), their combined length will be 28 nucleotides. The signature is likely to be unique, even though the variable segment of each probe is rather short. Because the sequence of every A-type fragment is already known, every intersite segment can be identified from its signature, and neighboring fragments from the first digest can be identified.

For example, FIG. 15 shows four previously sequenced fragments (M, N, O and P) produced by digestion of a DNA with restriction endonuclease A. Because the sequence of each A-type fragment is known, we can predict: the sites where these fragments will be cleaved by restriction enzyme B, the addresses in the sorting array where segments of these fragments will hybridize, and the signatures those segments will possess. Some of the fragments contain a restriction site for a second digestion with restriction enzyme B. The intersite segments are $M_L$, $M_R$, N, $O_L$, $O_I$, $O_R$, $P_L$, and $P_R$, as shown. ("I" refers to an internal segment). Some segments are bordered by one A-type restriction site and one B-type restriction site (such as segment $M_L$); some are bordered by two A-type restriction sites (such as segment N); and some are bordered by two B-type restriction sites (such as segment $O_I$). The signature oligonucleotides of each type are found at the 3' terminus of each strand of an intersite segment. Fragment O possesses two B-type restriction sites. Therefore, its internal segment, $O_I$, will not hybridize to the A-type sorting array, because it lacks an A-type restriction site. On the other hand, fragment N lacks B-type restriction sites. Accordingly, it is entirely contained in the intersite segment N whose signature consists of two A-type oligonucleotides. All the segments' signatures will be found at four addresses in the sorting array: A11, A23, A33, and A43.

FIG. 16 shows how the data obtained with the A-type and B-type survey arrays can be utilized to order the A-type fragments shown in FIG. 15. First, for each occupied address in the sorting array, a list of all surveyed oligonucleotides of the A and B type is prepared. From all possible pairwise combinations of these oligonucleotides, only those that are contained in the "key", as shown in FIG. 16, are chosen, because only those combinations correspond to the already known signatures of real intersite fragments. If every signature is unique (i.e., belongs to only one intersite segment), then the segments can be identified unambiguously. By comparing the sets of intersite segments found at different addresses, the intersite segments that occur together at more than one address can be determined. This identifies "companion" segments. Lack of a companion indicates that the segment occupies a terminal position in the DNA. We then use the information obtained to order the fragments, as shown at the bottom of FIG. 16.

If an A-type fragment is completely embedded in a B-type fragment, so that there are no B-type restriction sites within that fragment (as in fragment N), its position between the neighboring A-type fragments is established, though without regard to its orientation. It is also possible that a B-type fragment will include a number of A-type fragments. In this case, the location of the entire group of fragments between the outer segments of the B-type fragment will be established. However, the orientation of the internal A-type fragments and their position relative to one another will be unknown. We have devised a simple solution to this problem. The fragments from the B-type digest can be re-digested with a restriction enzyme whose recognition site is shorter. For example, if restriction endonucleases with a hexameric recognition sequence were employed to produce the A-type and B-type fragments, a restriction enzyme with a tetrameric recognition sequence would be appropriate. Since tetramers occur in nucleotide sequences 16 times as frequently as hexamers, there would be almost no A-type fragments that lack the tetrameric recognition site within their sequence. After hybridization of the secondary digest to an A-type sorting array, only $\frac{1}{16}$ of the original DNA will remain bound. An analysis of the signatures of the bound intersite segments that are bordered (on one side) by the tetrameric recognition site, performed as described above, will allow the fragments in a group to be ordered. In this case, in addition to the A-type survey array, a new binary survey array is used, whose oligonucleotides' constant segments include a sequence that is complementary to the tetrameric restriction site.

The resolving power of this method of identifying neighboring sequenced restriction fragments depends on three probabilistic factors. The first factor is the probability that two distant pairs of neighboring fragments will share the same combination of addresses in the sorting array. The second factor is the probability that the same signature will be shared by two or more segments that occur in the sequenced restriction fragments. If a human genome is digested with restriction endonucleases that have hexameric recognition sites, if the digest is sorted on an array containing variable octanucleotides, and if the A-type and B-type survey arrays also contain immobilized oligonucleotides with a variable octanucleotide sequence, then each of these two probabilities will be quite low except for fragments from highly repetitive regions of the genomic DNA. Most of the uncertainty in ordering fragments will result from a third factor, which is due to the fact that the two oligonucleotides that constitute a signature are determined independently. If fragments from DNA of the size of the human genome are being ordered, the survey data for each well in the sorting array will include, on average, about 22 A-type oligonucleotides and about 22 B-type oligonucleotides, which will result in approximately 750 different pairwise combinations of A:B and A:A types. Some of these combinations will correspond to signatures of intersite segments that actually occur in the genome, but are not present in that well, resulting in the segment being erroneously identified. However, even if this third factor is accounted for, about 99 percent of all neighboring fragments are expected to be identified in one round of the ordering procedure. Analysis of four to five alternate restriction digests, while not required for the invention, will allow virtually all the sequenced fragments to be ordered. Thus, for the human genome, only a few additional arrays would be needed to order all the fragments, and this is several orders of magnitude less expensive and time-consuming than repeating the entire sequencing procedure for each additional restriction digest.

Signatures of fragments could be obtained by other methods, such as by hybridizing each group of fragments to a survey array of oligonucleotides with long variable segments (in such a case, a signature would be defined to be one long oligonucleotide). However, to statistically predict that a signature will be unique in, for example, a human genome, it should be about 30 nucleotides long. If a 28 nucleotide long signature is chosen, it would result in variable segments 22 nucleotides long that are adjacent to a hexameric restriction site. A survey array containing all possible variable segments of such a length would contain approximately $10^{13}$ areas. That would be an extremely large array. Our method for obtaining composite (two-membered) signatures is much superior economically.

In our method, the uniqueness of a signature is achieved by surveying "half signatures" (signature oligonucleotides) on two relatively small survey arrays. If the variable segments in those arrays are 8-nucleotide-long, the overall number of individual areas in the two arrays is approximately 130,000, or approximately 100,000,000 times smaller than the single array that would be needed for detecting the same size signature (28 nucleotides).

Instead of surveying signature oligonucleotides, the intersite segments can also be identified in the wells of the sorting array by comprehensive surveys of all oligonucleotides that are contained in the strands sorted into that well. For example, comprehensive survey arrays similar to those described herein for surveying partials could be employed. The oligonucleotide pattern in each well of the sorting array would very likely be different and, since the oligonucleotide content of each intersite segment is known (because their sequences are known), one could try to decompose the oligonucleotide patterns into individual oligonucleotide sets of the intersite segments. However, inasmuch as the oligonucleotide patterns would be very complex, and the number of intersite segments is very large (more than a million if the restriction sites are hexameric), it would be a very difficult task. At the same time, comprehensive surveys of the oligonucleotides that are contained in the strands sorted into wells can be useful for resolving ambiguities that remain after analysis with arrays that identify signature oligonucleotides, especially for resolution of the ambiguities caused by the second and the third probabilistic factors discussed above. Since most of the intersite segments in a well of the sorting array will have been identified unambiguously, only a few alternative solutions need to be assessed to determine the remaining intersite segments. For this purpose the actual oligonucleotide pattern observed in the well can be compared with a simulated pattern obtained by combining the oligonucleotides in the known intersite segments with the oligonucleotides in the remaining alternative intersite segments.

If a diploid genome (such as a human genome) is sequenced, the ordered fragments will appear as a string of unlinked pairs of allelic fragments. What remains unknown is how the allelic fragments in each pair are distributed between the homologous (sister) chromosomes that came from each parent. Allocation of the allelic fragments to these "chromosomal linkage groups" requires knowledge of which fragment in each pair is linked to which fragment in a neighboring pair.

We have developed a method that uses oligonucleotide arrays for allocating allelic fragments to chromosomes, irrespective of what method was used for sequencing and ordering the fragments. The linkage of fragments in neighboring pairs can be achieved by sequencing a restriction fragment ("spanning fragment") from an alternate digest that spans at least one allelic difference in each of the pairs. However, since the sequences of the allelic fragments are known, there is no need to sequence the spanning fragment.

Instead, one can simply determine which oligonucleotides that harbor allelic differences in neighboring pairs of fragments accompany one another in the spanning fragment, i.e., which oligonucleotides occur in the same chromosome. This can be accomplished by surveying, at a selected address in a partialing array, partials generated from a selected group of restriction fragments from an alternate digest. A group of restriction fragments is selected that contains a spanning fragment, and an address in a partialing array is selected that encompasses a difference in one of the neighboring allelic pairs.

Figure 17A:
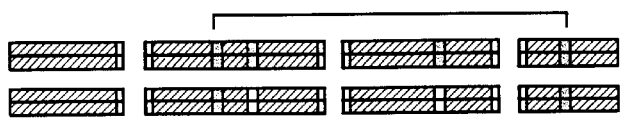
FIG. 17 shows the linking of fragments in neighboring allelic pairs.
Figure 17B:
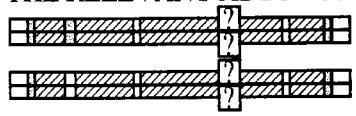
Figure 17C:
Figures 27D, 27E:
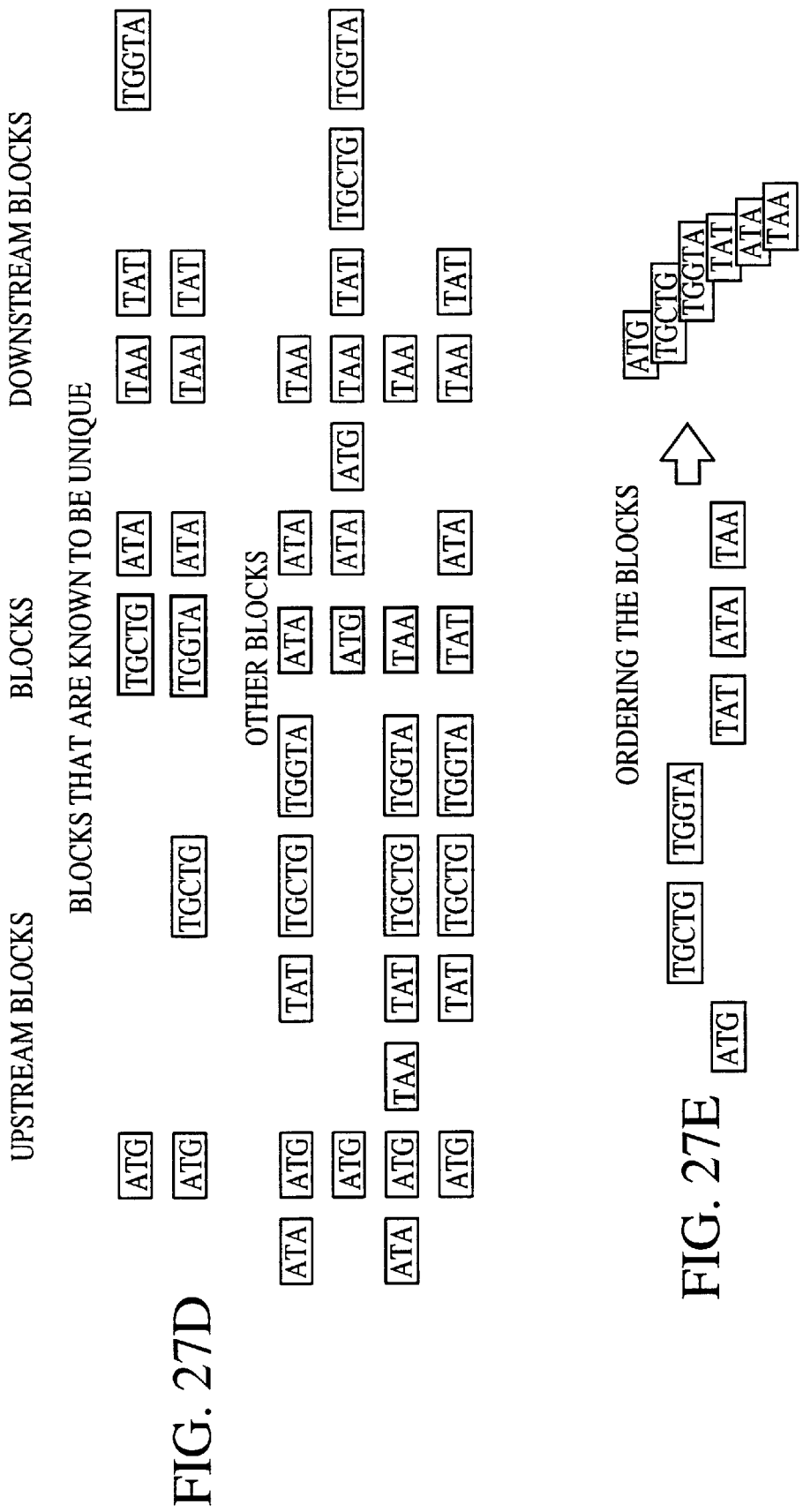

The top diagram in FIG. 17 shows a string of unlinked pairs of allelic fragments, whose order has been determined. The position in each pair of fragments where an allelic difference occurs is indicated by dissimilar symbols. Since the sequence of every fragment is known, it is possible to choose an alternate restriction fragment that spans the allelic differences in the neighboring pairs. A spanning restriction fragment, in fact, may already be present at a particular address in one of the sorting arrays used to sort alternate digests during the ordering procedure. The aim of the procedure, as illustrated in the figure, is to ascertain whether the allelic difference represented by a cross or a triangle occurs within the same spanning fragment as the allelic difference represented by a diamond or a circle. In the figure, the allelic difference represented by a diamond or a circle was arbitrarily chosen to serve as a reference point, with the allocation of the other pair of allelic differences being unknown.

The sorted strands are melted apart, and the mixture is hybridized to a particular well in the partialing array, whose address corresponds to an oligonucleotide that encompasses the reference point. In this illustration, two different wells are selected, each with an address that corresponds to an oligonucleotide that harbors the allelic difference represented by the circle or the diamond. Also, for this illustration the method of generating partials directly on a sectioned array is used (see Example 3.3, below). As discussed above, other methods of preparing partials could be used. After amplification of the partial strands, the oligonucleotides in the two wells are identified with a survey array. It can be seen from an examination of the survey arrays schematically depicted at the bottom of the figure that the oligonucleotides that encompass the allelic difference represented by a circle are accompanied by the oligonucleotides that encompass the allelic difference represented by a cross, while the oligonucleotides that encompass the allelic difference represented by a diamond are accompanied by the oligonucleotides that encompass the allelic difference represented by a triangle. We thus determine that the fragments containing the marker nucleotides represented by the diamond and the triangle are located on one chromosome, whereas the fragments containing the marker nucleotides represented by the circle and the cross are located on the other chromosome.

To allocate allelic pairs to chromosomal linkage groups, it may only be necessary to survey one oligonucleotide encompassing an allelic difference. The particular oligonucleotide that should be surveyed can be determined, if desired, by analyzing the known sequences of the partials in the mixture surveyed. Similarly, it may only be necessary to survey at one address in the partialing array. Having redundant data, however, is preferable, in order to avoid errors that can otherwise arise.

Since allelic differences occur roughly once every 1,000 basepairs in the human genome, most allelic fragments resulting from digestion with a restriction enzyme recognizing a hexameric sequence (resulting in about 4,096 average length) will differ from each other. If the variable oligonucleotide segments in the survey arrays are made of octanucleotides, then each allelic nucleotide substitution will give rise to eight different oligonucleotides in each of the allelic fragments. However, using our method, inspection of only one address in the partialing array is sufficient to reveal the linkage of the corresponding reference oligonucleotide to any one of the eight oligonucleotides that encompass the nucleotide substitution that occurs in the neighboring fragment on the same chromosome. Therefore, only one address in the partialing array is needed to reveal the linkages between every two neighboring allelic pairs. Thus, 65,536 linkages can be determined on a single comprehensive partialing array made of variable octanucleotides. With this method, only 10 to 20 of these arrays would be needed to complete the assembly of an entire diploid human genome that has been fragmented by a restriction endonuclease with a hexameric recognition site.

A power of the sequencing method of this invention is that the high redundancy in the information obtained allows the original hybridization data to be refined by computer analysis, thereby ensuring the reliability of the final results.

In a preferred embodiment described in detail above and in the examples, complementary strands of each DNA fragment of a first restriction digest bind at two addresses in a terminal sequence sorting array, each according to the identity of its 3'-terminal sequence. Subsequent amplification results in both complementary strands being present at both addresses. However, the complementary strands will be enmeshed in a different group of strands at these two addresses. The mixture of strands at each address (area of the sorting array) is separately sequenced by generating complete sets of partials for each, and separately surveying the oligonucleotide content of each well in the partialing array, as described. The different sequence contexts (in the two addresses of the sorting array) will interfere differently with the two strands' sequence determinations, allowing the exclusion of many ambiguities by comparing the information obtained at the two addresses. Furthermore, each of the complementary strands of the same restriction fragment will be sequenced independently within the two groups that the strands of the restriction fragment are sorted into. Because complementary sequences can be derived from each other, the complete set of data for each fragment will be independently collected four times during the entire procedure. Also, the data collected from complementary strands by our method provide an additional opportunity to discriminate against mismatched hybrids. In contrast to perfect matches, mismatches produced by the complementary strands with the immobilized oligonucleotides will result in different hybrid stabilities. For example, the relatively high stability of a G:T mismatch potentially produced by one strand contrasts with the lower stability of the C:A mismatch that can potentially be formed by the corresponding region of the complementary strand.

When strand sets are identified, all the oligonucleotides of each strand should occur in every pertinent address set. Thus, every strand set (or every pair of quasi-identical strand sets) will be determined as many times as the number of different oligonucleotides it contains.

If a strand set is determined incorrectly (i.e., if some oligonucleotides were missed or some were erroneously included), there will be unfilled gaps in the reconstructed sequence, or some blocks will occur that cannot be accommodated within any gap, thus indicating an error. And finally, with the method described herein of preparing strands by restriction digestion and end extension with priming regions, each strand will possess known restriction sequence tags at its ends (and only at the ends). This means that if a sequence does not begin with, or is not terminated by, those tag sequences, it is not a correct sequence and has resulted from errors in the data. Subsequent analysis can pinpoint possible reasons for the errors, and can provide the additional information needed to correct them.

Thus, there are many possibilities using the arrays and methods of this invention to filter out experimental errors that arise due to imperfections in the hybridization procedure. A basic feature of sequencing by hybridization is that every nucleotide position is reflected in n different independently identified oligonucleotides (where n is the length of the oligonucleotide probe). This ensures that no nucleotide in a sequence will be incorrectly deleted, inserted, or misidentified. In any case, a sequence error will not be overlooked, and all ambiguities that remain in a sequence can be identified and localized. Furthermore, most of the remaining ambiguities can be resolved when each sequence is verified by comparing it to the other version of that sequence that is found at another area in the strand sorting array, and by comparing it to the two versions of its complementary sequence.

Our methods for handling and manipulating the oligonucleotide information obtainable with our arrays and methods, can easily be converted into the form of computer algorithms by well-known techniques. Moreover, preliminary computer simulations can be used to further improve sequencing with particular embodiments. For these simulations, a number of different types of nucleotide sequences can be used as input. Natural sequences that are present in the GenBank library can be employed. Random sequences can also be constructed so that they resemble the human genome. Some of the characteristics that could be predetermined are nucleotide composition, dinucleotide frequency, frequency of restriction sites, the presence of telomeres and centromeres, and the presence of repeated segments.

A sequence (along with its complementary copy) can be algorithmically "digested" with a restriction enzyme, the ends provided with terminal priming regions, and the strands sorted into groups according to the identity of their terminal sequences. For the mixture of strands in a group, all possible one-sided partials can be generated, and then sorted according to the identity of oligonucleotide segments at their variable termini (addresses). For every address, a complete list can be prepared of the oligonucleotides that are present in the partials at that address. These upstream subsets can be used to generate the downstream subsets and the address sets of each address. The unindexed address sets can then be decomposed into strand sets, the sequence blocks from each strand set can be formed, and the order of the blocks can be established from their distribution among the upstream and downstream subsets of each address. After the sequences of the fragments in each of the groups has been determined, the sequences can be analyzed to identify restriction sites for those restriction endonucleases that are likely to be most useful in determining the order of the fragments. Collections of signature oligonucleotides can be generated that would occur at each address when fragments from alternate digests are sorted on an array. The distribution of signature oligonucleotides among the addresses in the sorting array can then be analyzed to order the sequenced fragments. A program that uses methods of analysis such as those described herein to determine nucleotide sequences (or a program that uses other methods of analysis) can be tested by comparing the assembled sequences to the input sequences.

To further develop useful methods of computer analysis, the mock "haploid genomes", represented by the input sequences, can be converted into "diploid genomes", by introducing random nucleotide substitutions into a copy of each of the original DNAs. Furthermore, insertions, deletions, inversions, transpositions, and recombinations can be introduced, in order to simulate the picture that is observed in a real genome. These diploid genomes can be analyzed as described above. After the "allelic pairs" are ordered, the fragments can be assembled into their original "chromosomes" from an analysis of the oligonucleotides that are present in selected partials from alternate restriction "digests." The results of these simulated sequence determinations can be analyzed, in order to improve the methods of analysis, and to find ways of reducing the number of ambiguities by purely algorithmic means.

The frequencies with which different types of ambiguities occur (when determining fragment sequences, and when linking fragments) can be assessed as a function of the sizes of the oligonucleotides used in the arrays. Simulations can be carried out in which the length of the variable segment within the immobilized oligonucleotides in each type of array is varied, in order to ascertain the combination of array sizes that is optimal (that is, to determine which combination of array sizes is likely to result in the lowest frequency of ambiguities, keeping in mind the need to minimize the time and expense of carrying out a total sequence analysis). Similarly, the effect of average fragment length (which depends on which restriction enzyme is used to cleave the nucleic acid(s) being analyzed) can be assessed.

Computational methods can be developed to minimize or eliminate errors that occur during partialing and surveying, by taking advantage of the high redundancy in the data. Such methods should take into account the following aspects of a preferred sequencing procedure: the sequence of every fragment is independently determined four times (by virtue of each strand and its complement being present at two different addresses in the sorting array); each strand set is determined in as many trials as the number of different oligonucleotides in that strand; every nucleotide in a strand is represented by as many different oligonucleotides as the length (of the variable segment) of the immobilized oligonucleotides in the survey array; the locations where a particular block can occur in a sequence are limited by the distribution of the blocks among the upstream and downstream subsets of each pertinent address; and the edges of a block must be compatible with the edges of each gap where that block is inserted. The following sources of error can be considered:

(1) Errors resulting from signal differences due to the different multiplicities of the oligonucleotides in the sample.

A threshold limit can be applied, thus excluding some rare oligonucleotides from the data. This altered data can then be offered to a sequence reconstruction program, in order to evaluate the tolerance of the method of analysis for the presence of those errors in the data. The outcome of these simulations can be used to predict the maximal DNA length and the maximal number of strands that can be present in a mixture, and still allow unambiguous sequence determination.

(2) Errors resulting from the presence of strong secondary structures in the strands.

Hairpin formation within a strand can compete with the formation of a hybrid, if undegraded partials are applied to a survey array. In order to simulate this situation, regions within an input sequence should be identified that have the potential to form such a secondary structure, and the signal strength of the corresponding hybrids should be reduced accordingly. This will result in the disappearance of some oligonucleotides from the input data, depending on their involvement in highly stable hairpins and on the relative content of those oligonucleotides in the strands. A sequence might be reconstructed, even if a set of overlapping oligonucleotides is missing from the data. The idea is to use the partialing information that can be obtained from complementary strands; in these strands, the gaps will occur on different sides of a hairpin.

(3) Errors resulting from false signals due to the presence of mismatched hybrids.

As was discussed above, related regions of complementary strands will give rise to mismatched hybrids with different stabilities, because a G:T mismatch is stronger than its C:A counterpart. A comparison of the sets of data obtained from each complementary strand can be used to distinguish between perfect and mismatched hybrids.

(4) Random errors.

Simulations can be carried out in which some data are randomly deleted from oligonucleotide lists, and false data is randomly inserted, in order to assess the ability of the method of analysis to tolerate random errors.

The goal of all such simulations is to select the optimal size for the oligonucleotides used in the different types of arrays. This information can also be used to predict the ratio of signal to noise that must be achieved in the hybridization procedures in each particular case.

Once optimal parameters for the various steps are established, further improvements can be achieved by the economical use of the space available in the arrays. For example, a preliminary survey of the signature oligonucleotides that are present at each address in the first sorting array, will indicate which groups of strands can be mixed together before analyzing them on a partialing array, without interfering with sequence determination. This can markedly reduce the number of partialing and survey arrays that are needed. In addition, the distribution of restriction sites within the sequenced fragments can be analyzed in order to select those restriction enzymes that will provide the most useful information for ordering the fragments. The sequenced fragments can also be analyzed to identify, for every two neighboring allelic pairs, a group of restriction fragments that contains a fragment that spans the allelic differences, and whose other fragments will not interfere with the identification of the oligonucleotides that encompass the allelic differences.

Using our genome sequencing method, one can use throughout essentially the same technology, i.e., hybridization of oligonucleotide probes and the amplification of nucleic acids by the polymerase chain reaction, both of which are well-studied, common laboratory techniques. The entire procedure can be performed by a specially designed machine, resulting in huge reductions in time and cost, and a marked improvement in the reliability of the data. Many arrays could be processed simultaneously on such a machine. The machine most preferably should be entirely computer-controlled, and the computer should constantly analyze intermediate results. As stated above, used arrays can be stored, both to serve as a permanent record of the results, and to provide additional material for subsequent analysis or for manipulating the sequenced strands and partials.

The route followed by each fragment through the described series of arrays is uniquely determined by its particular sequence. By discerning the path that each fragment takes, a computer associated with the machine can accurately reconstruct the sequence of a subject genome.

The result of the analysis of an individual's genomic DNA, using the method described above, is the complete nucleotide sequence of that individual's diploid genome. The genes, and their control elements, would be allocated into chromosomal linkage groups, as they appear in a single living organism. The sequence will thus describe an intact, functioning ensemble of genetic elements. This complete genome sequencing provides the ability to compare the genomes of many individuals, thereby enabling biologists to understand how genes function together, and to determine the basis of health and disease. The genomes of any species, whether haploid or diploid, can be sequenced.

The invention can be used not only for DNA's but as well for sequencing mixtures of cellular RNAs.

The invention is also useful to determine sequences in a clinical setting, such as for the diagnosis of genetic conditions.

EXAMPLES 1. sorting nucleic acids or their fragments on a binary oligonucleotide array whose immobilized oligonucleotides have free 3' termini, with their constant segments located upstream of the variable segments This method allows the immobilized oligonucleotides on the binary array to serve as primers for copying bound DNA or RNA strands, resulting in the formation of their complementary copies covalently linked to the surface of the array. In such an embodiment, the array can be vigorously washed after the extension of the immobilized oligonucleotides to remove any non-covalently bound material. Moreover, these arrays containing covalently bound strands can be stored and used as a permanent library from which additional copies of the sorted strands can be generated. If amplification of the sorted strands on the binary array is desired, the array can be sectioned. For example, strands can be sorted on a plain (unsectioned) binary array, and the array can be sectioned at a later date. Sorting need not be carried out on sectioned arrays. If amplification is not required using the methods of the examples, then sectioned arrays may not be necessary.

1.1. Sorting restriction fragments according to their terminal sequences, following the introduction of terminal priming regions DNA is digested using a restriction endonuclease. Recognition sites for the restriction endonuclease are restored in solution by introducing terminal extensions (adaptors) that contain a sequence which, together with the restored restriction site, form a universal priming region at the 3' terminus of every strand in the digest. This priming region is later used for amplification of the sorted strands by PCR. After melting fragment strands apart, the strands are sorted on a sectioned binary array. A sequence complementary to the generated priming region serves as both the constant segment of the oligonucleotides immobilized in the sectioned binary array, and as the primer for PCR amplification of the bound strands.

The sequence of the primer (as well as the priming region) is chosen in such a manner that it is well suited for PCR. The criteria for selecting good primers are discussed in detail by Sambrook et al. (1989), Erlich et al. (1991), and Wu, D. Y., Ugozzoli, L., Pal, B. K., Qian, J. and Wallace, R. B. (1991). The Effect of Temperature and Oligonucleotide Primer Length on the Specificity and Efficiency of Amplification by the Polymerase Chain Reaction, *DNA Cell Biol.* 10, 233–238. Briefly, the primers should be long enough (preferably 15–25 nucleotides) to be able to hybridize to a DNA strand at a temperature that is optimal for polymerization. The primer should not be self-complementary, to avoid the formation of an internal secondary structure within the primer molecule, and to avoid the formation of a duplex between two primer molecules.

It is preferable that all recognition sites of the endonuclease used for DNA digestion be eliminated from the fragments' internal regions during digestion. This further ensures that the fragments' strands are bound to the sorting array only by their terminal regions, and that PCR is always primed only at the strand ends, resulting in amplification of only full-sized copies of the strands.

Naturally occurring modification of some bases in DNA often inhibits DNA cleavage at modified sites. In higher vertebrates, including human beings, cytosine residues are believed to be the only bases that are modified (methylated), producing 5-methylcytosine [Doerfler, W. (1983). DNA Methylation and Gene Activity, Annu. Rev. Biochem. 52, 93–124], with modification occurring mainly within the CG dinucleotide [Cooper, D. N. (1983). Eukaryotic DNA Methylation, Human Genetics 64, 315–333]. Sites containing 5-methylcytosine are not cleaved by most restriction endonucleases [Kessler, C. and Höltke, H. J. (1986). Specificity of Restriction Endonucleases and Methylases—A Review, Gene 47, 1–153]. Complete DNA digestion can be achieved in higher vertebrates either by DNA demethylation prior to the digestion [Gjerset, R. A. and Martin, D. W., Jr. (1982). Presence of a DNA Demethylating Activity in the Nucleus of Murine Erythroleukemic Cells, J. Biol. Chem. 257, 8581–8583], by using restriction endonucleases whose recognition sites do not contain cytosine [such as Aha III/Dra I (site TTTAAA) or Ssp I (site AATATT)], or by using restriction endonucleases whose activity is not influenced by cytosine methylation [such as Taq I (site TCGA), Kpn I (site GGTACC), or HpaI (site GTTAAC)]. Such restriction endonucleases are known in the art, and many are reviewed by Kessler and Höltke (1986), supra.

1.1.1. Method in which a priming region is introduced by fragment ligation to double-stranded synthetic oligodeoxyribonucleotide adaptors DNA to be analyzed is first digested substantially completely with a chosen restriction endonuclease, and the fragments obtained are then ligated to synthetic double-stranded oligonucleotide adaptors essentially as described by Sambrook et al. (1989), supra, and also by Kintzler and Vogelstein [Kintzler, K. W. and Vogelstein, B. (1989). Whole Genome PCR: Application to the Identification of Sequences Bound by Gene Regulatory Proteins, Nucleic Acids Res. 17, 3645–3653]. The adaptors have one end that is compatible with the fragment termini. The other end is not compatible with the fragments' termini. The adaptors can therefore be ligated to the fragments in only one orientation. Means for making compatible and incompatible ends are well known to one skilled in the art.

The adaptors' strands are non-phosphorylated, as results from conventional oligonucleotide synthesis [Horvath, S. J., Firca, J. R., Hunkapiller, T., Hunkapiller, M. W. and Hood, L. (1987). An Automated DNA Synthesizer Employing Deoxynucleoside 3'-Phosphoramidites, Methods Enzymol. 154, 314–326], which prevents their self-ligation. The strands in the restriction fragments have their 5' termini phosphorylated, which results from their cleavage by a restriction endonuclease. This favors the ligation of the adaptors by a DNA ligase (such as the DNA ligase of T4 bacteriophage) to the restriction fragments, rather then to each other. Since DNA ligase catalyzes the formation of a phosphodiester bond between adjacent 3' hydroxyl and phosphorylated 5' termini in a double-stranded DNA, the phosphorylated 5' termini of the fragments are ligated to the adaptor strand whose 3' end is at the compatible side of the adaptor. The 3' termini of the fragments remain unligated. A DNA polymerase possessing a 5'-3' exonuclease activity (such as DNA polymerase I from Escherichia coli or Taq DNA polymerase from Thermus aquaticus) is then used to extend the 3' ends of the fragments, utilizing the ligated oligonucleotide as a template, concomitant with displacement of the unligated oligonucleotide. To make the ligated oligonucleotide resistant to the 5'-3'exonuclease, the ligated oligonucleotide can be synthesized from α-phosphorothioate precursors [Eckstein, F. (1985). Nucleoside Phosphorothioates, Annu. Rev. Biochem. 54, 367–402]. Synthesis of phosphorothioate oligonucleotides is known in the art [Matsukura, M., Zon, G., Shinozuka, K., Stein, C. A., Mitsuya, H., Cohen, J. S. and Broder, S. (1988). Synthesis of Phosphorothioate Analogs of Oligodeoxyribonucleotides and Their Antiviral Activity Against Human Immunodeficiency Virus, Gene 72, 343–347].

Although the oligonucleotide adaptors are provided in great excess during the ligation step, there is still a low probability that two restriction fragments will ligate to one another, rather then to the adaptor. To prevent this, the ligation products can again be treated with the restriction endonuclease used to generate the fragments, in order to cleave the formed interfragment dimers. The endonuclease will not cleave the ligated adaptors if they are synthesized from modified precursors (such as nucleotides containing $N^6$-methyl-deoxyadenosine), which are known and currently commercially available [e.g., from Pharmacia LKB]. Resistance of the ligated adaptors to digestion by the restriction endonuclease can be increased further if the ligated oligonucleotide is synthesized from phosphorothioates, and if phosphorothioate analogs of the nucleoside triphosphates are used as substrates for extension of the 3' termini of the fragments, instead of utilizing natural nucleoside triphosphates as substrates [Eckstein, F. and Gish, G. (1989). Phosphorothioates in Molecular Biology, Trends Biol. Sci. 14, 97–100].

It is not necessary that all these steps (digestion, ligation, extension, repetitive digestion) be performed separately. The necessary enzymes and substrates can be added into the same reaction mixture, without interference from one another. Moreover, the presence of the appropriate restriction endonuclease in the ligation mixture can be advantageous, because undesirable interfragment links will be destroyed as soon as they are formed.

After the priming regions have been added, the complementary strands are melted apart, such as by increasing temperature and/or by introducing denaturing agents such as guanidine isothiocyanate, urea, or formamide. The resulting strands are then hybridized to a binary sorting array, such as by following a standard protocol for the hybridization of DNA to immobilized oligonucleotides [Gingeras, T. R., Kwoh, D. Y. and Davis, G. R. (1987). Hybridization Properties of Immobilized Nucleic Acids, Nucleic Acids Res. 15, 5373–5390; Saiki, R. K., Walsh, P. S., Levenson, C. H. and Erlich, H. A. (1989). Genetic Analysis of Amplified DNA with Immobilized Sequence-specific oligonucleotide Probes, Proc. Natl. Acad. Sci., U.S.A. 86, 6230–6234]. Hybridization is performed so that formation of only perfectly matched hybrids is promoted. The hybrids have a length which is equal to that of the immobilized oligonucleotides. The binary array contains immobilized oligonucleotides that are attached to the array at their 5' termini and contain constant restriction site segments adjacent to a variable segment of predetermined length. Each strand will be bound to the array at its 3' terminus. Its location within the array will be determined by the identity of the oligonucleotide segment that is located in the strand immediately upstream from the restored restriction site at its 3' end, and that is complementary to the variable segment of the immobilized oligonucleotide to which the strand is bound. After hybridization and washing away all unbound material, the entire array is incubated with a DNA polymerase, such as Taq DNA polymerase deoxyribonucleotide 5' triphosphates or the DNA polymerase of bacteriophage T7, and substrates. As a result, the 3' end of each immobilized oligonucleotide to which a strand is bound will be extended to produce a complementary copy of the bound strand. The array is then vigorously washed under conventional conditions that remove the hybridized DNA strands and all other material that is not covalently bound to the surface. The wells in the array are then filled with a solution containing universal primer, an appropriate DNA polymerase, and the substrates and buffer needed to carry out a polymerase chain reaction. Preferably, the DNA polymerase is a highly processive and thermostable DNA polymerase with a high-temperature optimum, which can be used under conditions in which the secondary structure of single-stranded DNA is destabilized; for example, some variants of Taq DNA polymerase [Erlich et al. (1991)]). The array is then sealed, isolating the wells from each other, and exponential amplification is carried out, preferably simultaneously, in each well of the array. After amplification, the DNA in each well may be withdrawn for subsequent analysis.

1.1.2. Method in which a priming region is introduced by fragment ligation to single-stranded synthetic oligoribonucleotide adaptors After digestion of DNA with a restriction endonuclease, the 5' termini of the resulting fragments (which are phosphorylated) are ligated to a single-stranded 3',5'-hydroxyl oligoribonucleotide adaptor with an RNA ligase, such as the RNA ligase of bacteriophage T4 in order to restore the restriction recognition sequence and introduce a priming region. [Higgins, N. P., Gebale, A. P. and Cozzarelli, N. R. (1979). Addition of Oligonucleotides to the 5'-Terminus of DNA by T4 RNA Ligase, *Nucleic Acids Res.* 6, 1013–1024]. Synthesis of oligoribonucleotides is known in the art [Sampson, J. R. and Uhlenbeck, O. C. (1988). Biochemical and Physical Characterization of an Unmodified Yeast Phenylalanine Transfer RNA Transcribed in vitro, *Proc. Natl. Acad. Sci. U.S.A.* 85, 1033–1037; Chou, S. H., Flynn, P. and Reid, B. (1989). Solid-phase Synthesis and High-resolution NMR Studies of Two Synthetic Double-helical RNA Dodecamers: r(CGCGAAUUCGCG) and r(CGCGUAUACGCG), *Biochemistry* 28, 2422–2435]. To make the oligoribonucleotides of the adaptor more stable, they can be synthesized from α-phosphorothioate ribonucleotide precursors [Milligan, J. F. and Uhlenbeck, O. C. (1989). Determination of RNA-Protein Contacts Using Thiophosphate Substitutions, *Biochemistry* 28, 2849–2855].

After ligation, a reverse transcriptase is used to extend the 3' ends of the fragments, utilizing the ligated oligoribonucleotide as a template, essentially as described by Sambrook et al. (1989). Use of an enzyme that lacks ribonuclease H activity is preferable [Kotewicz, M. L., Sampson, C. M., D'Alessio, J. M. and Gerard, G. F. (1988). Isolation of Cloned Moloney Murine Leukemia Virus Reverse Transcriptase Lacking Ribonuclease H Activity, *Nucleic Acids Res.* 16, 265–277]. As in Example 1.1.1, above, all reactions can be performed in one reaction mixture, in which case, no re-digestion to eliminate dimers is necessary, because RNA ligase cannot ligate double-stranded DNA fragments.

The extended strands are then melted apart, hybridized to a sorting array and amplified there, as described in Example 1.1.1, above. For the extension of the immobilized oligonucleotide, however, reverse transcriptase is used instead of DNA polymerase, because reverse transcriptase can use both DNA and RNA as a template [Verma, I. M. (1981). Reverse Transcriptase, in *The Enzymes,* 3rd edition (P. D. Boyer, ed.), vol. 14, pp. 87–103, Academic Press, New York].

1.1.3. Method in which a priming region is introduced by fragment tailing with a homopolynucleotide sequence This method can be used where DNA is digested with a restriction endonuclease whose recognition site can be restored by the addition of only one type of nucleotide. For example, DNA can be digested with restriction endonuclease Aha III or Dra I, whose recognition site is TTTAAA. Cleavage occurs in the middle of the site, between T and A residues, leaving (5')p-AAA . . . and . . . TTT-OH(3') fragment termini. The restriction site is restored by extension of the 3' ends with poly(dA) through incubation with terminal deoxynucleotidyl transferase, essentially as described by Sambrook et al. (1989), in the presence of only one type of substrate, dATP. This produces . . . TTTAAAAAAAAAAAAAAAAAAA-AAA . . . (3'), which serves as a priming region for the binding of a primer of the (5')oligo(T)AAA-OH(3') type. The 5' termini of the fragments are then extended by ligation to non-phosphorylated oligo(dT) that is hybridized to the 3' terminal extension. Detailed protocols for the addition of homopolymeric tails and for oligonucleotide ligation to DNA fragments are given in Sambrook et al. (1989). After melting the extended strands apart, they are hybridized to a binary sorting array whose immobilized oligonucleotides' constant segment consists of (5')oligo(T)AAA(3'). All other operations are carried out as described in Example 1.1.1, above.

1.2. Sorting restriction fragments according to their terminal sequences, with 3' and 5' terminal priming regions being introduced, one before and one after strand sorting This procedure consumes larger amounts of enzymes and substrates than the procedure described in Example 1.1, however, only those strands that are correctly bound to the immobilized oligonucleotides acquire both priming regions necessary for PCR. Therefore, the possibility that non-specifically bound strands will be amplified, is minimized. Furthermore, using this procedure different priming regions can be introduced at different termini of a strand. It then becomes possible to: (1) perform "asymmetric" PCR, where only one of the complementary strands is accumulated in significant amounts, and remains in a single-stranded form; (2) introduce a transcriptional promoter into only one of the priming regions, in order to be able to obtain RNA transcripts of only one strand (without also producing its complement as in conventional PCR); (3) differentially label complementary strands; and (4) avoid self-annealing of the strand's terminal segments that can interfere with primer hybridization, therefore resulting in a lower PCR efficiency.

1.2.1. Method in which a priming region is introduced at a restriction fragment strand's 5' end by ligation to a double-stranded oligodeoxyribonucleotide adaptor before sorting, and another priming region is introduced at the 3' end after sorting In this example, digestion of DNA, adaptor ligation and re-digestion of fragments are carried out as described in Example 1.1.1, above. The 3' ends of the restriction fragments, however, are not extended by incubation with DNA polymerase. Instead, the strands ligated at their 5' ends to adaptors are melted apart from their unextended complements and the strands are hybridized to a binary sorting array. The binary sorting array contains immobilized oligonucleotides that are pre-hybridized with shorter complementary 5'-phosphorylated oligonucleotides that cover (mask) the immobilized oligonucleotides except for a segment which includes a variable region and a region complementary to the portion of the restriction site remaining at the fragments' (unrestored) 3' end. The masked region includes the rest of the restriction site and any other constant sequence, such as may be included in a priming region. Hybridization is carried out under conditions that promote the formation of only perfectly matched hybrids which are the length of the unmasked segment of the immobilized oligonucleotide. After washing away the unbound strands, the strands that remain bound are ligated to the masking oligonucleotides by incubation with DNA ligase. The correctly bound strands thus acquire a priming region at their 3' end, in addition to the priming region they already have at their 5' end. The two priming regions preferably correspond to different primers. The array is then washed under appropriately stringent conditions to remove all nucleic acids except the immobilized oligonucleotides and the ligated strands hybridized to them. A protocol for amplification can then be followed as described in Example 1.1.1, above, starting with extension of the immobilized primer by DNA polymerase, except that two different primers, rather than one universal primer, are used for PCR.

Using this procedure, only those strands that have been successfully ligated after sorting will be exponentially amplified during PCR, while other strands, if some remain after washing, will not be amplified, because they are missing one of the two priming regions.

1.2.2. Method in which one terminal priming region is introduced at the 5' end by ligation to a single-stranded oligoribonucleotide adaptor before sorting restriction fragment strands, and another priming region is introduced at the 3' end after sorting A priming region is generated at the 5' end of strands by fragment ligation to single-stranded oligoribonucleotides, as described in Example 1.1.2, above. The 3' ends are not extended. Then the strands are melted apart and hybridized to a binary sorting array as described in Example 1.2.1, above. Following ligation of the strands to the masking oligonucleotides and subsequent washing, the immobilized oligonucleotides are extended, and the covalently bound strands' copies are amplified, as described in Example 1.1.2, above.

1.2.3. Method in which a 3' priming region is generated before strand sorting, and a 5' priming region is generated after strand sorting, both extensions being generated by tailing the strands with a homopolynucleotide sequence As in Example 1.1.3, above, the procedure in this example can be used where DNA is digested with a restriction endonuclease whose recognition site can be restored by the addition of only one type of nucleotide. In this method, the 3' termini of the DNA fragment strands are extended by incubation with terminal deoxynucleotidyl transferase. Unlike the method described in Example 1.1.3, however, ligation of a homooligonucleotide to the 5' termini is omitted. Instead, the strands are melted apart and hybridized to a binary sorting array, and the immobilized primer is extended as described in Example 1.1.3. After synthesis of the bound strand's complementary copy, all the material that is not covalently linked to the surface of the array is washed away, and the 3' end of the copy strand, which corresponds to the 5' end of the original strand, is extended by incubation with terminal deoxynucleotidyl transferase, as described above. PCR is carried out utilizing a primer that consists of a 5'-terminal homooligonucleotide region that is complementary to the strand's homopolymeric tail, and a 3'-terminal region that is complementary to the part of the restriction site which has been restored by addition of the tail. A potential drawback to this method is that the strands acquire self-complementary terminal sequences. This method has the advantage, however, that only covalently bound strand copies receive the second priming region required for exponential amplification by PCR.

1.3. Sorting restriction fragments according to their terminal sequences, with priming regions at both 3' and 5' termini being introduced after strand sorting The procedure of this example provides the highest selectivity and the lowest background, because both the first and the second priming regions are generated only if a strand has been specifically bound to the immobilized oligonucleotides.

Unextended restriction fragments are melted into their constituent strands which are then hybridized to a binary sectioned array having immobilized oligonucleotides that are masked over their constant region, except for the portion of the constant region complementary to the partial restriction site remaining in the strands. The masking oligonucleotides are 5'-phosphorylated. The hybridized strands are then ligated to the masking oligonucleotides to generate the first priming region. Then, the immobilized oligonucleotides are extended, as described in Example 1.2.1, above. After additional (more vigorous) washing, in a manner that destroys all hybrids that have not been extended, the second priming region is generated in one of the following ways.

1.3.1. Method in which a second terminal priming region is generated by ligation of the 5' end of the bound strand to a single-stranded oligoribonucleotide adaptor This procedure is performed utilizing T4 RNA ligase, essentially as described for oligoribonucleotide ligation before sorting (see Example 1.1.2, above). Then, the immobilized copy of the bound strand is further extended by incubation with reverse transcriptase, utilizing the oligoribonucleotide extension as a template. The material that is not covalently bound is then washed away, and the strands that are covalently bound are amplified by PCR, as described in Example 1.2.1, above.

1.3.2. Method in which a second terminal priming region is generated by extension of the immobilized copy with a homopolymeric tail A homopolymer tail is added by extending the immobilized strand copy using the procedure described in Example 1.2.3, above. Two different primers, however, result because the first priming region in the immobilized oligonucleotide can be of any sequence. As in Examples 1.1.3 and 1.2.3, above, this method is applicable where the DNA is digested with a restriction endonuclease whose recognition site can be restored by the addition of only one type of nucleotide.

1.4. Sorting of DNA fragments that are not bounded by restriction recognition sequences, according to their terminal sequences.

Such fragments can be obtained by DNA digestion with restriction endonucleases whose recognition sequences are remote from their cleavage sites, or by a method that does not involve restriction endonucleases, such as by known enzymatic methods [e.g., Pei, D., Corey, D. R. and Schultz, P. G. (1990). Site-specific Cleavage of Duplex DNA by a Semisynthetic Nuclease via Triple-helix Formation, *Proc.*

Natl. Acad. Sci. U.S.A. 87, 9858–9862; Zuckermann, R. N. and Shultz, P. G. (1989). Site-selective Cleavage of Structured RNA by a Staphylococcal Nuclease-DNA Hybrid, Proc. Natl. Acad. Sci. U.S.A. 86, 1766–1770], or by known chemical methods [e.g. Chen, C. H. and Sigman, D. S. (1986). Nuclease Activity of 1,10-Phenanthroline-copper: Sequence-specific Targeting, Proc. Natl. Acad. Sci. U.S.A. 83, 7147–7151; Fedorova, O. S., Savitski, A. P., Shoikhet, K. G. and Ponomarev, G. V. (1990). Palladium(II)-coproporphyrin I as a Photoactivable Group in Sequence-specific Modification of Nucleic Acids by Oligonucleotide Derivatives, FEBS Lett. 259, 335–337]. Mixtures of relatively short DNA molecules can also be obtained by other known methods (e.g., cDNAs). In this method, the priming regions added to the fragments' termini, as well as the constant segments of the immobilized oligonucleotides, will not generally include a restriction recognition sequence. Specificity of hybridization and of priming at the fragments' termini is achieved by the addition of adaptors, utilizing the method described in Examples 1.1 to 1.3, above, which provide unique priming regions. The uniqueness of these priming regions can be checked in preliminary hybridization experiments.

The use of terminal deoxynucleotidyl transferase for the introduction of homopolymeric extensions has restricted applicability when the fragment termini do not possess restriction recognition sequences, because homopolymeric sequences frequently occur in genomes, and therefore hybridization and PCR priming would not always be confined to the fragment termini.

Some methods of DNA cleavage result in DNA "nicking", rather than in cleavage of the double-stranded fragments. Where nicking results from the fragmentation process, ligation of double-stranded adaptors is not preferable. Also, chemical cleavage of DNA often results in the appearance of 5'-hydroxyl and 3'-phosphoryl groups, i.e., the opposite of what is required for enzymatic ligation or extension. But preliminary dephosphorylation of 3' termini (with a phosphatase, such as bacterial alkaline phosphatase or calf intestine alkaline phosphatase) and then (if necessary) phosphorylation of 5' termini (with a kinase, such as the polynucleotide kinase of bacteriophage T4) can be carried out, as described by Sambrook et al. (1989). Alternatively, T4 polynucleotide kinase can be used for both phosphorylation of 5' ends and dephosphorylation of 3' ends of DNA, since this enzyme possesses both of those activities [Cobianchi, F. and Wilson, S. H. (1987). Enzymes for Modifying and Labeling DNA and RNA, Methods Enzymol. 152, 94–110].

1.5. Isolation of individual DNAs or DNA fragments, by sorting according to their terminal sequences If the number of different DNA strands in a sample is rather small relative to the number of areas in a sorting array, there is a high probability that, after one round of sorting on a sectioned binary sorting array, many wells in the sectioned array will either be unoccupied, or occupied by only one type of fragment. In the case of a complex mixture of DNA strands, such as a mixture of strands obtained upon restriction endonuclease digestion of an entire human genome, a number of different types of fragments will occupy each well of a sorting array having, e.g., 56,536 sections. In that case, the isolation of individual fragments is achieved by sorting each group of fragments from the first round of sorting on a second sectioned binary array. As a result of PCR amplification (following generation of priming regions as described above), each well (section) in the first array will contain both the original strands that were hybridized by their 3' termini and complementary copies of the original strands. The complementary strands will have 3' termini that are complementary to the 5'-terminal sequences of the original strands and will therefore be different from the 3' termini of the original strands. Thus, the complementary strands will bind to oligonucleotides in different wells within the new sectioned binary array, and, with a high probability, each strand will occupy a separate well, where it can then be amplified. As a result of this second round of sorting, almost all fragments will be separated from one another. In a diploid genome, however, virtually identical allelic fragments will, as a rule, accompany each other.

No matter which method of adding primers is utilized (see Examples 1.1 to 1.3, above), after the first round of sorting, each strand will already possess priming regions at both ends. Therefore each group of such strands can be directly hybridized to a second binary sectioned array having immobilized oligonucleotides thereon with a constant sequence complementary to the complementary strands' 3' terminal priming region. (The complementary strands' 3'-terminal priming region could have been made different from the 3'-terminal priming region of the original strands.) The complementary strands can therefore be amplified by using the same primers as were used in the first round of sorting. This procedure is analogous to that described above for sorting strands following the generation of priming regions (see Example 1.1, above).

Alternatively, in order to ensure a higher degree of selectivity, the second sorting can be performed concomitant with the substitution of new priming regions for the original priming regions. For example, if restriction sites were included in the priming region (and eliminated from the fragments' internal regions), the old adaptors can be cleaved off with a restriction endonuclease, thus regenerating the original restriction fragments, and new adaptors can be introduced, using procedures described in Examples 1.2 or 1.3, above.

There are a number of ways to use the second binary sorting arrays economically. First, smaller arrays having shorter variable sequences than in the first array can be employed. Second, because the number of wells in a second sorting array will usually be much greater than the number of different strands in a well from the first array, one array can be used for the simultaneous sorting of strands from many of the wells in the first array. To prevent strands from different groups interfering with one another's isolation, their 3' terminal sequences ("signature oligonucleotides") can be surveyed prior to the second sorting by using a binary survey array, as described in Example 5.1.4, below. The oligonucleotides of this latter array are comprised of a variable sequence and an adjacent constant sequence that is complementary to a part of the strands' 3'-terminal priming region (e.g., the terminal restriction site). After surveying the terminal sequences, groups of strands that would not interfere with one another's separation can be mixed together before the second round of sorting. Alternatively, the material from individual wells of the first array can be delivered to particular addresses in the second array that have been determined from the results of the surveys.

Depending on the specific aim of this separation procedure, the strands can be amplified by virtue of either standard ("symmetric") PCR, or by "asymmetric" PCR [Gyllensten, U. B. and Erlich, H. A. (1988). Generation of Single-Stranded DNA by the Polymerase Chain Reaction and Its Application to Direct Sequencing of the HLA-DQA Locus, Proc. Natl. Acad. Sci. U.S.A. 85, 7652–7656; U.S. Pat. No. 5,066,584, incorporated herein by reference]. Furthermore, RNA copies of the strands can be produced in the wells by incubation with a DNA-dependent RNA polymerase, such as the RNA polymerases of T7, T3, or SP6 bacteriophages [Tabor, S. (1989). DNA-Dependent RNA polymerases, in *Current Protocols in Molecular Biology* (Ausubel, F. M. et al., eds.), vol. 1, pp. 3.8.1–3.8.4, John Wiley and Sons, New York], if an RNA polymerase-specific promoter sequence is included in one of the two priming regions used for DNA amplification.

1.6. Sorting selected strands by their terminal sequences

There may be applications where it is desired to isolate and analyze only some selected strands from a complex strand mixture. There are 50,000 to 100,000 genes in the human genome, that together account for several percent of the genomic DNA, and that would be of primary interest for clinical diagnostics. Thus, it may be desirable that only 100,000 or so fragments be isolated and analyzed, instead of millions of restriction fragments from the patient's entire genome. Instead of preparing an array that includes all possible variable oligonucleotide segments of a certain length, a binary sorting array can be prepared that contains selected oligonucleotides whose variable segments are chosen so that they match the termini of every fragment of interest, and only the termini of those fragments, i.e. the segments are long enough to isolate only the fragment of interest. Once the first human genome is sequenced and all the genes are identified, and consequently all the accessible restriction sites and their adjacent regions are known, it will be possible to predict which restriction enzyme(s) would produce fragments encompassing genes, and which oligonucleotide sequences at each strand's terminus will be unique. For example, most of the 15-meric variable segments would be unique for the human genome (together with an adjacent hexameric restriction site they would form effective recognition sequences that are 21 nucleotide long). At the same time, different oligonucleotides can be made of different lengths to ensure that each would hybridize to only one type of strand. (Means of ensuring highly selective hybridization conditions for every oligonucleotide in the array, irrespective of its length and nucleotide composition, are described above in Section II). An array that contains 100,000 selected oligonucleotides with differing variable segments would be of virtually the same size as an array made of all possible variable octamers (65,536). If, for example, a human genome is digested with a chosen restriction enzyme(s), and the strands are hybridized and amplified within such an array according to the methods described in Examples 1.1 to 1.3, above, every fragment of interest will occupy a particular well, and will be essentially homogenous (except for minor sequence differences between allelic fragments, that will almost always possess identical terminal sequences and will therefore almost always occupy the same well). The fragments obtained (in either double-stranded or single-stranded form, depending on the type of amplification used, as described in Example 1.5, above) can then be analyzed directly. Because the DNA sequence is substantially similar for every individual, except for on average a few sequence differences per gene, it would be sufficient, for most genes, to merely survey the oligonucleotide content of the corresponding fragments (e.g., as described above in Section V), and to compare it to the genome sequences that have already been established, to identify the sequence differences. Alternatively, only some chosen fragments can be analyzed, and the array can be then stored as a comprehensive permanent bank of all of the patient's genes, for use in subsequent analyses, if desired.

1.7. Sorting RNAs according to their terminal sequences 1.7.1. Sorting of eukaryotic mRNAs Mature eukaryotic mRNAs all share some structural features that can help in their manipulation using arrays. All of these RNAs have a "cap" structure (such as a 7-methylguanosine residue attached to the RNA by a 5'-5' pyrophosphate bond) on their 5' end, and most of the RNAs also possess a 3'-terminal poly(A) tail, which is attached posttranscriptionally by a poly(A) polymerase. Because there are usually no long oligo(A) tracts in the internal regions of cellular RNAs, the poly(A) tail can serve as a naturally occurring terminal priming sequence in the sorting procedure. The size of mRNAs (several thousand nucleotides in length) allows these sequences to be amplified and analyzed directly, without prior cleavage into smaller fragments.

There are known methods for preparing essentially undegraded total cellular RNA [Sambrook et al., 1989]. Residual amounts of degraded RNA can be removed by treatment with a specific 5'-3'exoribonuclease that completely degrades uncapped RNAs while leaving capped RNAs intact [Murthy, K. G. K., Park, P. and Manley, J. L. (1991). A Nuclear Micrococcal-sensitive, ATP-dependent Exoribonuclease Degrades Uncapped but not Capped RNA Substrates, *Nucleic Acids Res.* 19, 2685–2692].

Total cellular RNA is converted into complementary DNA (cDNA) using an oligo(dT) primer and a reverse transcriptase (see Example 1.1.2, above) or *Thermus thermophilus* DNA polymerase (Tth DNA polymerase) [Myers, T. W. and Gelfand, D. H. (1991). Reverse Transcription and DNA Amplification by a Thermus thermophilus DNA Polymerase, *Biochemistry* 30, 7661–7666]. Then, omitting second strand synthesis, single-stranded cDNAs (which possess oligo(dT) extensions at their 5' end and variable 3' termini) are sorted according to their 3'-terminal oligonucleotide segments on a sectioned binary array and are ligated there (following the procedure described in Example 1.2.1, above) to pre-hybridized oligonucleotide adaptors of a pre-determined sequence that are complementary to the immobilized oligonucleotides' constant sequence, and that introduce into a cDNA molecule the 3'-terminal priming site. The procedure described in Example 1.2.1 is followed to amplify the cDNA, using two primers for PCR amplification: oligo (dT) and an oligonucleotide that is complementary to the ligated adaptor.

Alternatively, cellular RNAs are directly hybridized according to their poly(A)-tailed 3' termini to a sectioned binary array, whose immobilized oligonucleotides' constant sequence is comprised of oligo(dT). After washing away unbound RNAs, the immobilized primer is extended by incubation with a reverse transcriptase or Tth DNA polymerase, using the hybridized RNA as a template. The second priming site can be generated, and cDNA can then be amplified, by ligation of the 5' termini of the RNA molecules to oligoribonucleotide adaptors before sorting (as described in Example 1.1.2, above) or after sorting (as described in Example 1.2.2, above), or by extension of the immobilized DNA copies by the addition of a 3'-terminal homopolymeric tail (as described in Example 1.2.3, above). If oligoribonucleotide ligation to the 5' end of the RNA is used, the 5' terminal cap structure should first be removed by incubation with an appropriate enzyme, e.g., nucleotide pyrophosphatase from tobacco or potato cells, which results in the generation of phosphorylated 5' ends [Furuichi, Y. and Shatkin, A. J. (1989). Characterization of Cap Structures, *Methods Enzymol.* 180, 164–176]. To overcome potential interference with ligation resulting from the presence of RNA secondary structures, dimethylsulfoxide (up to 40% v/v) should be added to the ligation buffer to denature the RNA without appreciably decreasing the ligase activity (Romaniuk and Uhlenbeck, 1983).

The result of the above procedure is sorted and amplified cDNAs of all cellular mRNAs. A typical mammalian (including human) cell contains between 10,000 and 30,000 different mRNA sequences [Davidson, E. H. (1976). *Gene Activity in Early Development,* 2nd edition, Academic Press, New York]. For example, if an oligonucleotide array made of variable octamers is used (i.e., made of 65,536 different oligonucleotides) most of the different types of cDNAs will be obtained in an individual state. Again, as in other applications, the final amplified product can be synthesized as either a double-stranded or a single-stranded DNA or RNA (as described in Example 1.5, above).

One of the most significant problems in preparing comprehensive cDNA libraries is that the number of copies of different RNAs that occur in a cell can differ by several orders of magnitude [Williams, J. G. (1981). The Preparation and Screening of a cDNA Clone Bank, in *Genetic Engineering* (R. Williamson, ed.), vol. 1, p. 1, Academic Press, London]. Various rather complicated methods of enrichment of rare RNAs or their cDNAs in the sample are used to overcome this problem [Sambrook et al., 1989]. However, this problem does not arise if the above scheme is employed and the RNAs are sorted into different wells. Exponential amplification by PCR is allowed to continue until there is a leveling-off of the synthesis due to consumption of the substrates or primers. Then there will be a roughly equal amount of DNA product in each well, irrespective of the starting number of copies of a template. Put another way, PCR amplification using the invention results in an equalization in the number of cDNA copies of different cellular RNAs, no matter whether they are abundant or rare to begin with, avoiding the problem encountered with conventional cDNA library formation.

1.7.2. Sorting RNAs lacking a 3'-terminal poly(A) tail

In this case, the 3'-terminal poly(A) tail can first be introduced by using poly(A) polymerase [Sippel, A. E. (1973). Purification and Characterization of Adenosine Triphosphate: Ribonucleic Acid Adenyltransferase from *Escherichia coli,* Eur. J. Biochem. 37, 31–40], with subsequent steps essentially identical to those described in Example 1.7.1, above. If RNAs are sorted directly (i.e. without first synthesizing cDNA), the 5'-terminal priming regions are preferably introduced through ligation of RNA by incubation with RNA ligase to a non-phosphorylated oligoribonucleotide. For ligation to occur, the 5' terminus of the RNA must be phosphorylated; if not, phosphorylation should be performed by using polynucleotide kinase (as described in Example 1.4, above). If the 5' end is blocked by a triphosphate group (as in most prokaryotic RNAs), it should first be dephosphorylated by treatment with a phosphatase.

Alternatively, RNAs can be sorted according to their 3'-terminal oligonucleotide segments on a sectioned binary array and ligated there to pre-hybridized oligodeoxynucleotide adaptors, following the procedure described in Example 1.2.1, above. It has been shown that T4 DNA ligase efficiently joins the 3'-hydroxyl group of RNA to the 5'-phosphoryl group of DNA in mixed duplexes [Nath, K. and Hurwitz, J. (1974). Covalent Attachment of Polyribonucleotides to Polydeoxyribonucleotides Catalyzed by Deoxyribonucleic Acid Ligase, *J. Biol. Chem.* 249, 3680–3688; Selsing, E. and Wells, R. D. (1979). Polynucleotide Block Polymers Consisting of a DNA:RNA Hybrid Joined to a DNA:DNA Duplex. Synthesis and Characterization of $dG_n$:$rC_1dC_k$ Duplexes, *J. Biol. Chem.* 254, 5410–5416].

2. Sorting nucleic acids or their fragments by their internal sequences 2.1. Sorting DNA strands by their internal sequences on a binary array, according to a combination of a variable oligonucleotide segment and an adjacent restriction site This procedure can be used, for example, for sorting strands before surveying fragment signatures, to ascertain which sequenced fragments neighbor each other within a longer DNA. The purity of the sorted strands (i.e., free from contaminating irrelevant strands) is not as critical for this purpose as it is in sequencing. The only requirement is that the number of copies of each contaminating strand be low enough, compared with the number of copies of legitimately bound strands, that the hybridization signals that the legitimate strands produce in different areas of a signature survey array be reliably distinguishable from the signals produced by irrelevant strands.

2.1.1 Addition of both priming regions at the same time

After a DNA sample has been digested with a restriction endonuclease, terminal priming regions are added to both ends of the fragment strands by one of the methods described in Examples 1.1.1 to 1.1.3, above. Then the strands are melted apart and hybridized to a sectioned binary array whose immobilized oligonucleotides are comprised of a variable segment and a constant segment, the latter being complementary to a preselected restriction recognition sequence occurring in the DNA. If the procedure is performed to order previously sequenced restriction fragments, it is preferable that the constant segment be complementary to the recognition sequence of the restriction endonuclease used to produce the sequenced fragments. The oligonucleotides immobilized on in the array can have either end free, however, free 3' ends are preferable. In that case, after washing away the unbound strands, the immobilized oligonucleotides are preferably extended, using the bound strands as templates. The length of minimally extended hybrids of short strands will increase by the length of the sequence introduced at the fragment's 5' end, resulting in an increase in the melting temperature of the extended hybrids. The array is then washed under much more stringent conditions in which the only bound strands that remain are those that are hybridized to extended immobilized oligonucleotides. The wells in the array are then filled with a solution containing universal primer, an appropriate DNA polymerase, and the substrates and buffer needed to carry out a polymerase chain reaction. The array is then sealed, isolating the wells from each other, and exponential amplification is carried out in each well of the array. If the oligonucleotides in the array are linked to the surface by their 3' ends, the oligonucleotide extension step, as well as the second washing, is omitted.

2.1.2 Addition of two different priming regions in separate steps

In this method, the priming regions on the 3' and 5' ends of the strands are generated in two steps: 5' priming regions are introduced by ligation to either a double-stranded oligodeoxyribonucleotide adaptor (described in Example 1.2.1, above), or by ligation to a single-stranded oligoribonucleotide adaptor (as described in Example 1.2.2, above), whereas the 3' priming regions are introduced by extending the strands' 3' termini through the addition of a homopolymeric tail (as described in Example 1.2.3, above) after the 5'-terminally ligated strands have been melted apart and hybridized to a 3' or 5' binary array. (The order of 3'-terminal extension and 5'-terminal ligation to oligoribonucleotides can be reversed). The rest of the procedure is identical to that described in Example 2.1.1, above, with immobilized oligonucleotide extension and second washing being preferably included when the oligonucleotides are linked to the surface by their 5' ends.

2.2. Sorting nucleic acid strands by their internal sequences on an ordinary array This method can be used, for example, for sorting nucleic acids into groups of strands that share some sequence motif, or for isolating individual strands that contain unique sequence segments. The array can be 5' or 3'. The oligonucleotides need not contain a constant segment, and can, if desired, be rather long. The array can contain only selected oligonucleotides, whose sequence and length can be different from one another (rather than being a comprehensive array). Both DNAs and RNAs can be sorted, essentially following the procedures described in Example 2.1, above. In the case of RNA, a preferred scheme includes, first, addition of a poly(A) tail to the 3' end (if it is not present there) by incubation with a poly(A) polymerase, and then, after hybridization of the strands and extension of the immobilized oligonucleotides by a reverse transcriptase, the ligation of the 5' end of the RNAs to an oligoribonucleotide adaptor.

3. Preparing partial strands of nucleic acids on oligonucleotide arrays

There are two aspects to this procedure: first, the generation of partial strands, and second, the sorting of the partial strands into groups according to the identity of their terminal oligonucleotide segments. In one embodiment these two aims are achieved in a single step. Preparing partials has steps in common with strand sorting, described above; however, in strand sorting it is desirable to preserve the original strand intact, and to amplify precise copies of the original strand, whereas in preparing partials, truncated copies of the original strand are produced. All of the embodiments described below in this section are based on the following principle: in generating partials from a strand, one of the original strand ends is preserved (it will be referred to as the "fixed" end), whereas the other end is truncated to a different extent in the various partials (it will be referred to as the "variable" end). Although either the 5' or the 3' end of the original strand can serve as the fixed end, it is preferable that the 5' end be fixed. If amplification of sorted partials is desirable, it is preferable that the 5' end of the original strand, i.e., the fixed end, be provided with a priming region prior to strand partialing, by any of the methods described above and that the partialing be carried out on a sectioned array. Either an individual strand, or a mixture of strands can be subjected to a partialing procedure; however, if the mixture is very complex (such as a restriction digest of a large genome), it is desirable that the mixture first be sorted into less complex groups of strands, as described above. The groups of strands used for preparing partials should essentially be devoid of contaminating strands; therefore, sorting by terminal sequences is preferable for the preliminary sorting of strands. If preliminary sorting of strands is performed, the strands will already contain the terminal priming regions necessary for amplification of the partials. As with sorting, partialing can be performed on either DNA or RNA, the final product being either DNA or RNA, in either a double-stranded or a single-stranded state.

3.1. Methods employing enzymatic cleavage of DNA fragments

The purpose of the cleavage is to produce a set of partials of every possible length; therefore, DNA should be cleaved as randomly as possible, and to the extent that there is approximately one cut per strand. The extent of cleavage is determined by the enzyme concentration, temperature, and duration of incubation. Optimal reaction conditions can be determined in preliminary experiments for a given range of strand lengths.

3.1.1. Utilizing double-strand-specific deoxyribonucleases for cleaving double-stranded DNA fragments Deoxyribonuclease I from bovine pancreas (DNase I) cleaves both double-stranded and single-stranded DNA; however, double-stranded DNA is preferable as the starting material for preparing partials because of its essentially homogeneous secondary structure, so that every segment of a DNA molecule is equally accessible to cleavage. Double-stranded DNA fragments are produced as a result of "symmetric" PCR that can be carried out when sorting strands (as described in Example 1.2, above). An advantage of using DNase I is that it produces fragments with 5'-phosphoryl and 3'-hydroxyl termini, that are suitable for enzymatic ligation.

Cleavage of DNA by DNase I is not perfectly random under standard conditions; for example, DNase I cleaves phosphodiester bonds that are 5' from a deoxythymidine more frequently than other bonds [Laskowski, M., Sr. (1971). Deoxyribonuclease I, in *The Enzymes*, 3rd edition (P. D. Boyer, ed.), vol. 4, pp. 289–311, Academic Press, New York]. The bias of DNase I for cleaving at certain nucleotides is largely eliminated if the reaction buffer contains $Mn^{++}$ instead of $Mg^{++}$ [Anderson, S. (1981). Shotgun DNA Sequencing Using Cloned DNase I-generated Fragments, *Nucleic Acid Res.* 9, 3015–3027]. Moreover, the preference of DNase I for particular nucleotides can be either increased or decreased in a predictable way by including transition metal ions, such as $Cu^{++}$ or $Hg^{++}$, in the incubation buffer [Clark, P. and Eichhorn, G. L. (1974). A Predictable Modification of Enzyme Specificity. Selective Alteration of DNA Bases by Metal Ions to Promote Cleavage Specificity by Deoxyribonuclease, *Biochemistry* 13, 5098–5102]. Thus, DNA cleavage by DNase I can be made essentially random by manipulating the content of different transition metal ions in the reaction medium.

Another way to make cleavage more random is to use mixtures of different deoxyribonucleases, whose spectra of nucleotide specificity complement one another. For example, the nucleotide specificity spectrum of neutral DNase from crab (*Cancer pagurus*) testes is essentially complementary to that of DNAse I; moreover, this DNase also produces 5'-phosphoryl and 3'-hydroxyl termini [Bernardi, A., Gaillard, C. and Bernardi, G. (1975). The specificity of Five DNases as Studied by the Analysis of 5'-Terminal Doublets, *Eur. J. Biochem.* 52, 451–457].

The exact composition of the reaction mixture should be found in preliminary experiments with a terminally labeled DNA. The cleavage should result in a "ladder" of bands of essentially equal intensity when seen after polyacrylamide gel electrophoresis under denaturing conditions (Sambrook et al., 1989).

After cleavage of the double-stranded DNA fragments, DNase is removed, e.g., by phenol extraction (Sambrook et al., 1989). The (partial) strands are then melted apart and are hybridized to a sectioned binary array, wherein the immobilized oligonucleotides are pre-hybridized with shorter complementary 5'-phosphorylated oligonucleotides of a constant sequence that cover (mask) the immobilized oligonucleotides except for a segment that consists of a variable sequence. Hybridization is carried out under conditions that favor the formation of perfectly matched hybrids of a length that is equal to the length of the unmasked (variable) segment of the immobilized oligonucleotide, and that minimize the formation of imperfectly matched hybrids. After washing away unbound strands, the strands that remain bound are ligated to the masking oligonucleotides by incubation with a DNA ligase. The ligated masking oligonucleotides will themselves serve as the second (3'-terminal) priming region of a partial strand. (All the partials of a strand will share the same 5' priming sequence that had been introduced into the strand before generation of the partials). If restriction fragments are to be partialed that possess some restriction site at their termini and do not possess this site internally, it is preferable that the 3' terminal priming region added to the partials include that site. This increases the specificity of terminal priming during subsequent amplification of the partials by PCR. Subsequent extension, washing, and amplification steps are as described in Example 1.1.1, above, for sorted strands. If the partials are prepared for the purpose of sequence determination, asymmetric PCR can be performed. Asymmetric PCR results in only one of the complementary strands of each partial being accumulated in significant amounts. Alternatively, an RNA polymerase promoter sequence can be included in one of the two primers, and amplified DNA is then transcribed to produce multiple single-stranded RNA copies of one of the two complementary partial strands (as described in Example 1.5, above).

As is the case for strand sorting, covalently bound (complementary) copies of each partial strand will be generated within the array, the copy of each type of partial being present at a known location; therefore, the array can be stored as a permanent record of all generated partials. It can be used repeatedly for the synthesis of additional copies of the partial strands.

If two different primers are used to amplify the full-length strands before the generation of partials (e.g., during a strand sorting procedure), then complementary strands will possess different priming sequences at their 5' termini, which are preserved during strand partialing. Therefore, depending on the combination of primers used during partial strand amplification, the partials that originate from either of the complementary strands, or from both of them, will be amplified. For example, if the primer sequences that are present at the 5' ends (fixed ends) of complementary strands prior to the generation of partials are "a" and "b", and if after the generation of partials primer "c" is added to the truncated 3' ends (variable ends), then the presence of primers a and c in the amplification reaction will result in the synthesis of one set of partials, while the presence of primers b and c will result in the synthesis of the other set of partials. Thus, after partials of one strand in each complementary pair have been amplified by utilizing an appropriate pair of primers, the samples are withdrawn, the array is washed, and then partials of the complementary strands can be amplified by employing a different pair of primers.

3.1.2. Utilizing single-strand-specific endonucleases for cleaving single-stranded DNA fragments This method can be used for cleaving both single-stranded DNA, and double-stranded DNA, after the latter is denatured (i.e. melted into constituent complementary strands). The best choice for cleavage is, at present, nuclease S1 from *Aspergillus oryzae,* that cleaves single-stranded regions in both DNA and RNA, producing fragments with 5'-phosphoryl and 3'-hydroxyl termini. Cleavage is essentially non-specific with respect to nucleotide sequence. There may be, however, problems with the cleavage of double-stranded regions that occur as secondary structures in a single-stranded nucleic acid, because these double-stranded regions are resistant to attack by this nuclease. The solution for this problem lies in the stability of the nuclease at high temperatures (it remains active at temperatures as high as 65° C.), at low ionic strength, and at rather high concentrations of many denaturing agents (even 50% formamide is tolerable) [Shishido, K. and Ando, T. (1982). Single-strand-specific Nucleases, in Nucleases (S. M. Linn and R. J. Roberts, eds.), pp. 155–185, Cold Spring Harbor Laboratory Press, Cold Spring Harbor, N.Y.]. Under these conditions, secondary structure elements are either destroyed or significantly destabilized. The steps that follow DNA cleavage are essentially the same as described in Example 3.1.1, above, except that fragment melting is omitted.

3.1.3. Utilizing exonucleases for cleaving partially phosphorothioate-substituted nucleic acid strands An intrinsically random method of preparing partials, that is not dependent on the existence of nucleic acid secondary structures and that produces fragments whose termini are suitable for ligation, is carried out using α-phosphorothioate analogs of natural nucleotides. These nucleotide analogs are incorporated into DNA strands by DNA polymerase, and the phosphorothioate internucleotide linkages that are formed are fully resistant to cleavage by a 3'–5' exonuclease III, so that exonucleolytic cleavage from the 3' end of a strand stops immediately downstream of the first phosphorothioate bond [Putney, S. D., Benkovic, S. J. and Schimmel, P. R. (1981). A DNA Fragment with an α-Phosphorothioate Nucleotide at One End Is Asymmetrically Blocked from Digestion by Exonuclease III and Can Be Replicated in vivo, *Proc. Natl. Acad. Sci. U.S.A.* 78, 7350–7354]. Partials of every possible length are generated, as described by Labeit at al., except that all four phosphorothioate analogs are present in one reaction [Labeit, S., Lehrach, H. and Goody, R. S. (1986). A New Method of DNA Sequencing Using Deoxynucleoside α-Thiotriphosphates, *DNA* 5, 173–177]. The procedure described in Example 3.1.1, above, is then followed.

3.2. Methods employing chemical degradation of DNA

These methods are applicable to both double-stranded and single-stranded nucleic acids. Chemical degradation is, in most cases, essentially random, because it can be performed under conditions that destroy secondary structure, and because of the small size of the modifying chemicals, making the chemicals readily accessible to the nucleotides that are involved in secondary structures.

3.2.1. Chemical degradation of DNA strands containing. natural nucleotides

Both base-nonspecific reagents [Cartwright, I. L. and Elgin, S. C. R. (1982). Analysis of Chromatin Structure and DNA Sequence Organization: Use of the 1,10-Phenanthroline-cuprous Complex, *Nucleic Acids Res.* 10, 5835–5852; Cartwright, I. L., Hertzberg, R. P., Dervan, P. B. and Elgin, S. C. (1983). Cleavage of Chromatin with Methidiumpropyl-EDTA.iron(II), *Proc. Natl. Acad. Sci. U.S.A.* 80, 3213–3217; Kobayashi, S., Ueda, K., Morita, J., Sakai, H. and Komano, T. (1988). DNA Damage Induced by Ascorbate in the Presence of $CU^{2+}$, *Biochim. Biophys. Acta* 949, 143–147; Reed, C. J. and Douglas, K. T. (1991). Chemical Cleavage of Plasmid DNA by Glutathione in the Presence of Cu(II) Ions. The Cu(II)-thiol System for DNA Strand Scission, *Biochem. J.* 275, 601–608] and base-specific reagents [Maxam, A. M. and Gilbert, W. (1980). Sequencing End-labeled DNA with Base-specific Chemical Cleavages, *Methods Enzymol.* 65, 499–560] can be used. In the latter case, after base-specific cleavage is performed separately with several portions of the sample, the portions are mixed together to form a set of all possible partial DNA lengths.

The main drawback to chemical cleavage is that the location of the terminal phosphate groups on the fragments is opposite to what is required for enzymatic ligation: 5'-hydroxyl and 3'-phosphoryl groups are produced in most cases. To overcome this problem, enzymatic dephosphorylation of 3' ends can be carried out (as described in Example 1.4, above). Alternatively, (complementary) partial copies, that cover the distance included between the 3' termini of the original strands and the cleavage sites, can be produced in a linear fashion by incubation with a DNA polymerase. In this case, primer(s) complementary to the 3'-terminal priming region(s) should be used. The product strands will then possess the 3'-terminal hydroxyl groups necessary for ligation to masking oligonucleotides in the array. Subsequent steps for obtaining sorted partials are then carried out (as described in Example 3.1.1, above).

3.2.2. Cleavage of DNA strands whose natural nucleotides are substituted with their α-phosphorothioate analogs This method is based on the technique developed by Gish and Eckstein for sequencing nucleic acids. In their approach, four different DNA (or RNA) polymerization reactions are carried out, in each reaction one of the four natural nucleoside triphosphates is replaced with the corresponding α-thiotriphosphate nucleoside analog. The full-length product strands thus produced are treated with alkylating agents, such as 2-iodoethanol or 2,3-epoxy-1-propanol, producing phosphorothioate triesters that are more susceptible to hydrolysis than natural phosphodiester bonds. Hydrolysis mainly results in desulphurization, with regeneration of the natural phosphodiester bond, but some cleavage of the nucleic acid strand occurs. This cleavage occurs randomly along the strand, and does not depend on whether or not the corresponding region is involved in a secondary structure [Gish, G. and Eckstein, F. (1988). DNA and RNA Sequence Determination Based on Phosphorothioate Chemistry, *Science* 240, 1520–1522; Nakamaye, K. L., Gish, G., Eckstein, F. and Vosberg, H. P. (1988). Direct Sequencing of Polymerase Chain Reaction Amplified DNA Fragments through the Incorporation of Deoxynucleoside α-Thiotriphosphates, *Nucleic Acid Res.* 16, 9947–9959].

In order to generate all possible partials taking advantage of this approach, a DNA sample is pre-amplified in the presence of α-phosphorothioate substrates. This can be done during a strand sorting procedure as described above. In contradistinction to the original method of Gish and Eckstein, all four α-phosphorothioates are present together, in one reaction mixture. Subsequent treatment with iodoethanol results in random cleavage of the DNA strands. The desired extent of cleavage can be achieved both by appropriately controlling alkylation conditions, and by varying the proportion of natural substrates to their phosphorothioate analogs during DNA synthesis. Since cleavage results in a mixture of 3'-hydroxyl and 3'-phosphoryl termini (Gish and Eckstein, 1988), removal of 3' phosphates with a phosphatase is preferably carried out (as described in Example 1.4, above) before the partials are sorted (as described in Example 3.1.1, above).

3.3. Method of preparing partials directly on a sectioned array, without prior degradation of nucleic acids In this embodiment, the generation of partials and their sorting according to the identity of the sequences at their variable ends occur essentially in one step. First, a strand or a group of strands (if double-stranded nucleic acid is used as a starting material, the complementary strands are first melted apart), is directly hybridized to a sectioned ordinary array, whose oligonucleotides only comprise variable sequences of a pre-selected length, and that are immobilized on the surface of the array by their 5' termini. Optimally, hybridization is carried out under conditions in which hybrids can only form whose length is equal to the length of the immobilized oligonucleotide. Each strand is able to bind to many different locations within the array, dependent on which oligonucleotide segments are present in its sequence. If the array is comprehensive, then a hybrid is formed somewhere within the array for every oligonucleotide that occurs in a DNA's sequence. After hybridization, the entire array is washed and incubated with an appropriate DNA polymerase in order to extend the immobilized oligonucleotide, using the hybridized strand as a template. Each product strand is a partial (complementary) copy of the hybridized strand. Each partial begins at the place in the strand's sequence where it has been bound to the immobilized oligonucleotide and ends at the priming region at the 5' terminus of the strand. (If a priming region has not been introduced at the strand's 5' end before partialing, it can be generated at this step, after the hybrids that have not been extended, are eliminated by washing. This can be done either by ligating the 5' end of the bound strand to a single-stranded oligoribonucleotide adaptor, as described in Example 1.3.1, above, or by tailing the immobilized partial copy with a homopolynucleotide, as described in Example 1.3.2, above). The entire array is then vigorously washed under conditions that remove the original full-length strands and essentially all other material that is not covalently bound to the surface. Subsequent amplification of the immobilized partials can be carried out in different ways, dependent on whether it is desired to use linear amplification (which produces DNA or RNA copies of each partial), or exponential amplification (which is able to produce a much larger number of DNA copies).

3.3.1. Linear copying of partial strands

Linear copying results in only generating copies of partials of the parental strand and not complementary copies. This may be advantageous in analyzing the results of a subsequent survey of the oligonucleotide content of the partials. Linear copying takes advantage of the presence of the priming region on the 3' end of the immobilized partials (that is complementary to the 5'-terminal priming region of the original strand). If DNA copies are desired, a thermostable DNA polymerase and a primer that is complementary to that priming region, should be used. After the array is sealed to isolate individual wells from each other, temperature cycling is performed as in PCR. RNA copies can be produced by employing an RNA polymerase (as described in Example 1.5, above); in which case, the priming region should contain an appropriate promoter sequence. Linear amplification of partials in the form of RNA does not require temperature cycling and is more effective, since at least 700 full-length RNA copies can be produced from each DNA template with T7 RNA polymerase [Weitzmann, C. J., Cunningham, P. R. and Ofengand, J. (1990). Cloning, in vitro Transcription, and Biological Activity of *Escherichia coli* 23S Ribosomal RNA, *Nucleic Acids Res.* 18, 3515–3520]. An advantage of the linear copying of the partials prepared by the method of this embodiment is the absence of a priming region at the 3' end of the copies produced that could otherwise interfere with certain uses of the partials discussed below.

3.3.2. Exponential amplification of partial strands

Exponential copying results in the generation of partials, and their complements. For a strand to be exponentially amplified by PCR, both of its termini should be provided with a priming region, preferably different priming regions. The immobilized (complementary) partial (obtained by extension of the immobilized oligonucleotide) contains only one (3'-terminal) priming region, and a complementary copy produced by linear copying would also have only one priming region (on its 5' end). For RNA copies to have a priming region at their 5' ends, the immobilized partial copy should have been provided with an RNA polymerase promoter downstream of its 3' terminal priming region using the methods described herein. The second priming region that is needed for exponential amplification can be introduced at the 3' ends of the complementary copies as follows.

(a) The 3' termini of RNA copies can then be ligated to oligoribonucleotide or oligodeoxyribonucleotide adaptors which are phosphorylated at their 5' end and whose 3' end is blocked [Romaniuk, P. J. and Uhlenbeck, O. C. (1983). Joining of RNA Molecules with RNA Ligase, *Methods Enzymol.* 100, 52–59; Uhlenbeck, O. C. and Gumport, R. I. (1982). T4 RNA Ligase, in *The Enzymes,* 3rd edition (P. D. Boyer, ed.), vol. 15, pp. 31–58, Academic Press, New York]. Exponential PCR amplification can then be performed by utilizing the two primers that correspond to the two priming regions, and then incubating with Tth DNA polymerase (Myers and Gelfand, 1991).

(b) If the amplified copies are DNA molecules, they can be transferred, such as by blotting, (after melting them free of the immobilized partial) onto a binary array that is a mirror copy of the first array in the arrangement of the variable segments of its immobilized oligonucleotides. The constant segments of this binary array are pre-hybridized to masking oligonucleotides whose ligation to the 3' termini of the transferred DNAs (by DNA ligase, such as described in Example 1.2.1, above) results in generation of the second priming region. Exponential PCR amplification can then be performed by utilizing the two primers that correspond to the two priming regions, and an appropriate DNA polymerase.

In methods (a) and (b), both priming regions preferably contain, when applicable, the recognition sequence of the restriction endonuclease that was used to digest the genomic DNA before full-length strand sorting, and which had thus been substantially eliminated from the strands' internal regions.

(c) The priming region at the 3' terminus of a DNA or RNA copy can be introduced by extension of the terminus with a homopolymeric tail by incubation with terminal deoxynucleotidyl transferase or poly(A) polymerase, respectively. The complementary homooligonucleotide can be then used during PCR to prime from this region. This method, however, may not be desirable, since, similar homopolymeric stretches may occur somewhere within the partial, and the corresponding shortened sequence would then also be amplified.

(d) If partials are surveyed and it is desirable to detect only those oligonucleotides that occur in one complementary strand (such as detecting only parental oligonucleotides), then either only one of the two different primers should be labeled, or the primers should be labeled differently. It is also possible to use labeled substrates during asymmetric PCR.

3.4. Partialing RNAs

A 3'-poly(A)-tailed RNA can be converted into a cDNA (such as described in Example 1.7.1, above), after which any method described above for partialing DNA, can be applied. Alternatively, RNAs can be partialed directly. Prior to partialing, a 5'-terminal priming region should be introduced into RNAs (such as described in Example 1.7, above).

3.4.1. RNA partialing by enzymatic degradation

As with DNA, single-stranded RNA uncleaved by nuclease S1 randomly an in a sequence-nonspecific manner, but double-stranded secondary structure elements are essentially resistant to nuclease attack (see Example 3.1.2, above). Ribonuclease V1 from cobra venom, however, perfectly complements nuclease S1 by cleaving RNA mainly within double-stranded regions, and is also sequence-nonspecific [Vasilenko, S. K. and Ryte, V. C. (1975). Isolation of Highly Purified Ribonuclease from Cobra (*Naja oxiana*) Venom, *Biokhimia* (Moscow) 40, 578–583], so that by preparing mixtures of these enzymes an essentially uniform cleavage of an RNA strand can be obtained. 5'-phosphoryl and 3'-hydroxyl termini are produced upon action of either of these enzymes. If a double-stranded RNA is used as a starting material, it can be randomly cleaved by incubation with ribonuclease V1 alone.

A priming region can be introduced into the newly formed 3' hydroxyl termini of RNA partial strands in solution, either by addition of a poly(A) tail by incubation with poly(A) polymerase, or by ligation of an oligonucleotide adaptor by incubation with RNA ligase in solution (such as described in Example 3.3.2, above). Then the partials are hybridized to a sectioned binary array of oligonucleotides whose constant segment is complementary to the 3'-terminal extension of the fragments. Alternatively, the 3'-terminal priming region can be introduced by ligation of RNA partials to a masking oligonucleotide on a sectioned binary array (such as described in Example 1.7.2, above). The immobilized oligonucleotides are then extended by incubation with reverse transcriptase or Tth DNA polymerase, the array is washed to remove non-covalently bound material, and the immobilized partials are amplified, such as by methods described in Example 3.1.1, above).

3.4.2. RNA partialing by chemical degradation

Although there are many methods for chemical degradation of RNA, the simplest methods are alkaline hydrolysis [Donis-Keller, H., Maxam, A. M. and Gilbert, W. (1977). Mapping Adenines, Guanines, and Pyrimidines in RNA, *Nucleic Acids Res.* 4, 2527–2538] and RNA hydrolysis with $Mg^{++}$-formamide [Diamond, A. and Dudock, B. (1983). Methods of RNA Sequence Analysis, *Methods Enzymol.* 100, 431–453], that produce a fairly uniform ladder of different-length RNA bands when examined by electrophoresis through a denaturing polyacrylamide gel. As with DNA, chemical degradation results in fragments bearing 3'-phosphoryl groups that should be removed by incubation with a phosphatase (as described in Example 1.4, above), after which the procedure described in Example 3.4.1, above, is followed.

3.4.3. RNA partialing directly on an oligonucleotide array

This is carried out as described for DNA (in Example 3.3, above), the difference being that a reverse transcriptase (or a DNA polymerase that can copy RNA, such as Tth DNA polymerase) is used for the extension of the immobilized oligonucleotides. Thus, DNA partials of the RNA strands are generated.

4. Uses of sectioned oligonucleotide arrays for manipulating nucleic acids

In the examples described below, it is assumed that the sequences of the nucleic acids to be manipulated have already been established either by the method of the invention, or by some other technique. Therefore, it is assumed that sequence analysis has preceded the manipulations described here. Since the sequence of the nucleic acid sample is already known, it is not necessary, in these manipulations, that the sample be distributed across the entire array. Instead, a sample can be delivered directly to the well in the array where a particular oligonucleotide (or a particular strand) is immobilized. Other wells in the array can be either left unused in a particular procedure, or, preferably, used to carry out similar reactions in parallel. In these uses, the arrays can serve as a universal tool, enabling a very large number of specifically directed manipulations of nucleic acids to be carried out using a standard set of supplies, without recourse to synthesis of new oligonucleotides for each manipulation.

4.1. Isolation of individual partial strands 4.1.1. Separation of partials that share the same variable terminal oligonucleotide, but originate from different strands Partials sharing the same terminal oligonucleotide, but that originate from different strands possess, as a general rule, different sequences at their fixed ends (assuming that the fixed ends were not used for strand sorting). Therefore, individual partials almost always can be isolated from each other by sorting according to the terminal oligonucleotides at their fixed ends using arrays as described above.

4.1.2. Separation of partials that share the same variable terminal oligonucleotide and originate from the same strand If an address oligonucleotide occurs in a strand more then once, there will be two or more partials of different length in the same well which possess not only identical 3'-terminal oligonucleotides (assuming the variable end is the 3' end), but also identical 5'-terminal oligonucleotides. These partials can, of course, be separated by size, utilizing known gel-electrophoresis techniques (Sambrook et al., 1989). Even in this case, however, separation can be performed by using sectioned oligonucleotide arrays.

For example, there may be three identical oligonucleotides "P" in a strand, which are numbered, according to the order of their appearance in the parental strand in the 5' to 3' direction, $P_1$, $P_2$, and $P_3$. Accordingly, in the well where an oligonucleotide complementary to P is immobilized, three partials of different length are generated from the original strand, among which partial 1 is the shortest, and partial 3 is the longest. The method described below results in isolation of each of these three partials from one another.

Where the longest partial contains an oligonucleotide that does not occur in the shorter partials (i.e., an oligonucleotide that occurs between oligonucleotides $P_2$ and $P_3$, but does not occur upstream of $P_2$), its isolation is straightforward: the mixture is hybridized to a well containing the complementary oligonucleotide, wherein only the longest partial can bind.

For isolation of the shorter partials, a different (though similar) method is required, since any oligonucleotide that occurs in a shorter partial is also contained in a longer one. To prepare shorter partials, we first prepare a chosen partial from the parental strand, with a different variable terminus (i.e., not P). For example, to prepare partial 1 (the shortest partial), first a longer partial is prepared (using the technique described above) whose 3'-terminal oligonucleotide lies between oligonucleotides $P_1$ and $P_2$, but does not occur downstream of $P_2$. This is easily determined from an examination of the known sequence of the strand. Partial 1 is the only partial with 3'-terminal oligonucleotide P, that is prepared by partialing the truncated strand, and isolating the partial whose terminal oligonucleotide is P. To prepare partial 2 (of intermediate size), a partial is first prepared whose 3'-terminal oligonucleotide lies between $P_2$ and $P_3$, and does not occur down stream of $P_3$. From this partial, two partials are then generated with 3'-terminal oligonucleotide P, of which partial 2 is the longest one, and can now be isolated as described for partial 3.

If oligonucleotide P occurs n times in a strand, a partial "i" can be isolated by first preparing a partial (or partials) in which oligonucleotide $P_i$ is the P which is furthest downstream, i.e., a partial whose terminal oligonucleotide lies between $P_i$ and $P_{i+1}$ and does not occur downstream of $P_{i+1}$. Once partial $P_i$ is the longest partial in a mixture with shorter partials, it is isolated from the shorter partials by making use of an oligonucleotide that lies between $P_i$ and $P_{i-1}$, and does not occur upstream of $P_{i-1}$, as described above.

4.2. Preparation of partial strands that have both ends truncated

The methods described above in Examples 3.1 to 3.4 allow a nested set of all possible one-sided partials of a nucleic acid strand to be obtained. Desired one-sided partials can be prepared from either the direct or the complementary copies of a parental strand, or from a mixture of strands containing either the direct or complementary copies of each strand (for example a mixture of strands obtained by amplifying sorted strands in an asymmetric PCR to obtain either direct copies of the strands or their complementary copies). Partials can also be prepared from samples having both direct and complementary copies of parental strands present, such as a mixture of strands obtained by amplification of sorted strands in a symmetric PCR. Even using such a mixture, partials of the direct and complementary copies can be obtained separately. This can be carried out either on separate arrays, or on the same array. If one array is used for partialing both the direct and complementary copies of a parental strand, partials from either copy can be separately prepared by selectively amplifying partials of the direct copies or by selectively amplifying partials of the complementary copies at different times (using different combinations of primers as described in Example 3.1.1, above).

One-sided partials have one end fixed, and the other end variable, so that each partial corresponds to a parental strand having one end truncated to a different extent, i.e., a complete set of partials corresponds to the parental strand truncated at one end to all possible extents (see FIG. 9). Either end of the parental strand can be truncated. This can be done, for example, by randomly degrading a parental strand and sorting the partials obtained according to their 3' termini on a 3' binary array; or by sorting the partials according to their 5' termini on a 5' binary array. Alternatively, one-sided partials having either 3' ends truncated or 5' ends truncated, as desired, can be obtained by truncating either the direct copy or the complementary copy of a partial strand. For example, one-sided partials can be generated by truncation of either the direct or complementary copies at their 3' ends using an appropriate method of Examples 3.1 or 3.2. Asymmetric PCR can then be employed to amplify only direct copies of the partials of direct copies of the parental strand; or to amplify only complementary copies of the partials of complementary copies of the parental strand. Since the 3' end of a complementary strand corresponds to the 5' end of a direct strand, the first set of amplified partials will comprise the direct strand truncated at its 3' end, and the second set of amplified partials will comprise the direct strand truncated at its 5' end. Of course, asymmetric PCR can also be used to amplify only complementary copies of the direct strand partials, and to amplify only direct copies of the complementary strand partials, which will comprise the complementary strand truncated at the 5' end and the 3' end, respectively. Thus, every possible one-sided partial, comprising either the direct copy or the complementary copy of a parental strand, that is truncated at either the 3' end or the 5' end, can be prepared by the methods of this invention.

The one-sided partials obtained can themselves be subjected to second partialing according to the invention, wherein the former fixed end is truncated to any extent using the techniques described above for preparing one-sided partials (see Examples 3.1 to 3.4, above), thereby resulting in two-sided partials. If comprehensive arrays are used in each of the two consecutive rounds of strand partialing, the two-sided partials obtained can be any segments desired of the original parental strands.

For example, to prepare a segment bordered in a strand by two internal oligonucleotides, "a" and "b", one sided partials of the strand can first be produced, resulting in both "a" and "b" being at the variable termini of partials. Assuming that oligonucleotide "a" lies in the parental strand between oligonucleotide "b" and the fixed end, the contents of the well in the array where the partials terminating with "b" have been sorted to (i.e., the well containing an immobilized oligonucleotide complementary to "b"), is withdrawn and partialed again on a second array. The second array is chosen to prepare partials having oligonucleotide "b" at the fixed end. The segment bordered by "a" and "b" will be found in this second array in the well where the partials terminating with "a" have been sorted to (i.e., in-the well whose address is "a"). Of course, it is not necessary to prepare all one-sided partials of the original parental strand or all one sided partials of the partial strand terminating with "b" using comprehensive arrays. Rather, provided that the relative location of "a" and "b" in the strand is known, only two wells with addresses "a" and "b" in the arrays are required. In the first round of the procedure, a sample containing the parental strand is partialed in well "b" (wherein partials terminating with "b" are generated), and the contents of this well is partialed in well "a" in the second round. Wells "a" and "b" may even belong to the same array. Furthermore, a single array can be used for simultaneously preparing (in a two-stage procedure) a large number of segments bordered by any of chosen pairs of oligonucleotides in any of the strands that are present in a bank. Many variations of this technique will be apparent for obtaining the same results.

Using this technique, any desired segment of a nucleic acid strand of a known or partially known sequence can be precisely "excised" and amplified (e.g., by the use of "cleavable primers" as is described below), irrespective of the presence or absence of restriction sites, and without the need for synthesizing specific oligonucleotide primers.

Of course, if the combination of two oligonucleotides that border the excised segment occurs more than once in the group of partials that are present in the same well of a first partialing array, then there will be several different products of such a double truncation. If this occurs, individual two-sided partials can be isolated by the method described above in Example 4.1.2, by sorting according to their internal sequences (see Examples 2.1 and 2.2, above), or by any other separation technique known in the art (e.g., by gel electrophoresis, as described by Sambrook et al., 1989).

4.3. Cleavable primers

Amplification of strands and partials following separation (or generation) on a sectioned oligonucleotide array requires that their ends be provided with priming regions, either one (for linear amplification) or two (for exponential amplification). These priming regions (generally terminal extensions), however, can be undesirable in the subsequent use of the amplified strands or partials, such as the making of recombinants or site-directed mutants (see Examples 4.4 and 4.5, below). Additionally, for some uses of the amplified strands or partials it is desirable to substitute new priming regions for old priming regions. For those uses, the primers used for amplification must first be removed from the 5' ends of strands or partials. Where the junction of the primer and the strand (or partial) is contained within a unique restriction site, the primer can be removed by treating a double-stranded version of the strand (or partial) with a corresponding restriction endonuclease. However, restriction sites will often not be present at the junctions. A solution to this problem is to make the primer (or even only the junction nucleotide in the primer) chemically different from the rest of the strand (or partial), as described below. Below are several examples of such an approach. The primer in these examples resides at the strand's 5' terminus.

4.3.1. Cleavage of primers by alkaline hydrolysis or by ribonuclease digestion

This method is suitable for removal of oligoribonucleotide primers, or mixed RNA/DNA primers whose 3' terminal nucleotide (which becomes a junction nucleotide upon primer extension) is a ribonucleotide. Such primers are incorporated at the 5' end of DNA strands or partials during the strands' or partials' amplification described elsewhere herein.

Alkaline hydrolysis cleaves a phosphodiester bond that is on the 3' side of a ribonucleotide, and leaves intact a phosphodiester bond that is on the 3' side of a deoxyribonucleotide [Wyatt, J. R. and Walker, G. T. (1989). Deoxynucleotide-containing Oligoribonucleotide Duplexes: Stability and Susceptibility to RNase V1 and RNase H, *Nucleic Acids Res.* 17, 7833–7842]. After alkaline hydrolysis, the pH of the reaction mixture is returned to a neutral value by the addition of acid, and the sample can be used without purification.

Primers containing a riboadenylate or a riboguanylate residue at their 3' end can effectively be removed from a DNA strand or partial by treatment with $T_2$ ribonuclease [Scaringe, S. A., Francklyn, C. and Usman, N. (1990). Chemical Synthesis of Biologically Active Oligoribonucleotides Using β-Cyanoethyl Protected Ribonucleoside Phosphoramidites, *Nucleic Acids Res.* 18, 5433–5441]. After treatment, the sample is heated to 100° C. to inactivate the ribonuclease, and can be used without purification.

In both these cases, the released 5' terminus of the strand (or partial) is left dephosphorylated. Therefore, if the strand obtained is subsequently used for ligation, it should be phosphorylated by incubation with polynucleotide kinase (as described in Example 1.4, above).

4.3.2. Cleavage of primers from DNA strands (or partials) synthesized from phosphorothioate nucleotide precursors In this method, oligodeoxynucleotide or oligoribonucleotide primers are synthesized from natural nucleotides, but strand amplification is carried out in the presence of only α-phosphorothioate nucleotide precursors (as described in Example 3.2.2, above). Subsequent digestion of the synthesized strands with a 5'-3' exonuclease, such as calf spleen 5'-3' exonuclease results in the elimination of all primer nucleotides except the original 3', -terminal (junction) nucleotide of the primer, with the released 5'-terminal group of a strand or partial being unphosphorylated [Spitzer, S. and Eckstein, F. (1988). Inhibition of Deoxyribonucleases by Phosphorothioate Groups in Oligodeoxynucleotides, *Nucleic Acids Res.* 16, 11691–11704]. The junction nucleotide is not removed, because it is joined to the rest of the strand by a phosphorothioate diester bond. Therefore, the strand obtained has an extra nucleotide at its 5' end. This does not present a problem when the presence of the former junction nucleotide at the 5' end of the strand is compatible with the subsequent use of the strand. The presence of the extra nucleotide can also be useful for site-directed mutagenesis (described in 4.5, below).

If the primer-deprived strand obtained by this method is to be used for ligation, the use of spleen exonuclease, which leaves 5'-hydroxyl groups, must be then followed by phosphorylation of the strand utilizing polynucleotide kinase. Therefore, where the strand is to be ligated, the use of bacteriophage lambda or bacteriophage T7 5'-3' exonuclease is preferable over spleen exonuclease, since they leave 5'-phosphoryl groups at the site of cleavage [Sayers, J. R., Schmidt, W. and Eckstein, F. (1988). 5'-3' Exonucleases in Phosphorothioate-based Oligonucleotide-directed Mutagenesis, *Nucleic Acids Res.* 16, 791–802].

4.3.3. Removal of priming regions from 3' ends

After a primer is removed from the 5' end of a strand, the strand can be used as a template for the synthesis of complementary copies, such as described for the linear amplification of partials (see Example 3.3.1, above). The complementary product strands will not contain a 3'-terminal priming region. If desired, the primer used for this copying can be also made cleavable using one of the methods described above in Examples 4.3.1 or 4.3.2. Since any strand or partial can be obtained in any of the complementary versions (described in Examples 1.5 and 3.1.1, above), it is possible to deprive any strand or partial of either its 5' or 3' priming region, or both of them.

4.4. Generation of recombinant nucleic acids

With the ability using the invention to excise, amplify, and isolate any segment of any strand of known or partially known sequence, and with the ability to introduce and to remove priming regions at the segment's termini (and, therefore, to substitute one priming region for another, if necessary), it is possible to prepare any desired recombinant nucleic acid by employing a standard nucleic acid ligation technique (Sambrook et al., 1989), and then to amplify the recombinant by PCR. Using sectioned arrays, thousands of recombinants can be prepared simultaneously, if desired. Also, in many cases, specific recombinations can be carried out on the arrays without prior purification of one or both of the nucleic acids to be ligated.

In the methods described below, two nucleic acid strands are ligated in one round of ligation. It is of course possible to repeat the ligation process, ligating the recombinant product to another strand, and to keep repeating the process any desired number of times to ligate the desired number of strands.

4.4.1. Use of oligonucleotides immobilized on an array as sequence-specific "splints" for the ligation of nucleic acids In this example, a sectioned array contains immobilized oligonucleotides that consist of two portions, one being complementary to the 3'-terminal sequence of one of the moieties to be ligated, and the other being complementary to the 5' -terminal sequence of the other moiety to be ligated. The immobilized oligonucleotides can have either free 3' or 5' ends. The relevant termini of the nucleic acids to be ligated should be deprived of priming regions (as described in Example 4.3, above), but priming regions (preferably different) should be preserved at the opposite termini of the nucleic acids to allow amplification of the recombinants. After hybridization in an appropriate well of the array, the two nucleic acid strands are ligated to each other utilizing DNA ligase [Landegren, U., Kaiser, R., Sanders, J. and Hood, L. (1988). A Ligase-mediated Gene Detection Technique, *Science* 241, 1077–1080; Barany, F. (1991). Genetic Disease Detection and DNA Amplification Using Cloned Thermostable Ligase, *Proc. Natl. Acad. Sci. U.S.A.* 88, 189–193]. Unligated strands are then washed away. Only the ligated strands possess the two terminal priming regions that are required for subsequent PCR amplification. The strands that are to be ligated can be used in a mixture with other strands, provided that there are no other strands in the mixture with the same oligonucleotides at the termini that have been deprived of priming regions.

The sectioned array for performing ligation on can have immobilized oligonucleotides with either their 5' or 3' termini free. It is usually impracticable to use a comprehensive array for this purpose; rather, a new array is preferably prepared for the purpose of generating a particular set of recombinants that includes only the particular immobilized oligonucleotides that are required. These immobilized oligonucleotides can be relatively long to ensure a high specificity of hybridization. All of the required oligonucleotides can be synthesized simultaneously on the array before the recombination procedure is carried out utilizing, for example, a photolithographic technique (Foder et al., 1991).

A specific application of this method is to ligate many different strands to one particular strand or partial, for example, in order to produce many recombinant variations of one gene. In that case, one portion of the splint, i.e., the immobilized oligonucleotide, is a constant segment, and the other portion of the splint is a variable segment, i.e., the array used is a binary array. The constant segment binds to the strand that was chosen to be included in every recombinant and the variable segment binds to the end of another strand or partial that is chosen to be fused with the invariant strand.

4.4.2. Method for producing recombinants in which one nucleic acid to be combined is ligated to the free end of a hybrid formed between another nucleic acid to be combined and the immobilized oligonucleotide In one embodiment of this method, a blunt-ended double-stranded nucleic acid fragment is ligated in an individual area of an array to a single-stranded DNA (or RNA) that is hybridized by its terminus to the complementary oligonucleotides immobilized in that area. The array is an ordinary array and can be either 3' or 5', depending on whether the single-stranded nucleic acid is to be hybridized to the immobilized oligonucleotide by its 5' end or by its 3' end, respectively. The hybrids are ligated to the double-stranded fragment by incubation with a DNA ligase [Sambrook et al. 1989], and this can only occur when the free terminus of the immobilized oligonucleotide and the complementary terminus of the hybridized strand are perfectly aligned to produce a blunt end.

The single-stranded nucleic acid to be ligated is selected according to the identity of its hybridized end. Therefore, it need not be separated from other strands, provided that all the other strands in the mixture have dissimilar terminal sequences. On the other hand, the double-stranded fragment to be ligated is not selected using our method, and therefore it must be isolated from other fragments if it is desired to obtain an individual recombinant nucleic acid. The 5' termini to be ligated must be phosphorylated (this can apply to the immobilized oligonucleotide, if a 5' array is used). To ensure the proper orientation of the double-stranded fragment, the end of the fragment opposite to that which is to be ligated should not be compatible with ligation to the immobilized oligonucleotide/single-stranded nucleic acid hybrid. Means for making double-stranded nucleic acid ends incompatible are well known. The non-ligating ends of both the double-stranded fragment and the single-stranded nucleic acid should preferably be provided with priming regions before their ligation to each other, so that the ligated strands can be exponentially amplified in a subsequent PCR. Preferably, the priming regions are different, so that the ligated strands are selectively amplified. (If the end of the fragment which is not intended to be ligated in fact incorrectly ligates, the resulting product will not be amplified during PCR because the two primers will hybridize to the same strand).

The double-stranded fragment can be obtained, for example, by copying a strand that has had its 5'-terminal primer removed but retains a 3' terminal priming region (using techniques described elsewhere herein) (see Example 4.3, above). The primer-deprived end is the ligating end, and should be phosphorylated before copying the strands (if cleavage of the primer results in a 5'-hydroxyl group at this end). The primer used for copying the strand occurs at the non-ligating side of the fragment and should be non-phosphorylated to prevent ligation at that side. To prevent ligation of the 3' end at this fragment side, the 3'-hydroxyl group of the strand to be copied can be blocked by a conventional chemical modification. Alternatively, this side of the double-stranded fragment can be made not blunt by, during strand copying, using a primer whose 5'-terminal nucleotide is displaced in either direction with respect to the 3' terminal nucleotide of the copied strand. In other words, the primer is chosen to hybridize to the strand so that either it protrudes, or the strand protrudes, resulting in a non-blunt end which is incompatible with the ligating end of the immobilized oligonucleotide/single stranded nucleic acid hybrid. This approach can limit the amount of improper ligation.

Different pairs of single-stranded nucleic acids and double-stranded fragments can be ligated in each well of the array. Alternatively, if it is desired to have a collection of recombinants wherein only one moiety is varied and the other is the same, the double-stranded fragment can consist of a constant sequence and be ligated to variable single-stranded nucleic acids in wells of an array. In this method, as opposed to the method of Example 4.4.1, an array of specially designed oligonucleotides need not be prepared to produce a particular set of recombinants. Rather, one can use an ordinary comprehensive array of relatively short oligonucleotides immobilized thereon.

In another embodiment of this method, a purified double-stranded blunt-ended fragment is ligated to the 3' ends of oligoribonucleotides immobilized in a well of a 3' ordinary array by incubation with T4 RNA ligase (Higgins et al., 1979). After unligated material is washed away, a single-stranded nucleic acid, either isolated or in a mixture with other strands with different terminal sequences, is hybridized to the immobilized partially double-stranded complex and then ligated by its phosphorylated 5' end to the 3' end of the double-stranded fragment by incubation with DNA ligase.

4.5. Site-directed mutagenesis

The ability to prepare any partial of a strand according to the invention provides the opportunity to make nucleotide substitutions, deletions and insertions at any chosen position within a nucleic acid. Moreover, the use of sectioned arrays makes it possible to perform site-directed mutagenesis at a number of positions (even at all positions) at once, and in a particular embodiment, to determine, within individual wells of the array, properties of the encoded mutant proteins.

According to the methods described below for site directed mutagenesis, mutations are introduced into a nucleic acid strand by first preparing partials having variable ends that correspond to the segment of the strand to be mutated, that segment preceding the location of the intended mutation. Then mutagenic nucleotides or oligonucleotides are introduced into the partials at their variable ends. The mutated partials are then extended the length of the full sized strand using the complementary copy of the original non-mutated strand as a template.

Of course, more than one site directed mutation can be introduced into a strand in one procedure. For example, it may be desired to introduce mutations into a strand at positions "a", "b", and "c" (in the order those positions appear in the strand). A partial can first be prepared having on its variable 3' end an oligonucleotide segment that just precedes position "a" in the parental strand. Then a sequence containing a mutation at position "a" can be introduced into the variable end of the partial (i.e. 3' end). The resulting first mutated partial is extended using as a template a longer partial that is complementary to the partial that ends (in the parental strand) just in front of position "b". Then a sequence containing mutation "b" is introduced into the extended terminus of the partial that contains the mutation at position "a". The resulting double mutated partial is extended on a template that is complementary to the partial that ends just in front of position "c". The process is repeated with mutation "c" using for the last desired extension a template that encodes the remaining portion of the strand to be mutated (for example, this can be a complement of the full sized strand).

For mutagenesis, partials that have identical variable termini, but that originated from different parental strands, need not be separated from one another. However, if a particular oligonucleotide segment occurs more than once in a strand to be mutated, the corresponding partials must be separated from one another before mutagenesis, as described in Example 4.1.2, above.

4.5.1. Mutagenesis involving ligation of partial strands to immobilized oligonucleotides In this method, complements of nucleic acid partials (i.e., strands whose 5' termini are variable and 3' termini are fixed) are used. Their 5'-terminal priming regions are removed by complete alkaline digestion or by ribonuclease digestion of their incorporated cleavable primers (see Example 4.3.1, above). The resulting 5' termini are phosphorylated by incubation with polynucleotide kinase, and the partials are then ligated by incubation with RNA ligase to the free 3' hydroxyls of oligoribonucleotides that are immobilized on the surface of a 3' sectioned ordinary array. The sequence of the immobilized oligonucleotide to which a partial is ligated is identical to the oligonucleotide segment that occurs in the original (full-length) strand immediately adjacent to the end of the partial, except for one (or a few) nucleotide difference(s) that corresponds to mutation(s) to be introduced.

The nucleotide differences are preferably located at the 3' terminus of the immobilized oligonucleotide, and can correspond to a nucleotide substitution, insertion, or deletion. A deletion can be of any size. For a large insertion, the ligated partial, or the immobilized oligonucleotide, can first be fused to a nucleic acid containing all or part of the sequence to be inserted, using the method described in Example 4.4, above.

After washing away the material that is not covalently bound to the array, the immobilized strand is linearly copied, taking advantage of the priming region at its (fixed) 3' end. The copies obtained correspond to partials that have been extended by the oligonucleotides containing the mutation(s). These copies are then annealed to their complementary full-length strands, and their 3' termini extended by incubation with DNA polymerase, using the annealed complementary parental strand as a template. Finally, the extended mutant strands are amplified by PCR. It is important that the pair of primers utilized for amplification of a partial used for mutagenesis, are different from the primers used to amplify the original (non-mutant) full-length strand. This assures that only mutant strands are amplified.

If the aim of this procedure of the invention is protein engineering, then the amplified mutant strands can be transcribed and translated. Transcription and translation can be carried out either on the same array, or on a replica array. An RNA polymerase promoter should be included in advance in one of the primer regions of the mutant strand. For translation, the components of a cell-free translation system should be added to the reaction mixture in each well. [Anderson, C. W., Straus, J. W. and Dudock, B. S. (1983). Preparation of a Cell-free Protein-synthesizing System from Wheat Germ, *Methods Enzymol.* 101, 635–644; Bujard, H., Gentz, R., Lanzer, M., Stueber, D., Mueller, M., Ibrahimi, I., Haeuptle, M.-T. and Dobberstein, B. (1987). A T5 Promoter-based Transcription-translation System for the Analysis of Proteins in vitro and in vivo, *Methods Enzymol.* 155, 416–433; Tymms, M. J. and McInnes, B. (1988). Efficient in vitro Expression of Interferon α Analogs Using SP6 Polymerase and Rabbit Reticulocyte Lysate, *Gene Anal. Tech.* 5, 9–15; Baranov, V. I., Morozov, I. Yu., Ortlepp, S. A. and Spirin, A. S. (1989). Gene Expression in a Cell-free System on the Preparative Scale, *Gene* 84, 463–466; Ueda, T., Tohda, H., Chikazumi, N., Eckstein, F. and Watanabe, K. (1991). Phosphorothioate-containing RNAs Show mRNA Activity in the Prokaryotic Translation Systems in vitro, *Nucleic Acids Res.* 19, 547–552; Lesley, S. A., Brow, M. A. and Burgess, R. R. (1991). Use of in vitro Protein Synthesis from Polymerase Chain Reaction-generated Templates to Study Interaction of *Escherichia coli* Transcription Factors with Core RNA Polymerase and for Epitope Mapping of Monoclonal Antibodies, *J. Biol. Chem.* 266, 2632–2638]. The translation products in each well can then be assayed as desired. For example, the proteins can be assayed in situ for activity (if they are enzymes), or they can be assayed for the presence of particular antigenic determinants (for example, by determining the ability of each protein to bind to an array of immobilized antibodies).

4.5.2. Nucleotide substitution by the addition of a nucleotide to a partial's end If the purpose of mutagenesis is to substitute a single-nucleotide, a simpler method can be employed than is described in Example 4.5.1, above. The method described below involves the addition of a single mutagenic nucleotide to the variable end of a partial.

In one embodiment of this method, a primer that is made of natural oligonucleotides and that is present on the variable end of a partial strand that was synthesized from phosphorothioate precursors, is removed, as described above in Example 4.3.2, resulting in the appearance of an extra nucleotide at the partial's 5' end. By employing during amplification one of the four primers possible that differ in their 3'-terminal nucleotide, one can add any desired nucleotide to the partial's 5' variable end. The mutated partials are then copied by incubation with DNA polymerase, and the extra nucleotide appears at the 3' end of the copy. The copy is then annealed to a complementary full-length strand, and its 3' terminus is extended by incubation with DNA polymerase, using the full-length strand as a template. The extended mutant strand is then amplified by PCR using a pair of primers whose sequence is identical to the 5' terminal priming regions of the annealed mutated partial and the template.

Although the mutant partial's 3'-terminal nucleotide does not match its counterpart in the original full-length strand, conditions are employed whereby such unpaired termini are extended by DNA polymerase [Wu, D. Y., Ugozzoli, L., Pal, B. K. and Wallace, R. B. (1989). Allele-specific Enzymatic Amplification of Beta-globin Genomic DNA for Diagnosis of Sickle Cell Anemia. *Proc. Natl. Acad. Sci. U.S.A.* 86, 2757–2760]. The low efficiency of such extension is compensated for by subsequent exponential amplification of the extended mutant strands.

There is a chance that the unpaired nucleotide, which is loosely bound to the template, will be looped-out during extension, resulting in a nucleotide insertion rather than in a nucleotide substitution. To prevent the affected strands from being amplified, the heteroduplexes that consist of the mutant strand and the original strand, can be treated, prior to PCR amplification, with a single-strand-specific endonuclease, such as nuclease S1, that cleaves DNA at single-nucleotide bulges, but leaves intact single-base mismatches [Bhattacharyya, A. and Lilley, D. M. (1989). The Contrasting Structures of Mismatched DNA Sequences Containing Looped-Out Bases (Bulges) and Multiple Mismatches (Bubbles), *Nucleic Acids Res.* 17, 6821–6840].

An alternative approach is to generate a full-length mutant strand directly from the modified partial (with an extra nucleotide at its 5' end) without preparing a complementary copy of the modified partial. After the modified partial is annealed to a complementary full-length strand, the protruding single-stranded part of the duplex is filled in, by utilizing the Klenow fragment of DNA polymerase I (which will not displace the annealed modified partial) and a primer that is complementary to the 3'-terminal priming region of the full-length strand. Then, the extended primer and the annealed modified partial are ligated to each other by incubation with DNA ligase. The resulting full-length mutant strand is then amplified by PCR.

5. Surveying oligonucleotides with binary arrays

Surveying oligonucleotide content can be carried out in a conventional manner in the different embodiments of the invention, by hybridization of detectable nucleic acid strands or partials to an ordinary oligonucleotide array, and followed by detection of those hybridized. However, with this approach the signal-to-noise ratio is not high enough to always avoid ambiguous results. The most significant problem in this respect is inability to sufficiently discriminate against mismatched basepairs that occur at the ends of hybrids. That inability hampers the analysis of complex sequences [Drmanac, R., Strezoska, Z., Labat, I., Drmanac, S. and Crkvenjakov, R. (1990). Reliable Hybridization of Oligonucleotides as Short as Six Oligonucleotides, *DNA Cell Biol.* 9, 527–534]. The use of binary arrays in the manner discussed below helps to overcome this problem.

In some cases binary arrays are also useful for surveying longer oligonucleotides than are easily surveyed on an ordinary array (e.g., signature oligonucleotides) without increasing the size of the array over that of an ordinary array.

The oligonucleotides immobilized in a binary array that is used for surveys can have either free 5' or 3' ends, and the constant segment can be located either upstream or downstream from the variable segment. In most cases, it is preferable that the 3' ends of immobilized oligonucleotides be free, and that their constant segments be located upstream of the variable segments.

Surveying can be carried out by utilizing sectioned arrays. However, the use of plain arrays (i.e., not sectioned) is preferable because these arrays are less expensive and more amenable to miniaturization. The following methods are based on the use of plain binary arrays and involve fragmentation of the strands or partials prior to surveying.

5.1. Surveying DNA strands 5.1.1. Comprehensive surveys of DNA strands

In this format, every oligonucleotide segment that is present in a strand or in a partial, or in a group of strands or partials, is surveyed. If a survey of partials is performed in order to establish nucleotide sequences, it is preferable that each partial that is analyzed be represented by the same sense copies. Thus, there should be only one of the complementary strands in a sample or the complementary strands should be differentiable, e.g., one strand should produce either no detectable signal or a weaker signal. This can be accomplished by amplifying the partials linearly or by generating a great excess of one of the complementary strands over the other strand through the use of asymmetric PCR (see Example 3.1.1, above).

DNA strands (or partials) to be surveyed are preferably digested with nuclease S1 under conditions that destabilize DNA secondary structure (see Example 3.1.2, above). The digestion conditions are chosen so that the DNA pieces produced are as short as possible, but at the same time, most are at least one nucleotide longer than the variable segment of the oligonucleotides immobilized on the binary array. If the surveyed strands or partials have been previously sorted and amplified on a sectioned array, this degradation procedure can be performed simultaneously in each well of that array. Alternatively, if it is desired to store that array as a master array for later use, the array can be replicated by blotting onto another sectioned array (see Section I, above). The DNA is then amplified within the replica array by (asymmetric) PCR prior to digestion with nuclease S1.

After digestion, the nuclease is inactivated by, for example, heating to 100° C., and the DNA pieces are then hybridized to a binary array, whose immobilized oligonucleotides' constant segments are pre-hybridized to 5'-phosphorylated complementary masking oligonucleotides. Preferably, the constant segment contains a restriction site that has been eliminated from the internal regions of the DNA strands prior to strand sorting (such as described in Example 1.1, above), and is long enough so that its hybrid with the masking oligonucleotide is preserved during subsequent procedures. The binding of the masking oligonucleotide can be stabilized by introduction of an intercalating group at its 3' end [Asseline, U., Delarue, M., Lancelot, G., Toulmé, F., Thoung, N. T., Montenay-Garestier, T. and Hélène, C. (1984). Nucleic Acid-binding Molecules with High Affinity and Base Sequence Specificity: Intercalating Agents Covalently Linked to Oligodeoxynucleotides, *Proc. Natl. Acad. Sci. U.S.A.* 81, 3297–3301; Gottikh, M. B., Ivanovskaia, M. G., Skripkin, E. A. and Shabarova, Z. A. (1990). Design of New Oligonucleotide Derivatives Resistant to Cell Nucleases, *Bioorg. Khim.* (Moscow) 16, 514–523].

The array is then incubated with a DNA ligase (for example, as in Example 1.1.1, above), resulting in ligation of the masking oligonucleotides to only those hybridized DNA strands or partials whose 3' terminal nucleotide is immediately adjacent to the 5' end of the masking oligonucleotide, and matches its counterpart in the immobilized oligonucleotide. DNA ligase is especially sensitive to mismatches at the junction site [Landegren, U., Kaiser, R., Sanders, J. and Hood, L. (1988). A Ligase-mediated Gene Detection Technique, *Science* 241, 1077–1080].

After all non-ligated DNA pieces have been washed away under much more stringent conditions that were used during hybridization, the immobilized oligonucleotides are extended by incubation with a DNA polymerase, preferably by only one nucleotide, using the protruding part of the ligated DNA piece as a template, and preferably using the chain-terminating 2', 3'-dideoxynucleotides as substrates instead of the conventional 3'-deoxynucleotides. This extension is only possible, if the 3'-terminal base of the immobilized oligonucleotide forms a perfect basepair with its counterpart in the hybridized DNA piece. The use of the dideoxynucleotides ensures that all hybrids are extended by exactly one nucleotide, ensuring that all extended hybrids are of the same length. The array is then washed under conditions that are sufficiently stringent to remove unextended hybrids.

Thus, at each of the terminal positions of the hybrids, (where the nucleotides are most prone to form mismatches), there must be a perfectly matched basepair for a hybrid to survive washing and be detected.

Internal mismatches will also occur (at a lower frequency). Those mismatches can be essentially eliminated by "proofreading" the hybrids that are formed. This can be done by both chemical and enzymatic means described below. These methods are also applicable when surveying is carried out by utilizing ordinary (i.e., non-binary) arrays.

(a) Mismatched bases can be selectively modified by certain chemical reagents. For example, 1-cyclohexyl-3-(2-morpholino-ethyl)carbodiimide quantitatively reacts with mismatched guanidylate and thymidylate residues, while leaving perfect basepairs intact, including those that are located at the ends of duplexes [Novack, D. F., Casna, N. J., Fischer, S. G. and Ford, J. P. (1986). Detection of Single Base-pair Mismatches in DNA by Chemical Modification Followed by Electrophoresis in a 15% Polyacrylamide Gel, *Proc. Natl. Acad. Sci. U.S.A.* 83, 586–590]. This modification is very useful because G:T and G:A pairs are the most stable mismatches [Ikuta, S., Takagi, K., Wallace, R. B. and Itakura, K. (1987). Dissociation Kinetics of 19 Base Paired Oligonucleotide-DNA Duplexes Containing Different Single Mismatched Base Pairs, *Nucleic Acids Res.* 15, 797–811] and thus more likely to cause an erroneous signal. In addition, both hydroxylamine and osmium tetroxide selectively and quantitatively modify unpaired thymine and cytosine bases [Cotton, R. G. H., Rodrigues, N. R. and Campbell, R. D. (1988). Reactivity of Cytosine and Thymine in Single-base-pair Mismatches with Hydroxylamine and Osmium Tetroxide and Its Application to the Study of Mutations, *Proc. Natl. Acad. Sci. U.S.A.* 85, 4397–4401]. Because these modifications introduce bulky and/or highly hydrated groups into the mismatched basepair interface, the duplex structure is dramatically distorted, leading to a further decrease in the stability of the mismatched hybrids, while the stability of perfectly matched hybrids remains unchanged [Lebowitz, J., Chaudhuri, A. K., Gonenne, A. and Kitos, G. (1977). Carbodiimide Modification of Superhelical PM2 DNA: Considerations Regarding Reaction at Unpaired Bases and the Unwinding of Superhelical DNA with Chemical Probes, *Nucleic Acids Res.* 4, 1695–1711]. Thus, mere washing of the array after such a chemical treatment will eliminate almost all of the internally mismatched hybrids. Furthermore, the chemically modified nucleotide residues are recognized by repair enzymes, such as ABC excision nuclease, that specifically cleave DNA strands at the modified sites, resulting in the complete elimination of the corresponding mismatched hybrids [Thomas, D. C., Kunkel, T. A., Casna, N. J., Ford, J. P. and Sancar, A. (1986). Activities and Incision Patterns of ABC Excinuclease on Modified DNA Containing single-base Mismatches and Extrahelical Bases, *J. Biol. Chem.* 261, 14496–14505].

(b) If the array is made of oligoribonucleotides, rather than of oligodeoxyribonucleotides, the hybrids that are formed when surveying the oligonucleotides that are present in DNA can be edited by a ribonuclease treatment. Single-base mismatches in RNA:DNA heteroduplexes are recognized by ribonuclease A, which cleaves the RNA strand at the site of the mismatched basepair and nearby it. Cleavage predominantly occurs if the RNA strand contains a mismatched pyrimidine nucleotide. If the RNA strand contains a mismatched purine that is opposite to a pyrimidine nucleotide in the DNA strand, then the presence of the mismatch can be detected by analyzing the complementary DNA strand, where the relative position of the purines and pyrimidines is reversed and the mismatched pyrimidines will occur in the RNA strand, where it can be cleaved [Myers, R. M., Larin, Z. and Maniatis, T. (1985). Detection of Single Base Substitution by Ribonuclease Cleavage at Mismatches in RNA:DNA Duplexes, *Science* 230, 1242–1246]. The RNA:DNA duplexes can also be edited by the chemical means described in method (a).

With conventional hybridization methods, the ratio of the signal from a perfectly matched hybrid compared to the signal from a false hybrid containing a single internal mismatch is between 10 and 100 [Wilson, K. H., Blitchington, R., Hindenach, B. and Greene, R. (1988). Species-specific Oligonucleotide Probes for rRNA of *Clostridium difficile* and Related Species, *J. Clin. Microbiol.* 26, 2484–2488; Zhang, Y., Coyne, M. Y., Will, S. G., Levenson, C. H. and Kawasaki, E. S. (1991). Single-base Mutational Analysis of Cancer and Genetic Diseases Using Membrane Bound Modified Oligonucleotides, *Nucleic Acids Res.* 19, 3929–3933]. With hybrid proofreading techniques able to eliminate as many as 99% of mismatches, this ratio can be improved to between 1,000 to 10,000, a value that is comparable to the fidelity of most enzymatic reactions.

5.1.2. Detection of hybrids

Hybrids can be detected by a number of different means. Unlabeled hybrids can be detected by using surface plasmon resonance techniques, which currently can detect $10^8$ to $10_9$ hybrid molecules per square millimeter [Schwarz, T., Yeung, D., McDougall, A., Hawkins, E., Craven, F. C., Buckle, P. E. and Pollard-Knight, D. (1991). Detection of DNA Hybridization by Surface Plasmon Resonance, in *Advances in Gene Technology: The Molecular Biology of Human Genetic Disease* (Ahmad, F., Bialy, H., Black, S., Howell, R. R., Johnson, D. H., Lubs, H. A., Puett, J. D., Rabin, M. B., Scott, W. A., Van Brunt, J. and Whelan, W. J., eds.), vol. 1, p. 89, The Miami Bio/Technology Winter Symposium]. Alternatively, hybrids can be conventionally labeled, such as with radioactive or fluorescent groups [Landegren, U., Kaiser, R., Caskey, C. T. and Hood, L. (1988). DNA Diagnostics—Molecular Techniques and Automation, *Science* 242, 229–237]. Fluorescent labels are more convenient to use.

In order to ensure the lowest level of background labeling, it is preferable to label hybrids in a manner such that its detection is dependent on the success of both a ligation and an extension step. This can be accomplished within the scheme of oligonucleotide surveying described in Example 5.1.1, above, by labeling the masking oligonucleotides, and the 2',3'-dideoxynucleotides used for the extension of the immobilized oligonucleotides, with fluorescent dyes possessing different emission spectra. The fluorescence pattern of the array can then be scanned at different wavelengths, corresponding to the emission maxima of the two dyes, and only signals from those areas in the array that emit fluorescence of both colors are taken as a positive result. For example, dideoxynucleotides can be labeled with fluorescein (whose fluorescence is of green color), without interfering with their ability to serve as good substrates for both reverse transcriptases and DNA polymerases [Prober, J. M., Trainor, G. L., Dam, R. J., Hobbs, F. W., Robertson, C. W., Zagursky, R. J., Cocuzza, A. J., Jensen, M. A., and Baumeister, K. (1987). A System for Rapid DNA Sequencing with Fluorescent Chain-terminating Dideoxynucleotides, *Science* 238, 336–341]. On the other hand, masking oligonucleotides can be labeled with rhodamine (orange color) or Texas red (red color) [Smith, L. M., Sanders, J. Z., Kaiser, R. J., Hughes, P., Dodd, C., Connell, C. R., Heiner, C., Kent, S. B. H., and Hood, L. E. (1986). Fluorescence Detection in Automated DNA Sequence Analysis, *Nature* 321, 674–679].

After hybrids are extended (concomitant with labeling) and edited, the array is thoroughly washed to remove all unincorporated label, to destroy unextended hybrids, and to discriminate one more time against mismatched hybrids that might have remained in the array. A preferred method is to wash the array at steadily increasing temperature, with the signal from each individual area being read at a predetermined time, when the conditions ensure the highest selectivity for the particular hybrid that forms in that area [Khrapko, K. R., Lysov, Yu. P., Khorlin, A. A., Shik, V. V., Florentiev, V. L. and Mirzabekov, A. D. (1989). An Oligonucleotide Hybridization Approach to DNA Sequencing, *FEBS Lett.* 256, 118–122]. Other conditions (such as denaturant and/or salt concentration) can also be controlled over time. The fluorescence pattern can be recorded at predetermined time intervals with a scanning microfluorometer, such as an epifluorescence microscope [Fodor et al., 1991].

5.1.3. Surveys of selected oligonucleotides in DNA strands

Selected oligonucleotides present in a DNA strand, or a group of strands, can be surveyed on a binary array, whose immobilized oligonucleotides' variable segments comprise a collection of sequences that are complementary to the sequences of interest that may occur in the DNA sample being analyzed. These selected oligonucleotides may be, for example, a catalog of short oligonucleotide segments of a genome that are of special interest. For example, they may be segments whose alteration frequently results in (or accompanies) a disease. They may also be particularly variable segments whose identification, for example, can help to establish who the actual parents of a particular person are (i.e., they are rapidly evolving segments). In these cases, the variable regions of the immobilized oligonucleotide can be chosen so that they are long enough to be unique, or relatively unique, in the genome. The analyzed sample can, for example, be a group of genome fragments (see Examples 1.1 to 1.4 and Example 1.6), or a mixture of strands obtained, for example, through the use of whole-genome PCR utilizing a set of selected primers that are targeted to particular genome regions [Kinzler, K. W. and Vogelstein, B. Whole Genome PCR: Application to the Identification of Sequences Bound by Gene Regulatory Proteins, *Nucleic Acids Res.* 17, 3645–3653 (1989)].

5.1.4. Surveys of signature oligonucleotides

Binary arrays are useful for surveying signature oligonucleotides present in the sorted DNA fragments. The identification of signature oligonucleotides helps to establish the order of restriction fragments of digested chromosomes (see section V, above). A signature oligonucleotide consists of a variable oligonucleotide segment of a pre-selected length and an adjacent recognition site for a chosen restriction endonuclease. Accordingly, the constant segment of the immobilized oligonucleotide in the binary array includes, in this case, the sequence that is complementary to this restriction site. In contradistinction to comprehensive surveying, which is described in Example 5.1.1, above, a masking oligonucleotide should not protect this portion of the constant segment, so that this portion is able to hybridize to a signature oligonucleotide in the fragment. The procedure itself is that described in Examples 5.1.1 and 5.1.2, above. However, because the surveyed oligonucleotides are longer in this case, the DNA to be analyzed should be degraded into longer pieces.

5.2. Surveying RNA strands

As is the case for DNA strands, comprehensive surveys can be carried out to determine all the oligonucleotides that occur in RNA strands (e.g., for sequencing), or only selected oligonucleotides can be surveyed (e.g., to identify RNAs of a known sequence in a clinical sample). In contradistinction to DNA strands, RNA strands (or partials) can be degraded randomly under non-denaturing conditions (e.g., by treatment with a mixture of nuclease S1 and ribonuclease V1, as described in Example 3.4.1, above). The resulting RNA pieces can be ligated to masking oligonucleotides after hybridization to the array by utilizing DNA ligase (see Example 5.1.1, above). Alternatively, RNA 3' termini can be ligated in solution (after nuclease inactivation by heating) to an oligoribonucleotide or an oligodeoxyribonucleotide by utilizing RNA ligase (as described in Example 3.3.1, above). The extended RNA pieces are then hybridized to a binary array whose oligonucleotides' constant segments are complementary to the ligated oligonucleotide. After ligation, the procedure is as described for surveying DNA strands (Example 5.1.1, above). Double labeling of hybrids at their termini (as described in Example 5.1.2, above) is preferable, in order to enhance the specificity of hybrid detection. RNA hybrids can also be proofread by the methods described for DNA strand surveying (see Example 5.1.1, above). In that case, ribonuclease editing is more effective if the array contains immobilized oligoribonucleotides, because both strands of a hybrid can be cleaved when the hybrid contains mismatched pyrimidines.

6. Examples of interpretation of oligonucleotide information obtained from surveys of partial strands, for determining the nucleotide sequences of a mixture of nucleic acid strands

6.1 Determination of the nucleotide sequences of strands in a mixture when each strand possesses at least one oligonucleotide that does not occur in any other strand in the mixture FIGS. 18 to 28 depict the determination of the sequences of two mixed strands using the methods of the invention. The example demonstrates the power of the invention to identify all of the oligonucleotides that are present in a strand (i.e., its strand set) when that strand possesses at least one oligonucleotide that does not occur in any other strand in the mixture. In particular, the example demonstrates: (a) how the data obtained by surveying the partial strands generated from a mixture of strands and sorted by their variable termini (i.e., the upstream subset of each address) and the inferred downstream subset of each address (which together form the indexed address sets) are used to construct the unindexed address sets; and (b) how the unindexed address sets are compared to each other to identify prime sets, i.e., address sets that contain only one strand set. The example also demonstrates how the oligonucleotides that are contained in a strand set are assembled into the sequence of the strand, even though the primary data is obtained from a mixture of strands. In particular, the example demonstrates: (a) how the oligonucleotides in a strand set are assembled into sequence blocks; (b) how the contents of the indexed address sets are filtered so that only information pertaining to the oligonucleotides in a particular strand set remains; (c) how this filtered oligonucleotide data is re-expressed in terms of the sequence blocks that are contained in that particular strand; (d) how the information contained in the resulting "block sets" is used to identify those blocks that definitely occur only once in the strand ("unique blocks") and to identify those blocks that can potentially occur more than once in the strand; (e) how the information contained in the block sets of unique blocks is used to determine the relative order of the blocks that occur only once in the strand; (f) how the information contained in the block sets limits the positions at which the other blocks can occur (relative to other blocks); and (g) how a consideration of the sequences at the ends of blocks, in combination with a consideration of the relative positions of the blocks, leads to the unambiguous determination of the complete sequence of the strand. This example also illustrates: (a) how oligonucleotides that occur more than once in a strand are identified and located within the sequence, even though the survey data contain no information as to the number of times a particular oligonucleotide occurs in a partial or a mixture of partials having the same terminal oligonucleotide; and (b) how the sequences of different strands in a mixture can be determined separately, despite the fact that many of the oligonucleotides occur in more than one strand in the mixture.

FIG. 18a shows the sequences of two short strands (parental strands) that are assumed to be present in a mixture (with no other strands). It is also assumed that complete sets of partials have been generated from this mixture of strands, and that each set of partials has been separately surveyed, with the partials sharing the same address oligonucleotide being surveyed together. For the purpose of illustrating the method of analyzing the data, it is assumed that the address oligonucleotides and the surveyed oligonucleotides are three nucleotides in length. In practice, longer oligonucleotides should be used. However, for the purpose of illustration it is easier to comprehend an example based on trinucleotides. The same methods of analyzing the data apply when longer oligonucleotides are surveyed, when much longer strands are in the mixture, and when the mixture contains many more strands.

FIG. 18b shows the upstream subsets determined by surveying each relevant address in the partialing array (shown on the left), and the downstream subsets inferred by the method described above in section V (shown on the right), (i.e., FIG. 18b shows indexed address sets). The address oligonucleotides (shown in bold letters) are listed vertically in the center of the diagram. The oligonucleotides listed horizontally to the left of each address oligonucleotide are those oligonucleotides that were detected in a survey of the partials at that address (the upstream subset). The oligonucleotides listed horizontally to the right of each address oligonucleotide are those oligonucleotides that are inferred from the upstream subsets to occur downstream of that address oligonucleotide (the downstream subset). For example, oligonucleotide "ACC" is contained in the upstream subset of the address oligonucleotide "CCT". This means that oligonucleotide "CCT" occurs downstream of oligonucleotide "ACC" in at least one of the strands in the mixture. Therefore "CCT" is inferred to be in the downstream subset of address set "ACC". The remaining downstream oligonucleotides in all of the address sets are similarly inferred. Note that an address oligonucleotide is always a member of its own upstream and downstream subsets.

After the indexed address sets of all the addresses in the parental strands have been determined (as shown in FIG. 18b), the information is organized into unindexed address sets (FIG. 18c), having no division into downstream and upstream subsets, but merely listing, for each address oligonucleotide, those oligonucleotides that occur in either the upstream or downstream subset (or that occur in both subsets). In FIG. 18c, the address oligonucleotides (shown in bold letters) are listed vertically on the left side of the diagram. Note that the address oligonucleotide is always a member of its own unindexed address set.

Figure 18D:
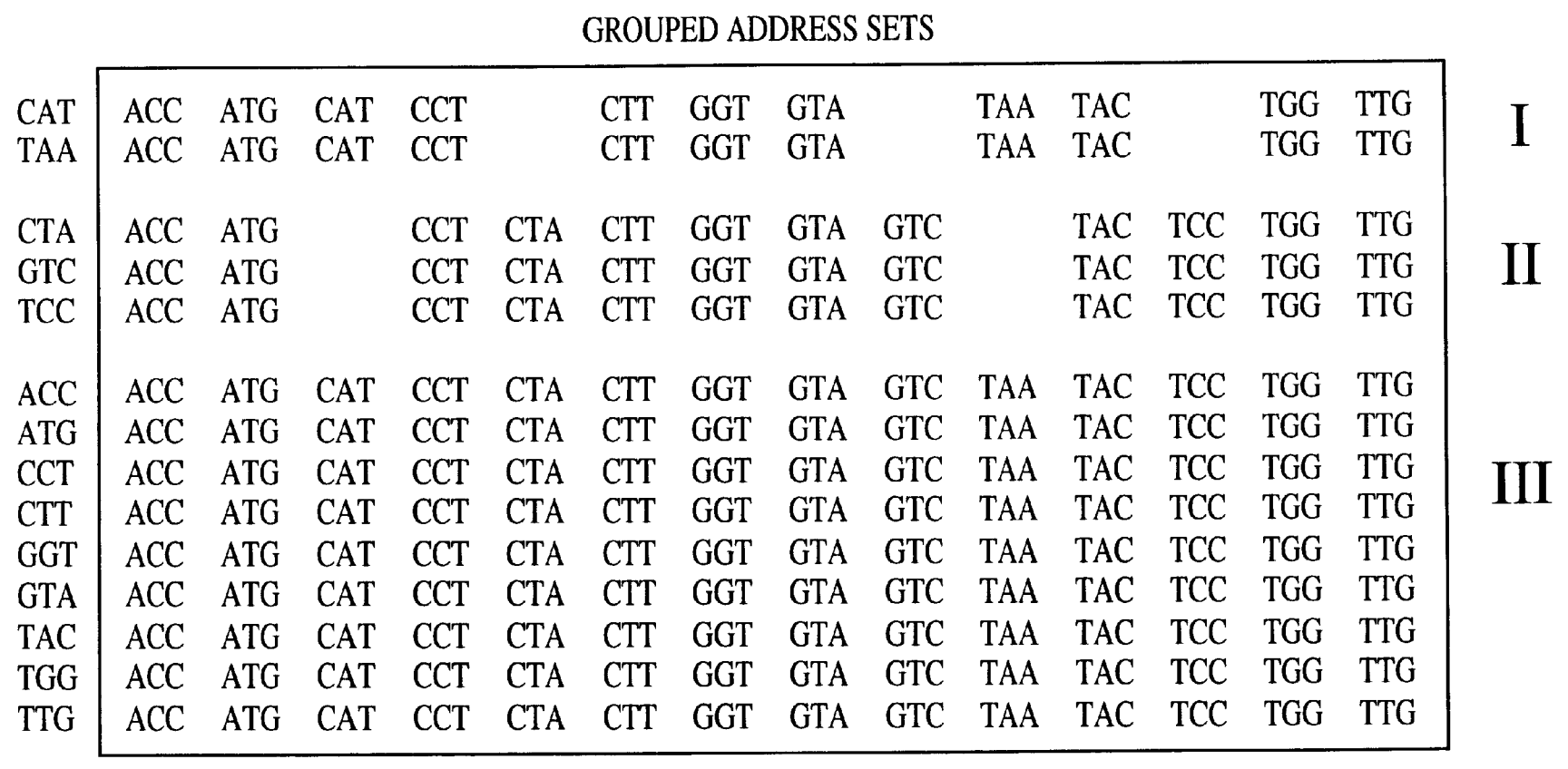

Unindexed address sets are then grouped together according to the identity of the oligonucleotides that they contain (FIG. 18d). Unindexed address sets that contain an identical set of oligonucleotides are grouped together. It can be seen that three groups of address sets are formed in this example. The groups are identified by the Roman numerals (I, II, and III). The address oligonucleotides of each group (for example, CTA, GTC, and TCC in group II) always occur together in a strand. The group of address oligonucleotides can occur together in more than one strand.

Each group of identical address sets is then compared to all other groups of identical address sets to see if its common address set appears to be a prime address set. This is accomplished for each address set by seeing whether any other address set is a subset of it. For example, in FIG. 17d, the address set common to group III is not a prime address set, because the address set common to group I is a subset of the address set common to group III. However, the address set common to group I does appear to be a prime address set, because neither the address set common to group II, nor the address set common to group III, is a subset of the address set common to group I. Similarly, the address set common to group II appears to be a prime address set.

Figure 19A:
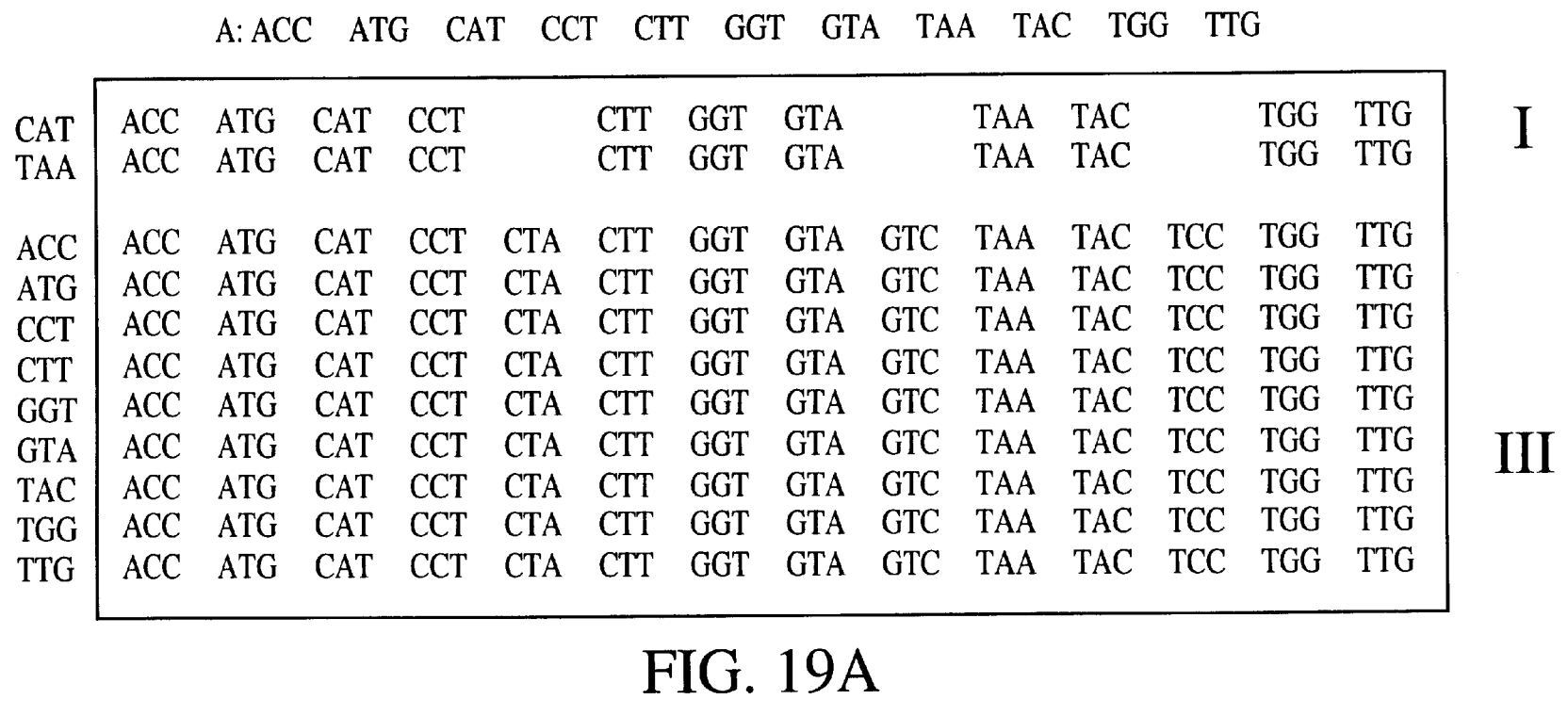
Figure 19B:
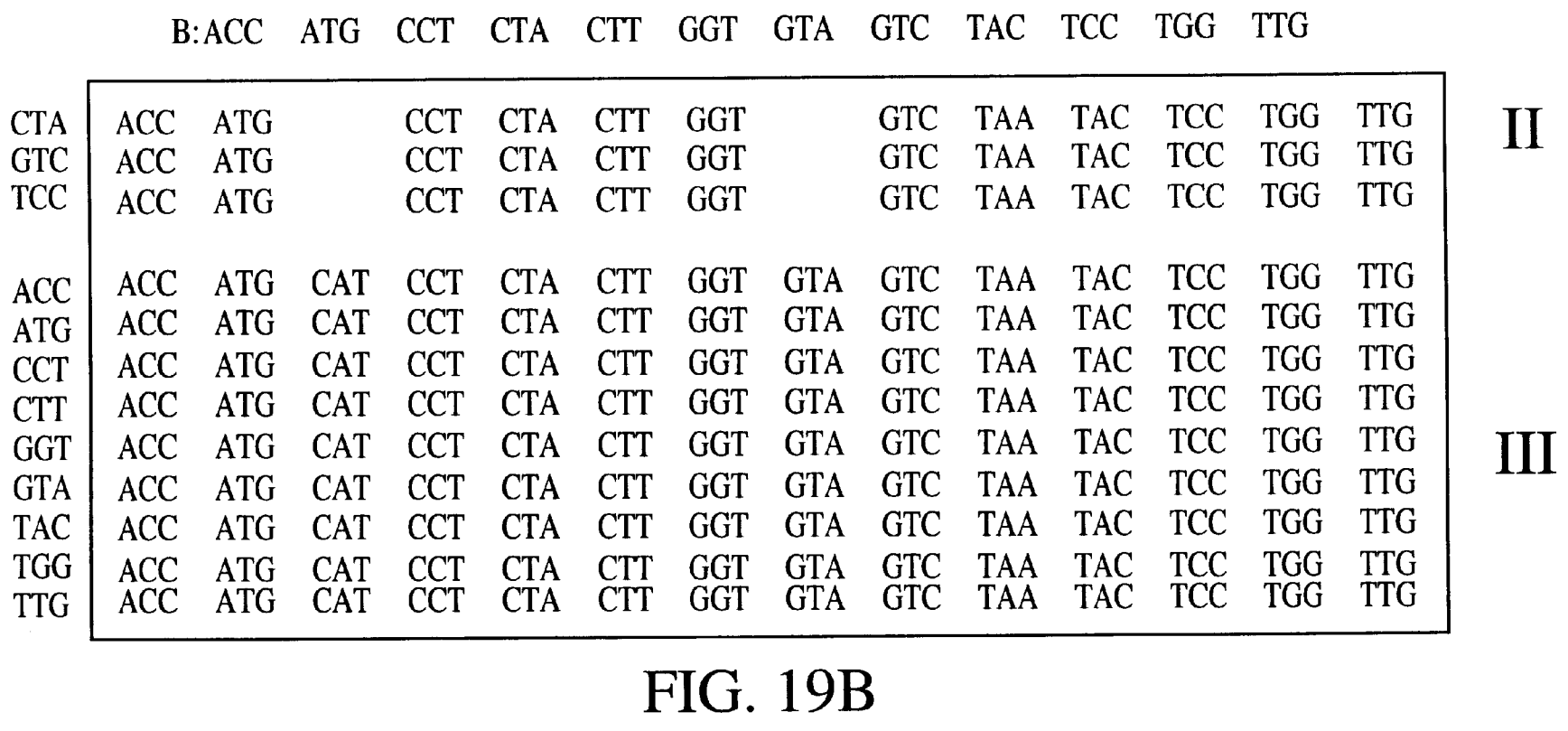

Each putative prime address set is then tested to see if it is a strand set. This is accomplished by examining all the address sets that contain all of the oligonucleotides that are present in the putative prime address set. For example, in FIG. 19a, all the address sets that contain all the oligonucleotides that are present in the putative prime address set common to group I are listed together (namely the address sets contained in groups I and III). The address oligonucleotides are shown in bold letters on the left side of the diagram, and the groups are identified by Roman numerals. The address set common to group I is indeed a prime address set (and therefore it contains a single strand set) because a list of the eleven oligonucleotides that are found in every address set in the diagram (they are seen as full columns) is identical to the list of eleven addresses on the left side of the diagram. Similarly, FIG. 19b shows why the address set common to group II is also a prime set. In particular, the twelve oligonucleotides common to every address set in the diagram are all found in the list of twelve addresses on the left side of the diagram. Had either of these putative prime address sets not turned out to indeed be a prime set (by the criterion described above), then it would have been identified as a pseudo-prime address set, and further analysis would have been required to decompose it into its constituent strand sets (as will be shown in Example 6.2, below).

Once the strand sets in a mixture have been identified; the oligonucleotides in each strand set can be assembled into the nucleotide sequence of the strand. This is accomplished in a series of steps, as illustrated in FIG. 20 (which utilizes the strand set determined in FIG. 19a).

First the oligonucleotides in the strand set are assembled into sequence blocks. A sequence block contains one or more uniquely overlapping oligonucleotides. Two oligonucleotides of length n, uniquely overlap each other if they share an identical sub-sequence that is n–1 nucleotides long and no other oligonucleotides in the same strand set share that sub-sequence. For example, for the strand set shown in FIG. 20a, the oligonucleotides "CAT" and "ATG" share the sub-sequence "AT" which does not occur in other oligonucleotides. These two oligonucleotides therefore uniquely overlap to form the sequence block "CATG", as shown in FIG. 20b. Similarly, oligonucleotide "TGG" uniquely overlaps oligonucleotide "GGT" by the common sub-sequence "GG", and oligonucleotide "GGT" also uniquely overlaps (on its other end) oligonucleotide "GTA" by the common sub-sequence "GT". Thus, the three oligonucleotides ("TGG", "GGT", and "GTA") can be maximally overlapped to form sequence block "TGGTA". In forming sequence blocks, the following rule is adhered to: two oligonucleotides can be included in the same block if they are the only oligonucleotides in the strand set to possess their common sub-sequence. Thus, "ATG" does not uniquely overlap "TGG", because the strand set contains a third oligonucleotide, "TTG", that shares the common sub-sequence "TG". If, following these rules, an oligonucleotide does not uniquely overlap any other oligonucleotide, then a sequence block consists of only that oligonucleotide. For example, "TAA" forms its own block. Following the above rules, the eleven oligonucleotides that occur in strand set A can be assembled into four sequence blocks.

Second, the data contained in the indexed address sets shown in FIG. 18b are filtered to remove extraneous information that does not pertain to strand set A. FIG. 20c shows the resulting filtered address sets. All address sets whose address oligonucleotide is not one of the oligonucleotides in strand set A are eliminated. In addition, all oligonucleotides that are not members of strand set A are removed from the upstream and downstream subsets of the remaining address sets. The resulting filtered address sets are then grouped together according to the oligonucleotides that are contained in each block. For example, the filtered address sets for address oligonucleotides "CAT" and "ATG" have been grouped together in FIG. 20c because these two oligonucleotides are contained in sequence block "CATG". In FIG. 20c, the address oligonucleotides found in the same block are identified by rectangular boxes. In addition, oligonucleotides that occur in the same block are grouped together within each upstream and downstream subset.

Third, the filtered address sets are converted into block sets, as shown in FIG. 20d. In a block set, the information from different address sets is combined. Instead of a different horizontal line for each filtered address set that pertains to a particular block, the information in all of the address sets that pertain to that particular block is combined into a single horizontal line. For example, in FIG. 19c, five different filtered address sets pertain to sequence block "TACCTTG". In FIG. 20d, these five lines are combined into a single line in which the address oligonucleotides are replaced by an "address block", shown as "TACCTTG" surrounded by a bold box. Similarly, the upstream oligonucleotides are replaced by upstream blocks, and the downstream oligonucleotides are replaced by downstream blocks. In substituting sequence blocks for the upstream (or downstream) oligonucleotides that are contained in the filtered address sets that pertain to a given address block, the following rule is adhered to: a sequence block only occurs in the upstream subset (or in the downstream subset) of an address block, if every oligonucleotide that is contained in that address block occurs in the upstream (or in the downstream) subset of every filtered address set that pertains to that address block. For example, sequence block "CATG" occurs in the upstream subset of Address Block "TACCTTG" because oligonucleotides "CAT" and "ATG" occur in the upstream subset of address oligonucleotides "TAC", "ACC", "CCT", "CTT", and "TTG".

Often, a sequence block does not occur in its own upstream or downstream subset. For example, sequence block "CATG" does not occur in the upstream or downstream subset of its own block set (i.e., in block set "CATG"), because Oligonucleotide "ATG" is not present in the upstream subset of address set "CAT" and oligonucleotide "CAT" is not present in the downstream subset of address set "ATG". When a sequence block does not occur in its own upstream or downstream subset, this indicates that that sequence block occurs only once in the nucleotide sequence of that strand. However, a sequence block may occur in both the upstream subset and in the downstream subset of its own block set. For example, sequence block "TGGTA" occurs in both the upstream subset and in the downstream subset of block set "TGGTA". When a sequence block does occur in its own upstream and downstream subsets, it indicates that the sequence block may occur more than once in the sequence. However, it does not indicate that the sequence block definitely occurs more than once in the sequence. The presence of more than one parental strand in the original mixture can introduce additional oligonucleotides into the filtered upstream and downstream subsets that can cause a block that actually occurs only once in a sequence to appear in both the upstream and downstream subsets of its own block set. However, further analysis of the data determines the multiplicity of each block in the strand (as described below), thus resolving these uncertainties. For convenience, block sets that pertain to blocks that definitely occur only once in the sequence are listed together. For example, in FIG. 20d, block set "CATG" and block set "TACCTTG" are listed together in the upper section of the block set diagram.

Fourth, the position of each sequence block relative to the other sequence blocks is determined. An examination of the block sets that pertain to unique blocks (blocks that definitely occur only once in the nucleotide sequence of the strand) indicates their relative positions. For example, in FIG. 20d, block set "CATG" indicates that unique sequence block "TACCTTG" occurs downstream of unique sequence block "CATG". This is confirmed by block set "TACCTTG", in which unique sequence block "CATG" occurs upstream of unique sequence block "TACCTTG". The relative position of the two unique sequence blocks is indicated in FIG. 20e, where the top line to the left of the arrow shows "CATG" upstream (to the left) of "TACCTTG". The relative position of the sequence blocks that can potentially occur more than once in the nucleotide sequence of the strand is determined from their presence or absence in the upstream and downstream subsets of other sequence blocks. For example, sequence block "TAA" occurs in the downstream subset of block set "CATG" (and does not occur in the upstream subset of block set "CATG"). Furthermore, sequence block "TAA" also occurs in the downstream subset of block set "TACCTTG" (and does not occur in the upstream subset of block set "TACCTTG"). Therefore, sequence block "TAA" must occur downstream of both unique sequence block "CATG" and unique sequence block "TACCTTG". This is indicated in FIG. 20e, where the bottom line to the left of the arrow shows "TAA" as occurring downstream of "CATG" and "TACCTTG". Furthermore, sequence block "TGGTA" occurs only in the downstream subset of block set "CATG". Therefore, it must occur downstream of "CATG" in the nucleotide sequence. On the other hand, sequence block "TGGTA" occurs in both the upstream and downstream subsets of block set "TACCTTG". This indicates that "TGGTA" can potentially occur in the sequence at positions both upstream and downstream of unique sequence block "TACCTTG". Finally, "TGGTA" only occurs upstream of "TAA". This is indicated in FIG. 20e, where the bottom line to the left of the arrow contains a bracket that shows the range of positions at which "TGGTA" can occur, relative to the positions of the other sequence blocks. At this point in the analysis, the diagram to the left of the arrow in FIG. 19c contains all the information obtained that pertains to strand set A.

Finally, the sequence of the strand is ascertained by taking into account both the relative position of the sequence blocks, as shown in the diagram to the left of the arrow in FIG. 20e, and the identity of the sequences at the ends of the sequence blocks. The object of this last step in sequence determination is to assemble the blocks into the final sequence. Four rules are followed: (a) each of the blocks must be used at least once; (b) the blocks must be assembled into a single sequence; (c) the ends of blocks that are to be joined must maximally overlap each other (i.e., if the surveyed oligonucleotides are n nucleotides in length, then two blocks maximally overlap each other if they share a terminal sub-sequence that is n−1 nucleotides in length); and (d) the order of the blocks must be consistent with their positions relative to one another, as ascertained from the block sets. For example, in FIG. 20e, "CATG" is upstream of "TACCTTG". "CATG" cannot be joined directly to "TACCTTG", since these two sequence blocks do not possess maximally overlapping terminal sequences (two nucleotides in length). However, an examination of the permissible positions at which other sequence blocks can occur indicates that "TGGTA" can occur in the gap between "CATG" and "TACCTTG". The ends of these sequence blocks are then examined to see whether the gap can be bridged. "CATG" can be joined to "TGGTA" by maximally overlapping their shared terminal sub-sequence "TG". Furthermore "TGGTA" can be joined to "TACCTTG" by maximally overlapping their shared terminal sub-sequence "TA". Similarly, the gap that occurs downstream of "TACCTTG" can potentially be filled by both "TAA" and "TGGTA". "TAA" must be used, because it was not used at any other location. However, "TACCTTG" cannot be directly joined to "TAA". The solution is to join "TACCTTG" to "TGGTA", and then to join "TGGTA" to "TAA". Thus, the sequence of strand A (which is shown in FIG. 20f) is unambiguously assembled by utilizing sequence block "TGGTA" twice (as summarized in the diagram to the right of the arrow in FIG. 20e).

The same procedure is followed to determine the nucleotide sequence of strand B (see FIG. 21). In this example, there are three sequence blocks that do not occur in their own upstream or downstream subsets, and they therefore definitely occur only once in the sequence of strand B (namely, sequence blocks "CTTG", "GTCC", and "TACC"). An examination of block set "GTCC" shows that "GTCC" occurs upstream of "CTTG" and "TACC". However, an examination of block set "CTTG" and an examination of block set "TACC" indicates that sequence blocks "CTTG" and "TACC" can both occur upstream and downstream of each other, which appears to conflict with the observation that these sequence blocks only occur once in the sequence of strand B. There is actually no conflict. Each of these sequence blocks does indeed occur only once in the sequence. It is just that their positions, relative to one another, in strand B are obscured by the presence of conflicting information from the relative positions of oligonucleotides that occur in strand A. This ambiguity (indicated by the identical positions of sequence blocks "CTTG" and "TACC" in the diagram to the left of the arrow in FIG. 21e) is resolved as the remainder of the information is taken into account. The positions of those sequence blocks that can potentially occur more than once in the sequence of strand B is determined from other block sets. First, the block sets of the sequence blocks that definitely occur only once in the sequence (namely, block sets "CTTG", "GTCC", and "TACC") are consulted. The range of positions at which these other sequence blocks can occur (relative to the positions of other blocks) is indicated in the diagram to the left side of the arrow in FIG. 21e.

The assembly of the nucleotide sequence of Strand B proceeds as follows: "ATG" is upstream of all other blocks. The uniquely occurring block immediately downstream of "ATG" is "GTCC". "ATG" and "GTCC" cannot be directly joined. However, "ATG" can be directly joined to "TGGT", so the correct order is to join "ATG" to "TGGC", and then to join "TGGC" to "GTCC". Neither "CTTG" nor "TACC" can be directly joined to "GTCC". Three different sequence blocks can be used to bridge this gap (namely, "CCT", "GTA", and "TGGT"). The only combination of these three sequence blocks that can fill this gap is "CCT" alone, which bridges the gap between "GTCC" and "CTTG". This resolves the ambiguity as to the relative positions of "CTTG" and "TACC". "CTTG" is therefore upstream of "TACC". "CTTG" cannot be directly joined to "TACC". Again, there are three different sequence blocks that can be used to fill this gap (namely, "CCT", "GTA", and "TGGT"). The only combination of these three sequence blocks that can fill this gap is "TGGT" and "GTA" (i.e., "GTTG" is joined to "TGGT", "TGGT" is joined to "GTA", and "GTA" is joined to "TACC"). And finally, "CTA", which occurs upstream of all other blocks, must be included in the sequence. However, "TACC" cannot be directly joined to "CTA". There are three different sequence blocks that can be used to fill this gap (namely, "CCT", "GTA", and "TGGT"). The only combination of these three sequence blocks that can fill this gap is "CCT" alone. Thus, the assembly of the nucleotide sequence of Strand B from its sequence blocks is completed. Note that some of the sequence blocks that could potentially occur in the sequence more than once, actually occur only once (e.g., "GTA"). Other sequence blocks that could potentially occur in the sequence more than once, actually occur more than once (e.g., "CCT").

Thus, using the methods of this invention, the entire sequence of strand B is unambiguously determined, despite the fact that some oligonucleotides occur more than once in its sequence, despite the fact that more than one sequence block can be assembled from the oligonucleotides that occur in the strand, despite the fact that the multiplicity of occurrence of each oligonucleotide is not determined during surveying, despite the fact that the strand is analyzed in a mixture of strands, and despite the fact that the other strand in the mixture possesses many of the same oligonucleotides.

6.2 Determination of the nucleotide sequences of strands in a mixture when some of the strands do not possess at least one oligonucleotide that does not occur in any other strand in the mixture FIGS. 22 to 28 depict the determination of the sequences of four strands in a mixture with each other using the methods of the invention. The example demonstrates the power of the invention to identify all of the oligonucleotides that are present in a strand (i.e., its strand set) when some of the strands (in this example, those of the four strands) do not possess even one oligonucleotide that does not occur in any other strand in the mixture.

Figure 22D:
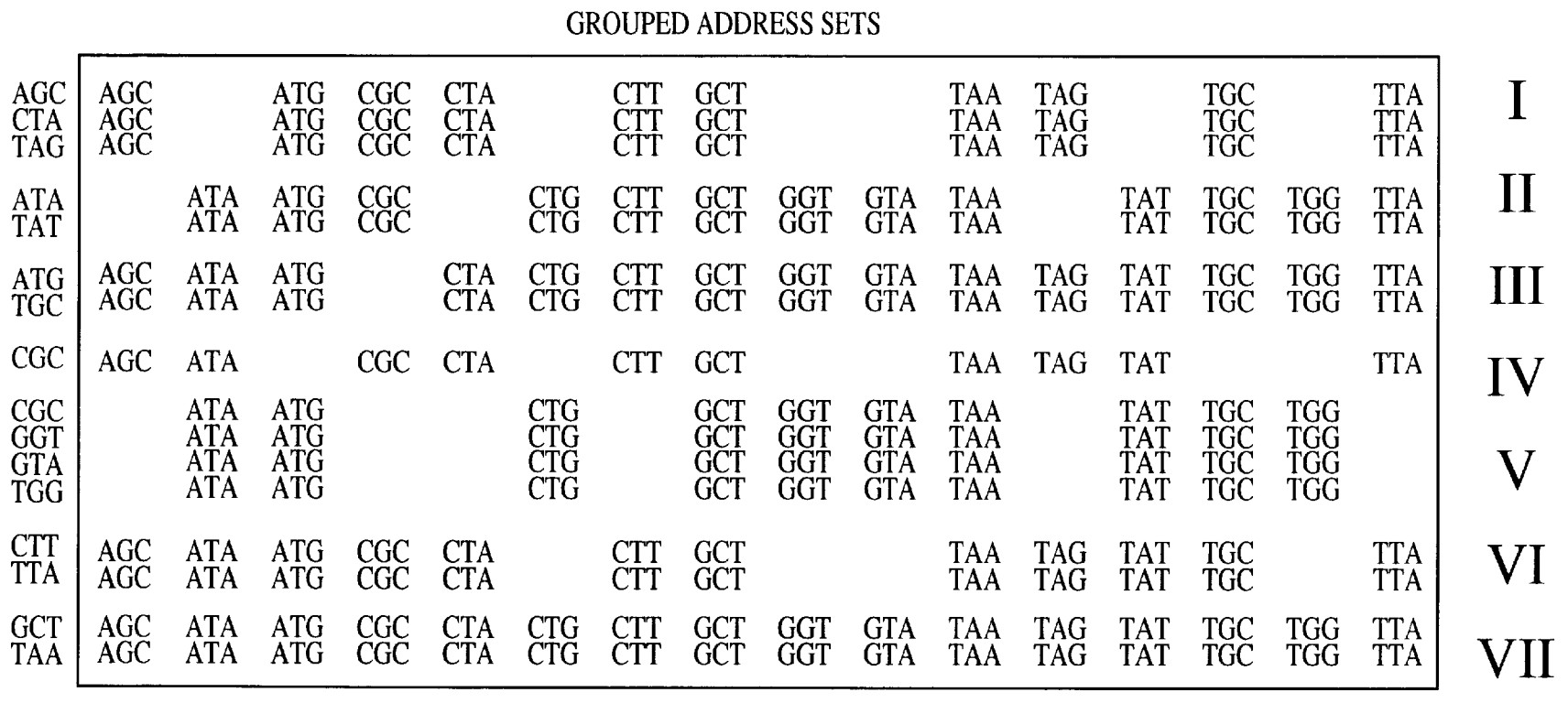

FIG. 22a shows the sequences of four short strands that are assumed to be present in a mixture. As in Example 6.1, above, it is assumed that complete sets of partials have been generated from this mixture of strands, and that each set of partials sharing the same address oligonucleotide has been separately surveyed. The address oligonucleotides and the surveyed oligonucleotides are assumed to be three nucleotides in length. FIG. 22b shows the indexed address sets determined for each relevant address in the partialing array. FIG. 22c shows the unindexed address sets, and FIG. 22d shows the unindexed address sets organized into groups according to the identity of the oligonucleotides that they contain. In this example, there are seven different groups of unindexed address sets.

As in Example 6.1, above, each group of identical address sets is compared to the other groups of identical address sets to see if its common address set appears to be a prime address set. This is accomplished for each address set by seeing whether any other address set is a subset of it. For example, in FIG. 22d, the address set common to group II is not a prime address set, because the address set common to group V is a subset of the address set common to group II. Similarly, group III is not prime, because group V is its subset, and both groups VI and VII are not prime, because group I is a subset of each of them. The remaining groups (namely, I, IV, and V) do not have subsets, and therefore appear to be comprised of prime address sets.

Each putative prime address set is then tested to see if it is indeed a prime set. This is accomplished by examining all the address sets that contain all of the oligonucleotides that are present in the putative prime address set. For example, in FIG. 23a, all the address sets that contain all the oligonucleotides that are present in the putative prime address set common to group I are listed together (namely the address sets contained in groups I, VI, and VII). Similarly, FIG. 23b lists all the address sets that contain all the oligonucleotides that are present in the putative prime address set common to group V; and FIG. 23c lists all the address sets that contain all the oligonucleotides that are present in the putative prime address set common to group IV. Each of these three putative prime address sets is then tested to see if it is indeed a prime set. The address set common to group V (analyzed in FIG. 23b) is indeed a prime set (and therefore contains a single strand set) because a list of those oligonucleotides that are found in every address set in the diagram is identical to the list of addresses on the left side of the diagram. The address set common to group I (analyzed in FIG. 23a), however, is not a prime set (and therefore does not contain a single strand set) because a list of those oligonucleotides that are found in every address set in the diagram (namely, AGC, ATG, CGC, CTA, CTT, GCT, TAA, TAG, TGC, and TTA) is not identical to the list of addresses on the left side of the diagram (namely, AGC, CTA, CTT, GCT, TAA, and TAG). The address set that is common to group I is therefore a pseudo-prime address set. Similarly, the address set common to group IV (analyzed in FIG. 23c) is also a pseudo-prime address set.

Pseudo-prime address sets are decomposed into strand sets by identifying the extra oligonucleotides that prevent the pseudo-prime address set from being a prime set. This is accomplished in the following manner: In the first step, a list is made of those oligonucleotides that are members of the pseudo-prime address set, but are not on the list of addresses whose address sets contain all the members of the pseudo-prime address set. For example, in FIG. 23a, pseudo-prime address set A consists of oligonucleotides: AGC, ATG, CGC, CTA, CTT, GCT, TAA, TAG, TGC, and TTA. However, the list of addresses shown in bold letters on the left of the diagram does not include: ATG, CGC, and TGC. In the second step, the groups associated with these "missed" addresses are identified. For example, from FIG. 22d, it can be seen that missed address oligonucleotides ATG and TGC belong to group VI, and missed address oligonucleotide CGC belongs to group IV. In the third step, new diagrams are prepared that include one or more of the "missed" groups. For example, FIG. 24a, is prepared by adding the address sets from group VI to the diagram from FIG. 23a. Similarly, FIG. 24b is prepared by adding the address set from group IV to the diagram from FIG. 23a. The set of oligonucleotides that are contained in every address set of this new diagram (they are seen as full columns) represents a putative strand set. For example, in FIG. 24a, the putative strand set consists of oligonucleotides AGC, ATG, CTA, CTT, GCT, TAA, TAG, TGC, and TTA. Similarly, in FIG. 24b, the putative strand set consists of oligonucleotides AGC, CGC, CTA, CTT, GCT, TAA, TAG, and TTA. The final step is to test each putative strand set to see if it is indeed a strand set. This is accomplished by seeing if the list of addresses on the left of the diagram is identical to the list of oligonucleotides in the putative strand set. For example, putative strand set A1, analyzed in FIG. 24a, is indeed a strand set, because the vertical list of nine addresses on the left of the diagram is identical to the list of nine oligonucleotides that are found in every one of the nine address sets. Similarly, putative strand set A2, analyzed in FIG. 24b, is also a strand set.

The decomposition of pseudo-prime address set C (identified in FIG. 23c) into its constituent strand sets illustrates an interesting aspect of this method. Its decomposition, shown in FIGS. 24c and 24d, gives rise to two strand sets, labeled "C1" and "C2". However, a comparison of all the strand sets identified indicates that strand set A2 is identical to strand set C2. Thus, there are four strands in the original mixture, represented by strand sets A1, A2, B, and C1.

The sequence of each of the four strands is then determined by: (a) assembling the oligonucleotides in the strand set into blocks, (b) filtering the indexed address sets to only include information that pertains to the oligonucleotides that are in the strand set, (c) converting the filtered address sets into block sets, (d) identifying the unique blocks (that only occur once in the sequence), (e) ascertaining the relative positions of the blocks from the information in the block sets, and (f) assembling the blocks into the nucleotide sequence of the strand by taking into account both the relative positions of the blocks and the sequences that occur at the termini of the blocks.

The power of this method is illustrated in FIGS. 25 to 28. For example, in the assembly of strand A1 (shown in FIG. 25), the top three block sets in FIG. 25d identify three blocks that definitely occur only once in the sequence (namely, "ATGC", "CTTA", and "TAGC"), and these three block sets also indicate the relative order of the three blocks. In addition, these block sets indicate that both "CTA" and "TAA" can only occur downstream of "TAGC", and that "GCT" can only occur downstream of "ATGC". Inspection of the lower three block sets in FIG. 25d shows that "GCT" occurs upstream of both "CTA" and "TAA", and that "TAA" occurs downstream of "CTA". The nucleotide sequence of Strand A1 is then assembled from a consideration of these positional constraints and a consideration of which blocks can maximally overlap each other. The gap between "ATGC" and "CTTA" is filled by "GCT". The gap between "CTTA" and "TAGC" cannot be filled by "GCT", however, "CTTA" is joined directly to "TAGC". The gap that occurs after "TAGC" can only be filled by joining "TAGC" to "GCT", then joining "GCT" to "CTA", and finally, joining "CTA" to "TAA" to complete the sequence.

In the assembly of Strand A2 (shown in FIG. 26), a consideration of the information in the two unique block sets ("CTTA" and "TAGC") indicates that: "CTTA" is upstream of "TAGC", "CGC" is upstream of "CTTA", both "CTA" and "TAA" are downstream of "TAGC", and "GCT" can occur at any position. It is easy to see that "GCT" occurs twice in the sequence, once to join "CGC" and "CTTA", and once again to join "TAGC" and "CTA". Although there is a gap between "CTTA" and "TAGC", it cannot be filled by "GCT", and the gap is filled by joining "CTTA" directly to "TAGC". The sequence is completed by joining "CTA" to "TAA".

In the assembly of strand B (shown in FIG. 27), "TGCTG" occurs upstream of "TGGTA". "ATG" occurs upstream of "TGCTG", and "TAT", "ATA", and "TAA" occur downstream of "TGGTA". It is easy to see that "ATG" is joined to "TGCTG", and "TGCTG" is joined to "TGGTA". It is also seen that "ATA" and "TAA" occur downstream of "TAT", and that "TAA" occurs downstream of "ATA". From a consideration of positional information and from a consideration of the sequence of the blocks, it follows that the only permissible way to fill in the gap that occurs downstream of "TGGTA" is to join "TGGTA" to "TAT", join "TAT" to "ATA", and then join "ATA" to "TAA", thus completing the sequence.

The assembly of strand C1 (shown in FIG. 28) is straightforward. There are two definitely unique sequence blocks ("CGCTTA" and "TATA"), and their order is known from their block sets ("CGCTTA" is upstream of "TATA"). The third block, "TAA", occurs downstream of both unique blocks. The sequence of Strand C1 is determined by joining "CGCTTA" to "TATA", and then joining "TATA" to "TAA".

We claim:

1. In a method wherein first and second nucleic acid strands are ligated to each other at their termini in order to form a recombinant product, the improvement comprising
    a) providing an array of immobilized oligonucleotides comprising predetermined areas on a surface of a solid support, each area having immobilized thereon copies of an oligonucleotide,
    b) hybridizing to said immobilized oligonucleotides first single-stranded terminal regions of first nucleic acid strands to be ligated, and
    c) ligating to the hybridized first termini of said hybridized first strands to said second nucleic acid strands.

2. The method of claim 1 wherein the first nucleic acid strands hybridized to the immobilized oligonucleotides have different nucleotide sequences in different areas of the array.

3. The method according to claim 1 wherein the second nucleic acid strands being ligated to the hybridized first strands have different nucleotide sequences in different areas of the array.

4. The method according to claim 1, wherein the array is a comprehensive array.

5. The method acording to claim 1, wherein the oligonucleotides immobilized in each area are of the same length.

6. A method according to claim 1, wherein the oligonucleotides consist of the group consisting of deoxyribonucleotides, ribonucleotides, mixed deoxyribonucleotides and ribonucleotides, modified deoxyribonucleotides, modified ribonucleotides, and non-standard nucleotides.

7. The method according to claim 1, wherein the second nucleic acid strands are not also hybridized to the immobilized oligonucleotides.

8. The method according to claim 7 wherein the second nucleic acid strands are strands of double stranded nucleic acids.

9. The method according to claim 8 wherein the second nucleic acid strands are the same in every area of the array.

10. The method according to claim 8 wherein the array is a sectioned array and the recombinant product is amplified in a polymerase chain reaction amplification.

11. The method according to claim 8 wherein the first nucleic acid strands being hybridized to the immobilized oligonucleotides are contained in at least one mixture containing additional strands also containing first single-stranded terminal regions, and wherein the first single-stranded terminal regions of said additional strands differ from the first terminal regions of said first nucleic acid strands.

12. The method according claim 8 wherein the double stranded nucleic acids have one end adapted for ligation to blunt ends formed by hybridization of the first termini of the first nucleic acid strands to the immobilized oligonucleotides.

13. The method according to claim 12 wherein nonligating termini of the first nucleic acid strands and the double stranded second nucleic acid strands contain priming regions for amplification.

14. The method according to claim 12 wherein the immobilized oligonucleotides are RNA and the double stranded second nucleic acid strands are ligated to the immobilized oligonucleotides using RNA ligase prior to ligation of the first nucleic acid strands to the second nucleic acid strands.

15. The method according to claim 1 wherein the array is a sectioned array.

16. The method according to claim 1 wherein the second nucleic acid strands have second single-stranded terminal regions to be ligated to the first single-stranded regions of said first nucleic acid strands and wherein, prior to ligation, the second single-stranded terminal regions of the second nucleic acid strands are hybridized to the immobilized oligonucleotides in the array.

17. The method according to claim 16 wherein the first nucleic acid strands being hybridized to the immobilized oligonucleotides are contained in at least one mixture containing first additional strands also containing first single-stranded terminal regions, and wherein the first single-stranded terminal regions of said first additional strands differ from the first terminal regions of said first nucleic acid strands; and, further, wherein the second nucleic acid strands being hybridized to the immobilized oligonucleotides are contained in at least one mixture containing second additional strands also containing second single-stranded terminal regions, and wherein the second single-stranded terminal regions of said second additional strands differ from the second terminal regions of said second nucleic acid strands.

18. The method according to claim 16 wherein the array is a binary oligonucleotide array whose immobilized oligonucleotides consist of a constant segment adjacent to a variable segment, and wherein the second nucleic acid strands are hybridized to the constant segment.

19. The method according to claim 16 wherein both the first and second nucleic acid strands contain priming regions at their non-ligating termini.

20. The method according to claim 19 wherein the array is a sectioned array and the recombinant product is amplified in a polymerase chain reaction.

21. A method of increasing the lengths of hybrids formed between nucleic acid strands and immobilized oligonucleotides in an array of immobilized oligonucleotides of different sequences, which hybrids have at least one single-stranded overhang that is a 3' extension, comprising the steps of annealing to the overhang an extender oligonucleotide prepared by hybridizing a primer to the overhang and extending the primer with a DNA polymerase, and enzymatically ligating the extender to the hybrid if it is annealed immediately adjacent to the hybrid.

22. A process for ligating on an array of first, immobilized oligonucleotides of different sequences comprising the steps of
   (a) incubating at least one nucleic acid strand with said immobilized oligonucleotides to form at least one hybrid having at least one single-stranded overhang comprising a 3' extension,
   (b) annealing to the overhangs a second oligonucleotide prepared by hybridizing a primer to the at least one overhang and extending the primer with a DNA polymerase, and
   (c) enzymatically ligating the second oligonucleotides to that at least one hybrid if it is annealed immediately adjacent thereto, thereby forming at least one hybrid of increased length.

23. A method of increasing the lengths of hybrids formed between nucleic acid strands of undetermined sequence in a sample and immobilized oligonucleotides in an array of immobilized oligonucleotides of different sequences, which hybrids have at least one single-stranded overhang, comprising the steps of annealing an extender oligonucleotide to the overhang and enzymatically ligating it to the hybrid if it is annealed immediately adjacent to the hybrid.

24. The method of claim 23 wherein the overhang is a 3' extension of the nucleic acid strands beyond the free 5' ends of the immobilized nucleotides.

25. A method of increasing the lengths of hybrids formed between nucleic acid strands and immobilized oligonucleotides in an array of immobilized binary oligonucleotides having different sequences and having a constant segment adjacent to a free-end variable segment, which hybrids have at least one single-stranded overhang, comprising the steps of annealing to the overhang an extender oligonucleotide that is hybridized to, and covers at least a part of, said constant segment, and enzymatically ligating it to the hybrid if it is annealed immediately adjacent to the hybrid.

26. The method of claim 25 wherein the extender oligonucleotide is annealed to the immobilized oligonucleotide prior to formation of the nucleic acid strand-immobilized oligonucleotide hybrid.

27. The method of claim 25 further comprising the subsequent step of washing under stringent conditions in which only extended hybrids will not be washed away.

28. A target-dependent process for ligating on an array of first, immobilized oligonucleotides of different sequences comprising the steps of
- (a) incubating a sample containing at least one nucleic acid strand of undetermined sequence with said immobilized oligonucleotides to form at least one hybrid having at least one single-stranded overhang,
- (b) annealing second oligonucleotides to the overhangs, and
- (c) enzymatically ligating the second oligonucleotides to the hybrids if they are annealed immediately adjacent thereto, thereby forming hybrids of increased length.

29. The process of claim 28 wherein step b) precedes step a).

30. The process of claim 28 further comprising the step of washing away strands not bound to the array by hybrids of increased length.

31. A method for introducing a plurality of site directed mutations into different copies of a parent nucleic acid strand on a sectioned oligonucleotide array using different-length partial copies of said parent strand, said copies corresponding to regions of the parent nucleic acid strand adjacent to the location of site directed mutations, comprising the steps of
- a) separately ligating said partial copies to free termini of immobilized oligonucleotides in said oligonucleotide array to obtain mutated partial copies of said strand, said oligonucleotide array comprising an array of predetermined areas on the surface of said support, each area having therein a different immobilized oligonucleotide having a sequence adapted to introduce a sequence containing a site directed mutation to a partial copy added to that area; and
- b) using the mutated partial copies to generate nucleic acid strands that are full-length mutant copies of the parent strand containing the site directed mutations.

32. The method according to claim 31 wherein step b is accomplished by
- (i) hybridizing a complementary copy of each mutated partial copy to a template having a sequence complementary to the remaining terminal portion of the parent nucleic acid strand which is not contained in said partial copy; and
- (ii) carrying out a polymerase chain reaction, a ligation reaction or both a polymerase chain reaction and a ligation reaction to join the remaining terminal portion of the parent nucleic acid strand to the mutated partial copy.

* * * * *

```
                           SEQUENCE LISTING

<160> NUMBER OF SEQ ID NOS: 18

<210> SEQ ID NO 1
<211> LENGTH: 16
<212> TYPE: DNA
<213> ORGANISM: Artificial Sequence
<220> FEATURE:
<223> OTHER INFORMATION: Synthetically derived DNA

<400> SEQUENCE: 1
atgagcctag atcggt                                                        16

<210> SEQ ID NO 2
<211> LENGTH: 12
<212> TYPE: DNA
<213> ORGANISM: Artificial Sequence
<220> FEATURE:
<223> OTHER INFORMATION: Synthetically derived DNA

<400> SEQUENCE: 2
acacacacac ac                                                            12

<210> SEQ ID NO 3
<211> LENGTH: 27
<212> TYPE: DNA
<213> ORGANISM: Artificial Sequence
<220> FEATURE:
<223> OTHER INFORMATION: Synthetically derived DNA

<400> SEQUENCE: 3
ggttgactga ctgactgact gacggtt                                            27

<210> SEQ ID NO 4
<211> LENGTH: 12
<212> TYPE: RNA
<213> ORGANISM: Artificial Sequence
<220> FEATURE:
<223> OTHER INFORMATION: Synthetically derived RNA

<400> SEQUENCE: 4
cgcgaauucg cg                                                            12

<210> SEQ ID NO 5
<211> LENGTH: 12
<212> TYPE: RNA
<213> ORGANISM: Artificial Sequence
<220> FEATURE:
<223> OTHER INFORMATION: Synthetically derived RNA

<400> SEQUENCE: 5
cgcguauacg cg                                                            12

<210> SEQ ID NO 6
<211> LENGTH: 24
<212> TYPE: DNA
<213> ORGANISM: Artificial Sequence
<220> FEATURE:
<223> OTHER INFORMATION: Synthetically derived DNA

<400> SEQUENCE: 6
tttaaaaaaa aaaaaaaaaa aaaa                                               24
```

```
<210> SEQ ID NO 7
<211> LENGTH: 15
<212> TYPE: DNA
<213> ORGANISM: Artificial Sequence
<220> FEATURE:
<223> OTHER INFORMATION: Synthetically derived DNA

<400> SEQUENCE: 7
atgagcctag atcgg                                                    15

<210> SEQ ID NO 8
<211> LENGTH: 14
<212> TYPE: DNA
<213> ORGANISM: Artificial Sequence
<220> FEATURE:
<223> OTHER INFORMATION: Synthetically derived DNA

<400> SEQUENCE: 8
atgagcctag atcg                                                     14

<210> SEQ ID NO 9
<211> LENGTH: 13
<212> TYPE: DNA
<213> ORGANISM: Artificial Sequence
<220> FEATURE:
<223> OTHER INFORMATION: Synthetically derived DNA

<400> SEQUENCE: 9
atgagcctag atc                                                      13

<210> SEQ ID NO 10
<211> LENGTH: 12
<212> TYPE: DNA
<213> ORGANISM: Artificial Sequence
<220> FEATURE:
<223> OTHER INFORMATION: Synthetically derived DNA

<400> SEQUENCE: 10
atgagcctag at                                                       12

<210> SEQ ID NO 11
<211> LENGTH: 11
<212> TYPE: DNA
<213> ORGANISM: Artificial Sequence
<220> FEATURE:
<223> OTHER INFORMATION: Synthetically derived DNA

<400> SEQUENCE: 11
atgagcctag a                                                        11

<210> SEQ ID NO 12
<211> LENGTH: 10
<212> TYPE: DNA
<213> ORGANISM: Artificial Sequence
<220> FEATURE:
<223> OTHER INFORMATION: Synthetically derived DNA

<400> SEQUENCE: 12
atgagcctag                                                          10

<210> SEQ ID NO 13
<211> LENGTH: 48
<212> TYPE: DNA
<213> ORGANISM: Artificial Sequence
<220> FEATURE:
```

```
<223> OTHER INFORMATION: Synthetically derived DNA

<400> SEQUENCE: 13
agcatgcctc tagaggccta gtgatagaga atccgggatg gttagtcg                    48

<210> SEQ ID NO 14
<211> LENGTH: 16
<212> TYPE: DNA
<213> ORGANISM: Artificial Sequence
<220> FEATURE:
<223> OTHER INFORMATION: Synthetically derived DNA

<400> SEQUENCE: 14
catggtacct tggtaa                                                       16

<210> SEQ ID NO 15
<211> LENGTH: 17
<212> TYPE: DNA
<213> ORGANISM: Artificial Sequence
<220> FEATURE:
<223> OTHER INFORMATION: Synthetically derived DNA

<400> SEQUENCE: 15
atggtccttg gtaccta                                                      17

<210> SEQ ID NO 16
<211> LENGTH: 12
<212> TYPE: DNA
<213> ORGANISM: Artificial Sequence
<220> FEATURE:
<223> OTHER INFORMATION: Synthetically derived DNA

<400> SEQUENCE: 16
atgctggtat aa                                                           12

<210> SEQ ID NO 17
<211> LENGTH: 12
<212> TYPE: DNA
<213> ORGANISM: Artificial Sequence
<220> FEATURE:
<223> OTHER INFORMATION: Synthetically derived DNA

<400> SEQUENCE: 17
atgcttagct aa                                                           12

<210> SEQ ID NO 18
<211> LENGTH: 11
<212> TYPE: DNA
<213> ORGANISM: Artificial Sequence
<220> FEATURE:
<223> OTHER INFORMATION: Synthetically derived DNA

<400> SEQUENCE: 18
cgcttagcta a                                                            11
```